United States Patent
Banks et al.

(12) 
(10) Patent No.: US 7,049,444 B2
(45) Date of Patent: *May 23, 2006

(54) 3-AZABICYCLO[3.1.0]HEXANE DERIVATIVES USEFUL IN THERAPY

(75) Inventors: Bernard Joseph Banks, Kent (GB); Robert James Crook, Kent (GB); Stephen Paul Gibson, Kent (GB); Graham Lunn, Kent (GB); Alan John Pettman, Kent (GB)

(73) Assignee: Pfizer Inc., New York, NY (US)

( * ) Notice: Subject to any disclaimer, the term of this patent is extended or adjusted under 35 U.S.C. 154(b) by 32 days.

This patent is subject to a terminal disclaimer.

(21) Appl. No.: 10/214,658

(22) Filed: Aug. 7, 2002

(65) Prior Publication Data

US 2003/0013875 A1    Jan. 16, 2003

Related U.S. Application Data

(60) Continuation of application No. 10/016,745, filed on Oct. 30, 2001, now abandoned, which is a division of application No. 09/467,871, filed on Dec. 20, 1999, now Pat. No. 6,313,312.

(30) Foreign Application Priority Data

Dec. 23, 1998 (GB) .................................... 9828485
May 27, 1999 (GB) .................................... 9912425

(51) Int. Cl.
    *C07D 209/52* (2006.01)

(52) U.S. Cl. ...................................... 548/452; 548/515

(58) Field of Classification Search .................. 458/452; 548/452, 515; 514/412
    See application file for complete search history.

(56) References Cited

U.S. PATENT DOCUMENTS 3,065,230 A * 11/1962 Baltzly .................... 260/247.1
6,313,312 B1* 11/2001 Banks et al. ................ 548/452

* cited by examiner

*Primary Examiner*—Golam M. M. Shameem
(74) *Attorney, Agent, or Firm*—Gregg C. Benson; Arlene K. Musser

(57) ABSTRACT

Compounds of formula (I), their salts and prodrugs thereof, where the substituents are as defined herein are disclosed as opiate binding agents useful in the treatment of opiate-mediated conditions. Also described are processes for making such substances.

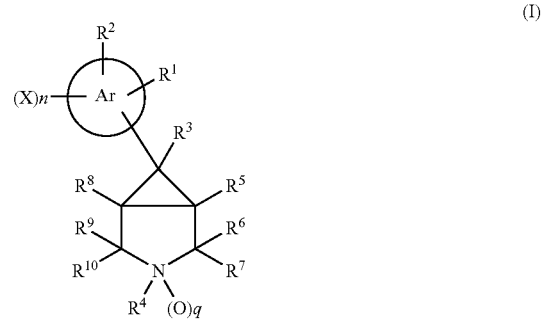

(I)

9 Claims, No Drawings

3-AZABICYCLO[3.1.0]HEXANE DERIVATIVES USEFUL IN THERAPY

RELATED APPLICATIONS

This application is a continuation of application U.S. Ser. No. 10/016,745, filed on Oct. 30, 2001, which is a divisional application and claims priority of U.S. patent application Ser. No. 09/467,871 filed on Dec. 20, 1999, now U.S. Pat. No. 6,313,312.

This invention relates to pharmaceutically useful compounds, in particular compounds that bind to opiate receptors (e.g. mu, kappa and delta opioid receptors). Compounds that bind to such receptors are likely to be useful in the treatment of diseases modulated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction, sexual dysfunction, shock, stroke, spinal damage and head trauma.

There is a particular need for an improved treatment of itching. Itching, or pruritus, is a common dermatological symptom that can give rise to considerable distress in both humans and animals. Pruritus is often associated with inflammatory skin diseases which may be caused by hypersensitivity reactions, including reactions to insect bites, such as flea bites, and to environmental allergens, such as house dust mite or pollen; by bacterial and fungal infections of the skin; or by ectoparasite infections.

Existing treatments that have been employed in the treatment of pruritus include the use of corticosteroids and antihistamines. However, both of these treatments are known to have undesirable side effects. Other therapies that have been employed include the use of essential fatty acid dietary supplements, though these have the disadvantages of being slow to act, and of offering only limited efficacy against allergic dermatitis. A variety of emollients such as soft paraffin, glycerine and lanolin are also employed, but with limited success.

Thus, there is a continuing need for alternative and/or improved treatments of pruritus.

Certain 4-arylpiperidine-based compounds are disclosed in inter alia European patent applications EP 287339, EP 506468 and EP 506478 as opioid antagonists. In addition, International Patent Application WO 95/15327 discloses azabicycloalkane derivatives useful as neuroleptic agents.

According to the invention there is provided a compound of formula I,

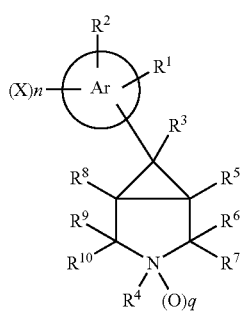

(I)

wherein the "Ar" ring represents an optionally benzo-fused phenyl or 5- or 6-membered heteroaryl ring;

$R^1$ when taken alone is H, halogen, $NO_2$, $NH_2$, $NY^2WY^1$, $Het^1$, AD, $CO_2R^7$, $C(O)R^8$, $C(=NOH)R^8$, or OE, $Y^2$ is H, $C_{1-6}$ alkyl, $C_{3-6}$ alkenyl (each of which alkyl and alkenyl is optionally substituted by aryl, aryloxy or $Het^1$), W is $SO_2$, CO, C(O)O, $P(Y^1)=O$, $P(Y^1)=S$, $Y^1$ is $C_{1-10}$ alkyl (optionally substituted by one or more substituents independently selected from halogen, OH, $C_{1-4}$ alkoxy, $C_{1-6}$ alkanoyloxy, $CONH_2$, $C_{1-6}$ alkoxycarbonyl, $NH_2$, aryl, mono- or di($C_{1-4}$ alkyl)amino, $C_{3-8}$ cycloalkyl, phthalimidyl, $Het^1$), $Het^1$, aryl (optionally substituted by one or more substituents independently selected from $C_{1-4}$ alkyl, $C_{1-4}$ haloalkyl and halogen), $NH_2$, $N(C_{1-6}$ alkyl$)_2$ or $NH(C_{1-6}$ alkyl), $Het^1$ is a heterocyclic group containing up to 4 heteroatoms selected from N, O and S, which may comprise up to 3 rings (preferably a heteroaryl group, optionally benzo- or pyrido-fused heteroaryl), optionally substituted by one or more substituents independently selected from $C_{1-6}$ alkyl, $C_{1-6}$ alkoxy, $C_{3-6}$ cycloalkyl, $C_{1-6}$ haloalkoxy, $C_{1-6}$ haloalkyl, $C_{3-6}$ halocycloalkyl, =O, OH, halogen, $NO_2$, $SiR^{19a}R^{19b}R^{19c}$, $CON^{20a}R^{20b}$, $NR^{20a}R^{20b}$, $SR^{21a}$, $NR^{21b}SO_2R^{22a}$, $NR^{21c}C(O)OR^{22b}$, $NR^{21d}COR^{22d}$, and $C_{1-6}$ alkoxycarbonyl, and if a S atom is present in a ring, it can be present as part of a —S—, S(O)— or —S(O$_2$)— group, and carbon atoms in the ring can be present as a part of a carbonyl moiety;

$R^{19a}$, $R^{19b}$, $R^{19c}$ each independently represent $C_{1-6}$ alkyl or aryl, $R^{20a}$ and $R^{20b}$ each independently represent H, $C_{1-6}$ alkyl, aryl, ($C_{1-4}$ alkyl)phenyl, each of which alkyl, aryl and alkylphenyl are optionally substituted by one or more $C_{1-4}$ alkyl, $C_{1-4}$ alkoxy, OH, $NO_2$, $NH_2$ and/or halogen, or $R^{20a}$ and $R^{20b}$ can be taken together with the N atom to which they are attached, to form a 4- to 6-membered ring optionally substituted by one or more substitutuents independently selected from one or more $C_{1-4}$ alkyl, $C_{1-4}$ alkoxy, OH, =O, $NO_2$, $NH_2$ and/or halogen, $R^{21a, b, c \, and \, d}$ each independently represent H, $C_{1-6}$ alkyl, aryl or $C_{1-4}$ alkylphenyl, each of which alkyl, aryl, and alkylphenyl are optionally substituted by one or more $C_{1-4}$ alkyl, $C_{1-4}$ alkoxy, OH, $NO_2$, halogen, $NH_2$, $R^{22a, b \, and \, c}$ each independently represent $C_{1-6}$ alkyl, aryl or $C_{1-4}$ alkylphenyl, each of which alkyl, aryl, and alkylphenyl are optionally substituted by one or more $C_{1-4}$ alkyl, $C_{1-4}$ alkoxy, OH, $NO_2$, halogen, $NH_2$, A is $C_{1-4}$ alkylene, $C_{2-4}$ alkenylene or $C_{2-4}$ alkynylene, each of which is optionally substituted by one or more $C_{1-4}$ alkyl, $C_{1-4}$ alkoxy, halogen and/or OH, D is H, OH, CN, $NR^{25}R_{26}$, $CONR^{25}R^{26}$, $NHR^{27}$, $CO_2R^{28}$, $COR^{29}$, $C(=NOH)R^{29}$, or AD is CN, $NR^{25}R^{26}$, $CONR^{25}R^{26}$, where $R^{25}$ and $R^{26}$ are either each independently H, $C_{1-3}$ alkyl, $C_{3-8}$ cycloalkyl, aryl, $C_{1-4}$ alkylphenyl (each of which $C_{1-3}$ alkyl, $C_{3-8}$ cycloalkyl, aryl and $C_{1-4}$ alkylphenyl are optionally substituted by one or more $NO_2$, halogen, $C_{1-4}$ alkyl and/or $C_{1-4}$ alkoxy, (each of which latter $C_{1-4}$ alkyl and $C_{1-4}$ alkoxy is optionally substituted by one or more halogen)), or $R^{25}$ and $R^{26}$ are taken together with the N atom to which they are attached and can form a 4- to 7-membered heterocyclic ring optionally incorporating one or more further hetero atoms selected from N, O and S, and which ring is optionally substituted by one or more $C_{1-4}$ alkyl, OH, =O, $NO_2$, $NH_2$ and/or halogen, $R^{27}$ is $COR^{30}$, $CO_2R^{31a}$, $SO_2R^{31b}$, $R^{28}$ and $R^{29}$ are each independently H, $C_{1-6}$ alkyl, $C_{3-8}$ cycloalkyl, aryl or $C_{1-4}$alkylphenyl, each of which $C_{1-6}$ alkyl, $C_{3-8}$ cycloalkyl, aryl and $C_{1-4}$ alkylphenyl are optionally substituted by one or more $NO_2$, halogen, $C_{1-4}$ alkyl, $C_{1-4}$ alkoxy (each of which latter $C_{1-4}$ alkyl and $C_{1-4}$ alkoxy are optionally substituted by one or more halogen), $R^{30}$ is H, $C_{1-4}$ alkyl, $C_{3-8}$ cycloalkyl, $C_{1-4}$ alkoxy, $C_{3-8}$ cycloalkyloxy, aryl, aryloxy, $C_{1-4}$ alkylphenyl, phenyl($C_{1-4}$)alkoxy, (each of which $C_{1-4}$ alkyl, $C_{3-8}$ cycloalkyl, $C_{1-4}$ alkoxy, $C_{3-8}$ cycloalkyloxy, aryl, aryloxy, $C_{1-4}$ alkylphenyl and phenyl($C_{1-4}$)alkoxy are optionally substituted by one or more $NO_2$, halogen, $C_{1-4}$ alkyl, $C_{1-4}$ alkoxy (which latter alkyl and alkoxy are optionally substituted by one or more halogen)), $R^{31a}$ and $R^{31b}$ are each independently $C_{1-4}$ alkyl, $C_{3-8}$ cycloalkyl, aryl or $C_{1-4}$ alkylphenyl, each of which is optionally substituted by one or more $NO_2$, halogen, $C_{1-4}$ alkyl or $C_{1-4}$ alkoxy, each of which latter alkyl and alkoxy is optionally substituted by one more halogen E is H, $CONR^{32}R^{33}$, $CSNR^{32}R^{33}$, $COR^{34}$, $CO_2R^{34}$, $COCH(R^{34a})NH_2$, $R^{35}$, $CH_2CO_2R^{35a}$, $CHR^{35b}CO_2R^{35a}$, $CH_2OCO_2R^{35c}$, $CHR^{35d}OCO_2R^{35c}$, $COCR^{36}=CR^{37}NH_2$, $COCHR^{36}CHR^{37}NH_2$, or $PO(OR^{38})_2$, $R^{32}$ and $R^{33}$ are each independently H, $C_{3-10}$ alkylalkenyl, $C_{3-7}$ cycloalkyl (optionally substituted by $C_{1-4}$ alkyl), phenyl (optionally substituted by $(X)_n$), $C_{1-10}$ alkyl (optionally substituted by $C_{4-7}$ cycloalkyl (optionally substituted by $C_{1-4}$ alkyl) or phenyl optionally substituted by $(X)_n$), or $R^{32}$ and $R^{33}$ can be taken together with the N atom to which they are attached and can form a 5- to 8-membered heterocycle optionally comprising further hetero atoms selected from N, O and S, which heterocycle is optionally substituted by $C_{1-4}$ alkyl, optionally substituted by one or more halogen, $R^{34}$ is H, $C_{4-7}$ cycloalkyl (optionally substituted by one or more $C_{1-4}$ alkyl), phenyl (optionally substituted by $(X)_n$, $C_{1-4}$ alkanoyloxy, $NR^{32}R^{33}$, $CONR^{32}R^{33}$ and/or OH), or $C_{1-6}$ alkyl (optionally substituted by one or more halogen, $C_{4-7}$ cycloalkyl (optionally substituted by one or more $C_{1-4}$ alkyl), or phenyl (optionally substituted by $(X)_n$, $C_{1-4}$ alkanoyloxy, $NR^{32}R^{33}$, $CONR^{32}R^{33}$ and/or OH)), $R^{34a}$ is H, $C_{1-6}$ alkyl (optionally substituted by one or more halogen, $C_{4-7}$ cycloalkyl (optionally substituted by one or more $C_{1-4}$ alkyl), or phenyl (optionally substituted by $(X)_n$, $C_{1-4}$ alkanoyloxy, $NR^{32}R^{33}$, $CONR^{32}R^{33}$ and/or OH)), $C_{4-7}$ cycloalkyl (optionally substituted by one or more $C_{1-4}$ alkyl), phenyl (optionally substituted by $(X)_n$, $C_{1-4}$ alkanoyloxy, $NR^{32}R^{33}$, $CONR^{32}R^{33}$ and/or OH) or a naturally occuring amino acid substituent, $R^{35}$ is $C_{4-7}$ cycloalkyl optionally substituted by one or more $C_{1-4}$ alkyl, phenyl optionally substituted by one or more $(X)_n$, $C_{1-4}$ alkanoyl, $NHR^{32}$, $CON(R^{32})_2$, and/or OH), $C_{1-6}$ alkyl (optionally substituted by $C_{4-7}$ cycloalkyl optionally substituted by one or more $C_{1-4}$ alkyl, or phenyl (optionally substituted by one or more $(X)_n$, $C_{1-4}$ alkanoyl, $NHR^{32}$, $CON(R^{32})_2$, and/or OH)), $C_{1-4}$ alkoxy($C_{1-4}$ alkyl), phenyl ($C_{1-4}$)alkyloxy($C_{1-4}$)alkyl, tetrahydropyranyl, tetrahydrofuranyl, cinnamyl or trimethylsilyl, $R^{35a,b,c\ and\ d}$ are each independently H, $C_{4-7}$ cycloalkyl optionally substituted by one or more $C_{1-4}$ alkyl, phenyl optionally substituted by one or more $(X)_n$ or $C_{1-6}$ alkyl (optionally substituted by $C_{4-7}$ cycloalkyl optionally substituted by one or more $C_{1-4}$ alkyl, or phenyl optionally substituted by one or more $(X)_n$), $R^{36}$ and $R^{37}$ each independently represent H, $C_{3-6}$ alkylalkenyl, $C_{4-7}$ cycloalkyl, phenyl optionally substituted by one or more $(X)_n$, or $C_{1-6}$ alkyl (optionally substituted by $C_{4-7}$ cycloalkyl optionally substituted by one or more $C_{1-4}$ alkyl, or phenyl optionally substituted by one or more $(X)_n$), $R^{38}$ is $C_{4-7}$ cycloalkyl optionally substituted by one or more $C_{1-4}$ alkyl, phenyl optionally substituted by one or more $(X)_n$, or $C_{1-6}$ alkyl (optionally substituted by $C_{4-7}$ cycloalkyl optionally substituted by one or more $C_{1-4}$ alkyl, or phenyl optionally substituted by one or more $(X)_n$), $R^2$ when taken alone is H or halogen;

or $R^1$ and $R^2$, when attached to adjacent carbon atoms, can be taken together with the carbon atoms to which they are attached, and may represent $Het^{1a}$;

$Het^{1a}$ is a heterocyclic group containing up to 4 heteroatoms selected from N, O and S, which may comprise up to 3 rings (and is preferably an optionally benzo-fused 5- to 7-membered heterocyclic ring) and which group is optionally substituted by one or more substituents independently selected from OH, =O, halogen, $C_{1-4}$ alkyl, $C_{1-4}$ haloalkyl, $C_{1-4}$ alkoxy and $C_{1-4}$ haloalkoxy, which $C_{1-4}$ alkyl, $C_{1-4}$ haloalkyl, $C_{1-4}$ alkoxy and $C_{1-4}$ haloalkoxy groups can be optionally substituted by one or more $C_{3-6}$ cycloalkyl, aryl($C_{1-6}$)alkyl, which aryl group is optionally substituted by one or more halogen, $C_{1-4}$ alkyl, $C_{1-4}$ haloalkyl, $C_{1-4}$ alkoxy and $C_{1-4}$ haloalkoxy, which latter $C_{1-4}$ alkyl, $C_{1-4}$ haloalkyl, $C_{1-4}$ alkoxy and $C_{1-4}$ haloalkoxy groups can be optionally substituted by one or more $NR^{23}R^{24}$, $NR^{23}S(O)_nR^{24}$, $NR^{23}C(O)_nR^{24}$, and if a S atom is present in a ring, it can be present as part of a —S—, S(O)— or —S(O$_2$)— group, which $R^{23}$ and $R^{24}$ when taken alone independently represent H, $C_{1-4}$ alkyl, or $C_{1-4}$ haloalkyl, or $R^{23}$ and $R^{24}$ can be taken together with the N atom to which they are attached, to form a 4- to 6-membered heterocyclic ring optionally comprising one or more further heteroatoms selected from, N, O, or S, and which heterocyclic ring is optionally substituted by one or more halogen, $C_{1-4}$ alkyl, $C_{1-4}$ haloalkyl, $C_{1-4}$ alkoxy and/or $C_{1-4}$ haloalkoxy groups, $R^3$ is H, CN, halogen, $C_{1-6}$ alkoxy, $C_{1-6}$ alkoxycarbonyl, $C_{2-6}$ alkanoyl, $C_{2-6}$ alkanoyloxy, $C_{3-8}$ cycloalkyl, $C_{3-8}$ cycloalkyloxy, $C_{4-9}$ cycloalkanoyl, aryl, aryloxy, heteroaryl, saturated heterocycle, $NR^{12}R^{13}$, $CONR^{12}R^{13}$, $NY^2WY^1$, $C_{1-6}$ alkyl, $C_{2-10}$ alkenyl, $C_{2-10}$ alkynyl, (each of which alkyl, alkenyl and alkynyl groups is optionally substituted by one or more CN, halogen, OH, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl, saturated heterocycle, $NR^{12}R^{13}$, $CONR^{12}R^{13}$ and/or $NY^2WY^1$), $R^4$ is $C_{1-10}$ alkyl, $C_{3-10}$ alkenyl or $C_{3-10}$ alkynyl each of which groups is linked to the N atom via a sp$^3$ carbon, and which is optionally substituted by one or more OH, CN, halogen, $C_{1-6}$ alkoxy (optionally substituted by aryl), aryloxy (optionally substituted by one or more halogen, $C_{1-6}$ alkyl(optionally substituted by one or more CN and/or halogen), $C_{1-4}$ alkoxy, $C_{1-4}$ haloalkoxy, OH and/or $NY^2WY$), $C_{1-6}$ alkoxycarbonyl, $C_{2-6}$ alkanoyl, $C_{2-6}$ alkanoyloxy, $C_{3-8}$ cycloalkyl, $C_{3-8}$ cycloalkyloxy, $C_{4-9}$ cycloalkanoyl, aryl (optionally substituted by one or more halogen, $C_{1-6}$ alkyl(optionally substituted by one or more CN and/or halogen), $C_{1-4}$ alkoxy, $C_{1-4}$ haloalkoxy, OH and/or $NY^2WY$), $C_{1-4}$ alkoxy, $C_{1-4}$ haloalkoxy, OH, $C_{1-4}$ haloalkoxy, and/or $NY^2WY$), heterocycle (optionally benzo-fused and optionally substituted by one or more halogen, $C_{1-6}$ alkyl(optionally substituted by one or more CN and/or halogen), $C_{1-4}$ alkoxy, OH, $C_{1-4}$ haloalkoxy, and/or $NY^2WY$), heterocyclyloxy (optionally substituted by one or more halogen, $C_{1-6}$ alkyl(optionally substituted by one or more CN and/or halogen), $C_{1-4}$ alkoxy, OH, $C_{1-4}$ haloalkoxy, and/or $NY^2WY$), adamantyl or $ZBNR^{14}R^{15}$, Z is a direct bond, CO or $S(O)_n$ group, B is $(CH_2)_p$, $R^{12}$ and $R^{13}$ each independently represent H or $C_{1-4}$ alkyl, or $R^{12}$ and $R^{13}$ can be taken together with the N atom to which they are attached to form a 4- to 7-membered heterocycle optionally comprising a further hetero moiety selected from $NR^{16}$, O and/or S, and which is optionally substituted by one or more $C_{1-4}$ alkyl, $R^{14}$ and $R^{15}$ each independently represent H, $C_{1-10}$ alkyl, $C_{3-10}$ alkenyl, $C_{3-10}$ alkynyl, $C_{3-8}$ cycloalkyl, aryl or heteroaryl, or $R^{14}$ and $R^{15}$ can be taken together with the N atom to which they are attached to form a 4- to 7-membered heterocycle optionally comprising a further hetero moiety selected from $NR^{16}$, O and/or S, and which is optionally substituted by one or more $C_{1-4}$ alkyl, $R^{16}$ is H, $C_{1-6}$ alkyl, $C_{3-8}$ cycloalkyl, $(C_{1-6}$ alkylene)$(C_{3-8}$ cycloalkyl) or $(C_{1-6}$ alkylene)aryl, $R^5$ and $R^8$ when taken separately are each independently H, $C_{1-6}$ alkyl, $R^5$ and $R^8$ can be taken together with the carbon atoms to which they are joined to form a $C_{3-8}$ cycloalkyl ring, $R^6$, $R^7$, $R^9$ and $R^{10}$ when taken separately are H, $R^5$ and $R^6$ or $R^7$ can be taken together with the carbon atoms to which they are joined to form a $C_{3-8}$ cycloalkyl ring, X is halogen, $C_{1-4}$ alkyl, $C_{1-4}$ alkoxy, $C_{1-4}$ haloalkyl or $C_{1-4}$ haloalkoxy, m is 1 or 2;

n is 0, 1 or 2;

p is 0, 1, 2, 3, 4, 5, 6, 7, 8, 9 or 10;

q is 0 or 1;

"Naturally occuring amino acid substituent" means the □-substituent that occurs in any one of the following natural amino acids, glycine, alanine, valine, leucine, isoleucine, phenylalanine, tryptophan, tyrosine, histidine, serine, threonine, methionine, cysteine, aspartic acid, glutamic acid, asparagine, glutamine, lysine, arginine or proline;

"Heteroaryl" represents an aromatic ring containing up to four heteroatoms independently selected from N, O and S, and if a S atom is present in the ring, it can be present as part of a —S—, S(O)— or —S(O)$_2$— group, and which may be joined to the remainder of the compound via any available atom(s);

"Heterocycle" is a group containing 1, 2 or 3 rings, and which contains up to 4 ring heteroatoms selected from N, O and S and up to 18 ring carbon atoms;

"Aryl", including in the definitions of "aryloxy", etc., means a group comprising a phenyl ring and which may incorporate a further carbocyclic ring fused to said phenyl ring and which may be joined to the remainder of the compound via any available atom(s) (examples of such groups include naphthyl, indanyl, etc.);

"Alkyl", "alkenyl" and "alkynyl" groups can be linear or branched if the number of carbon atoms allows;

"Cycloalkyl" groups can be polycyclic if the number of carbon atoms allows;

or a pharmaceutically or veterinarily acceptable derivative or prodrug thereof.

Where a fused heterocyclic group is present it can be attached to the remainder of the compound via any available atom(s).

"Haloalkyl", "haloalkoxy" groups and the like can contain more than one halogen atom, and for instance can be per-halogenated.

Certain of the compounds of the invention can exist in one or more geometric and/or stereoisomeric forms. The present invention includes all such individual isomers and salts and prodrugs thereof.

Certain compounds of the present invention may exist in more than one tautomeric form. Similarly certain compounds of the invention may have zwitterionic forms. It is to be understood that the invention embraces all such tautomers, zwitterions and their derivatives.

The pharmaceutically acceptable salts of the compounds of the formula (I) include the acid addition and the base salts thereof. Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts. Suitable base salts are formed from bases which form non-toxic salts and examples are the aluminium, calcium, lithium, magnesium, potassium, sodium, zinc and diethanolamine salts. For a review on suitable salts see Berge et al, J. Pharm. Sci., 66, 1–19 (1977).

It will be appreciated by those skilled in the art that certain protected derivatives of compounds of formula (I), which may be made prior to a final deprotection stage, may not possess pharmacological activity as such, but may, in certain instances, be transformed after administration into or onto the body, for example by metabolism, to form compounds of formula (I) which are pharmacologically active. Such derivatives are included in the term "prodrug". It will further be appreciated by those skilled in the art that certain moieties known to those skilled in the art as "pro-moieties", for example as described in "Design of Prodrugs" by H Bundgaard (Elsevier) 1985, may be placed on appropriate functionalities when such functionalities are present in compounds of formula (I), also to form a "prodrug". Further, certain compounds of formula I may act as prodrugs of other compounds of formula I. All protected derivatives, and prodrugs, of the compounds of formula I are included within the scope of the invention.

Preferably the "Ar" ring represents phenyl or pyridyl.

Most preferably the "Ar" ring represents a group of formula:

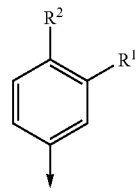

Preferably $R^1$ when taken alone is OH, CN, halogen, $NO_2$, $NH_2$, $NY^2WY^1$ or $Het^1$.

More preferably $R^1$ when taken alone is OH, CN, I, Cl, $NH_2$, $NO_2$, optionally benzo-fused heteroaryl, $NHSO_2Y^1$, $NHCOY^1$ or $NHCO_2Y^1$.

Yet more preferably $R^1$ when taken alone is OH, CN, I, Cl, $NH_2$, $NO_2$, 1,2,3-triazolyl, 1,2,4-triazolyl, imidazol-2-yl, pyridin-2-yl, thien-2-yl, imidazol-4-yl, benzimidazol-2-yl, $NHSO_2(C_{1-6}$ alkyl), $NHSO_2(C_{1-6}$ alkyl substituted by methoxy, $CONH_2$, OH, $CO_2(C_{2-6}$ alkyl), phthalimido, $NH_2$ or halogen), $NHSO_2NH_2$, $NHSO_2NH(C_{1-6}$ alkyl), $NHSO_2N$ $(C_{1-6}$ alkyl$)_2$, $NHSO_2Het_{1a}$, $NHCO(C_{1-6}$ alkyl) or $NHCO_2$ $(C_{1-6}$ alkyl).

Even more preferably $R^1$ is OH, $NHSO_2CH_3$, $NHSO_2C_2H_5$, $NHSO_2(n-C_3H_7)$, $NHSO_2(i-C_3H_7)$, $NHSO_2$ $(n-C_4H_7)$, $NHSO_2NH(i-C_3H_7)$, $NHSO_2$(N-methylimidazol-4-yl), $NHSO_2(CH_2)_2OCH_3$, $NHSO_2(CH_2)_2OH$, 1,2,4-triazolyl or imidazol-2-yl.

Most preferably $R^1$ is OH, $NHSO_2CH_3$, $NHSO_2C_2H_5$ or imidazol-2-yl.

Preferably $R^2$ when taken alone is H.

$R^1$ and $R^2$ when taken together with the carbon atoms to which they are attached are preferably an optionally benzo-fused 5- to 7-membered heteroaryl ring optionally substituted by $C_{1-4}$ alkyl or $C_{1-4}$ haloalkyl.

More preferably $R^1$ and $R^2$ when taken together with the carbon atoms to which they are attached are a 5-membered heteroaryl moiety optionally substituted by $C_{1-4}$ alkyl or $C_{1-4}$ haloalkyl.

Yet more preferably $R^1$ and $R^2$ when taken together with the carbon atoms to which they are attached are an imidazole group optionally 2-substituted by $CF_3$.

Preferably X is Cl.
Preferably n is 0.
Preferably q is 0.

Preferably $R^3$ is H, CN, $C_{1-6}$ alkyl (optionally substituted by one or more halogen, OH, $C_{1-6}$ alkoxy, $C_{1-6}$ alkoxycarbonyl, $C_{2-6}$ alkanoyl, $C_{2-6}$ alkanoyloxy, $C_{2-6}$ alkyloxycarbonyloxy, $NR^{12}R^{13}$, $CONR^{12}R^{13}$ and/or $NY^2WY^1$).

More preferably $R^3$ is H, $CH_3$, $C_2H_5$, $i-C_3H_7$, $n-C_3H_7$ or $CH_2OCH_3$.

Most preferably $R^3$ is $CH_3$.

Preferably $R^4$ is $C_{1-10}$ alkyl, $C_{3-10}$ alkenyl or $C_{3-10}$ alkynyl each of which groups is linked to the N atom via a $sp^3$ carbon, each of which is optionally substituted by $C_{3-8}$ cycloalkyl, aryl (optionally substituted by one or more methyl, ethyl, halogen, $CH_2CN$, $CF_3$, $NHSO_2CH_3$, OH, =O, methoxy, $OCF_3$), optionally benzo-fused heteroaryl (optionally substituted by one or more methyl, halogen, $CH_2CN$, $CF_3$, $NHSO_2CH_3$, methoxy, OH, =O, $OCF_3$), OH, aryloxy (optionally substituted by one or more methyl, halogen, $CH_2CN$, OH, =O, $CF_3$, $NHSO_2CH_3$, methoxy, $OCF_3$), CN, $CF_3$, $C_{1-6}$ alkoxy, $C_{3-8}$ cycloalkyloxy, CONH $(C_{3-8}$ cycloalkyl), adamantyl, or (optionally benzo-fused) heteroaryloxy (optionally substituted by one or more methyl, halogen, $CH_2CN$, $CF_3$, $NHSO_2CH_3$, OH, =O, methoxy, $OCF_3$).

More preferably $R^4$ is n-hexyl, 3-phenylpropyl, 3-phenyloxypropyl, 3-cyclohexylpropyl, 5-methylhexyl, 2-phenyloxyethyl, (4-cyanomethyl)benzyl, 2-cyclohexyloxyethyl, 2-benzyloxyethyl, 3-cyclohexylprop-2-en-1-yl, 2-(cyclohexylcarbonyl)ethyl, 3-(2-methylphenyl)propyl, 3-phenylprop-2-en-1-yl, 2-(indol-3-yl)ethyl, 3-cyclohexyl-3-hydroxypropyl, (indan-2-yl)methyl, 3-(4-fluorophenyl)propyl, 3-(thien-2-yl)propyl, 3-(thien-3-yl)propyl, 3-(pyrid-2-yl) propyl, 3-(3-methylthien-2-yl)propyl, 3-(thien-2-yl)prop-2-en-1-yl, 3-(thien-3-yl)prop-2-en-1-yl, 3-(pyrid-2-yl)prop-2-en-1-yl, 3-(3-methylthien-2-yl)prop-2-en-1-yl, 3-(3-methylpyrid-2-yl)prop-2-en-1-yl or 3-(2-methoxyphenyl) propyl.

Yet more preferably $R^4$ is n-hexyl, 3-phenylpropyl, (4-cyanomethyl)benzyl, 2-benzyloxyethyl, 3-cyclohexylprop-2-en-1-yl, 2-(indol-3-yl)ethyl, 3-(2-methylphenyl)propyl, 3-(4-fluorophenyl)propyl, 3-(pyrid-2-yl)propyl, 3-phenylprop-2-en-1-yl, 3-cyclohexyl-3-hydroxypropyl, 3-(thien-2-yl)propyl, 3-(thien-3-yl)propyl, 3-(3-methylthien-2-yl) propyl, 3-(thien-2-yl)prop-2-en-1-yl, 3-(thien-3-yl)prop-2-en-1-yl, 3-(pyrid-2-yl)prop-2-en-1-yl, 3-(3-methylthien-2-yl)prop-2-en-1-yl, 3-(6-methylpyrid-2-yl)prop-2-en-1-yl or 3-(2-methoxyphenyl)propyl.

Preferably $R^5$, $R^6$, $R^7$, $R^8$ $R^9$ and $R^{10}$ are each taken separately and are H.

A preferred group of substances are those in which the "Ar" ring, $R^1$, $R^2$, $R^3$, $R^4$, $R^5$, $R^6$, $R^7$, $R^8$, $R^9$, $R^{10}$, q and $(X)_n$ have the values as detailed in the Examples below.

A most preferred group of substances are those mentioned in the Examples, especially Examples 1, 5, 6, 10–13, 18, 20, 25–28, 32–34, 36, 38, 40, 42, 45, 47, 48, 57, 62, 67–69, 76, 79, 80, 84, 88, 90, 92, 97, 99, 102, 113, 114, 118, 119, 122–124, 136, 139 and 143, and the salts and prodrugs thereof, even more especially those of Examples 1, 5, 10, 12, 13, 26, 28, 36, 40, 45, 47, 48, 62, 68, 69, 79, 80, 84, 88, 90, 97, 99, 102, 113, 118, 114, 119, 122–124, 136, 139 and 143 and the salts and prodrugs thereof. Yet more preferred are the compounds of Examples 1, 10, 13, 26, 28, 62, 68, 69, 79, 80, 84, 88, 90, 97, 102, 113, 114, 118, 119, 12, 123, 124, 136, 139, and 143 and the salts and prodrugs thereof. Most preferred are the compounds of Examples 1, 10, 26, 79, 97, 102, 118, 139 and 143 and the salts and prodrugs thereof.

The invention further provides synthetic methods for the production of compounds and salts of the invention, which are described below and in the Examples and Preparations. The skilled man will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, VCH (1989 or later editions), "Advanced Organic Chemistry—Reactions, Mechanisms and Structure", J. March, Wiley-Interscience (3rd or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

It is to be understood that the synthetic transformation methods mentioned herein are exemplary only and they may be carried out in various different sequences in order that the desired compounds can be efficiently assembled. The skilled chemist will exercise his judgement and skill as to the most efficient sequence of reactions for synthesis of a given target compound. For example, substituents may be added to and/or chemical transformations performed upon, different intermediates to those mentioned hereinafter in conjunction with a particular reaction. This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein. Functional groups which may desirable to protect include oxo, hydroxy, amino and carboxylic acid. Suitable protecting groups for oxo include acetals, ketals (e.g. ethylene ketals) and dithianes. Suitable protecting groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

In the Methods below, unless otherwise specified, the substituents are as defined above with reference to the compounds of formula (I).

The invention provides a process for the preparation of compounds of formula I as defined above, or a pharmaceutically or veterinarily acceptable derivative thereof, which comprises:

(a) for compounds of formula I in which q is 0 and $R^1$ represents $NY^2WY^1$, reacting a compound of formula II,

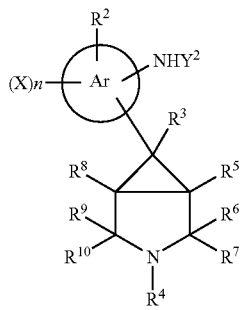

II with a compound of formula III, $Z^1$-$WY^1$    III wherein $Z^1$ is a suitable leaving group, such as halogen or $Y^1SO_2O$—;

(b) for compounds of formula I in which q is 0 and $R^6$ and $R^7$ both represent H, reduction of a compound of formula IV,

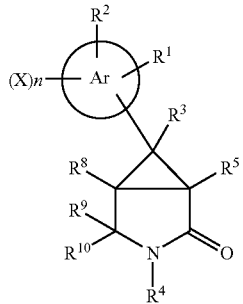

IV using a suitable reducing agent;

(c) for compounds of formula I in which q is 0 and $R^9$ and $R^{10}$ both represent H, reduction of a compound of formula V,

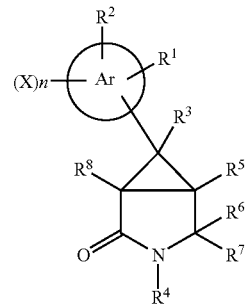

V using a suitable reducing agent;

(d) for compounds of formula I in which q is 0 and $R^1$ and $R^2$ are attached to adjacent carbon atoms and are taken together with the carbon atoms to which they are attached to represent $Het^{1a}$, in which $Het^{1a}$ represents an imidazolo unit, reaction of a corresponding compound of formula VI,

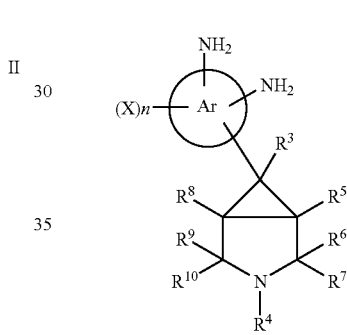

VI with a compound of formula VII, $R^yCO_2H$    VII wherein $R^y$ represents H or any of the optional substituents on $Het^{1a}$ (as defined above), preferably H, $C_{1-4}$ alkyl or $C_{1-4}$ haloalkyl;

(e) where q is 0, reacting a compound of formula VIII,

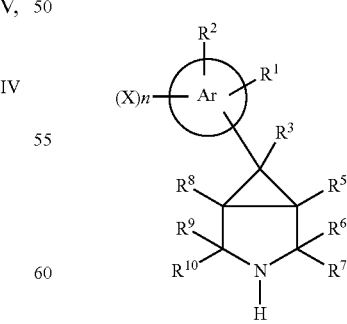

VIII with a compound of formula IX, $R^4$-Lg    IX wherein Lg is a leaving group;

(f) for compounds of formula I in which q is 0 and $R^6$, $R^7$, $R^9$ and $R^{10}$ are all H, reduction of a compound of formula X,

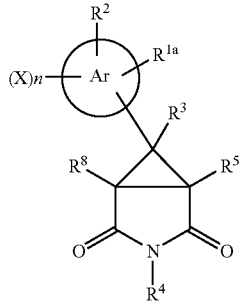

X with a suitable reducing agent;

(g) for compounds of formula I in which q is 0 and $R^1$ represents OH, reacting a compound of formula II in which $Y^2$ is H, as defined above, with fluoroboric acid and isoamyl nitrite;

(h) for compounds of formula I in which q is 0 and $R^1$ represents Cl, reacting a compound of formula II in which $Y^2$ is H, as defined above, with sodium nitrite in the presence of dilute acid, followed by reaction with copper (I) chloride in the presence of concentrated acid;

(i) for compounds of formula I in which q is 1, reacting a compound of formula I where q is 0 with a suitable oxidising agent such as aqueous hydrogen peroxide; or (j) for compounds of formula I where q is 0, by reduction of a corresponding compound of formula XXXI,

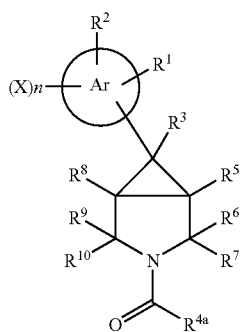

XXXI where $R^{4a}CH_2$ takes the same meaning as $R^4$ as defined above, and where desired or necessary converting the resulting compound of formula I into a pharmaceutically or veterinarily acceptable derivative or vice versa.

In process (a), the reaction may be carried out at between 0° C. and room temperature in the presence of a suitable base (e.g. pyridine) and an appropriate organic solvent (e.g. dichloromethane).

Compounds of formula II may be prepared by reduction of a corresponding compound of formula XI or formula XII,

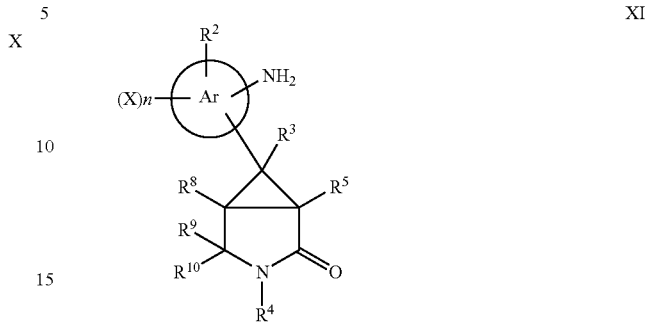

XI

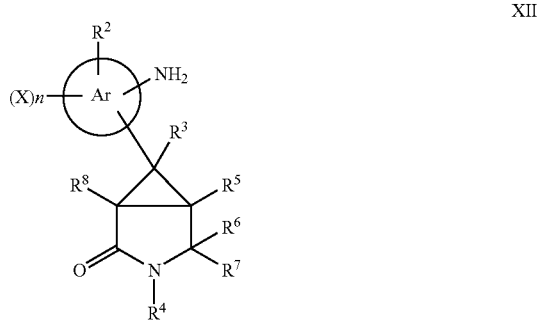

XII in the presence of a suitable reducing agent, such as lithium aluminium hydride. The reaction may be carried out at between room temperature and reflux temperature in the presence of a suitable solvent (e.g. tetrahydrofuran).

Compounds of formula XI and XII may be prepared by reduction of the corresponding —$NO_2$ compounds under conditions that are well known to those skilled in the art (e.g. using $H_2$/Raney Ni or in the presence of $CaCl_2$ and iron powder, in the presence of a suitable solvent system (e.g. EtOH, EtOAc and/or water)). The skilled person will appreciate that, in preparing a compound of formula II, in which $Y^2$ is H, from such a corresponding —$NO_2$ compound, the two above-mentioned reduction steps may be performed in the same step or sequentially in any order.

The said corresponding —$NO_2$ compounds may be prepared by reaction of a compound of formula XII or formula XIV, as appropriate,

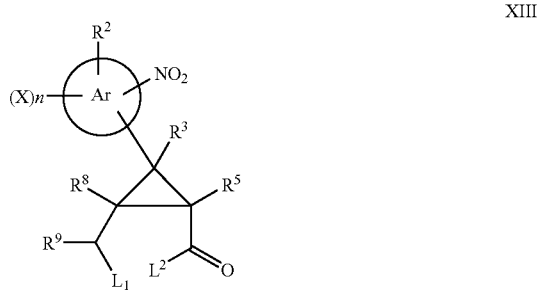

XIII

-continued

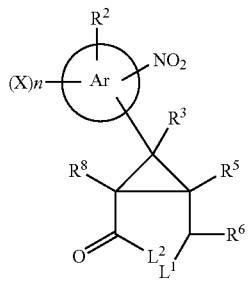

XIV wherein $L^1$ represents a suitable leaving group [such as halo (e.g. chloro or bromo)], $L^2$ represents a suitable leaving group (such as $C_{1-3}$ alkoxy) and $R^3$ is as defined above, with a compound of formula XV,

  XV

The reaction may be carried out at between room temperature and reflux temperature in the presence of a suitable base (e.g. NaHCO$_3$) and an appropriate organic solvent (e.g. dimethylformamide), or at a higher temperature (e.g. between 50 and 200° C., preferably between 100 and 160° C.) in the presence of neat compound of formula XV.

Compounds of formula XIII and XIV may be prepared in accordance with standard techniques. For example, compounds of formula XIII and XIV may be prepared by reacting a corresponding compound of formula XVI or XVII,

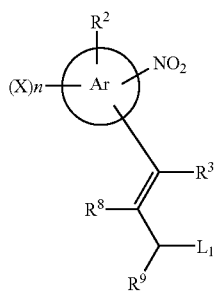

XVI

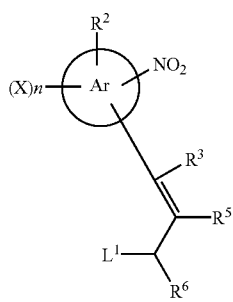

XVII with a compound of formula XVIII or XIX respectively,

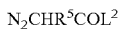  XVIII

  XIX wherein $L^2$ is as defined above. The reaction may be carried out at room temperature in the presence of a suitable catalyst [e.g. Rh$_2$(OAc)$_4$] and an appropriate non-protic organic solvent (e.g. dichloromethane).

Compounds of formula XVI and formula XVII are available or can be prepared using known techniques. Compounds of formula XVI and formula XVII may, for example, be prepared from corresponding compounds of formula XX,

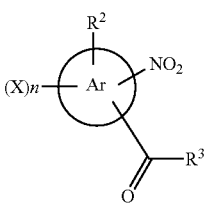

XX for example by performing a Wittig reaction using an appropriate provider of the nucleophilic group RO$_2$C—CR$^5$H$^-$ or RO$_2$C—CR$^8$H$^-$ (wherein R represents lower (e.g. $C_{1-3}$) alkyl), as appropriate, under conditions that are well known to those skilled in the art. The —CO$_2$R group of the resulting compound may be converted to an appropriate —CH$^2$L$^1$ group using standard techniques (e.g. reduction of the ester to the primary alcohol and conversion of the latter to an alkyl halide) under conditions that are well known to those skilled in the art.

In processes (b) and (c), suitable reducing agents include lithium aluminium hydride. The reaction may be carried out at between room temperature and reflux temperature in the presence of a suitable solvent (e.g. tetrahydrofuran).

Compounds of formula II may be prepared by reduction of the corresponding compound of formula XXX,

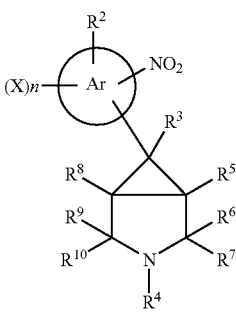

XXX by analogy to the process steps mentioned above.

Compounds of formula IV and V may be prepared respectively from compounds of formula XXI and XXII,

XXI

-continued

XXII

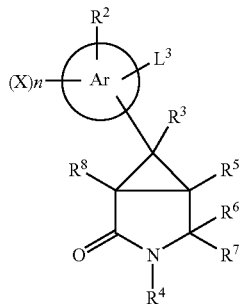

wherein L³ represents a group that is capable of undergoing functional group transformations (e.g. cyano) using standard functional group substitution or conversion techniques.

For example:

(1) Compounds of formula IV and V in which $R^1$ represents 1,2,4-triazol-3-yl may be prepared by reaction of an appropriate compound of formula XXI or XXII in which $L^3$ represents —CN with HCl (gas) in the presence of an appropriate lower alkyl alcohol (e.g. ethanol), for example at between 0° C. and room temperature, followed by reaction of the resultant intermediate with formic acid hydrazide (e.g. at reflux temperature, with or without the presence of a suitable organic solvent (e.g. methanol), followed by, if necessary, removing the solvent and heating the resultant residue to a high temperature (e.g. about 150° C.)).

(2) Compounds of formula IV and V in which $R^1$ represents imidazol-2-yl may be prepared by reaction of an appropriate compound of formula XXI or XXII in which $L^3$ represents —CN with HCl (gas) in the presence of an appropriate lower alkyl alcohol (e.g. ethanol), for example at between 0° C. and room temperature, followed by reaction of the resultant intermediate with aminoacetaldehyde dialkylacetal (e.g. dimethylacetal) (e.g. at or around reflux temperature in the presence of an appropriate solvent, such as methanol).

(3) Compounds of formula IV and V in which $R^1$ represents 1,2,3-triazol-5-yl may be prepared by reaction of an appropriate compound of formula XXI or XXII in which $L^3$ represents —CN with diazomethane, or a protected (e.g. trialkylsilyl) derivative thereof, for example at between 0° C. and room temperature in the presence of a suitable base (e.g. n-BuLi) and, optionally, an appropriate organic solvent (e.g. THF), followed by removal of the protecting group as necessary.

(4) Compounds of formula IV and V in which $R^1$ represents benzimidazol-2-yl may be prepared by reaction of an appropriate compound of formula XXI or XXII in which $L^3$ represents C=NH(OEt) with 1,2-diaminobenzene. The reaction may be carried out in a solvent such as methanol, at an elevated temperature (such as the reflux temperature of the solvent). Preparations 81, etc. provide further details.

Compounds of formula IV and V in which $R^1$ represents Het¹ may also be prepared from compounds of formula XI and XII respectively according to the following scheme:

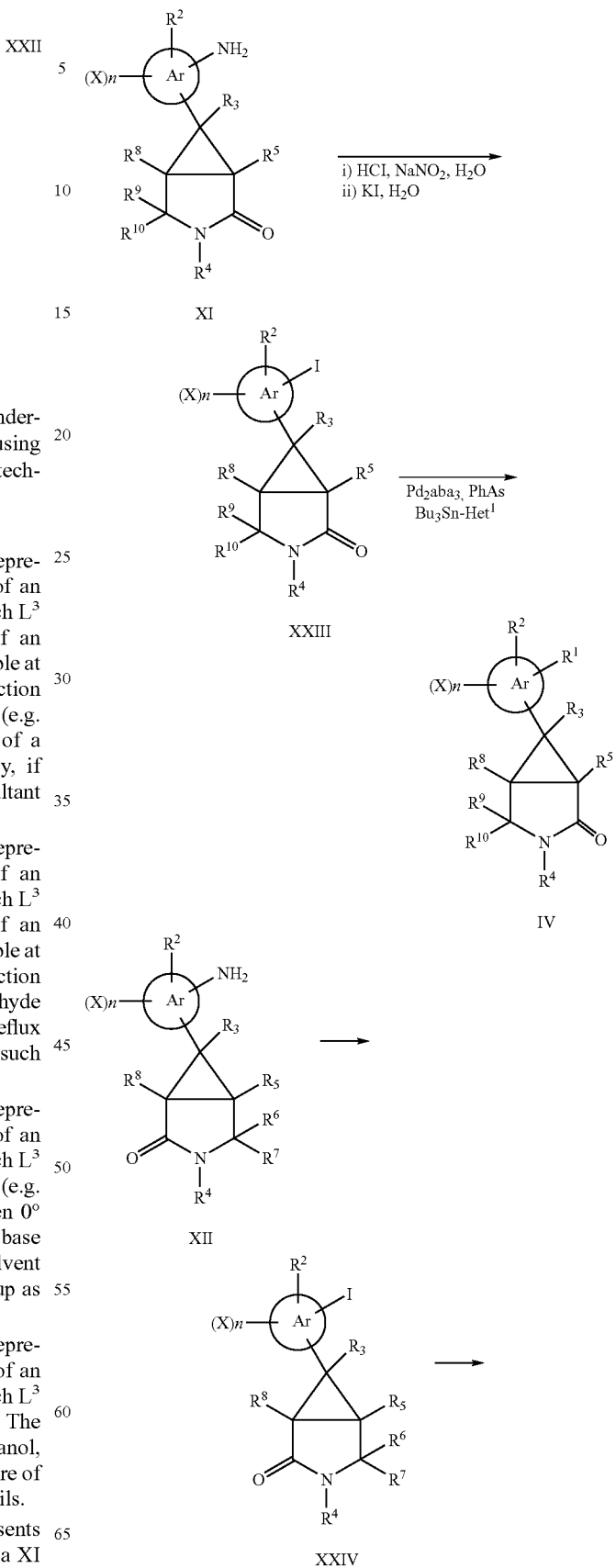

-continued

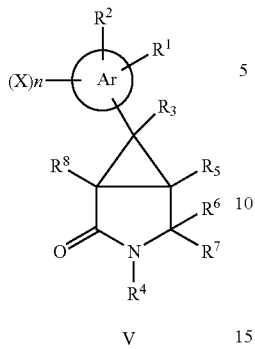

V wherein Het¹ is defined above. Further details may be found in Preparations 67, 68, etc. below.

Compounds of formula XXI and XXII may be prepared in analogous fashion to methods described herein, for example those described hereinbefore for preparation of compounds of formula II.

Other compounds of formula (IV) and (V) may be prepared by analogy with methods described herein (e.g. by analogy with methods described hereinbefore for preparation of compounds of formula XI and XII (and especially the corresponding —$NO_2$ compound)).

In process (d), the reaction may be carried out by heating under reflux, with or without the presence of an appropriate organic solvent.

Compounds of formula VI may be prepared using known techniques. For example, compounds of formula VI may be prepared by nitration (at the 4-position) of a corresponding 3-aminobenzene compound (a compound of formula II), which latter compound may be activated by converting the 3-amino group to a 3-amido group, followed by hydrolysis of the amide and reduction of the 4-nitrobenzene compound. All of these reactions may be performed using techniques that are familiar to the skilled person, and are illustrated in Preparations 45–48, etc. below.

In process (e), suitable leaving groups that Lg may represent include halogen, such as bromine, or a sulphonate group such as tosylate. The reaction may be carried out in a solvent that does not adversely affect the reaction (for example dimethylformamide), at an elevated temperature (for example 50° C.), in the presence of a base (for example sodium hydrogen carbonate). A catalyst such as sodium iodide may optionally be added.

Compounds of formula VIII may be prepared from compounds of formula XXV,

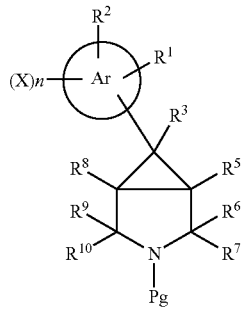

XXV wherein Pg represents a suitable protecting group. Suitable protecting groups include allyl, which may be removed using a palladium (0) catalyst and N,N-dimethylbarbituric acid (see Preparation 53, etc. below). Compounds of formula XXV may be prepared using analogous methods to those described herein for the preparation of compounds of formula I.

In process (f), suitable reducing agents include lithium aluminium hydride. The reaction may be carried out in a solvent that does not adversely affect the reaction (for example tetrahydrofuran), at an elevated temperature (for example the reflux temperature of the solvent).

Compounds of formula X may be prepared by reacting a compound of formula XXVI with a compound of formula XXVII in the presence of an oxidizing agent. Suitable oxidizing agents include manganese dioxide. The reaction may be carried out in a solvent that does not adversely affect the reaction (for example dioxan), at an elevated temperature such as the reflux temperature of the solvent (for example see Preparation 77, etc. below). The intermediate compounds XXIXa are isolatable using suitable conditions (e.g. see Preparation 58).

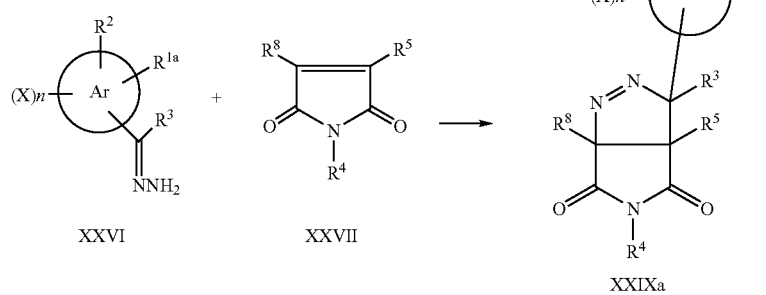

XXVI    XXVII    XXIXa

-continued

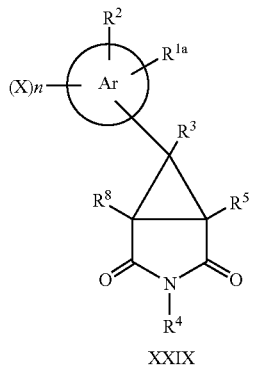

XXIX

Compounds of formula XXVI may be prepared from compounds of formula XXVIII, by reaction of the corresponding ketone with hydrazine monohydrate using known techniques (and as described in Preparation 76, etc. below).

Process (f) is particularly useful when Ar represents an optionally benzo-fused 5- or 6-membered heteroaryl ring. A similar methodology may be used to obtain compounds of formula II: the precursor nitro compound may be prepared from a compound of formula XX, as defined above, using the steps described above (see for example Preparations 57–61, etc.).

In process (g), the reaction may be carried out in a solvent that does not adversely affect the reaction (for example ethanol), first below room temperature and then at an elevated temperature (Examples 79, etc. provide further details).

In process (h), suitable acids include dilute aqueous hydrochloric acid and concentrated hydrochloric acid, respectively. The reaction may be carried out at or around room temperature, finishing at an elevated temperature (for example 90° C.). Examples 51 provide further details.

In process (j), the compound of formula XXXI may be prepared by acylation of the compound of formula VIII as defined above, with an acylating agent of the formula $R^{4a}CO-L_g$, where $L_g$ is a suitable leaving group as defined above with respect to (e), and includes halogen, (alkyl, haloalkyl or aryl)sulphonate, $OCOR^{4a}$ (i.e. an acid anhydride) and the like, well known to those practising in the art. See for example the conditions used for Preparation 47.

It will be apparent to those skilled in the art that compounds of formula I may be converted to other compounds of formula I using known techniques. For example, compounds of formula I in which $Y^1$ represents alkoxycarbonyl may be converted to compounds in which $Y^1$ represents alkyl substituted by OH, by reduction using $LiAlH_4$ (Example 57 provides further details). Similarly, intermediate compounds may be interconverted using known techniques (see for example Preparation 85).

The intermediate compounds such as those of formulae III, XV, XVIII, XIX, XX, VII, IX, XXVI, XXVII and XXVIII, and derivatives thereof, when not commercially available or not subsequently described, may be obtained either by analogy with the processes described herein, or by conventional synthetic procedures, in accordance with standard techniques, from readily available starting materials using appropriate reagents and reaction conditions.

The invention further provides the intermediate compounds of formulae II, IV, V, VI, VIII, X, $X^a$, XI, XII, XIII, XIV, XXI, XXII, XXIII, XXIV, XXV, XXIX, XXIXa, XXX, XXXI as defined above.

Where desired or necessary, the compound of formula (I) can be converted into a pharmaceutically acceptable salt thereof, conveniently by mixing together solutions of a compound of formula (I) and the desired acid or base, as appropriate. The salt may be precipitated from solution and collected by filtration, or may be collected by other means such as by evaporation of the solvent. Both types of salt may also be formed or interconverted using ion-exchange resin techniques.

The compounds of the invention may be purified by conventional methods, for example separation of diastereomers may be achieved by conventional techniques, e.g. by fractional crystallisation, chromatography or H.P.L.C. of a stereoisomeric mixture of a compound of formula (I) or a salt thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active base or acid.

The compounds of the invention are useful because they possess pharmacological activity in animals, especially mammals including humans. They are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the substances of the invention have been found to be useful in the treatment of diseases and conditions modulated via opiate receptors, such as irritable bowel syndrome; constipation; nausea; vomiting; pruritus; eating disorders; opiate overdoses; depression; smoking and alcohol addiction; sexual dysfunction; shock; stroke; spinal damage and/or head trauma; and conditions characterised by having pruritis as a symptom.

Thus, according to a further aspect of the invention there is provided the use of the compounds of the invention in the manufacture of a medicament for the treatment of a disease modulated via an opiate receptor. There is further provided the use of the compounds of the invention in the manufacture of a medicament for the treatment of as irritable bowel syndrome; constipation; nausea; vomiting; pruritus; eating disorders; opiate overdoses; depression; smoking and alcohol addiction; sexual dysfunction; shock; stroke; spinal damage and/or head trauma; and conditions characterised by having pruritis as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing a disease modulated via an opiate receptor. There is further provided a method of treating irritable bowel syndrome; constipation; nausea; vomiting; pruritus; eating disorders; opiate overdoses; depression; smoking and alcohol addiction; sexual dysfunction; shock; stroke; spinal damage and/or head trauma; or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (eg subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, eg fipronil, lufenuron, imidacloprid, avermectins (eg abamectin, ivermectin, doramectin), milbemycins, organophosphates, pyrethroids; antihistamines, eg chlorpheniramine, trimeprazine, diphenhydramine, doxylamine; antifungals, eg fluconazole, ketoconazole, itraconazole, griseofulvin, amphotericin B; antibacterials, eg enroflaxacin, marbofloxacin, ampicillin, amoxycillin; anti-inflammatories eg prednisolone, betamethasone, dexamethasone, carprofen, ketoprofen; dietary supplements, eg gamma-linoleic acid; and emollients. Therefore, the invention further provides a product containing a compound of the invention and one or more selected compounds from the above list as a combined preparation for simultaneous, separate or sequential use in the treatment of diseases modulated via opiate receptors The skilled person will also appreciate that compounds of the invention may be taken as a single dose or on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test method.

Biological Test

Compounds of the present invention have been found to display activity in three opioid receptor binding assays selective for the mu, kappa and delta opioid receptors in dog brain. The assays were conducted by the following procedure.

Laboratory bred beagles were used as a source of dog brain tissue. Animals were euthanaised, their brains removed and the cerebellum discarded. The remaining brain tissue was sectioned into small pieces approximately 3 g in weight and homogenised in 50 mM Tris pH 7.4 buffer at 4° C. using a Kinematica Polytron tissue homogeniser. The resulting homogenate was centrifuged at 48,400×g for 10 minutes and the supernatant discarded. The pellet was resuspended in Tris buffer and incubated at 37° C. for 10 minutes. Centrifugation, resuspension and incubation steps were repeated twice more, and the final pellet was resuspended in Tris buffer and stored at −80° C. Membrane material prepared in this manner could be stored for up to four weeks prior to use.

For mu, kappa and delta assays, increasing concentrations of experimental compound ($5 \times 10^{-12}$ to $10^{-5}$M), Tris buffer and $^3$H ligand, (mu=[D-Ala$^2$, N-Me-Phe$^4$,Gly-ol$^5$]-Enkephalin, DAMGO; kappa=U-69,593; delta=Enkephalin, [D-pen$^{2,5}$] DPDPE), were combined in polystyrene tubes. The reaction was initiated by the addition of tissue, and the mixture was incubated at room temperature for 90 minutes. The reaction was terminated by rapid filtration using a Brandel Cell Harvester™ through Betaplate™ GF/A glass fibre filters pre-soaked in 50 mM Tris pH 7.4, 0.1% polyethylenimine buffer. The filters were then washed three times with 0.5 ml ice-cold Tris pH 7.4 buffer. For mu and delta assays, washed filters were placed in bags and Starscint™ scintillant added, for the kappa assay Meltilex™ B/HS solid scintillant was used. Bags containing the filters and scintillant were heat sealed and counted by a Betaplate™ 1204 beta counter.

Duplicate samples were run for each experimental compound and the data generated was analysed using IC$_{50}$ analysis software in Graphpad Prism. Ki values were calculated using Graphpad Prism according to the following formula:

$$K_i = IC_{50}/1 + [^3H\ \text{ligand}]/K_D$$

where IC$_{50}$ is the concentration at which 50% of the $^3$H ligand is displaced by the test compound and $K_D$ is the dissociation constant for the $^3$H ligand at the receptor site.

Biological Activity

The Ki values of certain compounds of the present invention in the opioid receptor binding assays were determined, and the compounds of Examples 1, 6, 8, 14–16, 19 and 21–24 were found to have Ki values of 4000 nM or less for the μ receptor.

It is believed that the methods used in the following Examples produce compounds having the relative stereochemistry shown below, and such compounds are preferred:

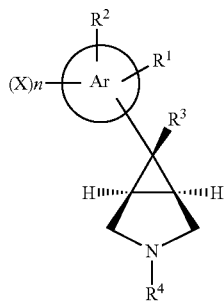

wherein R$^{1-4}$ and (X)$_n$ are as defined above.

The invention is illustrated by the following Examples and Preparations in which the following abbreviations may be used:

APCI=atmospheric pressure chemical ionization
DMF=dimethylformamide
DMSO=dimethylsulphoxide
d (in relation to time)=day
d (in relation to NMR)=doublet
ES (in relation to MS)=electrospray
EtOAc=ethyl acetate
EtOH=ethanol
h=hour
MeOH=methanol
min=minute
MS=mass spectrum
n-BuOH=n-butanol
ODS=octadecylsilyl
THF=tetrahydrofuran
TSP=thermospray Melting points were determined using a Gallenkamp melting point apparatus and are uncorrected. Nuclear magnetic resonance (NMR) spectral data relate to $^1$H and were obtained using a Varian Unity 300 or 400 spectrometer, the observed chemical shifts (δ) being consistent with the proposed structures. Mass spectral (MS) data were obtained on a Fisons Instruments Trio 1000, or a Fisons Instruments Trio 1000 APCI, or a Finnigan Navigator MS, or a Micromass Platform LC spectrometer. The calculated and observed ions quoted refer to the isotopic composition of lowest mass. Room temperature means 20 to 25° C. The mass spectrometer which is used as a detector on the analytical HPLC-MS system is a Micromass VG Platform II, running on Masslynx/Openlynx software. The system can run positive and negative ion with either Electrospray or APCI probes and is calibrated to 1972 Daltons, it collects full Diode array data from 190 nm to 600 nm.

HPLC means high performance liquid chromatography. HPLC conditions used were:

Condition 1: Rainin Dynamax™ column, 8μ ODS, 24×300 mm, column temperature 40° C., flow rate 45 ml/min, eluting with methanol:water (70:30), UV detection of product at 246 nm.

Condition 2: Rainin Dynamax™ column, 5μ ODS, 21.6× 250 mm, column temperature 40° C., flow rate 5 ml/min, eluting with acetonitrile:water (50:50), UV detection of product at 246 nm.

Condition 3: Rainin Dynamax™ column, 8μ ODS, 41×250 mm, column temperature 40° C., flow rate 45 ml/min, eluting with acetonitrile:0.1 M aqueous ammonium acetate buffer (50:50), UV detection of product at 235 nm.

Condition 4: Phenomenex Magellan™ column, 5μ C$_{18}$ silica, 21.2×150 mm, column temperature 40° C., flow rate 20 ml/min, eluting with a gradient of acetonitrile:0.1M aqueous ammonium acetate buffer (30:70 to 95:5 over 10 min), UV detection of product at 220 nm.

Condition 5: Phenomenex Magellan™ column, 5μ ODS, 21.2×150 mm, column temperature 40° C., flow rate 20 ml/min, eluting with a gradient of acetonitrile:0.1M aqueous ammonium acetate buffer (5:95 to 95:5 over 20 min), UV detection of product at 215 nm.

Condition 6: Phenomenex Magellan™ column, 5μ C$_{18}$ silica, 4.6×150 mm, column temperature 40° C., flow rate 1 ml/min, eluting with a gradient of acetonitrile:0.1M aqueous heptanesulphonic acid (10:90 to 90:10 over 30 min), UV detection of product at 220 nm.

Condition 7: Phenomenex Magellan™ column, 5μ C$_{18}$ silica, 21.2×150 mm, column temperature 40° C., flow rate 20 ml/min, eluting with a gradient of acetonitrile:0.05M aqueous ammonium acetate buffer (50:50 for 15 min then 50:50 to 90:10 over 5 min), UV detection of product at 220 nm.

Condition 8: Phenomenex Magellen™ column, 5μ C$_{18}$ silica, 21.2×150 mm, column temperature 40° C., flow rate 20 ml/min, eluting with a gradient of acetonitrile:0.1M aqueous ammonium acetate buffer (15:85 to 85:15), UV detection of product at 220 nm.

Condition 9: Phenomenex Magellen™ column, 5μ ODS, 10×150 mm, column temperature 40° C., flow rate 5ml/min, eluting with a gradient of acetonitrile:0.1M aqueous ammonium acetate buffer (5:95 to 30:70 over 5 min then 30:70 for a further 20 min), UV detection of product at 225 nm.

Condition 10: Phenomenex Magellan™ column, 5μ $C_{18}$ silica, 21.2×150 mm, column temperature 40° C., flow rate 20 ml/min, eluting with a gradient of acetonitrile:0.1M aqueous ammonium acetate (5:95 to 40:60 over 5 min then 40:60 for a further 25 min), UV detection of product at 210 nm.

Condition 11: Phenomenex Magellan™ column, 5μ ODS, 10×150 mm, column temperature 40° C., flow rate 5 ml/min, eluting with a gradient of acetonitrile:water (5:95 to 55:45 over 5 min), UV detection of product at 210 nm.

The free base form of the azabicycles could be obtained from the hydrochloride or acetate salts, for example, in the following way. The salt (0.3 mmol) was dissolved in dichloromethane (20 ml) and washed with saturated aqueous sodium hydrogen carbonate solution (20 ml). The basic mixture was separated and the aqueous layer was extracted with dichloromethane (2×20 ml). The combined organic extracts were dried ($Na_2SO_4$) and concentrated in vacuo to give the free base.

SPE cartridge refers to a solid phase extraction cartridge. These can be commercially obtained from Varian (Mega Bond Elut®) or Isolute™.

EXAMPLE 1

N-{3-[6-Methyl-3-(3-phenylpropyl)-3-azabicyclo[3.1.0]hex-6-yl]phenyl}methanesulfonamide

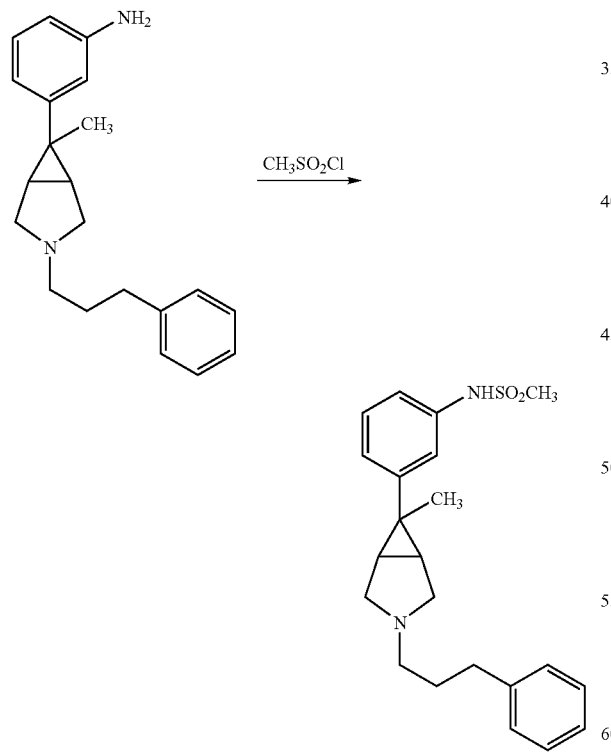

To a solution of 3-[6-methyl-3-(3-phenylpropyl)-3-azabicyclo[3.1.0]hex-6-yl]phenylamine (Preparation 8, 28 mg, 0.09 mmol) in dichloromethane (2 ml), at 0° C. under nitrogen was added pyridine (20 μl, 0.24 mmol) and then methanesulfonylchloride (25 μl, 37 mg, 0.32 mmol) over 5 minutes. The mixture was allowed to warm to room temperature and was then stirred for 2 hours. The mixture was concentrated in vacuo and the residue was purified by silica (5 g) column chromatography eluting with 80:20:1 ethyl acetate:hexane:ammonia solution (0.880). Product-containing fractions were combined and concentrated in vacuo to give the title compound as a colourless oil (18 mg, 52%).

NMR (CDCl$_3$) δ: 1.56 (s, 3H), 1.77 (m, 4H), 2.48 (t, 2H), 2.66 (t, 2H), 2.80 (d, 2H), 3.01 (s, 3H), 3.05 (d, 2H), 7.01 (d, 1H), 7.07 (m, 2H), 7.14–7.3 (m, 6H).

MS (thermospray): M/Z [MH$^+$] 385.4; $C_{22}H_{28}N_2SO_2$+H requires 385.2

EXAMPLE 2

N-{3-[6-Methyl-3-(3-phenylpropyl)-3-azabicyclo[3.1.0]hex-6-yl]phenyl}methanesulfonamide acetate salt N-{3-[6-Methyl-3-(3-phenylpropyl)-3-azabicyclo[3.1.0]hex-6-yl]phenyl}methanesulfon-amide (Example 1, 260 mg, 0.67 mmol) was purified further by preparative HPLC (condition 3). Combination and evaporation of pure fractions gave the title compound as a white solid (87 mg) mp 116–117° C.

NMR (CD$_3$OD) δ: 1.45 (s, 3H), 1.93 (m, 5H), 2.09 (s, 2H), 2.67 (t, 2H), 2.86 (t, 2H), 2.93 (s, 3H), 3.05 (d, 2H), 3.46 (d, 2H), 7.04 (m, 2H), 7.10–7.33 (m, 7H)

EXAMPLE 3

N-{3-[6-Methyl-3-(3-phenylpropyl)-3-azabicyclo[3.1.0]hex-6-yl]phenyl}-1-ethanesulfon-amide

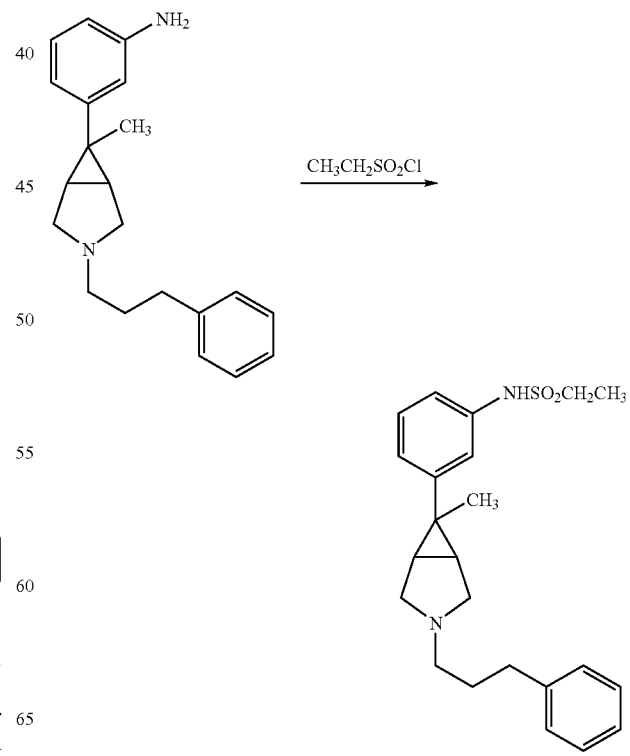

To a solution of 3-[6-methyl-3-(3-phenylpropyl)-3-azabicyclo[3.1.0]hex-6-yl]phenylamine (Preparation 8, 110 mg, 0.36 mmol) in dichloromethane (4 ml), at 0° C. under nitrogen was added pyridine (56 μl, 0.72 mmol) then dropwise over 5 minutes ethanesulfonylchloride (67 μl, 92 mg, 0.72 mmol). The mixture was allowed to warm to room temperature and was stirred for 16 hours. Further pyridine (56 μl, 0.72 mmol) and ethanesulfonylchloride (67 μl, 92 mg, 0.72 mmol) were added and the mixture was stirred for 2 hours. The crude mixture was purified by silica (40 g) column chromatography eluting with 80:20:1 ethyl acetate:hexane:ammonia solution (0.880). Product-containing fractions were combined and concentrated in vacuo to give the title compound as a colourless oil (48 mg, 34%).

NMR (CDCl$_3$) δ: 1.39 (t, 3H), 1.57 (s, 3H), 1.76 (m, 4H), 2.48 (t, 2H), 2.66 (t, 2H), 2.80 (d, 2H), 3.04 (d, 2H), 3.12 (q, 3H), 6.97–7.11 (m, 3H), 7.11–7.33 (m, 6H).

MS (thermospray): M/Z [MH$^+$] 399.2; C$_{23}$H$_{30}$N$_2$SO$_2$+H requires 399.2

EXAMPLE 4

N-{3-[3-(3-Cyclohexylpropyl)-6-methyl-3-azabicyclo[3.1.0]hex-6-yl]-phenyl}methanesulfonamide

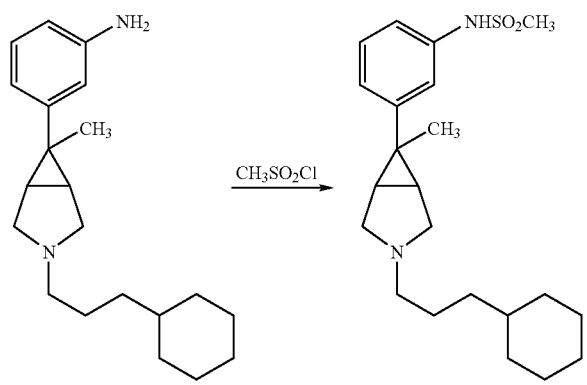

To a solution of 3-[3-(3-cyclohexylpropyl)-6-methyl-3-azabicyclo[3.1.0]hex-6-yl]phenylamine (Preparation 10, 25 mg, 0.08 mmol) in dichloromethane (2 ml) at 0° C. under nitrogen was added pyridine (20 μl, 0.24 mmol) then dropwise over 5 minutes methanesulfonylchloride (25 μl, 37 mg, 0.32 mmol). The mixture was allowed to warm to room temperature and was stirred for 90 minutes. Further methanesulfonylchloride (10 μl, 15 mg, 0.13 mmol) was added and the mixture was stirred for 1 hour. The mixture was concentrated in vacuo and the residue was purified by silica (5 g) column chromatography eluting with 80:20:1 ethyl acetate:hexane:ammonia solution (0.880). Product-containing fractions were combined and concentrated in vacuo to give the title compound as a pale yellow oil (18 mg, 58%).

NMR (CDCl$_3$) δ: 0.90 (m, 2H), 1.06–1.31 (m, 6H), 1.43 (m, 2H), 1.51 (s, 3H), 1.60–1.76 (m, 7H), 2.43 (t, 2H), 2.81 (d, 2H), 2.99 (d, 2H), 3.01 (s, 3H), 6.98–7.10 (m, 3H), 7.24 (m, 1H).

MS (thermospray): m/z [MH$^+$] 391.5.; C$_{22}$H$_{34}$N$_2$SO$_2$+H requires 391.2

EXAMPLE 5

N-{3-[3-(3-Cyclohexylpropyl)-6-methyl-3-azabicyclo[3.1.0]hex-6-yl]phenyl}-1-ethanesulfonamide

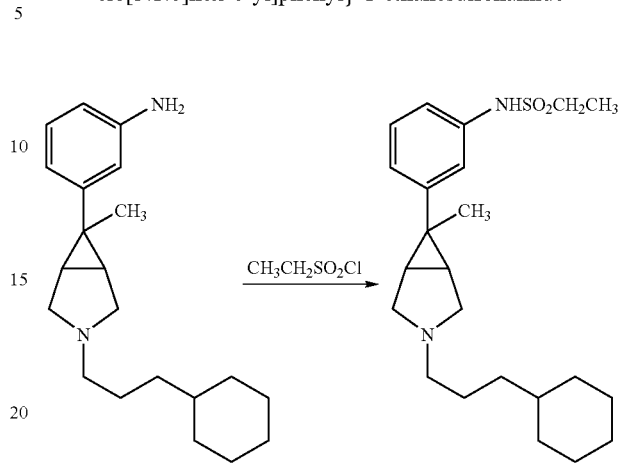

To a solution of 3-[3-(3-cyclohexylpropyl)-6-methyl-3-azabicyclo[3.1.0]hex-6-yl]phenylamine (Preparation 10, 25 mg, 0.08 mmol) in dichloromethane (2 ml) at 0° C. under nitrogen was added pyridine (20 μl, 0.24 mmol) then dropwise over 5 minutes ethanesulfonylchloride (25 μl, 34 mg, 0.26 mmol). The mixture was allowed to warm to room temperature and was stirred for 1.5 h. Further ethanesulfonylchloride (25 μl, 34 mg, 0.26 mmol) was added and the mixture was stirred for 2 hours. The mixture was concentrated in vacuo and the residue was purified by silica (5 g) column chromatography eluting with 80:20:1 ethyl acetate:hexane:ammonia solution (0.880). Product-containing fractions were combined and concentrated in vacuo to give the title compound as a pale yellow oil (21 mg, 65%).

NMR (CDCl$_3$) δ: 0.90 (m, 2H), 1.06–1.31 (m, 6H), 1.37 (t, 3H), 1.44 (m, 2H), 1.51 (s, 3H), 1.60–1.76 (m, 7H), 2.43 (t, 2H), 2.83 (d, 2H), 2.98 (d, 2H), 3.13 (q, 2H), 6.98–7.10 (m, 3H), 7.24 (t, 1H)

MS (thermospray): m/z [MH$^+$] 405.6.; C$_{23}$H$_{36}$N$_2$SO$_2$+H requires 405.3

EXAMPLE 6

N-[3-(3-Hexyl-6-methyl-3-azabicyclo[3.1.0]hex-6-yl)phenyl]methanesulfonamide

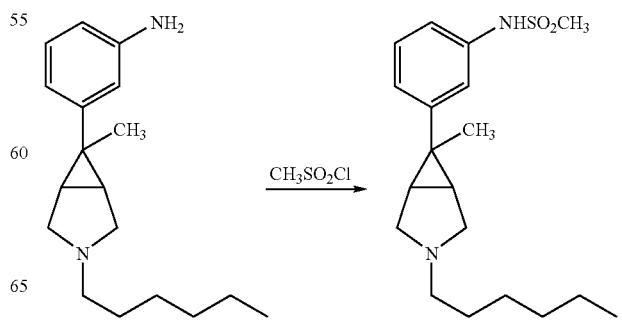

To a solution of 3-(3-hexyl-6-methyl-3-azabicyclo[3.1.0]hex-6-yl)phenylamine (Preparation 12, 200 mg, 0.735 mmol) in dichloromethane (5 ml) at room temperature was added pyridine (0.15 ml, 1.84 mmol) then dropwise over 5 minutes methanesulfonylchloride (0.11 ml, 158 mg, 1.38 mmol). The mixture was stirred for 48 h, concentrated in vacuo and the residue was purified by silica (10 g) column chromatography eluting with 90:10:1 ethyl acetate:methanol:ammonia solution (0.880), then in 80:20:1 ethyl acetate:methanol:ammonia solution (0.880). Product-containing fractions were combined and concentrated in vacuo to give the title compound as a pale yellow oil (212 mg, 82%).

NMR (CDCl$_3$) δ: 0.90 (t, 3H), 1.28 (m, 6H), 1.47 (s, 3H), 1.54 (m, 2H), 1.90 (s, 2H), 2.60 (t, 2H), 2.97 (d, 2H), 3.00 (s, 3H), 3.15 (m, 2H), 7.02 (d, 1H), 7.07–7.15 (m, 2H), 7.22 (m, 1H)

MS (thermospray): m/z [MH$^+$] 351.1; C$_{19}$H$_{30}$N$_2$SO$_2$+H requires 351.2

EXAMPLE 7

N-[3-(3-Hexyl-6-methyl-3-azabicyclo[3.1.0]hex-6-yl)phenyl]-1-ethanesulfonamide

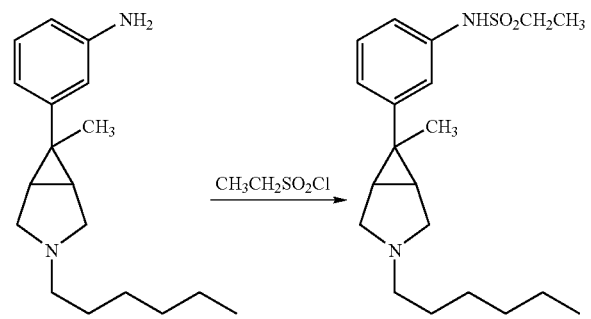

To a solution of 3-(3-hexyl-6-methyl-3-azabicyclo[3.1.0]hex-6-yl)phenylamine (Preparation 12, 200 mg, 0.735 mmol) in dichloromethane (5 ml) at room temperature was added pyridine (0.15 ml, 1.84 mmol) then dropwise over 5 minutes ethanesulfonylchloride (0.131 ml, 177 mg, 1.38 mmol). The mixture was stirred for 48 hours, concentrated in vacuo and the residue was purified by silica (10 g) column chromatography eluting with ethyl acetate then 90:10:1 ethyl acetate:methanol:ammonia solution (0.880). Product-containing fractions were combined and concentrated in vacuo to give the title compound as a pale yellow oil (140 mg, 52%).

NMR (CDCl$_3$) δ: 0.90 (t, 3H), 1.28 (m, 6H), 1.34 (t, 3H), 1.47 (s, 3H), 1.55 (m, 2H), 1.90 (s, 2H), 2.63 (m, 2H), 2.97 (m, 2H), 3.11 (q, 2H), 3.20 (m, 2H), 7.02 (d, 1H), 7.04–7.15 (m, 2H), 7.21 (m, 1H)

MS (thermospray): m/z [MH$^+$] 365.3; C$_{20}$H$_{32}$N$_2$SO$_2$+H requires 365.2

EXAMPLE 8

N-[3-(3-Hexyl-6-methyl-3-azabicyclo[3.1.0]hex-6-yl)phenyl]-1-propanesulfonamide

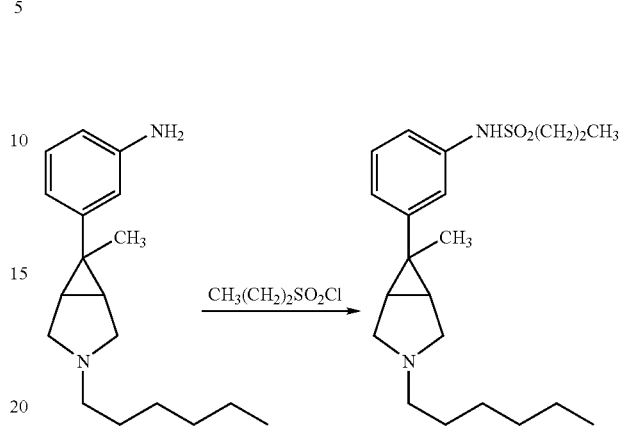

To a solution of 3-(3-hexyl-6-methyl-3-azabicyclo[3.1.0]hex-6-yl)phenylamine (Preparation 12, 200 mg, 0.735 mmol), in dichloromethane (5 ml) at room temperature was added pyridine (0.15 ml, 1.84 mmol) then dropwise over 5 minutes propanesulfonylchloride (0.16 ml, 202 mg, 1.42 mmol). The mixture was stirred for 48 hours, concentrated in vacuo and the residue was purified by silica (10 g) column chromatography eluting with ethyl acetate then 90:10:1 ethyl acetate:methanol:ammonia solution (0.880). Product-containing fractions were combined and concentrated in vacuo to give the title compound as a pale yellow oil (40 mg, 14%).

NMR (CDCl$_3$) δ: 0.90 (t, 3H), 1.02 (t, 3H), 1.30 (m, 6H), 1.46 (m, 2H), 1.50 (s, 3H), 1.77 (s, 2H), 1.87 (m, 2H), 2.47 (t, 2H), 2.87 (m, 2H), 2.93–3.07 (m, 4H), 6.97–7.09 (m, 3H), 7.22 (m, 1H)

MS (thermospray): m/z [MH$^+$] 379.2; C$_{21}$H$_{34}$N$_2$SO$_2$+H requires 379.2

EXAMPLE 9

N-[3-(3-Hexyl-6-methyl-3-azabicyclo[3.1.0]hex-6-yl)phenyl]-3-pyridinesulfonamide

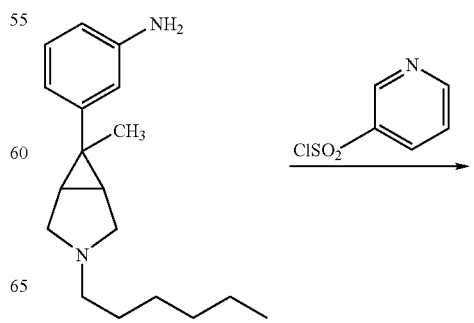

-continued

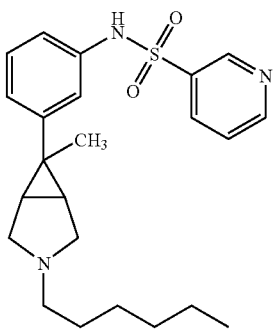

To a solution of 3-(3-hexyl-6-methyl-3-azabicyclo[3.1.0]hex-6-yl)phenylamine (Preparation 12, 220 mg, 0.809 mmol) in dichloromethane (5 ml) at room temperature was added pyridine (0.196 ml, 2.42 mmol) then dropwise over 5 minutes 3-pyridinesulfonylchloride (198 mg, 1.21 mmol). The mixture was stirred for 48 hours, concentrated in vacuo and the residue was purified by silica (10 g) column chromatography eluting with ethyl acetate then 90:10:1 ethyl acetate:methanol:ammonia solution (0.880). Product-containing fractions were combined and concentrated in vacuo to give the title compound as a pale orange oil (200 mg, 60%).

NMR (CDCl$_3$) δ: 0.89 (t, 3H), 1.30 (m, 6H), 1.40 (s, 3H), 1.52 (m, 2H), 1.77 (s, 2H), 2.58 (t, 2H), 2.91 (d, 2H), 3.11 (m, 2H), 6.91–7.04 (m, 3H), 7.13 (t, 1H), 7.35 (m, 1H), 8.06 (d, 1H), 8.73 (d, 1H), 8.94 (s, 1H)

MS (thermospray): m/z [MH$^+$] 414.2; $C_{23}H_{31}N_3SO_2$+H requires 414.2

EXAMPLE 10

N-{3-[6-ethyl-3-(3-phenylpropyl)-3-azabicyclo[3.1.0]hex-6-yl]phenyl}methanesulfonamide acetate salt

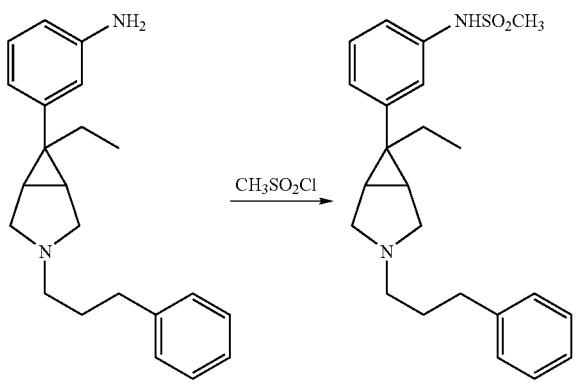

To a solution of 3-[6-ethyl-3-(3-phenylpropyl)-3-azabicyclo[3.1.0]hex-6-yl]phenylamine (Preparation 18, 500 mg, 1.56 mmol) in dichloromethane (20 ml), at 0° C. under nitrogen was added pyridine (0.20 ml, 2.6 mmol) then dropwise over 5 minutes methanesulfonylchloride (0.20 ml, 300 mg, 2.6 mmol). The mixture was allowed to warm to room temperature and was stirred for 18 h. The mixture was concentrated in vacuo and the residue was purified by silica (25 g) column chromatography eluting with 70:30:1 ethyl acetate:hexane:ammonia solution (0.880). Product-containing fractions were combined and concentrated in vacuo to give the title compound as a pale yellow oil. This was further purified by preparative HPLC (condition 3). Combination and evaporation of pure fractions gave the title compound as a white solid (140 mg, 20%).

NMR (CDCl$_3$) δ: 0.82 (t, 3H), 1.76 (q, 2H), 1.92 (m, 2H), 2.05 (m, 5H), 2.65 (t, 2H), 2.73 (t, 2H), 2.82 (d, 2H), 2.97 (s, 3H), 3.50 (d, 2H), 7.05 (m, 3H), 7.14–7.33 (m, 6H)

M/S: m/z [MH$^+$] 399.1; $C_{23}H_{30}N_2O_2S$+H requires 399.2

EXAMPLE 11

N-{3-[6-Ethyl-3-(3-phenylpropyl)-3-azabicyclo[3.1.0]hex-6-yl]phenyl}-1-ethanesulfonamide acetate salt

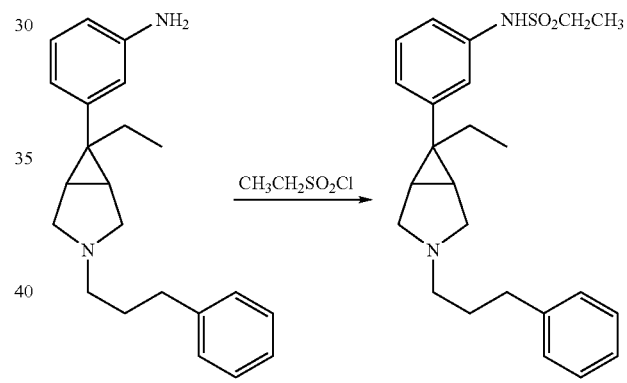

To a solution of 3-[6-ethyl-3-(3-phenylpropyl)-3-azabicyclo[3.1.0]hex-6-yl]phenylamine (Preparation 18, 500 mg, 1.56 mmol) in dichloromethane (20 ml), at 0° C. under nitrogen was added pyridine (0.20 ml, 2.6 mmol) then dropwise over 5 minutes ethanesulfonylchloride (0.20 ml, 0.27 g, 2.1 mmol). The mixture was allowed to warm to room temperature and was stirred for 18 hours. The mixture was concentrated in vacuo and the residue was purified by silica (25 g) column chromatography eluting with 50:50:1 ethyl acetate:hexane:ammonia solution (0.880). Product-containing fractions were combined and concentrated in vacuo to give the title compound as a pale yellow oil. This was further purified by preparative HPLC (condition 3). Combination and evaporation of pure fractions gave the title compound as a white solid (120 mg, 17%).

NMR (CDCl$_3$) δ: 0.80 (t, 3H), 1.32 (t, 3H), 1.74 (q, 2H), 1.89 (m, 2H), 1.99 (m, 5H), 2.62 (t, 2H), 2.72 (t, 2H), 2.81 (d, 2H), 3.08 (q, 2H), 3.43 (d, 2H), 6.97 (d, 1H), 7.07–7.37 (m, 8H)

M/S: m/z [MH$^+$] 413.1; $C_{24}H_{32}N_2O_2S$+H requires 413.2

EXAMPLE 12

N-[3-(6-Ethyl-3-hexyl-3-azabicyclo[3.1.0]hex-6-yl)phenyl]methanesulfonamide

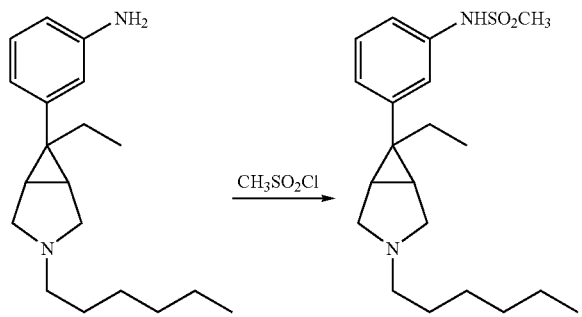

To a solution of 3-(6-ethyl-3-hexyl-3-azabicyclo[3.1.0]hex-6-yl)phenylamine (Preparation 20, 500 mg, 1.56 mmol) in pyridine (5 ml) at 0° C. under nitrogen was added dropwise over 5 minutes methanesulfonylchloride (0.20 ml, 0.30 g, 2.6 mmol). The mixture was allowed to warm to room temperature and was stirred for 18 hours. The mixture was concentrated in vacuo and the residue was purified by silica (25 g) column chromatography eluting with 50:50:1 ethyl acetate:hexane:ammonia solution (0.880). Product-containing fractions were combined and concentrated in vacuo to give the title compound as a pale yellow oil (180 mg, 33%).

NMR (CDCl$_3$) δ: 0.85 (m, 6H), 1.27 (m, 6H), 1.44 (m, 2H), 1.77 (m, 2H), 1.94 (q, 2H), 2.43 (m, 2H), 2.81 (m, 2H), 2.98 (m, 2H), 2.99 (s, 3H), 7.00–7.13 (m, 3H), 7.24 (t, 1H).

MS (electrospray): m/z [MH$^+$]; 365.1 $C_{20}H_{32}N_2O_2S+H$ requires 365.2

EXAMPLE 13

N-[3-(6-Ethyl-3-hexyl-3-azabicyclo[3.1.0]hex-6-yl)phenyl]-1-ethanesulfonamide

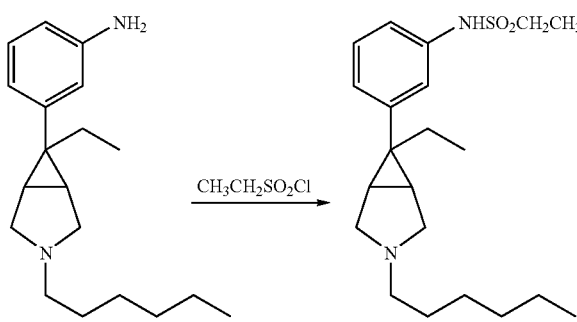

To a solution of 3-[6-ethyl-3-(3-phenylpropyl)-3-azabicyclo[3.1.0]hex-6-yl]phenylamine (Preparation 20, 500 mg, 1.56 mmol) in pyridine (5 ml), at 0° C. under nitrogen was added dropwise over 5 minutes ethanesulfonylchloride (0.25 ml, 0.34 g, 2.6 mmol). The mixture was allowed to warm to room temperature and was stirred for 18 hours. The mixture was concentrated in vacuo and the residue was purified by silica (25 g) column chromatography eluting with 50:50:1 ethyl acetate:hexane:ammonia solution (0.880). Product-containing fractions were combined and concentrated in vacuo to give the title compound as a pale yellow oil (150 mg, 31%).

NMR (CDCl$_3$) δ: 0.80 (t, 3H), 0.88 (t, 3H), 1.29 (m, 6H), 1.35 (t, 3H), 1.44 (m, 2H), 1.77 (m, 2H), 1.93 (q, 2H), 2.45 (t, 2H), 2.82 (m, 2H), 2.97 (d, 2H), 3.10 (q, 2H), 7.02–7.29 (m, 4H)

MS (electrospray): m/z [MH$^+$] 379.1; $C_{21}H_{34}N_2O_2S+H$ requires 379.2

EXAMPLE 14

N-[3-(3-{3-Phenylpropyl}-3-azabicyclo[3.1.0]hex-6-yl)phenyl]-methanesulfonamide

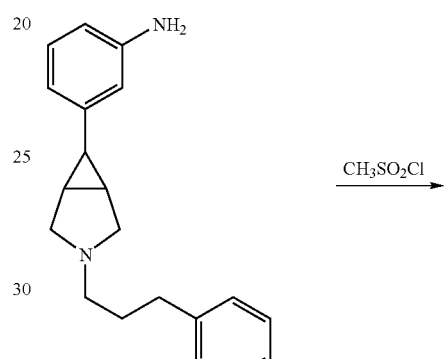

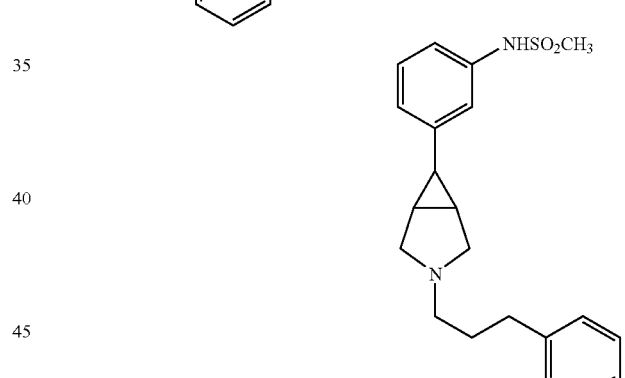

To a solution of 3-[3-(3-phenylpropyl)-3-azabicyclo[3.1.0]hex-6-yl]phenylamine (Preparation 25, 34 mg, 0.11 mmol) in dichloromethane (2 ml) at 0° C. under nitrogen was added pyridine (20 μl, 0.24 mmol) then methanesulfonylchloride (13 mg, 10 μl, 0.11 mmol). The mixture was allowed to warm to room temperature and was stirred for 1.5 hours. The mixture was concentrated in vacuo and the residue was purified by silica (5 g) column chromatography eluting with 80:20:1 ethyl acetate:hexane:ammonia solution (0.880). Product-containing fractions were combined and concentrated in vacuo to give the title compound as a pale yellow oil (29 mg, 71%).

NMR (CDCl$_3$) δ: 1.66 (s, 2H), 1.80 (m, 2H), 2.26 (s, 1H), 2.41 (d, 2H), 2.47 (t, 2H), 2.65 (t, 2H), 3.00 (s, 3H), 3.19 (d, 2H), 6.85 (d, 1H), 6.90 (s, 1H), 6.98 (d, 1H), 7.20 (m, 4H), 7.29 (m, 2H)

M/S: m/z [MH$^+$] 371.0; $C_{21}H_{26}N_2O_2S+H$ requires 371.2

EXAMPLE 15

3-Hexyl-6-phenyl-3-azabicyclo[3.1.0]hexane

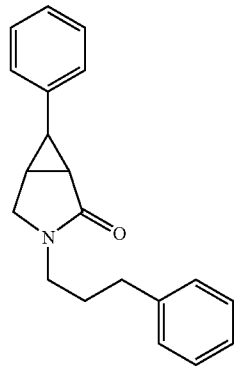

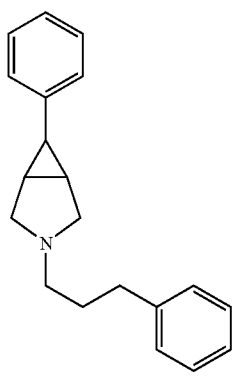

To a solution of 3-hexyl-6-phenyl-3-azabicyclo[3.1.0]hexan-2-one (Preparation 27, 40 mg, 0.15 mmol) in anhydrous tetrahydrofaran (2 ml) at room temperature under nitrogen, was added dropwise a solution of lithium aluminium hydride 1.0 M in tetrahydrofuran (0.3 ml, 0.3 mmol), then the mixture was heated to 60° C. for 4 hours, cooled and stirred at room temperature for 64 hours. Water (30 ml) was carefully added, then the mixture was extracted with ethyl acetate (2×25 ml). The combined extracts were washed with water (30 ml), dried (Na$_2$SO$_4$), filtered and concentrated in vacuo. The residue was purified by silica (1.5 g) column chromatography eluting with 80:20:1 ethyl acetate:hexane:ammonia solution (0.880). Product-containing fractions were combined and concentrated in vacuo to give the title compound as a pale yellow oil (14 mg, 38%).

NMR (CDCl$_3$) δ: 0.90 (t, 3H), 1.30 (m, 6H), 1.44 (m, 2H), 1.65 (s, 2H), 2.16 (t, 1H), 2.42 (m, 4H), 3.19 (d, 2H), 7.04 (d, 2H), 7.12 (m, 1H), 7.24 (m, 2H)

MS (APCI): m/z [MH$^+$] 244.4; C$_{17}$H$_{25}$N+H requires 244.2

EXAMPLE 16

N-{3-[6-Methyl-3-(3-phenylpropyl)-3-azabicyclo[3.1.0]hex-6-yl]phenyl}benzenesulfonamide acetate salt

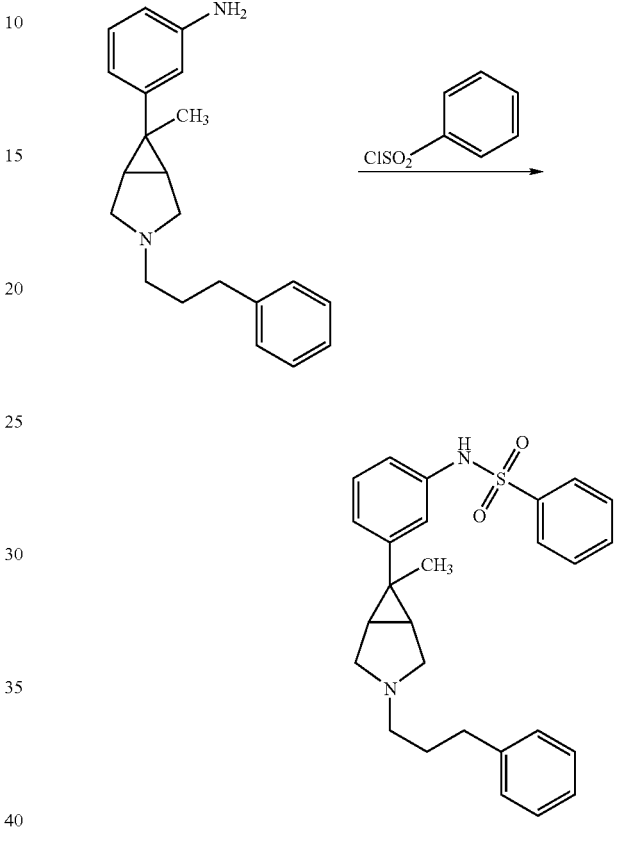

To a solution of 3-[6-methyl-3-(3-phenylpropyl)-3-azabicyclo[3.1.0]hex-6-yl]phenylamine (Preparation 8, 200 mg, 0.65 mmol) in pyridine (2 ml) under nitrogen at 0° C. was added benzenesulfonylchloride (172 mg, 0.98 mmol), then the mixture was stirred at room temperature for 16 hours. Water (5 ml) and dichloromethane (5 ml) were added, and the mixture was stirred for 30 minutes. The organic phase was washed further with water (5 ml) for 30 minutes, separated, dried (MgSO$_4$), filtered and concentrated in vacuo. The residue was purified by silica (10 g) column chromatography eluting with 20:80:1 ethyl acetate:hexane:ammonia solution (0.880), then 50:50:1 ethyl acetate:hexane:ammonia solution (0.880). Product-containing fractions were combined and concentrated in vacuo. The residue was further purified by preparative HPLC (condition 4). Combination and evaporation of appropriate fractions gave the title compound as a pale brown solid (5 mg, 2%).

NMR (CDCl$_3$) δ: 1.39 (s, 3H), 1.84 (s, 2H), 1.89 (m, 2H), 2.06 (s, 3H), 2.65 (m, 4H), 2.90 (d, 2H), 3.23 (br.d, 2H), 6.89 (m, 2H), 6.97 (d, 1H), 7.07–7.35 (m, 6H), 7.43 (m, 2H), 7.52 (m, 1H), 7.73 (d, 2H)

MS (electrospray): m/z [MH$^+$] 447.2; C$_{27}$H$_{30}$N$_2$O$_2$S+H requires 447.2

EXAMPLE 17

N,N-Dimethyl-N'-{3-[6-methyl-3-(3-phenylpropyl)-3-azabicyclo[3.1.0]hex-6-yl]phenyl}sulfamide acetate salt

EXAMPLE 18

N-{3-[6-Methyl-3-(3-phenylpropyl)-3-azabicyclo[3.1.0]hex-6-yl]-phenyl}propanesulfon-amide acetate salt

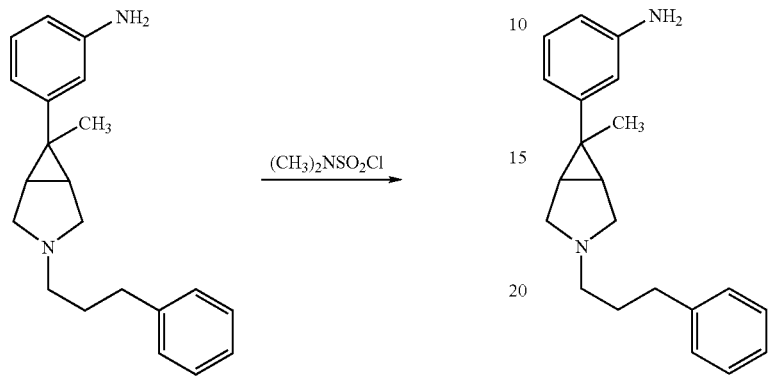
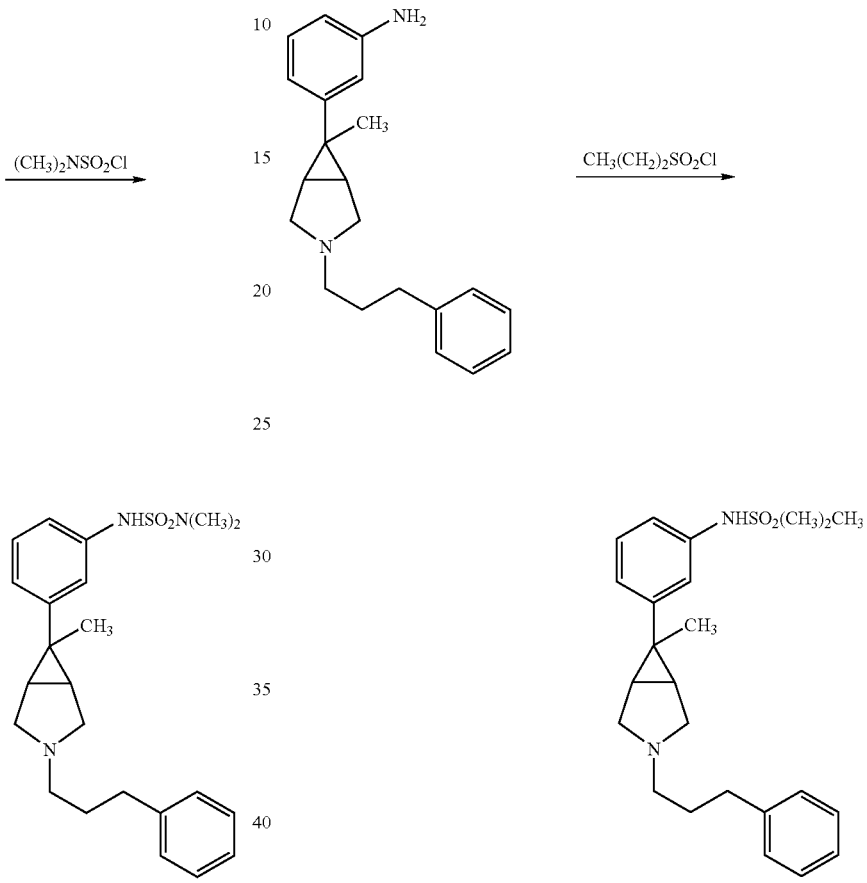

To a solution of 3-[6-methyl-3-(3-phenylpropyl)-3-azabicyclo[3.1.0]hex-6-yl]phenylamine (Preparation 8, 200 mg, 0.65 mmol) in pyridine (2 ml) under nitrogen at 0° C. was added dimethylsulfamoyl chloride (140 mg, 0.98 mmol), then the mixture was stirred at room temperature for 16 hours. Water (5 ml) and dichloromethane (5 ml) were added, and the mixture was stirred for 30 minutes. The organic phase was washed further with water (5 ml) for 30 minutes, separated, dried (MgSO$_4$), filtered and concentrated in vacuo. The residue was purified by silica (10 g) column chromatography eluting with ethyl acetate:hexane:ammonia solution (0.880) (20:80:1 then 50:50:1). Product-containing fractions were combined and concentrated in vacuo. The residue was further purified by preparative HPLC (condition 4). Combination and evaporation of appropriate fractions gave the title compound as a pale brown solid (7 mg, 3%).

NMR (CDCl$_3$) δ: 1.46 (s, 3H), 1.89 (m, 2H), 1.94 (s, 2H), 2.06 (s, 3H), 2.66 (m, 4H), 2.84 (s, 6H), 2.92 (m, 2H), 3.27 (br.d, 2H), 6.95–7.07 (m, 4H), 7.14–7.33 (m, 5H).

MS (electrospray): m/z [MH$^+$] 414.3; C$_{23}$H$_{31}$N$_3$O$_2$S+H requires 414.2.

To a solution of 3-[6-methyl-3-(3-phenylpropyl)-3-azabicyclo[3.1.0]hex-6-yl]phenylamine (Preparation 8, 200 mg, 0.65 mmol) in pyridine (2 ml) under nitrogen at 0° C. was added n-propanesulfonyl chloride (140 mg, 0.98 mmol), then the mixture was stirred at room temperature for 16 hours. Water (5 ml) and dichloromethane (5 ml) were added, and the mixture was stirred for 30 minutes. The organic phase was washed further with water (5 ml) for 30 minutes, separated, dried (MgSO$_4$), filtered and concentrated in vacuo. The residue was purified by silica (10 g) column chromatography eluting with ethyl acetate:hexane:ammonia solution (0.880) (20:80:1 then 50:50:1). Product-containing fractions were combined and concentrated in vacuo. The residue was further purified by preparative HPLC (condition 4). Combination and evaporation of appropriate fractions gave the title compound as a pale brown solid (11 mg, 4%).

NMR (CDCl$_3$) δ: 1.04 (t, 3H), 1.50 (s, 3H), 1.84 (m, 6H), 2.06 (s, 3H), 2.54–2.70 (m, 4H), 2.95 (d, 2H), 3.08 (m, 4H), 7.00–7.12 (m, 3H), 7.12–7.32 (m, 6H).

MS (electrospray): m/z [MH$^+$] 413.3; C$_{24}$H$_{32}$N$_2$O$_2$S+H requires 413.2.

EXAMPLE 19

N-{3-[6-Methyl-3-(3-phenylpropyl)-3-azabicyclo[3.1.0]hex-6-yl]phenyl}-3,5-dimethyl-4-isoxazole-sulfonamide acetate salt

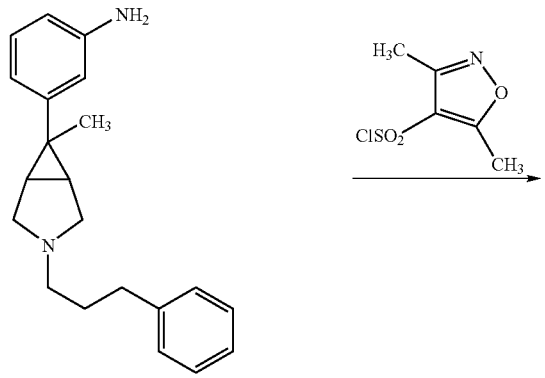

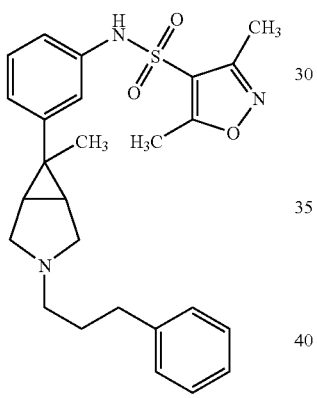

To a solution of 3-[6-methyl-3-(3-phenylpropyl)-3-azabicyclo[3.1.0]hex-6-yl]-phenyl-amine (Preparation 8, 200 mg, 0.65 mmol) in pyridine (2 ml) under nitrogen at 0□ C. was added 3,5-dimethylisoxazolesulfonyl chloride (190 mg, 0.98 mmol), then the mixture was stirred at room temperature for 16 h. Water (5 ml) and dichloromethane (5 ml) were added, and the mixture stirred for 10 minutes. The organic phase was washed further with water (5 ml), separated, dried (MgSO$_4$), filtered and concentrated in vacuo. The residue was purified by silica (10 g) column chromatography eluting with ethyl acetate:hexane:ammonia solution (0.880) (20:80:1 then 60:40:1). Product-containing fractions were combined and concentrated in vacuo. The residue was further purified by preparative HPLC (condition 4). Combination and evaporation of appropriate fractions gave the title compound as a pale brown solid (18 mg, 6%).

NMR (CDCl$_3$) δ: 1.42 (s, 3H), 1.87 (br.s, 2H), 1.95 (m, 2H), 2.09 (s, 3H), 2.25 (s, 3H), 2.43 (s, 3H), 2.55–2.76 (m, 6H), 2.95 (m, 2H), 6.91 (d, 1H), 7.00 (s, 1H), 7.05 (d, 1H), 7.13–7.34 (m, 6H)

MS (electrospray): m/z [MH$^+$] 466.3; C$_{26}$H$_{31}$N$_3$O$_3$S+H requires 466.2

EXAMPLE 20

N-{3-[6-Methyl-3-(3-phenylpropyl)-3-azabicyclo[3.1.0]hex-6-yl]phenyl}-2-methoxy-1-ethanesulfonamide

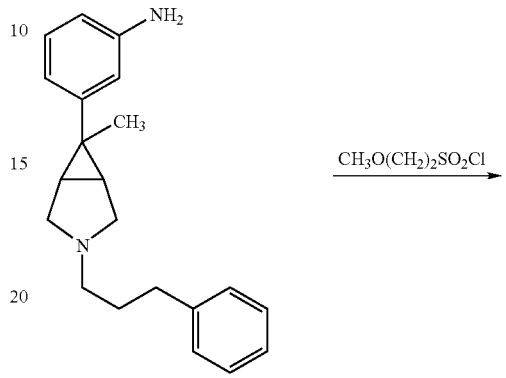

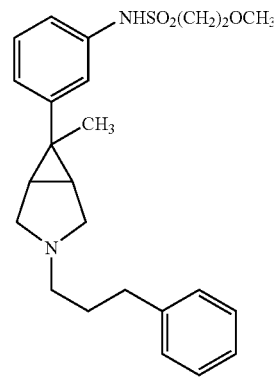

To a solution of 3-[6-methyl-3-(3-phenylpropyl)-3-azabicyclo[3.1.0]hex-6-yl]phenylamine (Preparation 8, 200 mg, 0.65 mmol) in pyridine (2 ml) under nitrogen at 0□ C. was added 2-methoxy-1-ethanesulfonyl chloride (J. Chem. Soc., 1968, 2895; 155 mg, 0.98 mmol), then the mixture was stirred at room temperature for 16 hours. Water (5 ml) and dichloromethane (5 ml) was added, and the mixture stirred for 10 minutes. The organic phase was washed further with water (5 ml), separated, dried (MgSO$_4$), filtered and concentrated in vacuo. The residue was purified by silica (10 g) column chromatography eluting with ethyl acetate:hexane:ammonia solution (0.880) (20:80:1 then 60:40:1). Product-containing fractions were combined and concentrated in vacuo. The residue was further purified by preparative HPLC (condition 4). Combination and evaporation of appropriate fractions gave the title compound as a pale brown solid (3 mg, 1%).

NMR (CDCl$_3$) δ: 1.55 (s, 3H), 1.82 (m, 4H), 2.55 (m, 2H), 2.66 (t, 2H), 2.80–3.05 (br.m, 4H), 3.23 (t, 2H), 3.42 (s, 3H), 3.84 (t, 2H), 7.00–7.33 (m, 9H)

MS (electrospray): m/z [MH$^+$] 429.3; C$_{24}$H$_{32}$N$_2$O$_3$S+H requires 429.2

EXAMPLE 21

N-{3-[6-Methyl-3-(3-phenylpropyl)-3-azabicyclo[3.1.0]hex-6-yl]phenyl}(phenyl)methanesulfonamide acetate salt

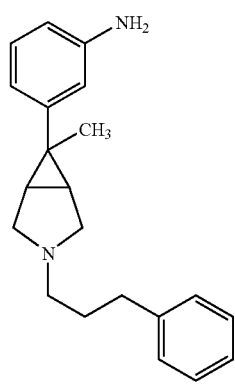
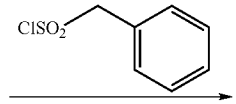
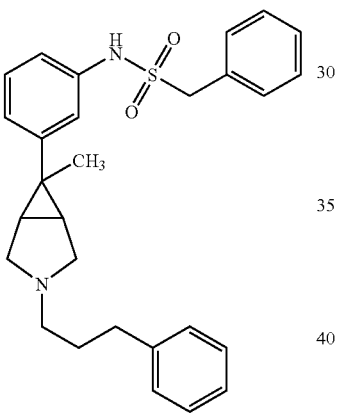

To a solution of 3-[6-methyl-3-(3-phenylpropyl)-3-azabicyclo[3.1.0]hex-6-yl]phenylamine (Preparation 8, 200 mg, 0.65 mmol) in pyridine (2 ml) under nitrogen at 0☐ C. was added α-toluenesulfonyl chloride (186 mg, 0.98 mmol), then the mixture was stirred at room temperature for 16 hours. Water (5 ml) and dichloromethane (5 ml) were added and the mixture was stirred for 10 minutes. The organic phase was washed further with water (5 ml), separated, dried (MgSO$_4$), filtered and concentrated in vacuo. The residue was purified by silica (10 g) column chromatography eluting with ethyl acetate:hexane:ammonia solution (0.880) (20:80:1 then 60:40:1). Product-containing fractions were combined and concentrated in vacuo. The residue was further purified by preparative HPLC (condition 4). Combination and evaporation of appropriate fractions gave the title compound as a pale brown solid (3 mg, 1%).

NMR (CDCl$_3$) δ: 1.48 (s, 3H), 1.87 (m, 4H), 2.06 (s, 3H), 2.65 (m, 4H), 2.96 (d, 2H), 3.16 (br.d, 2H), 4.32 (s, 2H), 6.93–7.06 (m, 3H), 7.14–7.40 (m, 11H)

MS (electrospray): m/z [MH$^+$] 461.3; C$_{28}$H$_{32}$N$_2$O$_2$S+H requires 461.2

EXAMPLE 22

N-[3-(3-Benzyl-6-methyl-3-azabicyclo[3.1.0]hex-6-yl)phenyl]methanesulfonamide

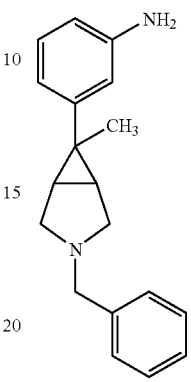
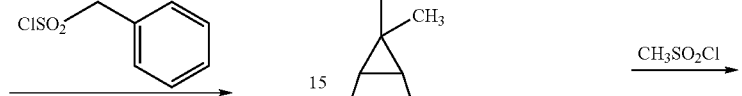
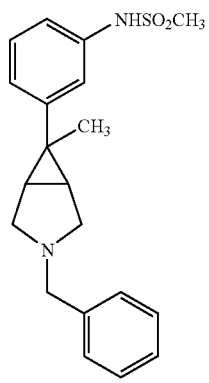

To a solution of 3-(3-benzyl-6-methyl-3-azabicyclo[3.1.0]hex-6-yl)phenylamine (Preparation 30, 1.58 g, 5.68 mmol) in pyridine (10 ml) under nitrogen at 0☐ C. was added methanesulphonyl chloride (0.66 ml, 8.52 mmol) dropwise to the solution, and the mixture was stirred for 14 hours at room temperature. The pyridine was evaporated in vacuo and the residue was partitioned between dichloromethane (50 ml) and dilute aqueous sodium hydrogen carbonate solution (1 M, 50 ml). The layers were separated and the organic extract was dried (Na$_2$SO$_4$), filtered and concentrated in vacuo. The residue was purified by silica (60 g) column chromatography eluting with ethyl acetate:hexane (5:95) then ethyl acetate:hexane:triethylamine (5:95:0.1 increasing to 80:20:0.1). Appropriate fractions were combined and concentrated in vacuo to give the title compound as an off-white solid (1 g, 50%).

mp 117–118☐ C.

NMR (CDCl$_3$) δ: 1.62 (s, 3H), 1.77 (s, 2H), 2.83 (d, 2H), 3.00 (s, 3H), 3.07 (d, 2H), 3.68 (s, 2H), 6.27 (br.s, 1H), 7.01 (d, 1H), 7.08 (m, 2H), 7.24–7.33 (m, 6H)

MS (thermospray): m/z [MH$^+$] 356.9; C$_{20}$H$_{24}$N$_2$O$_2$S+H requires 357.2

EXAMPLE 23

6-Methyl-3-(3-phenylpropyl)-6-[3-(1H-1,2,3-triazol-5-yl)phenyl]-3-azabicyclo[3.1.0]hexane

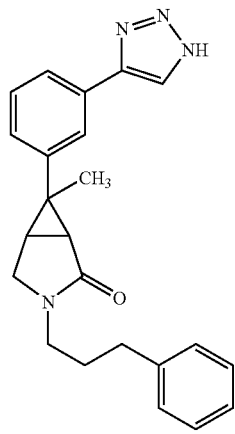

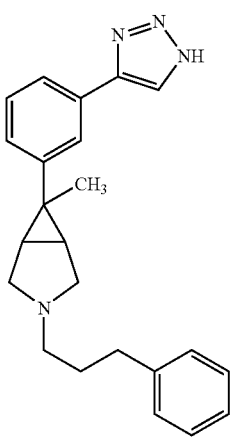

To a solution of 6-methyl-3-(3-phenylpropyl)-6-[3-(1H-1,2,3-triazol-5-yl)phenyl]-3-azabicyclo[3.1.0]hexan-2-one (Preparation 41, 32 mg, 0.087 mmol) in tetrahydrofuran (2 ml) at room temperature was added lithium aluminium hydride (0.43 ml, 0.43 mmol, 1.0 M in THF) dropwise over a few minutes. The mixture was stirred at room temperature for 6 hours and then quenched by the cautious addition of 2N sodium hydroxide (0.5 ml) at 0° C. Excess solid sodium hydrogen carbonate and ethyl acetate (5 ml) were then added and the mixture was stirred rapidly for 30 minutes and then filtered through celite washing with ethyl acetate. The solvent was evaporated in vacuo and the crude residue was purified by silica column chromatography eluting first with hexane:ethyl acetate (1:1) and then hexane:ethyl acetate: ammonia solution (0.880) (10:90:1) to afford the title compound as a colourless oil (15.0 mg, 48%).

NMR (CDCl$_3$) δ: 1.38 (s, 3H), 1.79–1.90 (m, 4H), 2.50 (t, 2H), 2.65 (t, 2H), 2.84 (m, 2H), 3.03 (m, 2H), 7.17–7.40 (m, 7H), 7.60 (d, 1H), 7.74 (br. s, 1H), 7.97 (s, 1H).

MS (thermospray): m/z [MH$^+$] 359.4; C$_{23}$H$_{26}$N$_4$+H requires 359.2.

EXAMPLE 24

3-Hexyl-6-methyl-6-[3-(1H-1,2,3-triazol-5-yl)phenyl]-3-azabicyclo[3.1.0]hexane

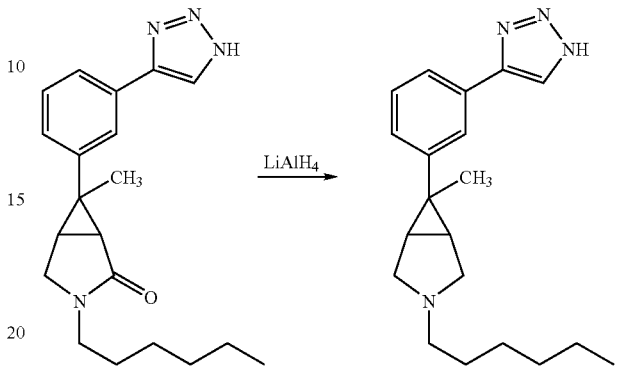

To a solution of 3-hexyl-6-methyl-6-[3-(1H-1,2,3-triazol-4-yl)phenyl]-3-azabicyclo[3.1.0]hexan-2-one (Preparation 40, 2.88 mmol) in tetrahydrofuran (25 ml) at 0° C. was added lithium aluminium hydride (5.8 ml, 5.76 mmol, 1.0M in THF) dropwise over a few minutes. The mixture was stirred at room temperature for 2 hours and then quenched by the cautious addition of 2N sodium hydroxide (3 ml) at 0° C. Ethyl acetate (15 ml) was then added and the mixture was stirred rapidly for 30 minutes and then filtered through celite washing with ethyl acetate. The solvent was evaporated in vacuo and the crude residue was purified by silica column chromatography eluting with hexane:ethyl acetate (1:1) then ethyl acetate:methanol:ammonia solution (0.880) (95:5:1) to afford the title compound (301 mg, 32% over 2 steps) as a colourless oil.

NMR (CDCl$_3$) δ: 0.85–0.95 (m, 3H), 1.25–1.40 (m, 6H), 1.42–1.55 (m, 2H), 1.58 (s, 3H), 1.84 (m, 2H), 2.46 (m, 2H), 2.84–3.00 (4H, m), 7.23–7.40 (m, 2H), 7.58 (d, 1H), 7.76 (br. s, 1H), 7.98 (s, 1H).

MS (thermospray): m/z [MH$^+$] 325.0; C$_{20}$H$_{28}$N$_4$+H requires 325.2.

EXAMPLE 25

3-Hexyl-6-methyl-6-[3-(4H-1,2,4-triazol-3-yl)phenyl]-3-azabicyclo[3.1.0]hexane

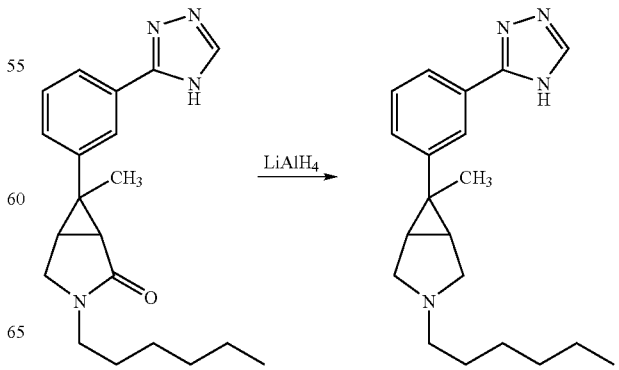

To a solution of 3-hexyl-6-methyl-6-[3-(4H-1,2,4-triazol-3-yl)phenyl]-3-azabicyclo[3.1.0]hexan-2-one (Preparation 43, 220 mg, 0.65 mmol) in tetrahydrofuran (5 ml) at room temperature was added lithium aluminium hydride (1.3 ml, 1.30 mmol, 1.0M in THF) dropwise over a few minutes. The mixture was then heated under reflux for 2 hours and then cooled to 0° C. 2N sodium hydroxide (1.0 ml) was added cautiously followed by ethyl acetate (10 ml) and the mixture was stirred rapidly for 30 minutes, then filtered through celite. The filtrate was concentrated in vacuo and the residue was purified by silica column chromatography eluting with ethyl acetate:methanol:ammonia solution (0.880) (80:20:1) to afford the title compound (190 mg, 90%) as a colourless oil.

NMR (CDCl$_3$) δ: 0.82–0.92 (m, 3H), 1.25–1.38 (m, 6H), 1.40 (s, 3H), 1.50–1.65 (m, 2H), 1.99 (m, 2H), 2.70 (m, 2H), 2.85 (m, 2H), 3.46 (m, 2H), 7.18–7.38 (m, 2H), 7.89–7.92 (m, 2H), 8.18 (s, 1H).

MS (thermospray): m/z 325.1 [MH$^+$]; C$_{20}$H$_{28}$N$_4$+H requires 325.2

EXAMPLE 26

3-Hexyl-6-[3-(1H-imidazol-2-yl)phenyl]-6-methyl-3-azabicyclo[3.1.0]hexane

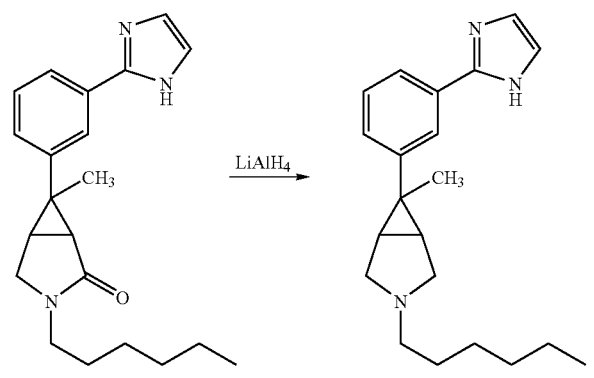

To a solution of 3-hexyl-6-[3-(1H-imidazol-2-yl)phenyl]-6-methyl-3-azabicyclo[3.1.0]hexan-2-one (Preparation 44, 190 mg, 0.56 mmol) in tetrahydrofuran (5 ml) at room temperature was added lithium aluminium hydride (1.1 ml, 1.12 mmol, 1.0 M in THF) dropwise over a few minutes. The mixture was heated under reflux for 1 hour and then cooled to 0° C. 2N sodium hydroxide (1.0 ml) was added cautiously followed by ethyl acetate (10 ml) and the mixture was stirred rapidly for 30 minutes, then filtered through celite. The filtrate was concentrated in vacuo and the residue was purified by silica column chromatography eluting with ethyl acetate:methanol:ammonia solution (0.880) (90:10:1) to afford the title compound (140 mg, 74%) as a white solid.

NMR (CDCl$_3$) δ: 0.85–0.95 (m, 3H), 1.24–1.36 (m, 6H), 1.39–1.45 (m, 2H), 1.50 (s, 3H), 1.78 (m, 2H), 2.42 (m, 2H), 2.80 (m, 2H), 2.95 (m, 2H), 7.10–7.35 (m, 4H), 7.58 (d, 1H), 7.79 (s, 1H)

MS (thermospray): m/z 324.1 [MH$^+$]; C$_{21}$H$_{29}$N$_3$+H requires 324.2

EXAMPLE 27

5-(3-Hexyl-6-methyl-3-azabicyclo[3.1.0]hex-6-yl)-1H-benzimidazole

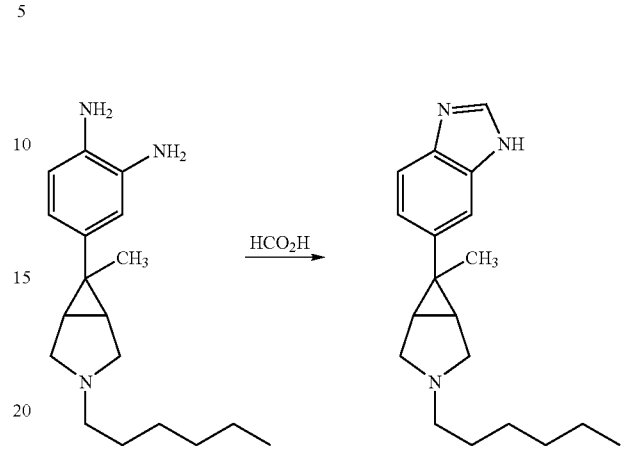

A solution of 2-amino-4-(3-hexyl-6-methyl-3-azabicyclo[3.1.0]hex-6-yl)phenylamine (Preparation 48, 112 mg, 0.39 mmol) in formic acid (2.0 ml) was heated under reflux for 1 h. The mixture was cooled, diluted with water (3 ml) and the pH adjusted to 10 with 5N sodium hydroxide. The aqueous layer was extracted with diethyl ether (3×5 ml) and ethyl acetate (2×5 ml). The combined organic layers were dried (MgSO$_4$), filtered and the solvent removed in vacuo. The crude residue was purified by silica column chromatography eluting with ethyl acetate then ethyl acetate:methanol:ammonia solution (0.880) (80:20:1) to afford the title compound (46 mg, 40%) as a colourless oil.

NMR (CDCl$_3$) δ: 0.85–0.95 (m, 3H), 1.22–1.56 (m, 11H), 1.83 (m, 2H), 2.50 (t, 2H), 2.92–3.00 (m, 4H), 7.20 (d, 1H), 7.50 (s, 1H), 7.56 (d, 1H), 8.00 (s, 1H)

MS (thermospray): m/z 298.2 [MH$^+$]; C$_{19}$H$_{27}$N$_3$+H requires 298.2.

EXAMPLE 28

5-(3-Hexyl-6-methyl-3-azabicyclo[3.1.0]hex-6-yl)-2-(trifluoromethyl)-1H-benzimidazole

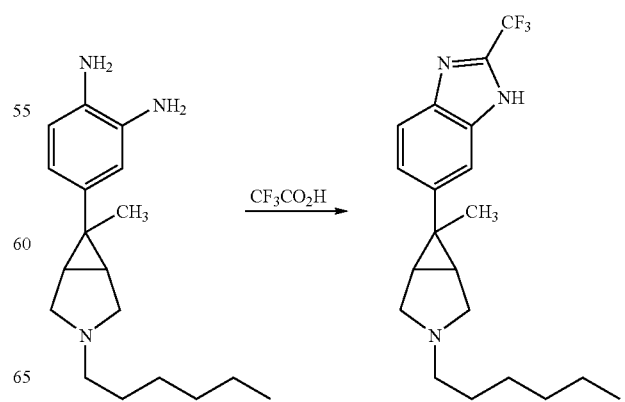

A solution of 2-amino-4-(3-hexyl-6-methyl-3-azabicyclo[3.1.0]hex-6-yl)phenylamine (Preparation 48, 99.0 mg, 0.345 mmol) in trifluoroacetic acid (2.0 ml) was heated under reflux for 1 hour. The mixture was cooled and the solvent was removed in vacuo. The residue was suspended in 2N sodium hydroxide (5 ml) and the aqueous layer was extracted with diethyl ether (3×5 ml). The combined extracts were dried (MgSO$_4$), filtered and concentrated in vacuo. The crude residue was purified by silica column chromatography eluting with ethyl acetate to afford the title compound (67 mg, 54%) as a colourless oil.

NMR (CDCl$_3$) δ: 0.85–0.95 (m, 3H), 1.25–1.52 (m, 8H), 1.56 (s, 3H), 1.83 (m, 2H), 2.50 (t, 2H), 2.92–3.00 (m, 4H), 7.30 (d, 1H), 7.56 (s, 1H), 7.62 (d, 1H)

MS (thermospray): M/Z [MH$^+$] 366.4; C$_{20}$H$_{26}$F$_3$N$_3$+H requires 366.2

EXAMPLE 29

N-[3-(3-Hexyl-6-methyl-3-azabicyclo[3.1.0]hex-6-yl)phenyl]-2-methylbenzenesulfonamide

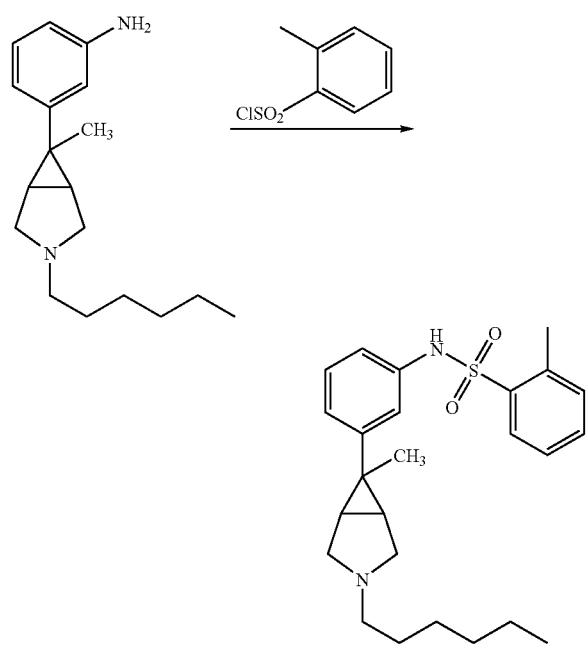

A solution of 3-(3-hexyl-6-methyl-3-azabicyclo[3.1.0]hex-6-yl)phenylamine (Preparation 12, 0.10 g, 0.37 mmol) in pyridine (5 ml) cooled at 0° C. was treated with 2-methylbenzenesulfonyl chloride (0.08 g, 0.44 mmol). The reaction mixture was stirred at room temperature for 3 h, water (30 ml) was added and the product was extracted with diethyl ether (30 ml×3). The combined organic extracts were dried (Na$_2$SO$_4$) and then concentrated in vacuo. The crude products were purified by preparative HPLC (condition 5) to give the acetate salt as a brown gum, (30 mg, 20%).

NMR (CDCl$_3$, selected data for the acetate salt): 0.9 (m, 3H), 1.1–1.2 (m, 9H), 1.6 (m, 2H), 2.0 (m, 2H), 2.6 (s, 3H), 2.9 (m, 2H), 3.0 (m, 2H), 3.55 (m, 2H), 6.8–7.9 (m, 8H).

MS (ES): M/Z (MH$^+$) 427.3; C$_{25}$H$_{34}$N$_2$O$_2$S+H requires 427.2.

EXAMPLE 30

2-Chloro-N-[3-(3-hexyl-6-methyl-3-azabicyclo[3.1.0]hex-6-yl)phenyl]benzenesulfonamide

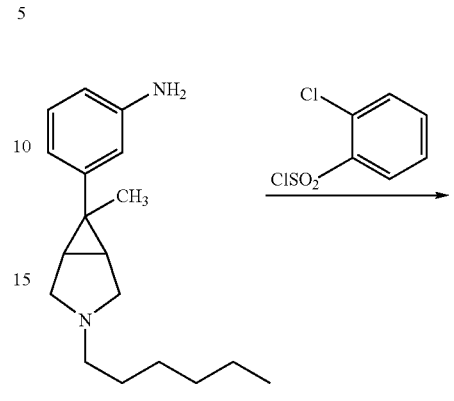

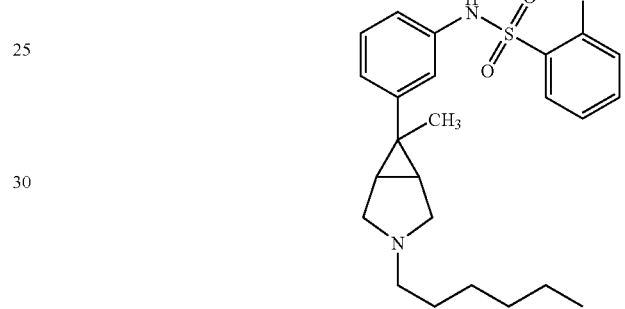

The title compound was prepared by the method of Example 29 substituting 2-methylbenzenesulfonyl chloride with 2-chlorobenzenesulfonyl chloride (90 mg, 0.44 mmol) to give a light brown gum (30 mg, 18%).

NMR (CDCl$_3$, selected data for the acetate salt): 0.9 (m, 3H), 1.1–1.2 (m, 9H), 1.6 (m, 2H), 2.8 (m, 2H), 3.0 (m, 2H), 3.4 (m, 2H), 6.85–6.95 (m, 2H), 7.05 (s, 1H), 7.1 (t, 1H), 7.4 (m, 1H), 7.5–7.6 (m, 2H), 8.0 (d, 1H).

MS (ES): M/Z (MH$^+$) 447.3; C$_{24}$H$_{31}$ClN$_2$O$_2$S+H requires 447.2.

EXAMPLE 31

4-Chloro-N-[3-(3-hexyl-6-methyl-3-azabicyclo[3.1.0]hex-6-yl)phenyl]benzenesulfonamide

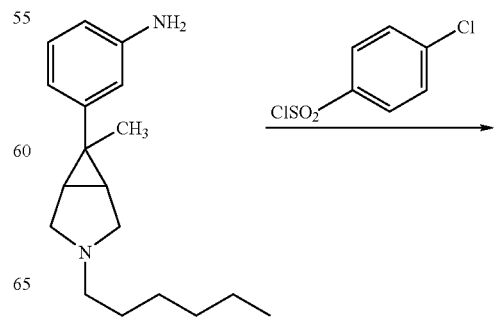

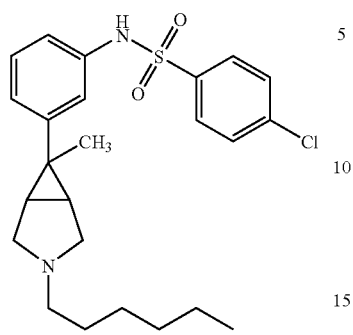

A solution of 3-(3-hexyl-6-methyl-3-azabicyclo[3.1.0]hex-6-yl)phenylamine (Preparation 12, 0.10 g, 0.37 mmol) in pyridine (5 ml) cooled at 0° C. was treated with 4-chlorobenzenesulfonyl chloride (90 mg, 0.44 mmol). The reaction mixture was stirred at room temperature for 3 h, water (30 ml) was added and the product was extracted with diethyl ether (30 ml×3). The combined organic extracts were dried (Na$_2$SO$_4$) and then concentrated in vacuo. The crude products were purified by preparative HPLC (condition 5). The acetate salt obtained was basified with saturated aqueous sodium hydrogen carbonate solution (20 ml) and extracted with dichloromethane (2×20 ml). The combined organic extracts were dried (Na$_2$SO$_4$) and concentrated in vacuo to give a colourless oil, (20 mg, 13%).

NMR (CDCl$_3$, selected data for the free base): 0.85 (m, 3H), 1.2–1.35 (m, 6H), 1.4 (s, 3H), 1.7 (m, 2H), 2.5 (m, 2H), 2.9 (m, 2H), 6.8 (d, 1H), 6.9 (s, 1H), 7.0 (d, 1H), 7.1 (t, 1H), 7.4 (d, 2H), 7.65 (d, 2H).

MS (ES): M/Z (MH$^+$) 447.3; C$_{24}$H$_{31}$ClN$_2$O$_2$S+H requires 447.2.

EXAMPLE 32

N-[3-(3-Hexyl-6-methyl-3-azabicyclo[3.1.0]hex-6-yl)phenyl]-N'-isopropylsulfamide

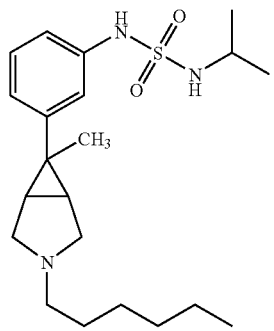

The title compound was prepared by the method of Example 31 substituting 4-chlorobenzenesulfonyl chloride with 2-[(chlorosulfonyl)amino]propane (Preparation 49, 70 mg, 0.44 mmol) to give a colourless oil (20 mg, 14%).

NMR (CDCl$_3$, selected data for the acetate salt): 0.85 (m, 3H), 1.15 (d, 6H), 1.2–1.4 (m, 9H), 1.4 (m, 2H), 1.8 (m, 2H), 2.4 (m, 2H), 2.8 (m, 2H), 2.95 (m, 2H), 3.55 (m, 1H), 4.25 (br, 1H), 6.9–7.05 (m, 3H), 7.2, t, 1H).

MS (ES): M/Z (MH$^+$) 394.3; C$_{21}$H$_{35}$N$_3$O$_2$S+H requires 394.3.

EXAMPLE 33

N-[3-(3-Hexyl-6-methyl-3-azabicyclo[3.1.0]hex-6-yl)phenyl]-1-butanesulfonamide

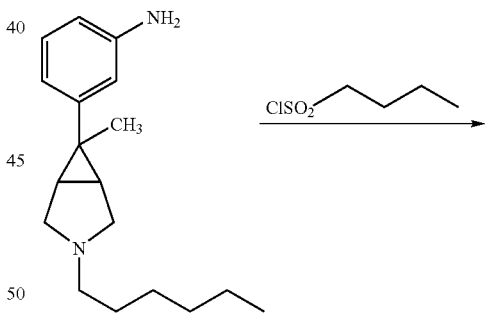

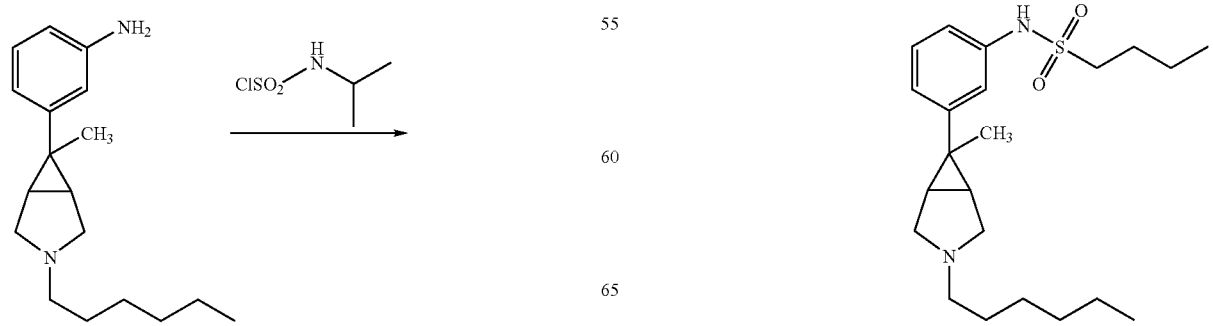

The title compound was prepared by the method of Example 31 substituting 4-chlorobenzenesulfonyl chloride with 1-butanesulfonyl chloride (69 mg, 0.44 mmol) to give a colourless oil (20 mg, 14%).

MS (ES): M/Z (MH$^+$) 393.3; $C_{22}H_{36}N_2O_2S$+H requires 393.3.

Analytical HPLC purity: 95%, retention time 17.6 min (condition 6).

EXAMPLE 34

N-[3-(3-Hexyl-6-methyl-3-azabicyclo[3.1.0]hex-6-yl)phenyl]-1-methyl-1H-imidazole-4-sulfonamide

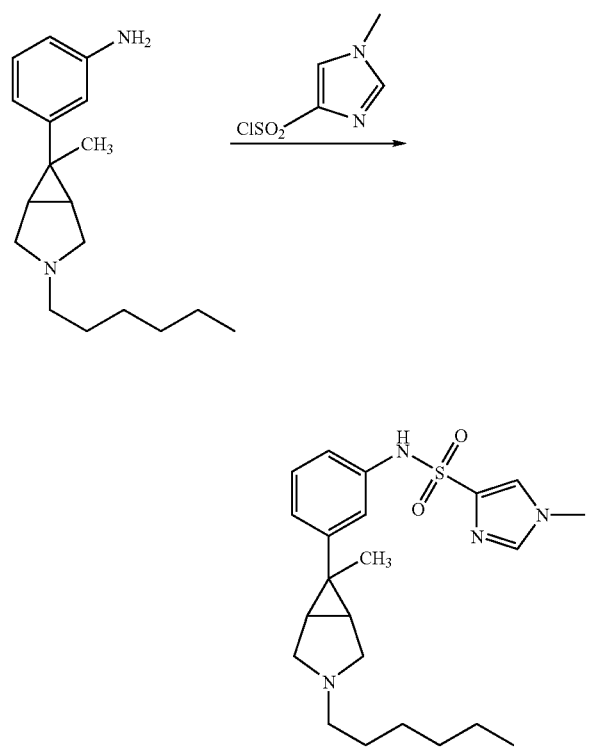

A solution of 3-(3-hexyl-6-methyl-3-azabicyclo[3.1.0]hex-6-yl)phenylamine (Preparation 12, 0.10 g, 0.37 mmol) in pyridine (5 ml) cooled at 0° C. was treated with 1-methyl-1H-imidazole-4-sulfonyl chloride (0.08 g, 0.44 mmol). The reaction mixture was stirred at room temperature for 3 h, water (30 ml) was added and the product was extracted with dichloromethane (30 ml×3). The combined organic extracts were dried ($Na_2SO_4$) and then concentrated in vacuo. The crude products were purified by preparative HPLC (condition 5). The acetate salt obtained was basified with saturated aqueous sodium hydrogen carbonate solution (20 ml) and extracted with dichloromethane (2×20 ml). The combined organic extracts were dried ($Na_2SO_4$) and concentrated in vacuo to give an off-white solid, (30 mg, 20%).

NMR (CDCl$_3$, selected data for the free base): 0.9 (t, 3H), 1.2–1.35 (m, 6H), 1.4 (s, 3H), 1.65 (m, 2H), 2.45 (m, 2H), 2.8 (m, 2H), 2.95 (d, 2H), 3.65 (s, 3H), 6.9–7.2 (m, 4H), 7.3, (s, 1H), 7.45 (s, 1H).

MS (ES): M/Z (MH$^+$) 417.0; $C_{22}H_{32}N_4O_2S$+H requires 417.2.

EXAMPLE 35

N-[3-(3-Hexyl-6-methyl-3-azabicyclo[3.1.0]hex-6-yl)phenyl]-2,1,3-benzoxadiazole-4-sulphonamide

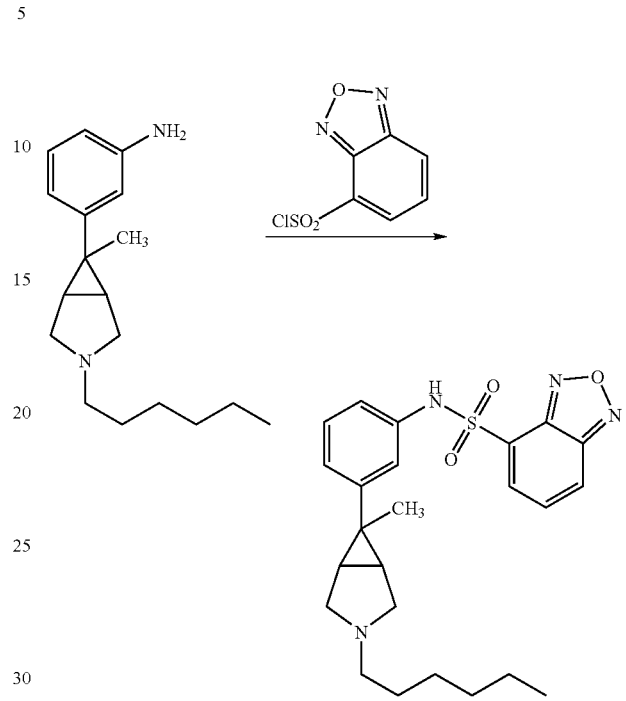

A solution of 3-(3-hexyl-6-methyl-3-azabicyclo[3.1.0]hex-6-yl)phenylamine (Preparation 12, 0.10 g, 0.37 mmol) in pyridine (5 ml) cooled at 0° C. was treated with 2,1,3-benzoxadiazole-4-sulfonyl chloride (0.1 g, 0.44 mmol). The reaction mixture was stirred at room temperature for 3 h, water (30 ml) was added and the product was extracted with diethyl ether (30 ml×3). The combined organic extracts were dried ($Na_2SO_4$) and then concentrated in vacuo. The crude products were purified by preparative HPLC (condition 1), to give the acetate salt as an off-white gum (14 mg, 8%).

NMR (CDCl$_3$, selected data for the acetate salt): 0.85 (t, 3H), 1.2–1.30 (m, 6H), 1.35 (s, 3H), 1.5 (m, 2H), 1.6 (m, 2H), 2.45 (m, 2H), 2.8–2.95 (m, 4H), 3.65 (s, 3H), 3.7 (br, 1H), 6.8 (d, 1H), 6.85–6.95 (m, 2H), 7.0 (t, 1H), 7.45 (m, 1H), 7.9–8.1 (m, 2H).

MS (ES): M/Z (MH$^+$) 455.3; $C_{24}H_{30}N_4O_3S$+H requires 455.2.

EXAMPLE 36

N-{3-[6-Methyl-3-(5-methylhexyl)-3-azabicyclo[3.1.0]hex-6-yl]phenyl}methanesulfonamide

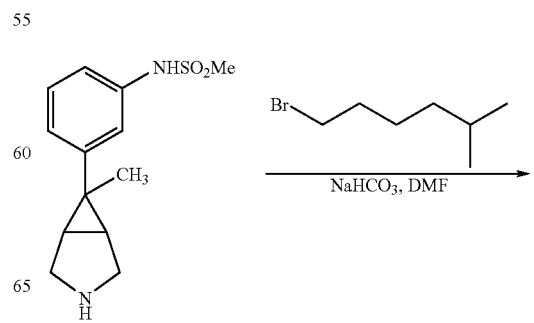

-continued

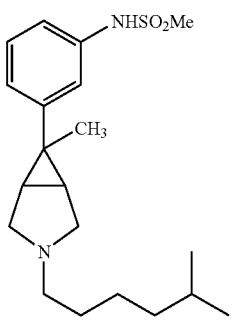

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate solution (63 mg, 0.75 mmol) and 1-bromo-5-methyl hexane (37 mg, 0.20 mmol). The reaction mixture was heated for 30 h at 50° C., and then cooled to room temperature. Diethyl ether (5 ml) was added followed by water (10 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (32 mg, 49%).

NMR ($CDCl_3$, selected data for the free base): 0.85 (d, 6H), 1.15–1.6 (m, 8H), 1.5 (s, 3H), 1.75 (m, 2H), 2.5 (m, 2H), 2.8–3.0 (m, 4H), 3.0 (s, 3H), 7.0–7.1 (m, 3H), 7.2 (t, 1H).

MS (ES): M/Z ($MH^+$) 365.2; $C_{20}H_{32}N_2O_2S+H$ requires 365.2.

EXAMPLE 37

N-[3-(6-Methyl-3-phenethyl-3-azabicyclo[3.1.0]hex-6-yl]phenyl}methanesulfonamide

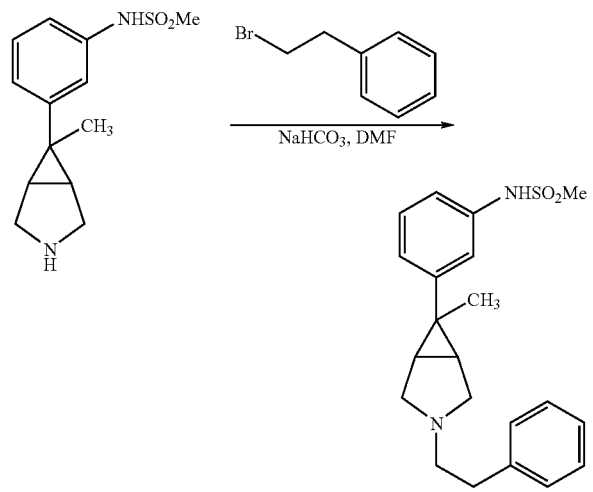

To a solution of the hydrochloride salt of N-[3-(6-methyl-3-azabicyclo[3.1.0]hex-6-yl)phenyl]methanesulfonamide (Preparation 53, 68 mg, 0.23 mmol) in N,N-dimethylformamide (2 ml) was added sodium hydrogen carbonate solution (76 mg, 0.90 mmol) and (2-bromoethyl)benzene (46 mg, 0.25 mmol). The reaction mixture was heated for 17 h at 50° C., and then cooled to room temperature. Diethyl ether (5 ml) was added followed by water (10 ml), the organic extracts were separated and the aqueous layer was washed further with diethyl ether (3×6 ml). The combined organic extracts were dried over ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as a pale yellow oil (35 mg, 41%).

NMR ($CDCl_3$, selected data for the free base): 1.6 (s, 3H), 1.8 (m, 2H), 2.75–2.85 (m, 4H), 2.9–3.1 (m, 7H), 6.9–7.1 (m, 3H), 7.15–7.3 (m, 6H).

MS (ES): M/Z ($MH^+$): 371.0, $C_{21}H_{26}N_2O_2S+H$ requires 371.2.

EXAMPLE 38

N-{3-[6-Methyl-3-(2-phenoxyethyl)-3-azabicyclo[3.1.0]hex-6-yl]phenyl}methanesulfonamide

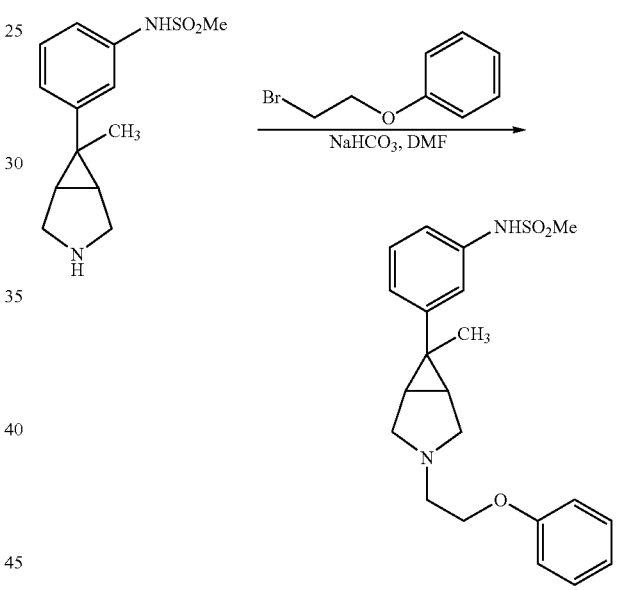

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate solution (63 mg, 0.75 mmol) and 2-(bromoethoxy)benzene (42 mg, 0.20 mmol). The reaction mixture was heated for 30 h at 50° C., and then cooled to room temperature. Diethyl ether (5 ml) was added followed by water (10 ml), the organic extracts were separated and the aqueous layer was washed further with diethyl ether (2×5 ml). The combined organic extracts were dried over ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (41 mg, 59%).

NMR ($CDCl_3$, selected data for the free base): 1.5 (s, 3H), 1.8 (m, 2H), 2.9–3.1 (m, 9H), 4.05 (m, 2H), 6.85–6.95 (m, 3H), 7.0–7.1 (m, 3H), 7.2–7.35 (m, 3H).

MS (ES): M/Z ($MH^+$)387.3; $C_{21}H_{26}N_2O_3S+H$ requires 387.2.

EXAMPLE 39

2-{[3-(3-Hexyl-6-methyl-3-azabicyclo[3.1.0]hex-6-yl)anilino]sulfonyl}acetamide

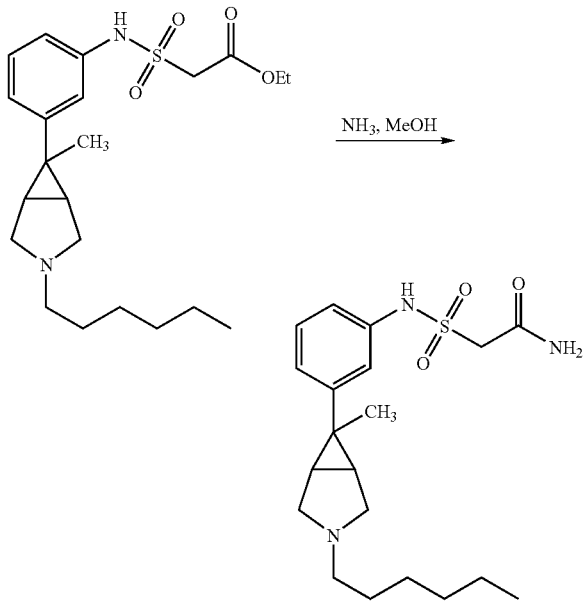

A solution of ethyl 2-{[3-(3-hexyl-6-methyl-3-azabicyclo[3.1.0]hex-6-yl)anilino]sulfonyl}acetate (Example 41, 0.13 g, 0.38 mmol) in ammonia (2M in methanol, 3.0 ml, 1.5 mmol) was heated to 60° C. for 12 h in a sealed tube. The mixture was cooled, concentrated in vacuo and then purified by chromatography on silica gel eluting with methanol:ethyl acetate (2:98) to give the product as a pale yellow foam (80 mg, 53%).

NMR (CDCl$_3$, selected data for the free base): 0.9 (m, 3H), 1.25–1.4 (m, 6H), 1.4–1.5 (m, 5H), 1.8 (m, 2H), 2.5 (m, 2H), 2.85–3.0 (m, 4H), 3.85 (s, 2H), 5.8 (br, 1H), 6.3 (br, 1H), 7.1–7.25 (m, 4H).

MS (ES): M/Z (MH+) 394.4; $C_{20}H_{31}N_3O_3S$+H requires 394.2.

EXAMPLE 40

N-[3-(3-Hexyl-6-methyl-3-azabicyclo[3.1.0]hex-6-yl)phenyl]-2-methoxy-1-ethanesulfonamide

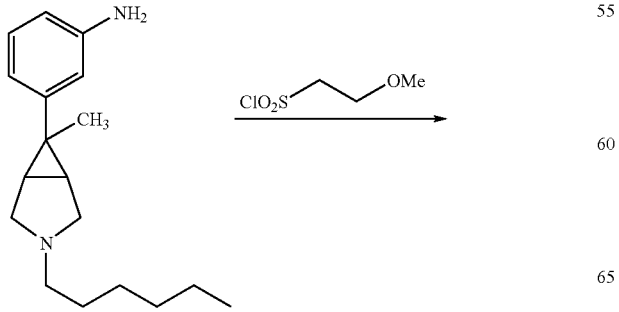

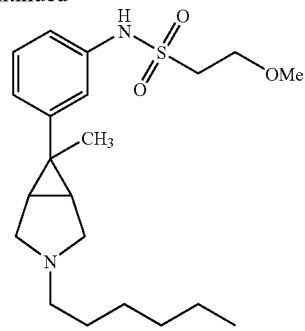

To a solution of 3-(3-hexyl-6-methyl-3-azabicyclo[3.1.0]hex-6-yl)phenylamine (Preparation 12, 0.11 g, 0.40 mmol) in dichloromethane (1.5 ml) was added pyridine (64 mg) in dichloromethane (0.75 ml) and 2-methoxy-1-ethanesulfonyl chloride (J. F. King, J. Y. L. Lam, S. Kronieczny, J. Am. Chem. Soc., 1992, 114 (5), 1743; 0.96 g, 0.60 mmol). The reaction mixture was stirred at room temperature for 16 h and then concentrated in vacuo. The crude residue was purified by chromatography on silica gel eluting with ethyl acetate:2M ammonia in methanol (99:1).

NMR (CDCl$_3$, selected data for the free base): 0.9 (m, 3H), 1.2–1.4 (m, 6H), 1.45 (m, 2H), 1.5 (s, 3H), 1.8 (m, 2H), 2.4 (m, 2H), 2.8 (m, 2H), 3.0 (m, 2H), 3.2 (m, 2H), 3.4 (s, 3H), 3.8 (m, 2H), 6.95–7.15 (m, 3H), 7.25 (m, 1H).

MS (ES): M/Z (MH+) 395.2; $C_{21}H_{34}N_2O_3S$+H requires 395.2

EXAMPLE 41

Ethyl 2-{[3-(3-hexyl-6-methyl-3-azabicyclo[3.1.0]hex-6-yl)anilino]sulfonyl}acetate

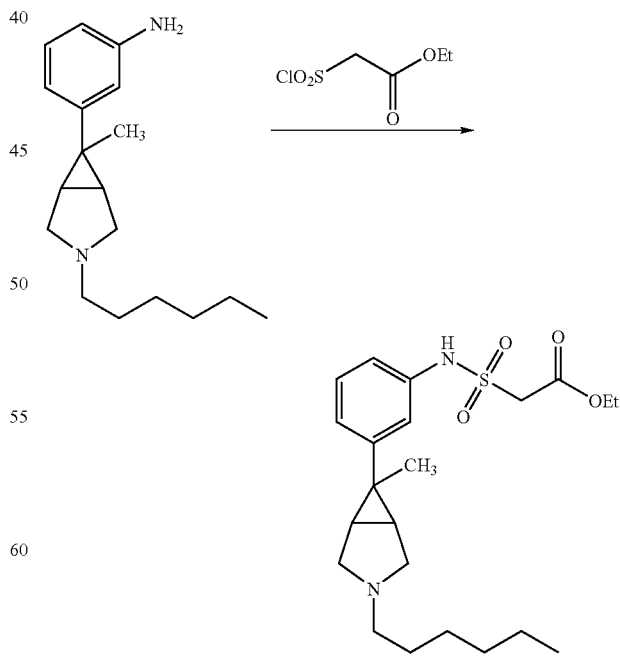

To a solution of 3-(3-hexyl-6-methyl-3-azabicyclo[3.1.0]hex-6-yl)phenylamine (Preparation 12, 0.50 g, 1.84 mmol)

in dichloromethane (5.0 ml) was added pyridine (0.27 ml) in dichloromethane (2.5 ml) and ethyl (2-chlorosulfonyl)acetate (J. E. Oliver, A. B. DeMilo, Synthesis, 1975, 321, 0.48 g, 2.5 mmol). The reaction mixture was stirred at room temperature for 8 h, saturated aqueous sodium hydrogen carbonate solution (10 ml) was added, the organic extracts were separated and the aqueous layer was further extracted with dichloromethane (2×10 ml). The combined organic layers were dried (MgSO$_4$) and concentrated in vacuo. The crude extracts were purified by chromatography on silica gel eluting with ethyl acetate:hexane (10:1) to give a colourless oil which solidified upon cooling (0.70 g, 91%).

NMR (CDCl$_3$, selected data for the free base): 0.85 (m, 3H), 1.2–1.4 (m, 9H), 1.4 (m, 2H), 1.5 (s, 3H), 1.7 (m, 2H), 2.4 (m, 2H), 2.8 (m, 2H), 3.0 (m, 2H), 3.85 (s, 2H), 4.25 (q, 2H), 7.05–7.2 (m, 4H).

MS (ES): M/Z (MH+) 423.2; C$_{22}$H$_{34}$N$_2$O$_4$S+H requires 423.2

EXAMPLE 42

N-[3-(3-Hexyl-6-methyl-3-azabicyclo[3.1.0]hex-6-yl)phenyl]-2-propanesulfonamide

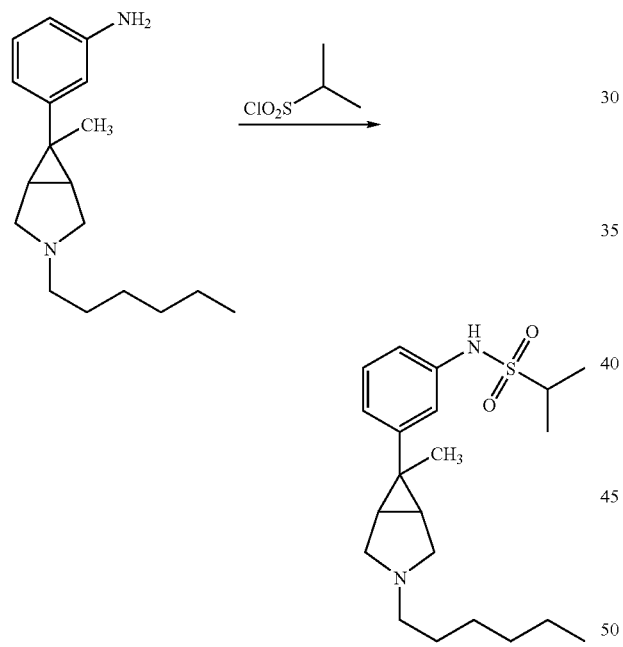

A solution of 3-(3-hexyl-6-methyl-3-azabicyclo[3.1.0]hex-6-yl)phenylamine (Preparation 12, 0.75 g, 0.28 mmol) in pyridine (1.5 ml) cooled at 0° C. was treated with 2-propanesulfonyl chloride (0.05 g, 0.33 mmol). The reaction mixture was stirred at room temperature for 16 h. The reaction mixture was concentrated in vacuo and the crude red residue was purified by chromatography on silica gel (5 g) eluting with hexane:ethyl acetate:0.880 ammonia (50:50: 0.5) to give the product as a light green gum (15 mg, 14%).

NMR (CDCl$_3$, selected data for the free base): 0.9 (t, 3H), 1.05–1.15 (m, 12H), 1.2–1.35 (m, 5H), 1.8 (m, 2H), 2.5 (m, 2H), 2.8 (m, 2H), 3.0 (m, 2H), 3.2 (m, 1H), 6.95–7.1 (m, 2H), 7.15–7.25 (m, 2H).

MS (ES): M/Z (MH+) 379.4; C$_{21}$H$_{34}$N$_2$O$_2$S+H requires 379.2.

EXAMPLE 43

N-{3-[3-(5-Cyanopentyl)-6-methyl-3-azabicyclo[3.1.0]hex-6-yl]phenyl}methanesulfonamide

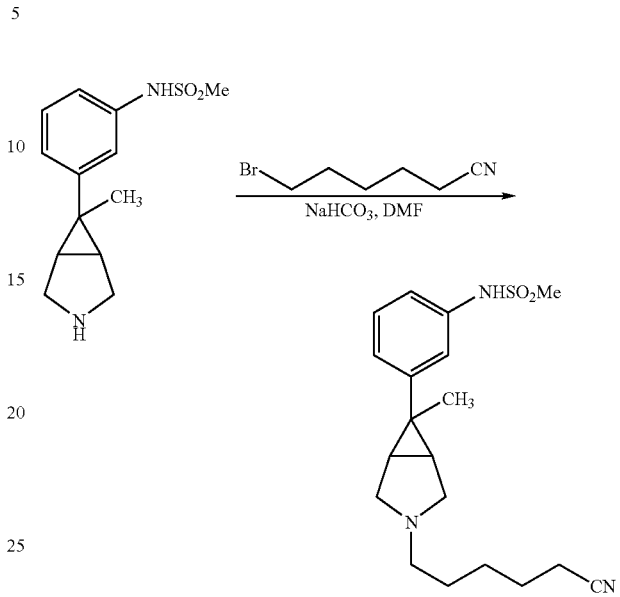

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate solution (63 mg, 0.75 mmol) and 6-bromohexanenitrile (36 mg, 0.20 mmol). The reaction mixture was heated for 30 h at 50° C., and then cooled to room temperature. Diethyl ether (5 ml) was added followed by water (10 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (32 mg, 49%).

NMR (CDCl$_3$, selected data for the free base): 1.4–1.6 (m, 7H), 1.7 (m, 2H), 1.8 (m, 2H), 2.3 (m, 2H), 2.5 (m, 2H), 2.8 (m, 2H), 2.9–3.0 (m, 5H), 6.95–7.1 (m, 3H), 7.25 (t, 1H).

MS (ES): M/Z (MH+) 362.2; C$_{19}$H$_{27}$N$_3$O$_2$S+H requires 362.2.

EXAMPLE 44

N-{3-[6-Methyl-3-(4,4,4-trifluorobutyl)-3-azabicyclo[3.1.0]hex-6-yl]phenyl}methanesulfonamide

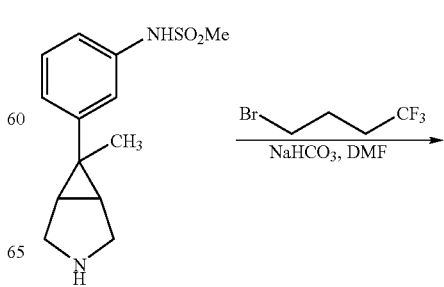

-continued

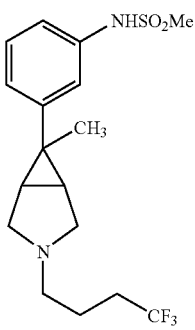

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate solution (63 mg, 0.75 mmol) and 4-bromo-1,1,1-trifluorobutane (40 mg, 0.20 mmol). The reaction mixture was heated for 30 h at 50° C., before addition of further 4-bromo-1,1,1-trifluorobutane (20 mg, 0.10 mmol). The reaction mixture was cooled to room temperature, diethyl ether (5 ml) was added followed by water (10 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (29 mg, 43%).

NMR (CDCl$_3$, selected data for the free base): 1.5 (s, 3H), 1.65–2.85 (m, 4H), 2.15 (m, 2H), 2.6 (m, 2H), 2.8–3.1 (m, 4H), 3.0 (s, 3H), 7.0–7.15 (m, 3H), 7.2 (m, 1H).

MS (ES): M/Z (MH$^+$) 377.3; C$_{17}$H$_{23}$F$_3$N$_2$O$_2$S+H requires 377.2.

EXAMPLE 45

N-{3-[6-Methyl-3-(3-phenoxypropyl)-3-azabicyclo[3.1.0]hex-6-yl]phenyl}methanesulfonamide

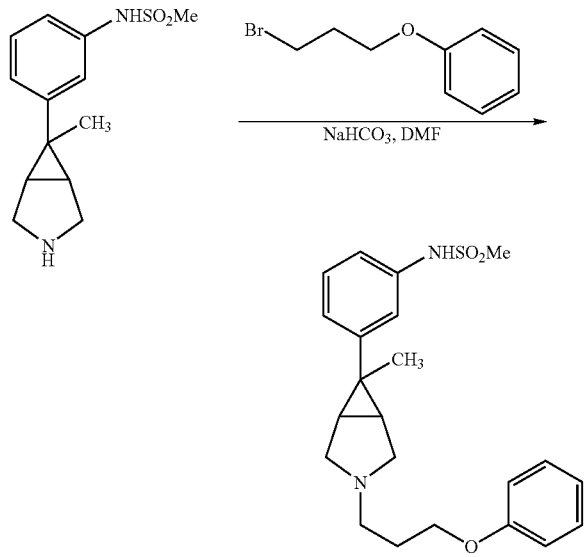

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate solution (63 mg, 0.75 mmol) and 3-phenoxypropyl bromide (45 mg, 0.20 mmol). The reaction mixture was heated for 30 h at 50° C., and then cooled to room temperature. Diethyl ether (5 ml) was added followed by water (10 ml), the organic extracts were separated and the aqueous layer was washed further with diethyl ether (2×5 ml). The combined organic extracts were dried over (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (40 mg, 55%).

NMR (CDCl$_3$, selected data for the free base): 1.55 (s, 3H), 1.8 (m, 2H), 1.95 (m, 2H), 2.65 (m, 2H), 2.9 (m, 2H), 3.0 (s, 3H), 3.05 (m, 2H), 4.0 (t, 2H), 6.85–6.95 (m, 3H), 7.0–7.1 (m, 3H), 7.2–7.35 (m, 3H).

MS (ES): M/Z (MH$^+$) 401.3; C$_{22}$H$_{28}$N$_2$O$_3$S+H requires 401.2.

EXAMPLE 46

N-[3-(3-Hexyl-6-methyl-3-azabicyclo[3.1.0]hex-6-yl)phenyl]-5-isoquinolinesulfonamide

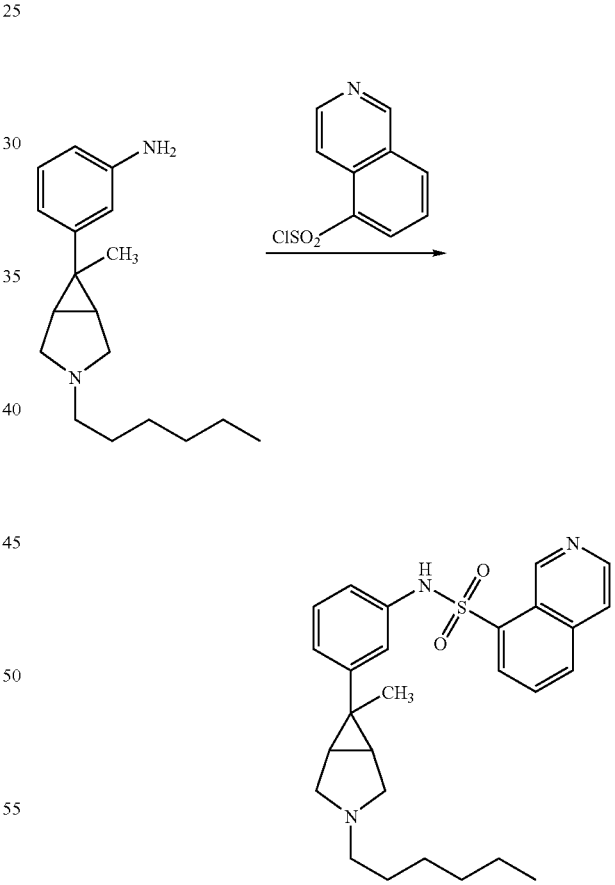

A solution of 3-(3-hexyl-6-methyl-3-azabicyclo[3.1.0]hex-6-yl)phenylamine (Preparation 12, 0.10 g, 0.37 mmol) in pyridine (10 ml) cooled at 0° C. was treated with 5-isoquinolinesulfonyl chloride (0.10 g, 0.44 mmol). The reaction mixture was stirred at room temperature for 16 h before addition of more 5-isoquinolinesulfonyl chloride (0.05 g, 0.22 mmol). The reaction mixture was concentrated in vacuo and the crude red residue was dissolved in dichloromethane (20 ml) and washed with saturated aqueous sodium hydrogen carbonate solution (20 ml), the aqueous phase was extracted with dichloromethane (2×20 ml). The combined organic extracts were dried ($Na_2SO_4$), filtered and concentrated in vacuo. The crude product was purified by chromatography on silica gel (5 g) eluting with hexane:ethyl acetate:0.88 ammonia (30:70:0.5 and then 0:100:0.5) to give the product as a yellow gum (90 mg, 52%).

NMR ($CDCl_3$, selected data for the free base): 0.85 (m, 3H), 1.2–1.35 (m, 9H), 1.3–1.6 (m, 4H), 2.45 (m, 2H), 2.8–3.0 (br, 3H), 6.75 (d, 1H), 6.8 (s, 1H), 6.9 (d, 1H), 7.0 (t, 11H), 7.6 (t, 1H), 8.15 (d, 1H), 8.3–8.4 (m, 2H), 8.6 (m, 1H), 9.3 (m, 1H).

MS (ES): M/Z ($MH^+$) 464.2; $C_{27}H_{33}N_3O_2S$+H requires 464.2.

EXAMPLE 47

N-[3-(3-Hexyl-6-isopropyl-3-azabicyclo[3.1.0]hex-6-yl)phenyl]-methanesulphonamide

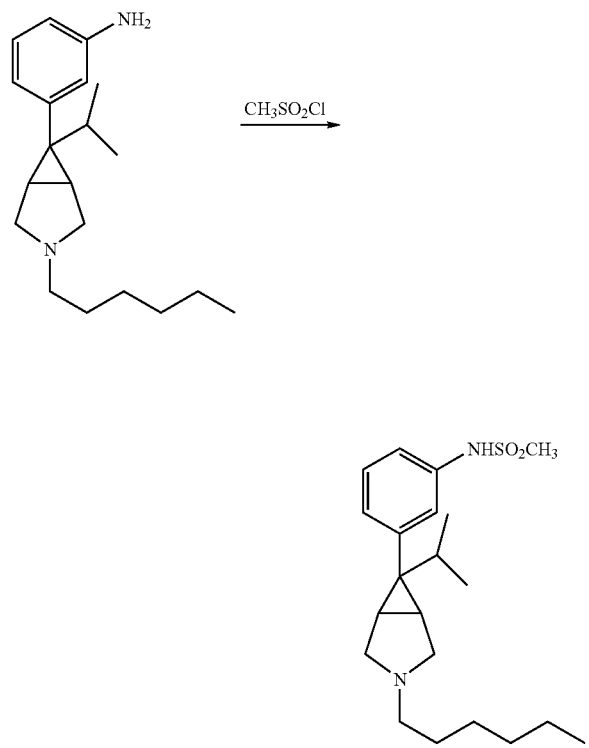

To a stirred solution of 3-(3-hexyl-6-isopropyl-3-azabicyclo[3.1.0]hex-6-yl)aniline (Preparation 61, 0.17 g, 0.57 mmol) in dichloromethane (5 ml) under nitrogen was added pyridine (0.07 ml, 0.91 mmol) and the reaction mixture was cooled to −5° C. Methanesulfonyl chloride (0.05 ml, 0.68 mmol) was added dropwise so that the internal temperature was maintained below −2° C. The reaction mixture was stirred for 3 h and then treated with water (40 ml) and extracted with dichloromethane (3×50 ml). The combined organic extracts were washed with brine (50 ml), dried ($Na_2SO_4$) and concentrated in vacuo to give an amber oil. The crude product was purified by chromatography on a Biotage Flash12™ cartridge packed with silica gel (8 g), the product was eluted with ethyl acetate:0.880 ammonia (99:1) to give the purified product (0.12 g, 56%).

NMR ($CDCl_3$, selected data for the free base): 0.8 (d, 6H), 0.9 (m, 3H), 1.2–1.4 (m, 6H), 2.4 (m, 2H), 2.8 (m, 2H), 2.9 (m, 2H), 3.0 (s, 3H), 7.0–7.25 (m, 4H), MS (ES): M/Z ($MH^+$) 379.0; $C_{21}H_{34}N_2O_2S$+H requires 379.2.

EXAMPLE 48

N-[3-(3-Hexyl-6-propyl-3-azabicyclo[3.1.0]hex-6-yl)phenyl]methanesulphonamide

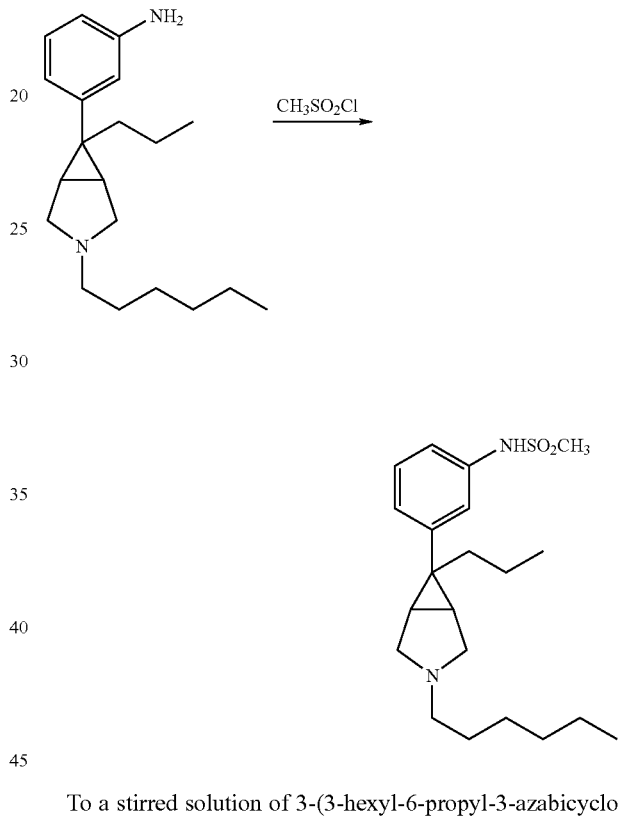

To a stirred solution of 3-(3-hexyl-6-propyl-3-azabicyclo[3.1.0]hex-6-yl)aniline (Preparation 66, 1.0 g, 3.32 mmol) in dichloromethane (52 ml) under nitrogen was added pyridine (53 μl, 6.56 mmol) and the reaction mixture was cooled to 0° C. Methanesulfonyl chloride (280 μl, 3.61 mmol) was added dropwise and then the reaction mixture was stirred at room temperature for 16 h. The crude residue was dissolved in dichloromethane:2M ammonia solution in methanol (80:20), filtered through a pad of silica gel and then through a syringe filter and concentrated in vacuo to give the hydrochloride salt which was then treated with 0.880 ammonia:water (1:3) and extracted with diethyl ether. The combined organic extracts were dried ($Na_2SO_4$) and concentrated in vacuo to give an orange oil (1.18 g, 94%).

NMR ($CDCl_3$, selected data for the free base): 0.8–1.0 (m, 6H), 1.2–1.4 (m, 8H), 1.45 (m, 2H), 1.8 (m, 2H), 1.9 (m, 2H), 2.5 (m, 2H), 2.8 (m, 2H), 2.9–3.0 (m, 5H), 7.0–7.1 (m, 3H), 7.2 (t, 1H).

MS (APCI): M/Z ($MH^+$) 379.1; $C_{21}H_{34}N_2O_2S$+H requires 379.2.

EXAMPLE 49

3-Hexyl-6-methyl-6-[3-(2-pyridyl)phenyl]-3-azabicyclo[3.1.0]hexane

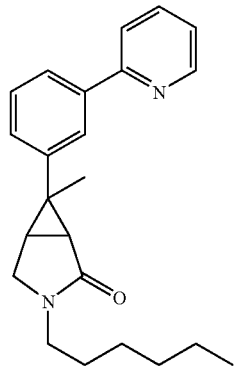 LiAlH₄ →

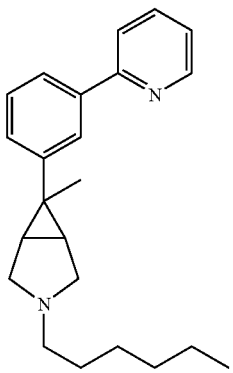

3-Hexyl-6-methyl-6-[3-(2-pyridinyl)phenyl]-3-azabicyclo[3.1.0]hexan-2-one (Preparation 68, 33 mg, 0.09 mmol) was dissolved in tetrahydrofuran (10 ml) at 0° C. Lithium aluminium hydride (1M in tetrahydrofuran, 0.2 ml, 0.2 mmol) was added under nitrogen and then the reaction mixture was stirred at room temperature for 16 h. The reaction mixture was quenched by adding aqueous sodium hydroxide solution (2N, 0.4 ml), followed by solid sodium hydrogen carbonate and ethyl acetate. The reaction mixture was stirred vigorously and then filtered through Celite®. The filtrate was concentrated in vacuo and the residue was chromatographed on silica gel eluting with ethyl acetate to give the product as a colourless oil (13 mg, 41%).

NMR (CDCl$_3$, selected data for the free base): 0.9 (m, 3H), 1.2–1.4 (m, 6H), 1.55–1.65 (m, 5H), 1.8 (m, 2H), 2.45 (m, 2H), 2.8 (m, 2H), 3.0 (m, 2H), 7.2–7.4 (m, 4H), 7.7–7.8 (m, 2H), 7.9 (m, 1H), 8.7 (m, 1H).

MS (TSP): M/Z (MH$^+$) 335.6; C$_{23}$H$_{30}$N$_2$+H requires 335.2.

EXAMPLE 50

3-Hexyl-6-methyl-6-[3-(2-thienyl)phenyl]-3-azabicyclo[3.1.0]hexane

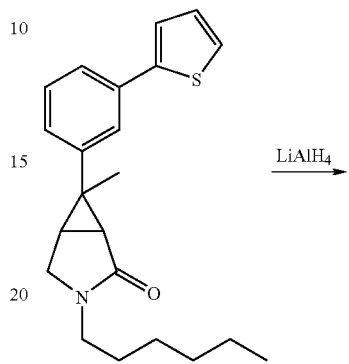 LiAlH₄ →

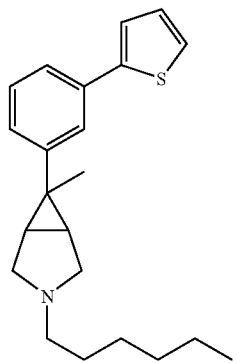

3-Hexyl-6-methyl-6-[3-(2-thienyl)phenyl]-3-azabicyclo[3.1.0]hexan-2-one (Preparation 69, 64 mg, 0.19 mmol) was dissolved in tetrahydrofuran (20 ml) at 0° C. Lithium aluminium hydride (1M in tetrahydrofuran, 0.4 ml, 0.4 mmol) was added under nitrogen and then the reaction mixture was stirred at room temperature for 16 h. The reaction mixture was quenched by adding aqueous sodium hydroxide solution (2N, 0.8 ml), followed by solid sodium hydrogen carbonate and ethyl acetate. The reaction mixture was stirred vigorously and then filtered through Celite®. The filtrate was concentrated in vacuo and the residue chromatographed on silica gel eluting the product with hexane:ethyl acetate (2:1) as a colourless oil (66 mg, 64%).

NMR (CDCl$_3$, selected data for the free base): 0.8 (m, 3H), 1.2–1.4 (m, 6H), 1.45 (m, 2H), 1.55 (s, 3H), 1.8 (m, 2H), 2.45 (m, 2H), 2.8 (m, 2H), 3.0 (m, 2H), 7.0 (t, 1H), 7.15 (d, 1H), 7.2–7.35 (m, 3H), 7.4 (d, 1H), 7.5 (s, 1H).

MS (TSP): M/Z (MH$^+$) 340.3; C$_{22}$H$_{29}$NS+H requires 340.2.

EXAMPLE 51

6-(3-Chlorophenyl)-3-hexyl-6-methyl-3-azabicyclo[3.1.0]hexane

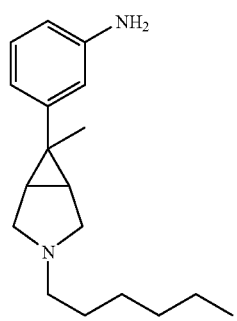

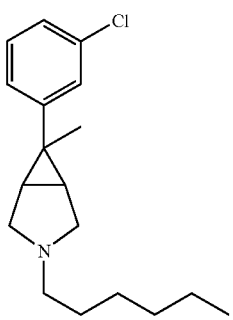

A solution of sodium nitrite (97 mg, 1.4 mmol) dissolved in water (2 ml) was added to 3-(3-hexyl-6-methyl-3-azabicyclo[3.1.0]hex-6-yl)phenylamine (Preparation 12, 0.17 g, 0.61 mmol) dissolved in aqueous hydrochloric acid (2.0 M, 2 ml) over a few minutes at 0° C. After 30 min at 0° C., the reaction mixture was added to copper (I) chloride (1.57 g, 15.8 mmol) in concentrated hydrochloric acid (4.0 ml). After stirring the reaction mixture at room temperature for 45 min, the reaction mixture was heated to 90° C. for 5 min. The reaction mixture was poured cautiously on to solid, prewetted sodium hydrogen carbonate and the product was extracted firstly with diethyl ether and then ethyl acetate. The combined organic extracts were dried (MgSO$_4$) and then concentrated in vacuo. The crude residue was purified by chromatography on silica gel eluting with hexane:ethyl acetate (8:1) to give the product (69 mg, 39%).

NMR (CDCl$_3$, selected data for the free base): 0.9 (m, 3H), 1.2–1.4 (m, 6H), 1.4 (m, 2H), 1.5 (m, 3H), 1.75 (m, 2H), 2.4 (m, 2H), 2.75 (m, 2H), 2.95 (m, 2H), 7.0–7.3 (m, 4H).

MS (TSP): M/Z (MH$^+$) 292.2; C$_{18}$H$_{26}$ClN+H requires 292.2.

EXAMPLE 52

3-Hexyl-6-[3-(1H-imidazol-5-yl)phenyl]-6-methyl-3-azabicyclo[3.1.0]hexane

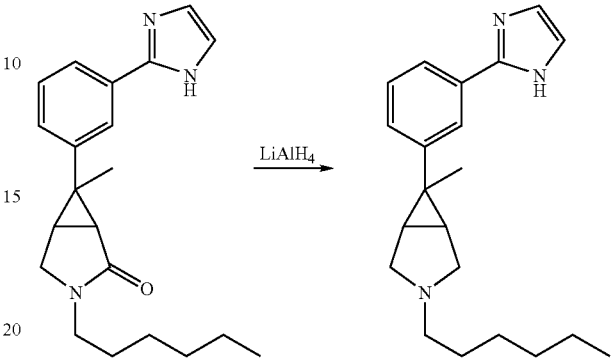

To a solution of 3-hexyl-6-[3-(1H-imidazol-5-yl)phenyl]-6-methyl-3-azabicyclo[3.1.0]hexan-2-one (Preparation 75, 21 mg, 62.3 µmol) in tetrahydrofuran (1.5 ml) at room temperature was added lithium aluminium hydride (1.0 M in tetrahydrofuran, 0.12 ml, 0.12 mmol) over 2 min. The reaction mixture was stirred at room temperature for 30 min and then heated under reflux for 2 h before cooling to room temperature. Aqueous sodium hydroxide solution (1 M, a few drops) and excess ethyl acetate were added followed by solid sodium hydrogen carbonate. The reaction mixture was stirred rapidly for 1 h before filtering. The mother liquor was concentrated in vacuo and the crude residue was chromatographed on silica gel eluting with ethyl acetate and then ethyl acetate:methanol (80:20) to give the product as a colourless semi-solid (15 mg, 75%).

NMR (CDCl$_3$, selected data for the free base: 0.85 (m, 3H), 1.2–1.4 (m, 6H), 1.45 (m, 2H), 1.5 (s, 3H), 1.8 (m, 2H), 2.5 (m, 2H), 2.85–3.0 (m, 4H), 7.15 (d, 1H), 7.2–7.25 (m, 2H), 7.5 (m, 1H), 7.65 (m, 1H), 7.7 (s, 1H).

MS (ES): M/Z (MH$^+$) 324.3; C$_{21}$H$_{29}$N$_3$+H requires 324.2.

EXAMPLE 53

3-Benzyl-6-methyl-6-(3-pyridinyl)-3-azabicyclo[3.1.0]hexane

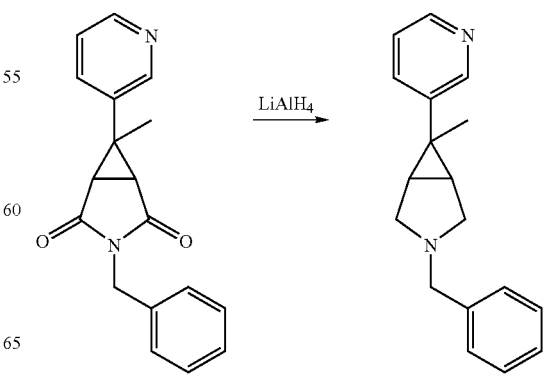

To a solution of 3-benzyl-6-methyl-6-(3-pyridinyl)-3-azabicyclo[3.1.0]hexane-2,4-dione, (Preparation 77, 1.0 g, 3.42 mmol) in tetrahydrofuran (50 ml), was added lithium aluminium hydride (1.0 M in tetrahydrofuran, 13.7 ml, 14.0 mmol). The reaction mixture was heated under reflux for 2 h, cooled to room temperature for 16 h and then refluxed for a further 3 h. The reaction mixture was cooled to room temperature, aqueous sodium hydroxide solution (5M, 14 ml) was added followed by ethyl acetate (20 ml). The reaction mixture was filtered through Celite® and the filtrate was concentrated in vacuo. The crude residue was purified by chromatography on silica gel, eluting with methanol:dichloromethane:0.880 ammonia (2:97:1 and then 5:94:1) to give the product (0.30 g, 33%).

NMR (CDCl$_3$, selected data for the free base): 1.2 (s, 3H), 1.4 (m, 2H), 2.8 (s, 2H), 3.4 (s, 2H), 4.6 (s, 2H), 7.2–7.3 (m, 4H), 7.4–7.45 (m, 2H), 7.6 (m, 1H), 8.5–8.6(m, 2H).

MS (TSP): M/Z (MH$^+$) 265.1; C$_{18}$H$_{20}$N$_2$+H requires 265.2.

EXAMPLE 54

3-Hexyl-6-methyl-6-(3-pyridinyl)-3-azabicyclo[3.1.0]hexane

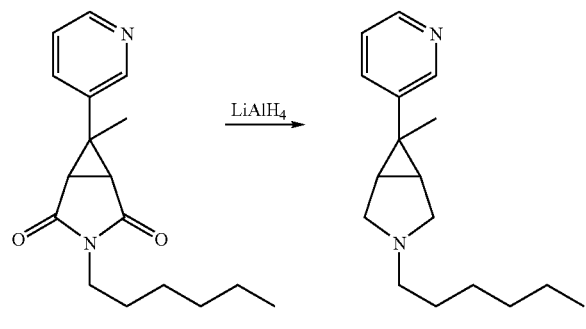

To a solution of 3-hexyl-6-methyl-6-(3-pyridinyl)-3-azabicyclo[3.1.0]hexane-2,4-dione (Preparation 78, 0.22 g, 0.78 mmol) in tetrahydrofuran (15 ml) was added lithium aluminium hydride (1.0 M in tetrahydrofuran, 1.6 ml, 1.6 mmol). The reaction mixture was heated under reflux for 3 h before cooling to room temperature and stirring for 16 h. Water (2 ml) was added followed by ethyl acetate (5 ml). The reaction mixture was filtered through Celite® and concentrated in vacuo. The crude residue was purified on silica gel eluting with dichloromethane:methanol:0.880 ammonia (99:0:1 and then 89:10:1) to give the pure product (0.13 g, 64%).

NMR (CDCl$_3$, selected data for the free base): 0.9 (m, 3H), 1.2–1.4 (m, 6H), 1.5 (m, 2H), 1.55 (s, 3H), 1.8 (m, 2H), 2.5 (m, 2H), 2.85 (m, 2H), 3.05 (m, 2H), 7.15 (m, 1H), 7.55 (m, 1H), 8.4 (m, 1H), 8.55 (m, 1H).

MS (TSP): M/Z (MH$^+$) 259.9; C$_{17}$H$_{26}$N$_2$+H requires 259.2.

EXAMPLE 55

6-Methyl-3-(3-phenylpropyl)-6-(3-pyridinyl)-3-azabicyclo[3.1.0]hexane

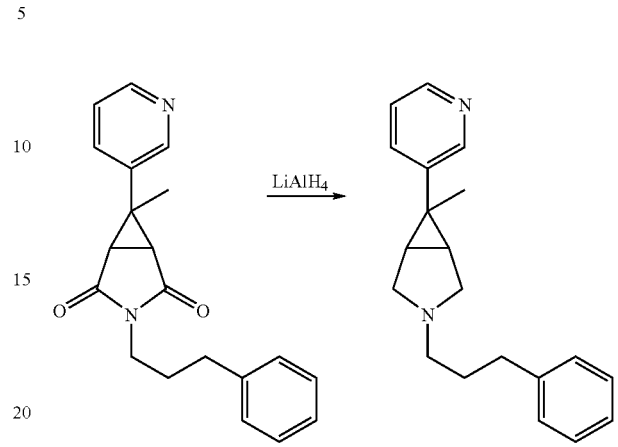

To 6-methyl-3-(3-phenylpropyl)-6-(3-pyridinyl)-3-azabicyclo[3.1.0]hexane-2,4-dione (Preparation 79, 0.23 g, 0.72 mmol) dissolved in tetrahydrofuran (15 ml) was added lithium aluminium hydride (1.0 M in tetrahydrofuran, 1.4 ml, 1.4 mmol). The reaction mixture was heated under reflux for 4 h before cooling to room temperature and adding water (2 ml) and ethyl acetate (5 ml). The reaction mixture was filtered through Celite® and concentrated in vacuo. The crude residue was purified on silica gel (10 g) eluting with dichloromethane:methanol:0.880 ammonia (99:0:1 and then 89:10:1) to give the pure product (0.2 g, 95%).

NMR (CDCl$_3$, selected data for the free base): 1.6 (s, 3H), 1.75 (m, 4H), 2.45 (m, 2H), 2.65 (m, 2H), 2.8 (m, 2H), 3.1 (m, 2H), 7.05–7.3 (m, 6H), 7.5 (m, 1H), 8.4 (m, 1H), 8.5 (s, 1H).

MS (TSP): M/Z (MH$^+$) 293.0; C$_{20}$H$_{24}$N$_2$+H requires 293.2.

EXAMPLE 56

N-[3-(3-Allyl-6-methyl-3-azabicyclo[3.1.0]hex-6-yl)phenyl]methanesulfonamide

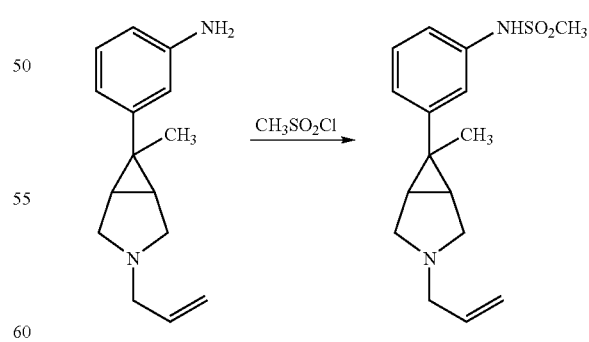

To 3-(3-allyl-6-methyl-3-azabicyclo[3.1.0]hex-6-yl)aniline (Preparation 52, 8.5 g, 37.2 mmol) dissolved in pyridine (70 ml) at 0° C. was added methanesulphonyl chloride (4.32 ml, 55.8 mmol) dropwise over 20 min. The reaction mixture was allowed to stir for 16 h and was then quenched with ice (5 g). The reaction mixture was concentrated in vacuo and the residue was dissolved in dichloromethane and washed with saturated aqueous sodium hydrogen carbonate solution, followed by water. The organic extracts were concentrated in vacuo and then purified by flash chromatography on silica gel, eluting with ethyl acetate:dichloromethane:2N ammonia in methanol (30:69:1). The product was obtained as a viscous brown oil (7.7 g, 68%).

NMR (CDCl$_3$, selected data for the free base): 1.5 (s, 3H), 1.8 (m, 2H), 2.8 (m, 2H), 2.95–3.05 (m, 5H), 3.1 (m, 2H), 5.05 (m, 1H), 5.2 (m, 1H), 5.85 (m, 1H), 7.0–7.1 (3H), 7.2 (t, 1H).

MS (ES): M/Z (MH$^+$) 307.0; $C_{16}H_{22}N_2O_2S$+H requires 307.1.

EXAMPLE 57

N-[3-(3-Hexyl-6-methyl-3-azabicyclo[3.1.0]hex-6-yl)phenyl]-2-hydroxy-1-ethanesulfonamide

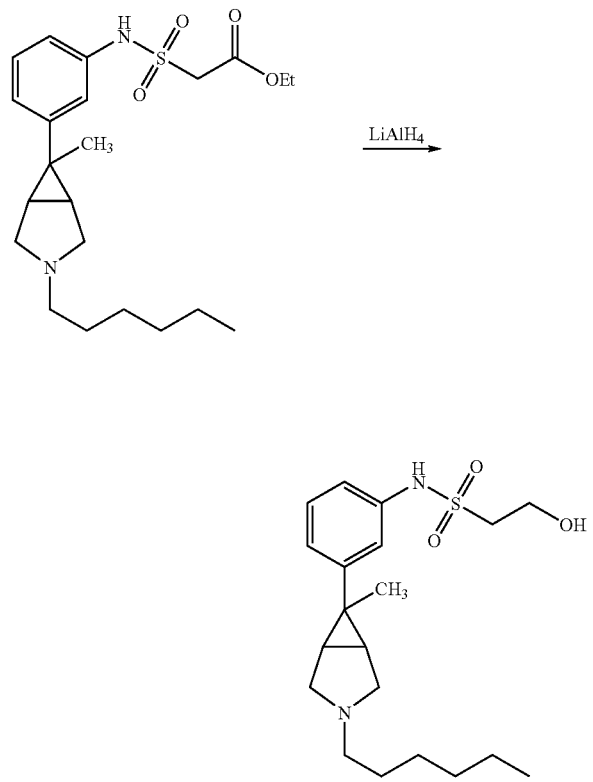

To a solution of ethyl 2-{[3-(3-hexyl-6-methyl-3-azabicyclo[3.1.0]hex-6-yl)anilino]sulfonyl}acetate (Example 41, 0.17 g, 0.43 mmol) in diethyl ether (6.5 ml) was added lithium borohydride (20 mg, 0.91 mmol) followed by methanol (37 μl) in diethyl ether (0.5 ml). The reaction mixture was stirred at room temperature for 5 h and then quenched with saturated aqueous sodium hydrogen carbonate solution. The organic extracts were extracted with ethyl acetate, dried (MgSO$_4$) and then concentrated in vacuo. The crude residue was purified by chromatography on silica gel eluting with ethyl acetate, and then ethyl acetate:methanol:0.880 ammonia (94:5:1) to give the product as a colourless oil (10 mg, 6%).

NMR (CDCl$_3$, selected data for the free base): 0.85 (m, 3H), 1.2–1.4 (m, 6H), 1.4 (m, 2H), 1.45 (s, 3H), 1.8 (m, 2H), 2.45 (m, 2H), 2.8 (m, 2H), 3.0 (m, 2H), 3.2 (m, 2H), 4.1 (m, 2H), 7.0–7.15 (m, 3H), 7.2 (m, 1H).

MS (ES): M/Z (MH$^+$) 381.1; $C_{20}H_{32}N_2O_3S$+H requires 381.2.

EXAMPLE 58

N-{3-[3-(2-Butoxyethyl)-6-methyl-3-azabicyclo[3.1.0]hex-6-yl]phenyl}methanesulfonamide

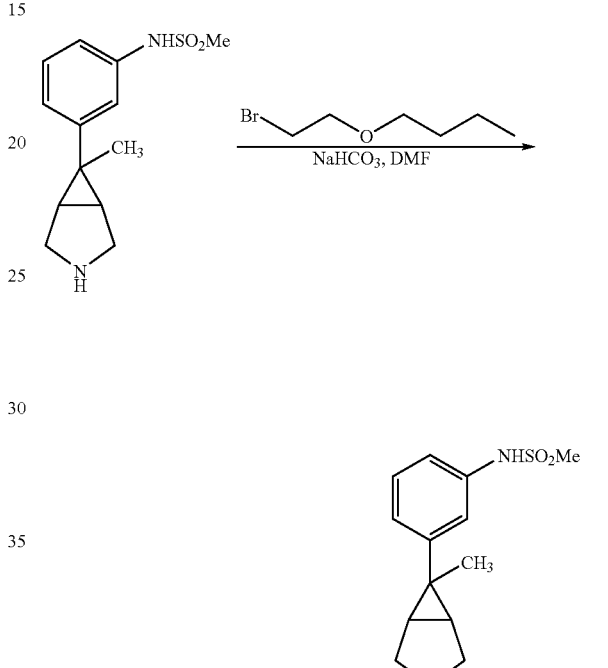

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethoxy)butane (38 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (29 mg, 44%).

NMR (CDCl$_3$, selected data for the free base): 0.95 (t, 3H), 1.35 (m, 2H), 1.45 (s, 3H), 1.55 (m, 2H), 1.75 (m, 2H), 2.7 (m, 2H), 2.9–3.05 (m, 7H), 3.45 (m, 2H), 3.5 (m, 2H), 7.0–7.15 (m, 3H), 7.25 (t, 1H).

MS (ES): M/Z (MH$^+$) 367.1; $C_{19}H_{30}N_2O_3S$+H requires 367.2.

EXAMPLE 59

N-{3-[6-Methyl-3-(3-methylphenethyl)-3-azabicyclo[3.1.0]hex-6-yl]phenyl}methanesulfonamide

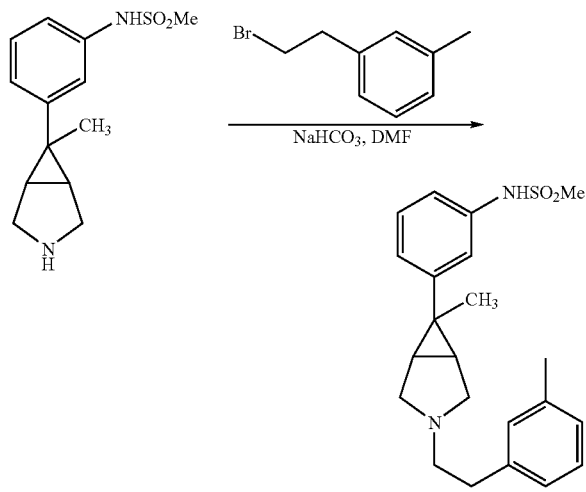

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethyl)-3-methylbenzene (A. Mitre, and S. Ghoshe, Ind. J. Chem. Sect. B, 1996, 35B, 785; 41 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (20 mg, 29%).

NMR (CDCl$_3$, selected data for the free base): 1.45 (s, 3H), 1.8 (m, 2H), 2.35 (s, 3H), 2.7–2.8 (m, 4H), 2.85–3.1 (m, 7H), 7.0–7.3 (m, 8H).

MS (ES): M/Z (MH$^+$) 385.5; C$_{22}$H$_{28}$N$_2$O$_2$S+H requires 385.2.

EXAMPLE 60

N-(3-{3-[2-(4-Fluorophenoxy)ethyl]-6-methyl-3-azabicyclo[3.1.0]hex-6-yl}phenyl)methanesulfonamide

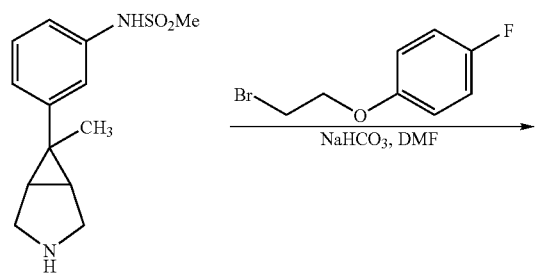

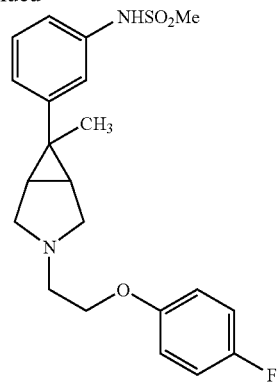

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 4-fluorophenoxyethyl bromide (45 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (18 mg, 25%).

NMR (CDCl$_3$, selected data for the free base): 1.5 (s, 3H), 1.8 (s, 2H), 2.9–3.15 (m, 9H), 4.05 (m, 2H), 6.8–6.9 (m, 2H), 6.95–7.15 (m, 5H), 7.25 (m, 1H).

MS (ES): M/Z (MH$^+$) 405.3; C$_{21}$H$_{25}$FN$_2$O$_3$S+H requires 405.2.

EXAMPLE 61

N-{3-[3-(5-Hexenyl)-6-methyl-3-azabicyclo[3.1.0]hex-6-yl]phenyl}methanesulfonamide

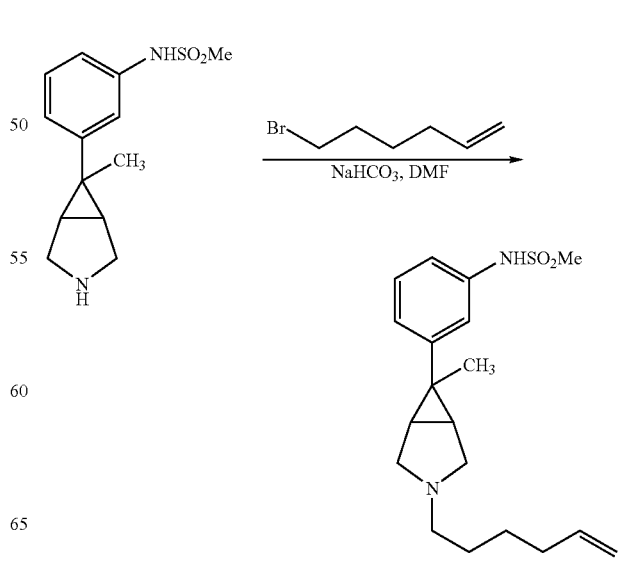

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 6-bromo-1-hexene (34 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (29 mg, 46%).

NMR (CDCl$_3$, selected data for the free base): 1.4–1.45 (m, 4H), 1.5 (s, 3H), 1.75 (m, 2H), 2.1 (m, 2H), 2.5 (m, 2H), 2.85 (m, 2H), 2.95–3.05 (m, 5H), 4.9–5.05 (m, 2H), 5.8 (m, 1H), 7.0–7.15 (m, 3H), 7.25 (t, 1H).

MS (ES): M/Z (MH$^+$) 349.5; C$_{19}$H$_{28}$N$_2$O$_2$S+H requires 349.2.

EXAMPLE 62

N-(3-{3-[4-(Cyanomethyl)benzyl]-6-methyl-3-azabicyclo[3.1.0]hex-6-yl}phenyl)methanesulfonamide

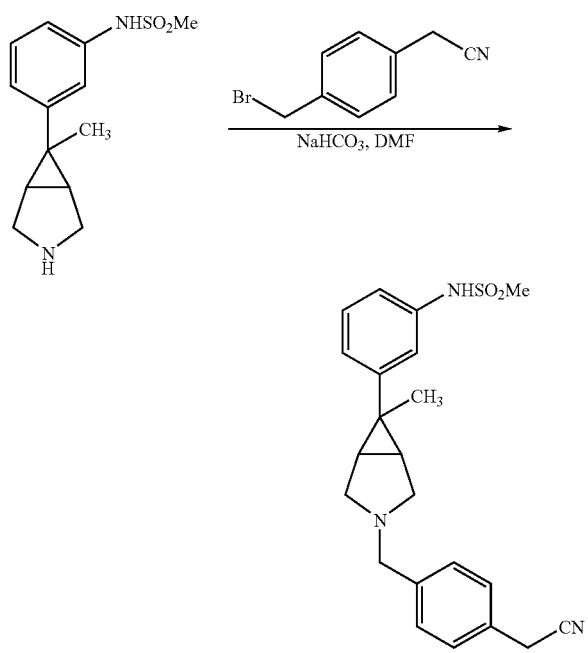

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 2-[4-(bromomethyl)phenyl]acetonitrile (E. Laurent, B. Marquet and R. Tardivel, Tetrahedron, 1991, 47, 3969) (44 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (31 mg, 43%).

NMR (CDCl$_3$, selected data for the free base): 1.6 (s, 3H), 1.80 (m, 2H), 2.85 (m, 2H), 3.0–3.1 (m, 5H), 3.7 (s, 2H), 3.75 (s, 2H), 6.75 (br, 1H), 7.0–7.1 (m, 3H), 7.2–7.4 (m, 5H).

MS (ES): M/Z (MH$^+$) 396.0; C$_{22}$H$_{25}$N$_3$O$_2$S+H requires 396.2.

EXAMPLE 63

N-{3-[3-(4-Fluorophenethyl)-6-methyl-3-azabicyclo[3.1.0]hex-6-yl]phenyl}methanesulfonamide

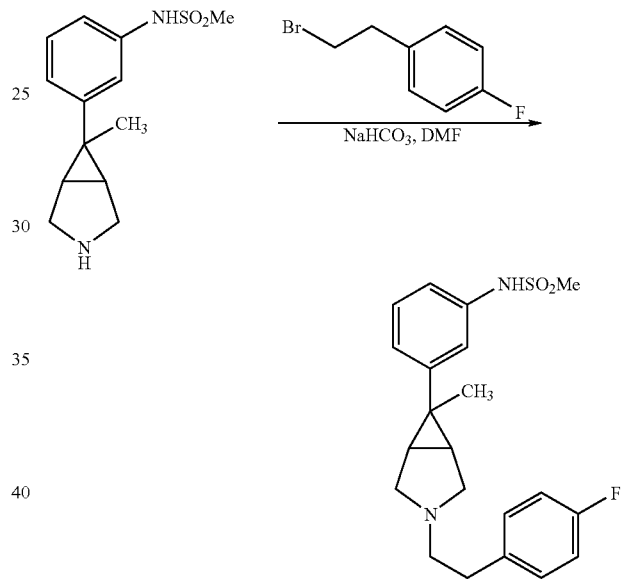

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethyl)-4-fluorobenzene (C. M. Suter, and A. W. Weston, J. Am. Chem. Soc., 1941, 63, 602; 42 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (18 mg, 26%).

NMR (CDCl$_3$, selected data for the free base): 1.65 (s, 3H), 1.8 (m, 2H), 2.75–2.85 (m, 4H), 2.9–3.1 (m, 7H), 6.9–7.3 (m, 8H).

MS (ES): M/Z (MH$^+$) 389.0; C$_{21}$H$_{25}$FN$_2$O$_2$S+H requires 389.2.

EXAMPLE 64

N-{3-[3-(2-Chlorophenethyl)-6-methyl-3-azabicyclo[3.1.0]hex-6-yl]phenyl}methanesulfonamide

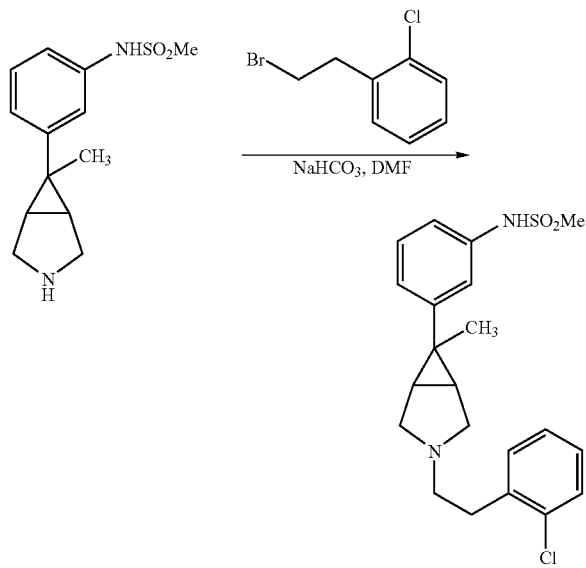

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethyl)-2-chlorobenzene (R. A. Glennon, et al., J. Med. Chem., 1981, 24, 678; 45 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (19 mg, 26%).

NMR (CDCl$_3$, selected data for the free base): 1.45 (s, 3H), 1.8 (m, 2H), 2.75 (m, 2H), 2.85–3.1 (m, 9H), 7.0–7.4 (m, 8H).

MS (ES): M/Z (MH$^+$) 405.0; C$_{21}$H$_{25}$ClN$_2$O$_2$S+H requires 405.1.

EXAMPLE 65

N-(3-{3-[2-(2-Chlorophenoxy)ethyl]-6-methyl-3-azabicyclo[3.1.0]hex-6-yl}phenyl)methanesulfonamide

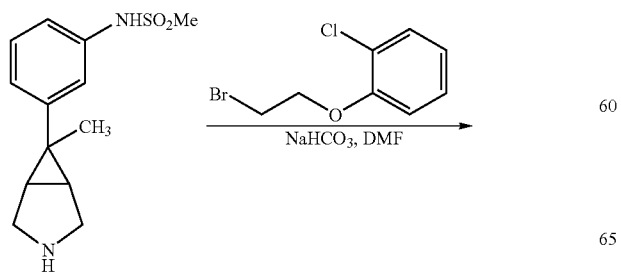

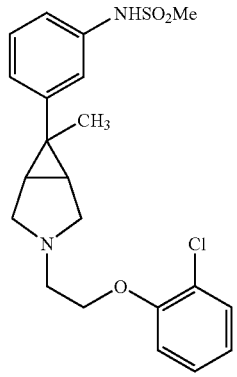

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethoxy)-2-chlorobenzene (J. D. Genzer, C. P. Huttrer, and G. C. van Wessem, J. Am. Chem. Soc., 1951, 73, 3159; 49 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried (Na$_2$SO$_4$) and concentrated in vacuo. The residues were purified by flash chromatography on an SPE cartridge containing silica gel (5 g) eluting with dichloromethane:ethanol:0.880 ammonia (200:8:1) to give the product as an oil (30 mg, 40%).

NMR (CDCl$_3$, selected data for the free base): 1.50 (s, 3H), 1.8 (m, 2H), 3.0–3.2 (m, 9H), 4.15 (m, 2H), 6.85–6.95 (m, 2H), 7.05–7.15 (m, 3H), 7.20–7.25 (m, 2H), 7.35 (m,1H).

MS (ES): M/Z (MH$^+$) 421.0; C$_{21}$H$_{25}$ClN$_2$O$_3$S+H requires 421.1.

EXAMPLE 66

N-(3-{6-Methyl-3-[2-(2-methylphenoxy)ethyl]-3-azabicylco[3.1.0]hex-6-yl}phenyl)methanesulfonamide

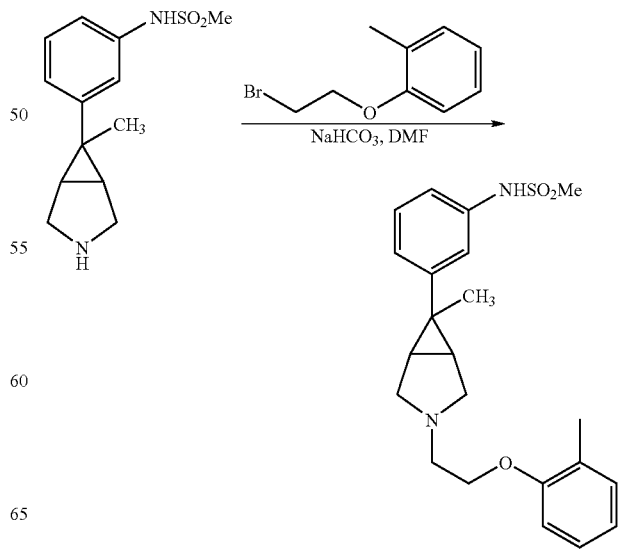

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-bromoethoxy)-2-methylbenzene (45 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (12 mg, 17%).

NMR ($CDCl_3$, selected data for the free base): 1.5 (s, 3H), 1.8 (m, 2H), 2.25 (s, 3H), 2.95–3.1 (m, 5H), 3.15–3.2 (m, 4H), 4.1 (m, 2H), 6.8–6.9 (m, 2H), 7.0–7.3 (m, 6H).

MS (ES): M/Z ($MH^+$) 401.0; $C_{22}H_{28}N_2O_3S$+H requires 401.2.

EXAMPLE 67

N-(3-{3-[2-(Cyclohexyloxy)ethyl]-6-methyl-3-azabicyclo[3.1.0]hex-6-yl}phenyl)methanesulfonamide

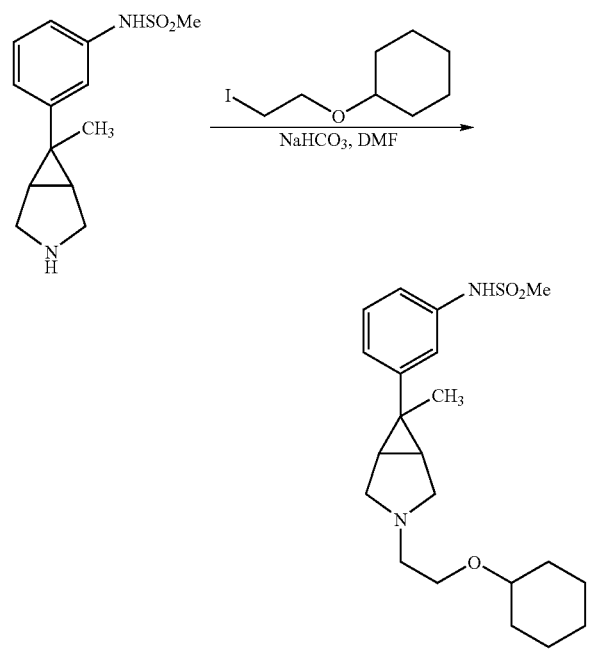

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(2-iodoethoxy)cyclohexane (Preparation 87, 53 mg, 0.20 mmol). The reaction mixture was heated for 30 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (33 mg, 47%).

NMR ($CDCl_3$, selected data for the free base): 1.15–1.35 (m, 5H), 1.45 (s, 3H), 1.5 (m, 1H), 1.65–1.8 (m, 4H), 1.9 (m, 2H), 2.7 (m, 2H), 2.9–3.1 (m, 7H), 3.25 (m, 1H), 3.55 (m, 2H), 7.0–7.15 (m, 3H), 7.25 (t, 1H).

MS (ES): M/Z ($MH^+$) 393.1; $C_{21}H_{32}N_2O_3S$+H requires 393.2.

EXAMPLE 68

N-(3-{3-[2-(Benzyloxy)ethyl]-6-methyl-3-azabicyclo[3.1.0]hex-6-yl}phenyl)methanesulfonamide

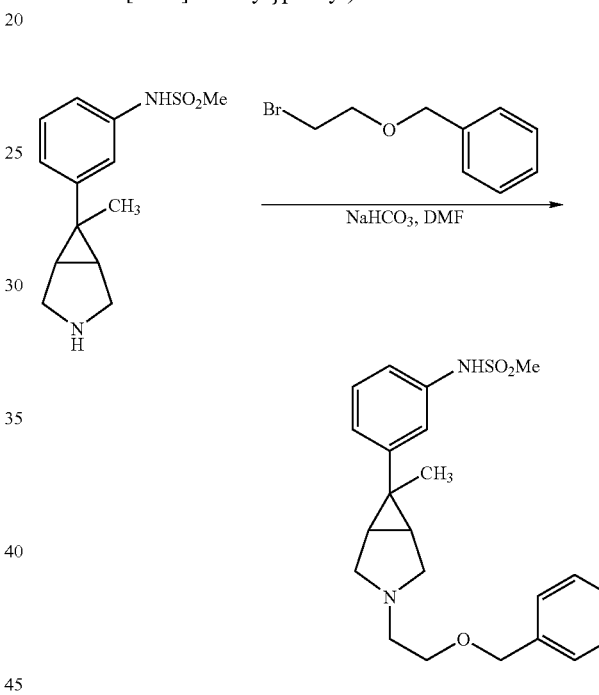

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-[(2-iodoethoxy)methyl]benzene (Preparation 90, 54 mg, 0.20 mmol). The reaction mixture was heated for 15 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (36 mg, 50%).

NMR ($CDCl_3$, selected data for the free base): 1.5 (s, 3H), 1.8 (s, 2H), 2.75 (m, 2H), 2.95–3.05 (m, 7H), 3.55 (m, 2H), 4.55 (s, 2H), 7.0–7.1 (m, 3H), 7.2–7.4 (m, 6H).

MS (ES): M/Z ($MH^+$) 401.0; $C_{22}H_{28}N_2O_3S$+H requires 401.2.

EXAMPLE 69

N-(3-{3-[(E)-3-Cyclohexyl-2-propenyl]-6-methyl-3-azabicyclo[3.1.0]hex-6-yl}phenyl)methanesulfonamide

EXAMPLE 70

N-{3-[6-Methyl-3-(3,4,4-trifluoro-3-butenyl)-3-azabicyclo[3.1.0]hex-6-yl]phenyl}methanesulfonamide

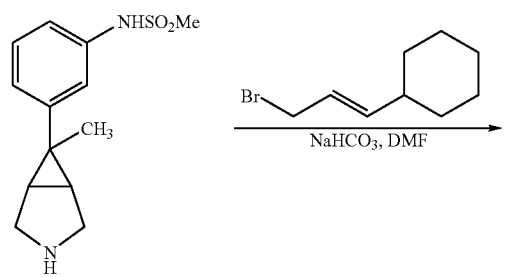

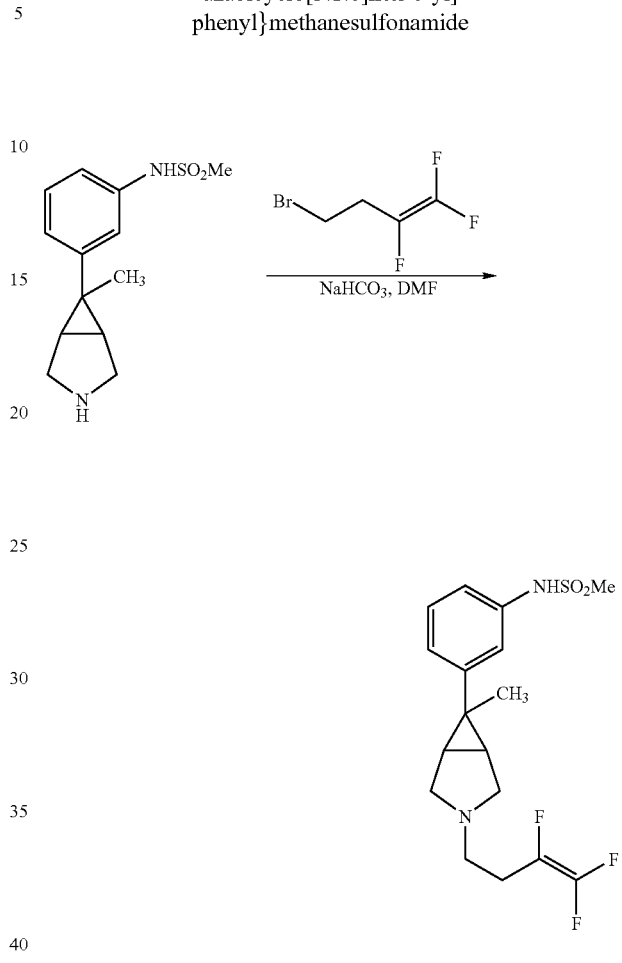

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-[(E)-3-bromo-1-propenyl]cyclohexane (Preparation 88, 42 mg, 0.20 mmol). The reaction mixture was heated for 15 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (30 mg, 43%).

NMR ($CDCl_3$, selected data for the free base): 1.0–1.35 (m, 6H), 1.5 (s, 3H), 1.6–1.75 (m, 4H), 1.8 (m, 2H), 1.95 (m, 1H), 2.85–2.95 (m, 4H), 3.0 (s, 3H), 3.1 (m, 2H), 5.4–5.6 (m, 2H), 7.0–7.15 (m, 3H), 7.15 (dd, 1H).

MS (ES): M/Z ($MH^+$) 389.1; $C_{22}H_{32}N_2O_2S+H$ requires 389.2.

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 4-bromo-1,1,2-trifluorobut-1-ene (39 mg, 0.20 mmol). The reaction mixture was heated for 30 h at 50° C., then further 4-bromo-1,1,2-trifluorobut-1-ene (19 mg, 0.10 mmol) was added and the reaction mixture was heated for a further 13 h. After the reaction had cooled to room temperature, diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (18 mg, 27%).

NMR ($CDCl_3$, selected data for the free base): 1.5 (s, 3H), 1.75 (m, 2H), 2.45 (m, 2H), 2.7 (m, 2H), 2.85 (m, 2H), 3.0 (s, 3H), 3.1 (m, 2H), 6.7 (br, 1H), 7.05–7.15 (m, 3H), 7.25 (t, 1H).

MS (ES): M/Z ($MH^+$) 375.0; $C_{17}H_{21}F_3N_2O_2S+H$ requires 375.1.

EXAMPLE 71

N-{3-[6-Methyl-3-(3-phenyl-2-propynyl)-3-azabicyclo[3.1.0]hex-6-yl]phenyl}methanesulfonamide

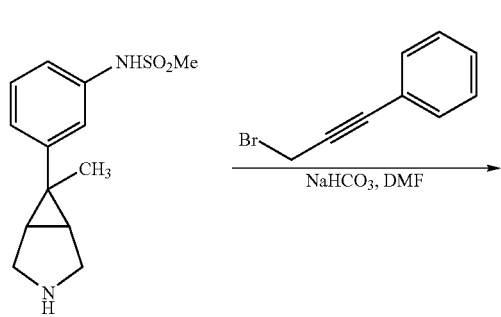

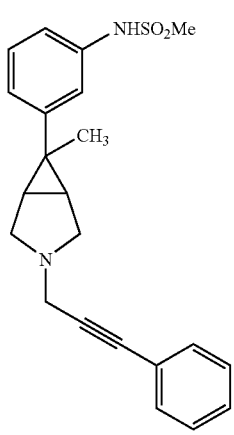

To a solution of the hydrochloride salt of N-[3-(6-methyl-3-azabicyclo[3.1.0]hex-6-yl)phenyl]methanesulfonamide (Preparation 53, 57 mg, 0.18 mmol) in N,N-dimethylformamide (2 ml) was added sodium hydrogen carbonate (63 mg, 0.75 mmol) and 1-(3-bromo-1-propynyl)benzene (P. Place, C. Vernière and J. Goré, Tetrahedron, 1981, 37, 1359) (40 mg, 0.20 mmol). The reaction mixture was heated for 15 h at 50° C., and then cooled to room temperature. Diethyl ether (5 ml) was added followed by water (7 ml), the organic extracts were separated and the aqueous layer was washed further with diethyl ether (2×5 ml). The combined organic extracts were dried ($Na_2SO_4$) and concentrated in vacuo. The residues were purified by flash chromatography on an SPE cartridge containing silica gel (5 g) eluting with dichloromethane:ethanol:0.880 ammonia (200:8:1) to give the product as an oil (27 mg, 39%).

NMR (CDCl$_3$, selected data for the free base): 1.55 (s, 3H), 1.8 (m, 2H), 3.0 (s, 3H), 3.1 (m, 2H), 3.2 (m, 2H), 3.65 (s, 2H), 7.0–7.15 (m, 3H), 7.2–7.35 (m, 4H), 7.4–7.45 (m, 2H).

MS (ES): M/Z (MH$^+$) 381.0; $C_{22}H_{24}N_2O_2S$+H requires 381.2.

EXAMPLE 72

2-[3-(3-Hexyl-6-methyl-3-azabicyclo[3.1.0]hex-6-yl)phenyl]-1H-benzimidazole

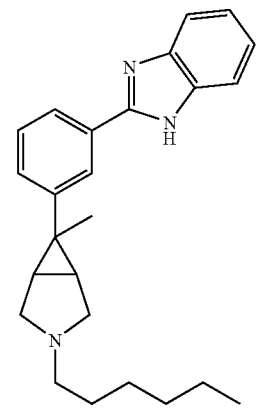

To 6-[3-(1H-benzimidazol-2-yl)phenyl]-3-hexyl-6-methyl-3-azabicyclo[3.1.0]hexan-2-one (Preparation 81, 61 mg, 1.58 mmol) in tetrahydrofuran (4 ml) stirred under nitrogen was added lithium aluminium hydride (1M in tetrahydrofuran, 0.4 ml, 0.39 mmol) dropwise over several minutes. The reaction mixture was stirred at room temperature for 16 h, further lithium aluminium hydride (1M in tetrahydrofuran, 0.4 ml, 0.39 mmol) was added and the reaction mixture was heated under reflux for 1 h and then cooled to room temperature. The reaction mixture was quenched with aqueous sodium hydroxide solution (2M, 1.0 ml) and excess solid sodium hydrogen carbonate was added followed by ethyl acetate (15 ml). The reaction mixture was stirred rapidly for 30 min, filtered through Celite® and after washing with ethyl acetate (15 ml) the combined organic solution was concentrated in vacuo. The crude residue was purified by chromatography on silica gel eluting with ethyl acetate and then ethyl acetate: methanol:0.880 ammonia (90:10:1) to give the product as a white solid (31 mg, 53%).

NMR (CDCl$_3$, selected data for the free base): 0.85 (m, 3H), 1.2–1.4 (m, 6H), 1.4–1.5 (m, 5H), 1.6 (m, 2H), 2.4 (m, 2H), 2.75 (m, 2H), 2.85 (m, 2H), 7.2–7.3 (m, 3H), 7.35 (m, 1H), 7.5 (m, 1H), 7.75–7.9 (m, 2H), 8.0 (s, 1H).

MS (TSP): M/Z (MH$^+$) 374.1; $C_{25}H_{31}N_3$+H requires 374.3.

EXAMPLE 73

2-(1,3-Dioxo-1,3-2H-isoindol-2-yl-N-[3-(3-hexyl-6-methyl-3-azabicyclo[3.1.0]hex-6-yl)phenyl]-1-ethanesulfonamide

EXAMPLE 74

2-Amino-N-[3-(3-hexyl-6-methyl-3-azabicyclo[3.1.0]hex-6-yl)phenyl]-1-ethanesulfonamide

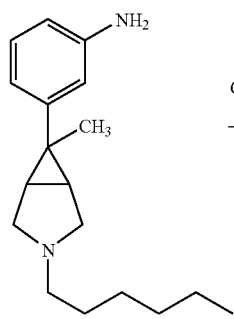 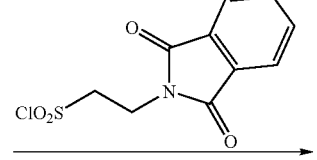 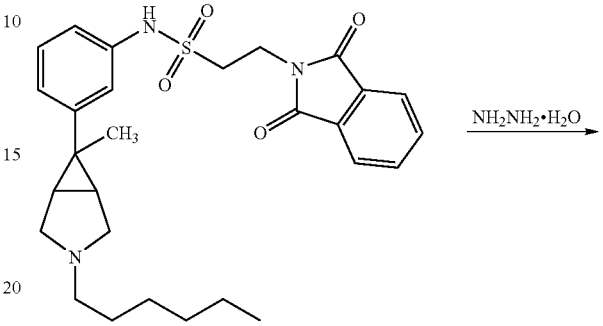

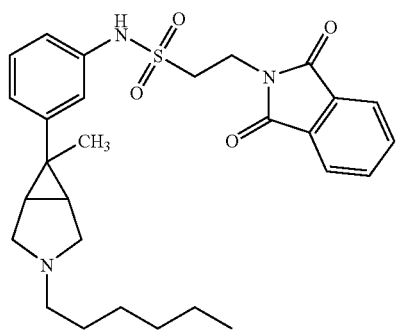 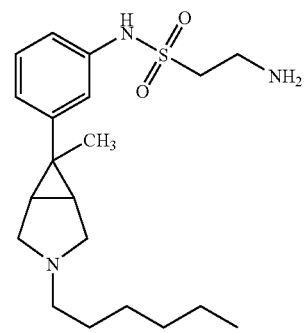

A solution of 3-(3-hexyl-6-methyl-3-azabicyclo[3.1.0]hex-6-yl)phenylamine (Preparation 12, 0.10 g, 0.37 mmol) in pyridine (8 ml) stirred under nitrogen was treated with 2-(1,3-dioxo-1,3-dihydro-2H-isoindol-2-yl)-1-ethanesulfonyl chloride (0.50 g, 1.84 mmol). The reaction mixture was stirred at room temperature for 16 h and then concentrated in vacuo. The crude residue was dissolved in dichloromethane (30 ml) and washed with saturated aqueous sodium hydrogen carbonate solution (100 ml), the aqueous phase was extracted with dichloromethane (2×30 ml). The combined organic extracts were dried ($Na_2SO_4$), filtered and concentrated in vacuo. The crude dark red gum was triturated with diethyl ether to give the product as a brown powder (80 mg, 42%).

NMR ($CDCl_3$, selected data for the free base): 0.8 (t, 3H), 1.2–1.4 (m, 6H), 1.45 (m, 2H), 1.5 (s, 3H), 1.75 (m, 2H), 2.45 (m, 2H), 2.8 (m, 2H), 2.95 (m, 2H), 3.5 (m, 2H), 4.05 (m, 2H), 7.0 (d, 1H), 7.1 (d, 1H), 7.15–7.25 (m, 2H), 7.75 (m, 2H), 7.85 (m, 2H).

MS (ES): M/Z (MH$^+$) 510.1; $C_{28}H_{35}N_3O_4S$+H requires 510.2.

A solution of 2-(1,3-dioxo-1,3-2H-isoindol-2-yl-N-[3-(3-hexyl-6-methyl-3-azabicyclo[3.1.0]hex-6-yl)phenyl]-1-ethanesulfonamide (Example 73, 0.70 mg, 0.14 mmol) in ethanol (3 ml) was treated with hydrazine monohydrate (6.7 µl, 0.4 mmol). The reaction mixture was heated under reflux for 3 h, the reaction mixture was cooled and filtered, the white precipitate was washed with ethanol and the filtrate was concentrated in vacuo. The residue was purified by chromatography on silica gel (5 g) eluting the product with a gradient of methanol:ethyl acetate:0.88 ammonia solution (10:90:1 and then 20:80:1) to give the product as a yellowish gum (50 mg, 94%).

NMR ($CDCl_3$, selected data for the free base): 0.9 (m, 3H), 1.2–1.4 (m, 6H), 1.45 (m, 2H), 1.35 (s, 3H), 1.8 (m, 2H), 2.45 (m, 2H), 2.8 (m, 2H), 3.0 (m, 2H), 3.2 (m, 2H), 3.3 (m, 2H), 7.0–7.15 (m, 3H), 7.2 (m, 1H).

MS (TSP): M/Z (MH$^+$) 380.1; $C_{20}H_{33}N_3O_2S$+H requires 380.2.

EXAMPLE 75

N-[3-(3-Hexyl-6-methyl-3-azabicyclo[3.1.0]hex-6-yl)phenyl]sulfamide

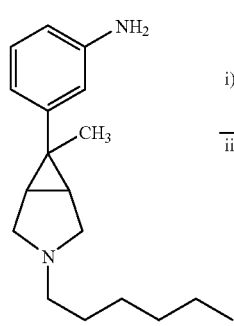
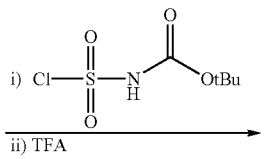

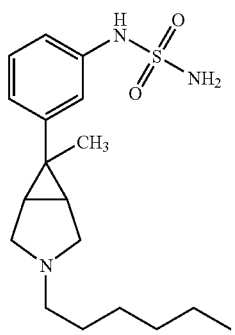

A solution of 3-(3-hexyl-6-methyl-3-azabicyclo[3.1.0]hex-6-yl)phenylamine (Preparation 12, 0.25 g, 0.93 mmol) in pyridine (10 ml) stirred under nitrogen was treated at 0° C. with [(tert-butoxycarbonyl)amino](chloro)dioxo-$\lambda^6$-sulfane (Preparation 83, 0.24 g, 1.12 mmol). The reaction mixture was allowed to warm to room temperature and was stirred overnight before concentrating in vacuo. The crude gum was treated with saturated sodium hydrogen carbonate solution (100 ml) and the product was extracted with dichloromethane (3×30 ml). The combined organic solution was dried (Na$_2$SO$_4$) and concentrated in vacuo to give an insoluble off white solid (0.28 g, 0.62 mmol). The white solid was suspended in dichloromethane (5 ml) cooled to 0° C. and treated dropwise with trifluoroacetic acid (1.5 ml). The reaction mixture was allowed to warm to room temperature and then stirred for 2 h. The reaction mixture was poured onto 0.1M aqueous sodium carbonate solution (50 ml) and ice (~50 g). The mixture was stirred for 10 min and then extracted with dichloromethane (3×20 ml). The combined organics were dried (Na$_2$SO$_4$) and concentrated in vacuo to give a yellow solid, (130 mg, 60%).

NMR (CDCl$_3$, selected data for the free base): 0.9 (m, 3H), 1.25–1.4 (m, 6H), 1.4–1.5 (m, 2H), 1.5 (s, 3H), 1.75 (m, 2H), 2.45 (m, 2H), 2.8 (m, 2H), 2.95 (m, 2H), 7.0–7.1 (m, 3H), 7.25 (m, 1H).

MS (ES): M/Z (MH$^+$) 352.1; C$_{18}$H$_{29}$N$_3$O$_2$S+H requires 352.2.

EXAMPLE 76

3-(3-Hexyl-6-methyl-3-azabicyclo[3.1.0]hex-6-yl)phenol

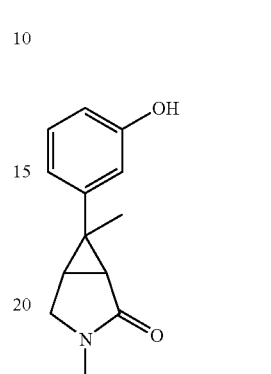

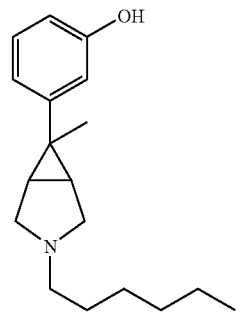

3-Hexyl-6-(3-hydroxyphenyl)-6-methyl-3-azabicyclo[3.1.0]hexan-2-one (Preparation 84, 0.34 g, 1.2 mmol) was dissolved in tetrahydrofuran (10 ml). Lithium aluminium hydride (1M in diethyl ether, 1.5 ml, 1.5 mmol) was added under nitrogen and the reaction mixture was stirred for 1 h, before adding more lithium aluminium hydride (1M in diethyl ether, 3.0 ml, 3.0 mmol) and stirring the reaction mixture for 16 h. The reaction mixture was quenched by the addition of aqueous sodium hydroxide solution (1M, 50 ml) and the product was extracted with dichloromethane (150 ml). The organic extracts were dried (Na$_2$SO$_4$) and concentrated in vacuo to give a brown waxy solid. The product was purified by chromatography on silica gel, (20 g) eluting with ethyl acetate to give the pure product as a yellow solid (0.17 g, 51%).

NMR (CDCl$_3$, selected data for the free base): 0.85 (m, 3H), 1.2–1.4 (m, 6H), 1.4 (s, 3H), 1.5 (m, 2H), 1.9 (m, 2H), 2.5 (m, 2H), 2.8 (m, 2H), 3.2 (m, 2H), 6.6–6.7 (m, 2H), 6.8 (d, 1H), 7.1 (dd, 1H).

MS (ES): M/Z (MH$^+$) 274.1; C$_{18}$H$_{27}$NO+H requires 274.2.

EXAMPLE 77

Trifluoro-N-[3-(3-hexyl-6-methyl-3-azabicyclo[3.1.0]hex-6-yl)phenyl]-methanesulfonamide

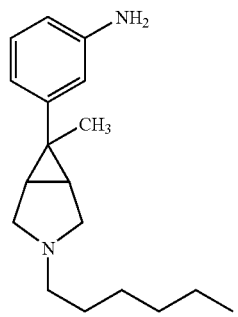

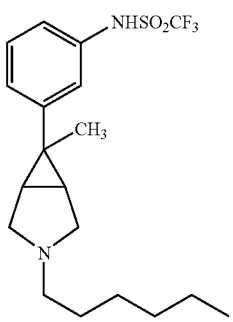

A solution of 3-(3-hexyl-6-methyl-3-azabicyclo[3.1.0]hex-6-yl)phenylamine (Preparation 12, 0.10 g, 0.37 mmol) in pyridine (10 ml) cooled at 0° C. was treated with trifluoromethanesulphonyl chloride (0.14 g, 0.88 mmol) and 4-dimethylaminopyridine (5 mg). The reaction mixture was stirred at room temperature for 3 h. The reaction mixture was concentrated in vacuo and the residue was poured into saturated aqueous sodium hydrogen carbonate solution (100 ml) and extracted with dichloromethane (3×50 ml). The combined organics were dried ($Na_2SO_4$) and then concentrated in vacuo. The crude residue was purified by preparative HPLC (condition 7) to give a brown solid, (17 mg, 12%).

NMR ($CD_3OD$, selected data for the free base): 0.9 (m, 3H), 1.3–1.5 (m, 6H), 1.65 (m, 2H), 1.95 (s, 3H), 2.2 (m, 2H), 3.3–3.15 (m, 4H), 3.8 (m, 2H), 6.85 (d, 1H), 6.95 (d, 1H), 7.0 (s, 1H), 7.05 (t, 1H).

MS (ES): M/Z (MH$^+$) 405.0; $C_{19}H_{27}F_3N_2O_2S$+H requires 405.2.

EXAMPLE 78

2,2,2-Trifluoro-N-[3-(3-hexyl-6-methyl-3-azabicyclo[3.1.0]hex-6-yl)phenyl]-1-ethanesulfonamide

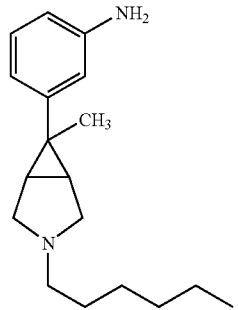

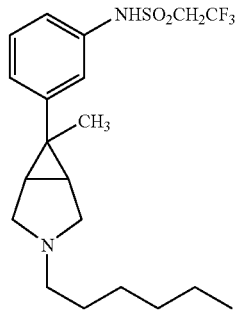

A solution of 3-(3-hexyl-6-methyl-3-azabicyclo[3.1.0]hex-6-yl)phenylamine (Preparation 12, 0.10 g, 0.37 mmol) in pyridine (8 ml) cooled at 0° C. was treated with 2,2,2-trifluoroethanesulphonyl chloride (0.08 g, 0.44 mmol). The reaction mixture was allowed to warm to room temperature and then stirred for 16 h. The reaction mixture was concentrated in vacuo and the residue was poured into saturated aqueous sodium hydrogen carbonate solution (100 ml) and extracted with dichloromethane (3×50 ml). The combined organics were dried ($Na_2SO_4$) and then concentrated in vacuo. The crude residue was purified by preparative HPLC (condition 7) to give a yellow solid, (15 mg, 10%).

NMR ($CD_3OD$, selected data for the free base): 0.9 (m, 3H), 1.2–1.4 (m, 6H), 1.45 (s, 3H), 1.5–1.6 (m, 2H), 2.0 (m, 2H), 2.65 (m, 2H), 2.9 (m, 2H), 3.2 (m, 2H), 4.05 (m, 2H), 7.05–7.10 (m, 2H), 7.15 (s, 1H), 7.2–7.3 (t, 1H).

MS (ES): M/Z (MH$^+$) 419.0; $C_{20}H_{29}F_3N_2O_2S$+H requires 419.2.

EXAMPLE 79

3-[6-Methyl-3-(3-phenylpropyl)-3-azabicyclo[3.1.0]hex-6-yl]phenol

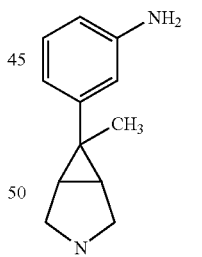

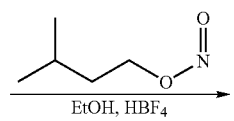

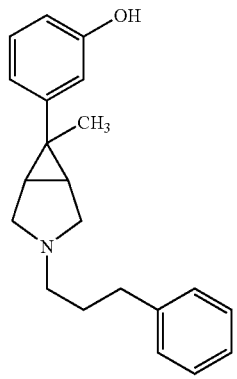

To a stirred solution of 3-[6-methyl-3-(3-phenylpropyl)-3-azabicyclo[3.1.0]hex-6-yl]phenylamine (Preparation 8, 100 mg, 0.33 mmol) in absolute ethanol (0.5 ml) at 0° C., was added fluoroboric acid (50% in water, 0.082 ml, 0.66 mmol). The reaction mixture was cooled to −5° C. and isoamyl nitrite (0.2 ml, 1.5 mmol) was added over 10 minutes. After stirring the reaction mixture for 30 minutes at −5° C., a red gum had formed. The supernatant solution was removed and concentrated sulphuric acid (1.5 ml) in water (4.5 ml) was added. The reaction mixture was stirred at 50° C. for 30 minutes and then at room temperature for 12 h before diluting with water (50 ml) and washing with dichloromethane (25 ml×3). The aqueous layer was basified to pH 10 with 0.880 ammonia solution and extracted with dichloromethane (3×25 ml). The latter organic extracts were dried (Na$_2$SO$_4$) and concentrated in vacuo to give a yellow oil. This crude residue was purified by chromatography on Florisil™ (5 g) eluting with dichloromethane:methanol:0.880 ammonia (98:1.5:0.5) to give a yellow oil (20 mg, 20% yield).

NMR (CDCl$_3$, selected data for the free base) 1.45 (s, 3H), 1.75–1.85 (m, 4H), 2.50 (m, 2H), 2.65 (m, 2H), 2.85 (m, 2H), 3.10 (m, 2H), 6.6–6.7 (m, 2H), 6.80 (d, 1H), 7.10–7.25 (m, 6H).

MS (APCI): M/Z (MH$^+$) 307.9, C$_{21}$H$_{25}$NO+H requires 308.2

EXAMPLE 80

N-(3-{6-methyl-3-[3-(3-methylphenyl)propyl]-3-azabicyclo[3.1.0]hex-6-yl}phenylmethanesulfonamide

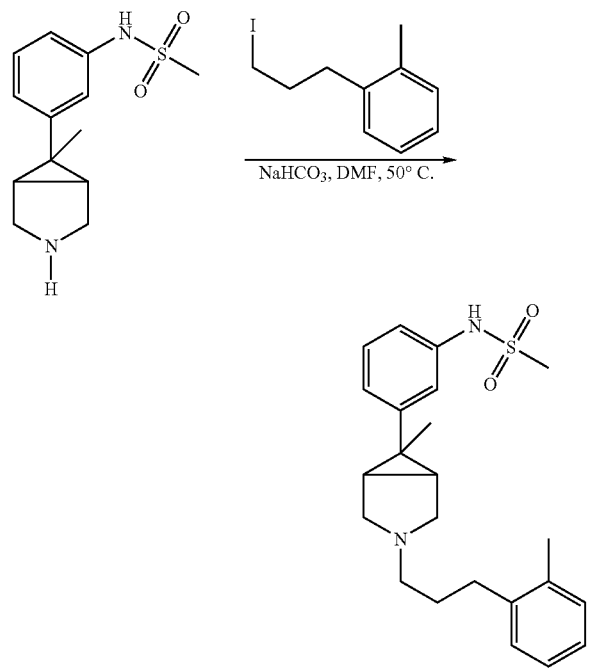

To a solution of the hydrochloride salt of N-[3-(6-methyl-3-azabicyclo[3.1.0]hex-6-yl)phenyl]methanesulfonamide (Preparation 53, 57 mg, 0.19 mmol) in N,N-dimethylformamide (2 ml) was added sodium hydrogen carbonate (630 mg, 7.52 mmol) and 1-(3-iodopropyl)-2-methylbenzene (EP279681 A2, 41 mg, 0.16 mmol) and the reaction mixture was heated at 50° C. for 20 h. After cooling, diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g) eluting with dichloromethane:ethanol:0.88 ammonia solution (200:8:1) to afford the title compound as an oil (23 mg, 30%).

NMR (CDCl$_3$, selected data for the free base): 1.6 (s, 3H), 1.8 (m, 2H), 2.3 (s, 3H), 2.5 (m, 2H), 2.6 (m, 2H), 2.8 (m, 2H), 3.0 (s, 3H), 3.1 (m, 2H), 7.0–7.2 (m, 6H), 7.2–7.3 (m, 2H).

MS (thermospray): M/Z (MH$^+$) 399.1; C$_{23}$H$_{30}$N$_2$O$_2$S+H requires 399.2.

EXAMPLE 81

N-{3-[3-(4-ethylbenzyl)-6-methyl-3-azabicyclo[3.1.0]hex-6-yl]phenyl}methanesulfonamide

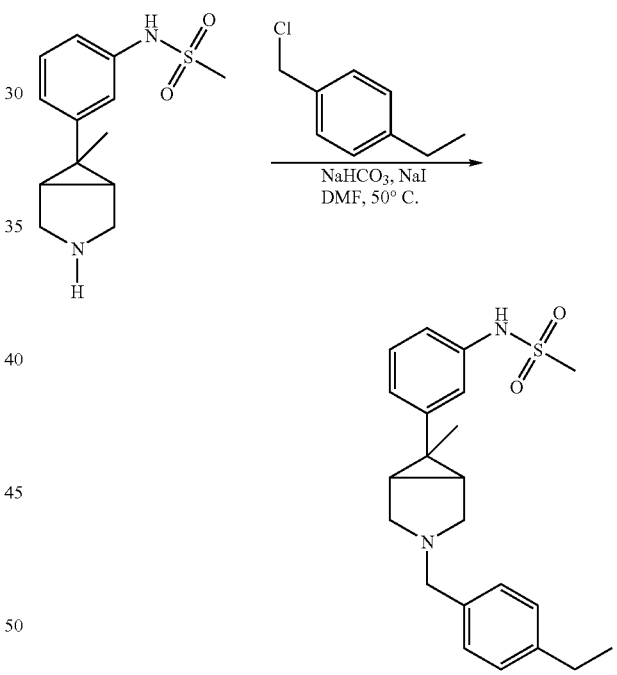

To a solution of the hydrochloride salt of N-[3-(6-methyl-3-azabicyclo[3.1.0]hex-6-yl)phenyl]methanesulfonamide (Preparation 53, 57 mg, 0.19 mmol) in N,N-dimethylformamide (2 ml) was added sodium hydrogen carbonate (630 mg, 7.52 mmol), 1-(chloromethyl)-4-ethylbenzene (32 mg, 0.20 mmol) and sodium iodide (catalytic) and the reaction mixture was heated at 50° C. for 20 h. After cooling, diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g)

eluting with dichloromethane:ethanol:0.88 ammonia solution (200:8:1) to afford the title compound as an oil (30 mg, 41%).

NMR (CDCl$_3$, selected data for the free base): 1.2 (t, 3H), 1.6 (s, 3H), 2.6 (q, 2H), 3.0 (s, 3H), 3.1 (m, 2H), 3.6 (m, 2H), 7.0–7.3 (m, 8H).

MS (thermospray): M/Z (MH$^+$) 384.8; C$_{22}$H$_{28}$N$_2$O$_2$S+H requires 385.2.

EXAMPLE 82

N-(3-{3-[(E)-2-hexenyl]-6-methyl-3-azabicyclo[3.1.0]hex-6-yl}phenyl)methanesulfonamide

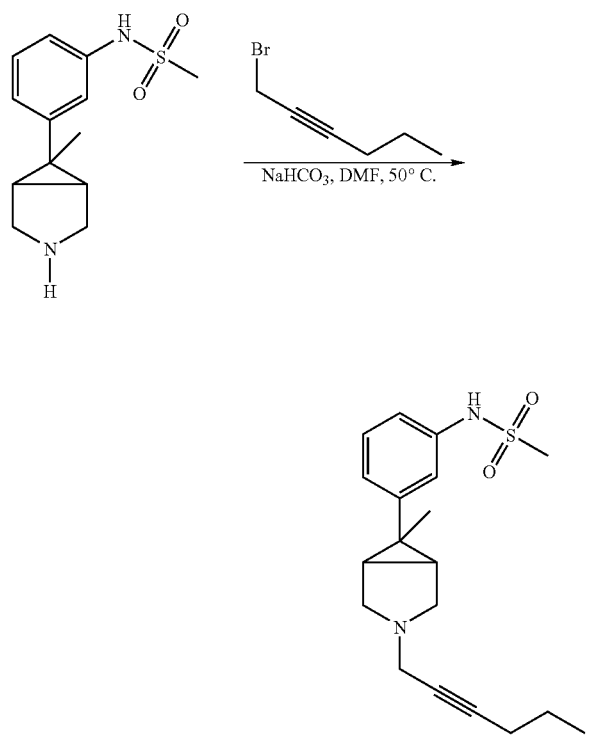

To a solution of the hydrochloride salt of N-[3-(6-methyl-3-azabicyclo[3.1.0]hex-6-yl)phenyl]methanesulfonamide (Preparation 53, 57 mg, 0.19 mmol) dissolved in N,N-dimethylformnamide (2 ml) was added sodium hydrogen carbonate (630 mg, 7.52 mmol) and 1-bromo-2-hexyne (H. A. J. Charles, and R. J. Batten, J. Chem. Soc., Perkin Trans 1, 1987, 1999, 33 mg, 0.2 mmol) and the reaction mixture was heated at 50° C. for 20 h. After cooling diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g) eluting with dichloromethane:ethanol:0.88 ammonia solution (200:8:1) to afford the title compound as an oil (33 mg, 50%).

NMR (CDCl$_3$, selected data for the free base): 1.0 (t, 3H), 1.45–1.6 (m, 5H), 1.8 (m, 2H), 2.2 (t, 2H), 2.95–3.1 (m, 7H), 3.4 (m, 2H), 7.0–7.1 (m, 3H), 7.25 (m, 1H).

MS (thermospray): M/Z (MH$^+$) 347.0; C$_{19}$H$_{26}$N$_2$O$_2$S+H requires 347.2.

EXAMPLE 83

N-cyclohexyl-2-(6-methyl-6-{3-[(methylsufonyl)amino]phenyl}-3-azabicyclo[3.1.0]hex-3-yl)acetamide

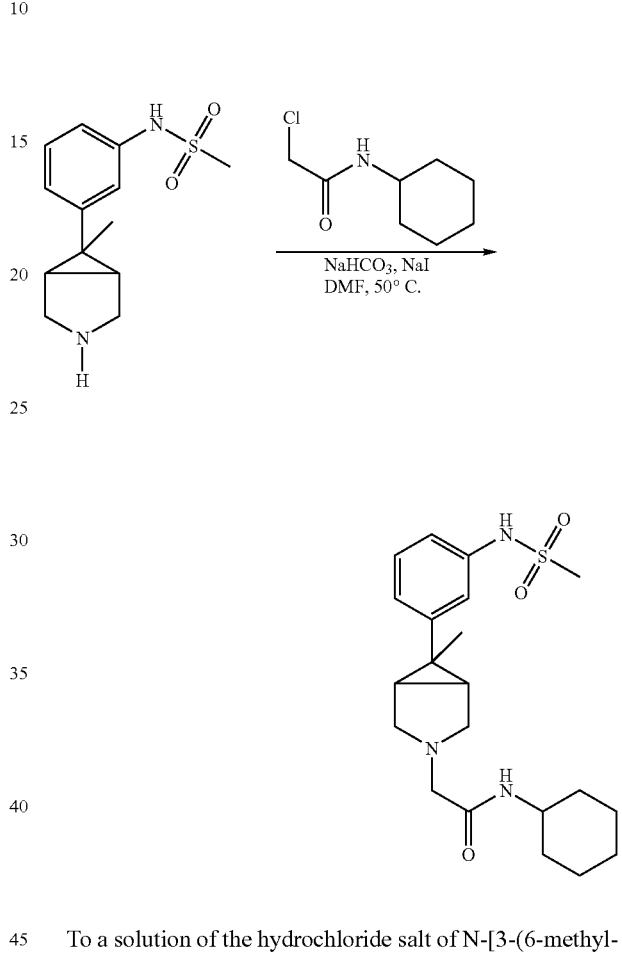

To a solution of the hydrochloride salt of N-[3-(6-methyl-3-azabicyclo[3.1.0]hex-6-yl)phenyl]methanesulfonamide (Preparation 53, 57 mg, 0.19 mmol) in N,N-dimethylformamide (2 ml) was added sodium hydrogen carbonate (630 mg, 7.52 mmol), 2-chloro-N-cyclohexylacetamide (36 mg, 0.2 mmol) and sodium iodide (catalytic) and the reaction was heated at 50° C. for 20 h. After cooling diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g) eluting with dichloromethane:ethanol:0.88 ammonia solution (200:8:1) to afford the title compound as an oil (22 mg, 28%).

NMR (CDCl$_3$, selected data for the free base): 1.1–1.3 (m, 3H), 1.3–2.0 (m, 12H), 2.9–3.2 (m, 10H), 3.8 (m, 2H), 6.6 (br, 1H), 6.8 (m, 1H), 7.0–7.3 (m, 4H).

MS (electrospray): M/Z (MH$^+$) 406.1; C$_{21}$H$_{31}$N$_3$O$_3$S+H requires 406.2.

EXAMPLE 84

N-{3-[3-(3-cyclohexyl-3-oxopropyl)-6-methyl-3-azabicyclo[3.1.0]hex-6-yl]phenyl}methanesulfonamide

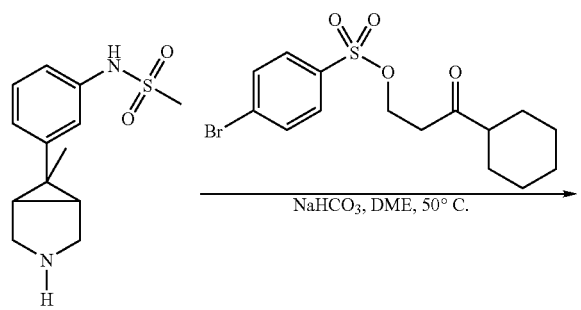

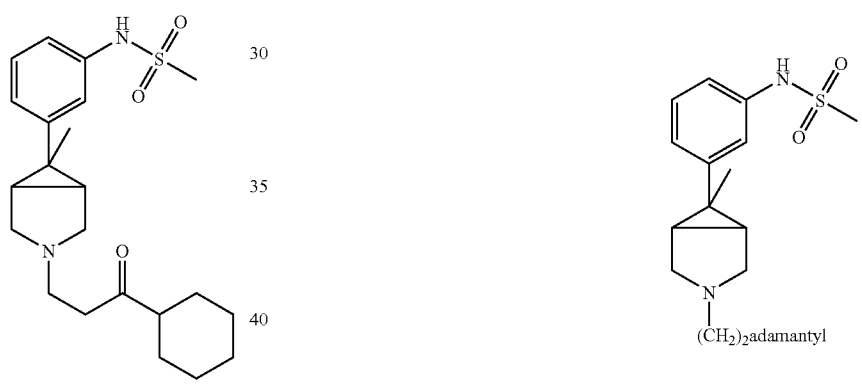

To a solution of the hydrochloride salt of N-[3-(6-methyl-3-azabicyclo[3.1.0]hex-6-yl)phenyl]methanesulfonamide (Preparation 53, 57 mg, 0.19 mmol) in dimethoxyethyl ether (2 ml) was added sodium hydrogen carbonate (630 mg, 7.52 mmol), and 3-cyclohexyl-3-oxopropyl-4-bromobenzenesulfonate (Preparation 91, 75 mg, 0.2 mmol) and the reaction mixture was heated at 50° C. for 20 h. After cooling, diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g) eluting with dichloromethane:ethanol:0.88 ammonia solution (200:8:1) to afford the title compound as an oil (42 mg, 52%).

NMR (CDCl$_3$, selected data for the free base): 1.1–1.3 (m, 6H), 1.6–1.9 (m, 10H), 2.3 (m, 1H), 2.6 (t, 2H), 2.7–2.85 (m, 4H), 3.0–3.1 (m, 5H), 7.0–7.15 (m, 3H), 7.2 (m, 1H).

MS (electrospray): M/Z (MH$^+$) 405.1; C$_{22}$H$_{32}$N$_2$O$_3$S+H requires 405.2.

EXAMPLE 85

N-(3-{3-[2-(1-Adamantyl)ethyl]-6-methyl-3-azabicyclo[3.1.0]hex-6-yl}phenyl)methanesulfonamide

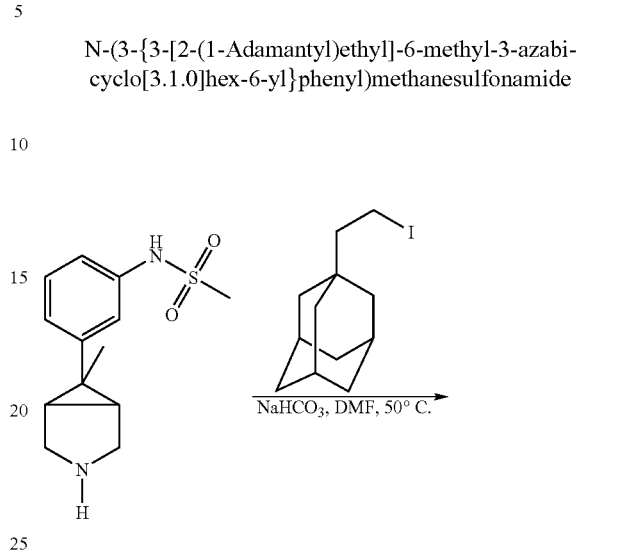

To a solution of the hydrochloride salt of N-[3-(6-methyl-3-azabicyclo[3.1.0]hex-6-yl)phenyl]methanesulfonamide (Preparation 53, 57 mg, 0.19 mmol) in N,N-dimethylformamide (2 ml) was added sodium hydrogen carbonate (630 mg, 7.52 mmol) and 1-adamantyl-2-iodoethane (Preparation 93, 58 mg, 0.2 mmol) and the reaction was heated at 50° C. for 20 h. After cooling diethyl ether (5 ml) and water (7 ml) were added and the reaction mixture was stirred vigorously for 5 min. The phases were separated and the aqueous layer was further extracted with diethyl ether (2×5 ml). The combined organic extracts were dried (Na$_2$SO$_4$), filtered and concentrated in vacuo. The residual oil was purified by flash column chromatography using a Sep-Pak™ cartridge packed with silica gel (5 g) eluting with dichloromethane:ethanol:0.88 ammonia solution (200:8:1) to afford the title compound as an oil (32 mg, 39%).

NMR (CDCl$_3$, selected data for the free base): 1.2 (m, 3H), 1.5–1.8 (m, 13H), 1.9 (m, 2H), 2.8–2.9 (m, 2H), 3.0 (s, 3H), 7.0–7.3 (m, 4H).

MS (electrospray): M/Z (MH$^+$) 429.2; C$_{25}$H$_{36}$N$_2$O$_2$S+H requires 429.3.

EXAMPLE 86

6-(3-Iodophenyl)-6-methyl-3-(3-phenylpropyl)-3-azabicyclo[3.1.0]hexane

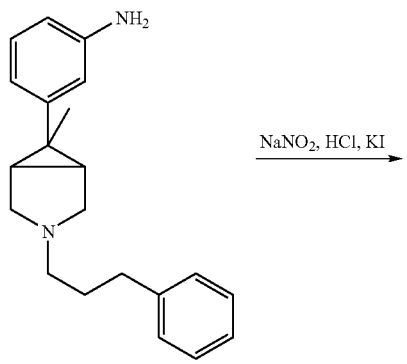

NaNO₂, HCl, KI →

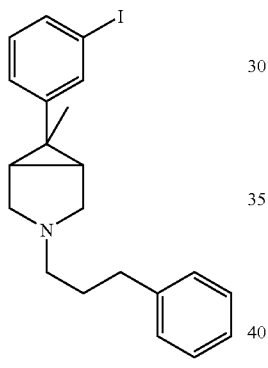

A solution of 3-(3-hexyl-6-methyl-3-azabicyclo[3.1.0]hex-6-yl)phenylamine (Preparation 12, 2.7 g, 8.8 mmol) in hydrochloric acid (2 M, 20 ml) was cooled in an ice bath and treated dropwise with a solution of sodium nitrite (1.3 g, 19 mmol) in water (20 ml). The reaction mixture was stirred for 30 minutes and then a solution of potassium iodide (3.1 g, 19 mmol) in water (20 ml) was added slowly. The reaction mixture was allowed to warm to room temperature over 3 h and then heated at 90° C. for 5 minutes, before cooling and slowly pouring onto aqueous saturated sodium hydrogen carbonate (100 ml). The reaction mixture was then extracted with ethyl acetate (4×75 ml) and the dark organic extracts were washed with aqueous sodium thiosulphate (10% w/w, 100 ml). The combined organic extracts were dried (MgSO₄) and then concentrated in vacuo to give a black oil (1.2 g). The crude residue was purified by chromatography on silica gel (100 g) eluting with hexane:ethyl acetate (70:30 and then 30:70) to give a black oil (160 mg, 12%).

NMR (CDCl₃, selected data for the free base): 1.55 (s, 3H), 1.70–1.85 (m, 4H), 2.50 (t, 2H), 2.65 (t, 2H), 2.80 (m, 2H), 3.05 (m, 2H), 7.00 (m, 1H), 7.05–7.20 (m, 6H), 7.50 (d, 1H), 7.65 (s, 1H).

MS (APCI): M/Z (MH⁺) 418.0: $C_{21}H_{24}{}^{129}IN+H$ requires 418.1.

EXAMPLE 87

3-[6-methyl-3-(3-phenylpropyl)-3-azabicyclo[3.1.0]hex-6-yl]benzonitrile

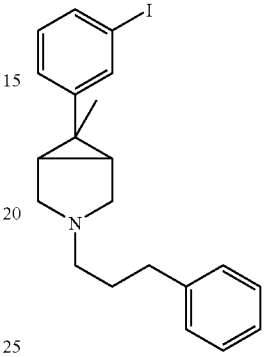

Pd(PPh₃)₄, KCN →

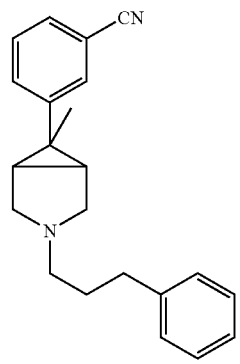

To a degassed solution of 6-(3-iodophenyl)-6-methyl-3-(3-phenylpropyl)-3-azabicyclo[3.1.0]hexane (Example 86, 490 mg, 1.18 mmol) in toluene (20 ml) was added tetrakistriphenylphosphine palladium (0) (0.68 g, 0.60 mmol) and a finely crushed mixture of potassium cyanide (320 mg, 5.0 mmol) and neutral activated alumina (640 mg) under nitrogen. The reaction mixture was heated to 80° C. for 3 h, and then at reflux for 30 minutes before cooling to room temperature and concentrating in vacuo. The mixture was absorbed onto silica gel (7 g) and then purified by chromatography on silica gel (100 g) eluting with hexane: ethyl acetate (95:5 and then 50:50) to give a red solid (165 mg, 44%).

NMR (CDCl₃, selected data for the free base): 1.60 (s, 3H), 1.70–1.85 (m, 4H), 2.50 (t, 2H), 2.65 (t, 2H), 2.80 (m, 2H), 3.10 (m, 2H), 7.10–7.60 (m, 9H).

MS (APCI): M/Z (MH⁺) 317.0: $C_{22}H_{24}N_2+H$ requires 317.2

EXAMPLE 88

N-{3-[3-(3-hydroxypropyl)-6-methyl-3-azabicyclo[3.1.0]hex-6-yl]phenyl}methanesulfonamide

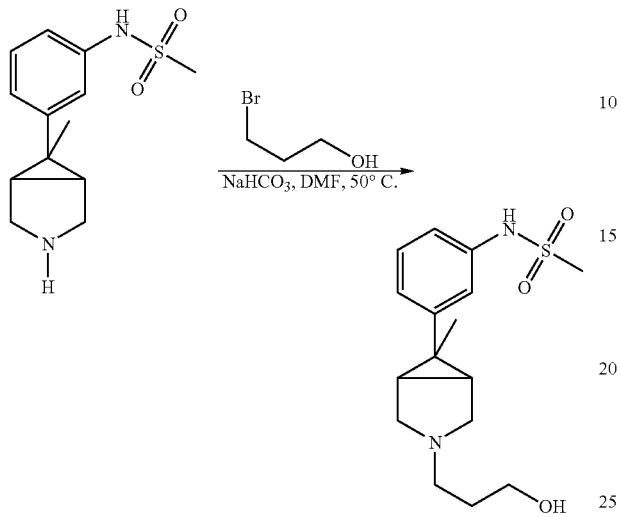

To a solution of the hydrochloride salt of N-[3-(6-methyl-3-azabicyclo[3.1.0]hex-6-yl)phenyl]methanesulfonamide (Preparation 53, 200 mg, 0.89 mmol) in N,N-dimethylformamide (8 ml) was added sodium hydrogen carbonate (3 g, 36 mmol) and 3-bromo-1-propanol (0.08 ml, 0.89 mmol), the reaction mixture was heated at 50° C. for 20 h. After cooling, diethyl ether (15 ml) and water (15 ml) were added and the reaction mixture was stirred vigorously for 5 min. The phases were separated and the aqueous layer was further extracted with diethyl ether (2×15 ml). The combined organic extracts were dried (Na$_2$SO$_4$), filtered and concentrated in vacuo. The residual oil was purified by flash column chromatography using a Sep-Pak™ cartridge packed with silica gel (10 g) eluting with dichloromethane:ethanol:0.88 ammonia solution (200:8:1) to afford the title compound as an oil (42 mg, 15%).

NMR (CDCl$_3$, selected data for the free base): 1.4 (s, 3H), 1.7 (m, 2H), 2.0 (m, 2H), 2.8 (m, 2H), 3.0–3.2 (m, 5H), 3.8 (m, 2H), 7.8–7.1 (m, 3H), 7.3 (m, 1H)

MS (thermospray): M/Z (MH$^+$) 325.1; C$_{16}$H$_{24}$N$_2$O$_3$S+H requires 325.2.

EXAMPLE 89

N-(3-{6-methyl-3-[(E)-3-phenyl-2-propenyl]-3-azabicyclo[3.1.0]hex-6-yl}phenyl)methanesulfonamide

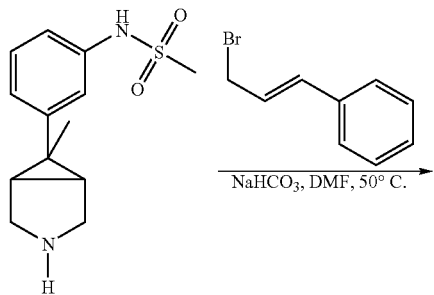

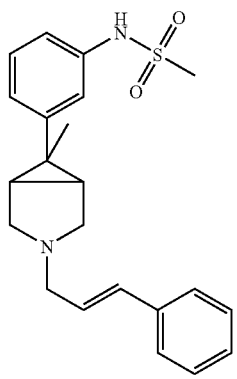

To a solution of the hydrochloride salt of N-[3-(6-methyl-3-azabicyclo[3.1.0]hex-6-yl)phenyl]methanesulfonamide (Preparation 53, 200 mg, 0.89 mmol) in N,N-dimethylformamide (8 ml) was added sodium hydrogen carbonate (3 g, 36 mmol) and 1-[(E)-3-bromo-1-propenyl]benzene (0.13 ml, 0.89 mmol) and the reaction mixture was heated at 50° C. for 20 h. After cooling, diethyl ether (15 ml) and water (15 ml) were added and the reaction mixture was stirred vigorously for 5 min. The phases were separated and the aqueous layer was further extracted with diethyl ether (2×15 ml). The combined organic extracts were dried (Na$_2$SO$_4$), filtered and concentrated in vacuo. The residual oil was purified by flash column chromatography using a Sep-Pak™ cartridge packed with silica gel (10 g) eluting with dichloromethane:ethanol:0.88 ammonia solution (200:8:1) to afford the title compound as an oil (40 mg, 12%).

NMR (CDCl$_3$, selected data for the free base): 1.6 (s, 3H), 1.8 (m, 2H), 2.9–3.1 (m, 9H), 3.3 (m, 2H), 6.25 (m, 1H), 6.5 (d, 1H), 7.0–7.1 (m, 7H)

MS (thermospray): M/Z (MH$^+$) 383.3; C$_{22}$H$_{26}$N$_2$O$_2$S+H requires 383.2.

EXAMPLE 90

N-{3-[3-(3-Cyclohexyl-3-hydroxypropyl)-6-methyl-3-azabicyclo[3.1.0]hex-6-yl]phenyl}methanesulfonamide

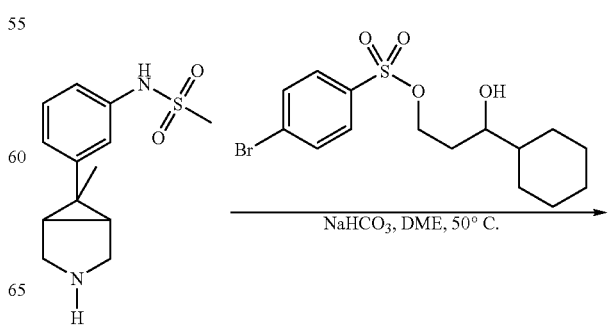

-continued

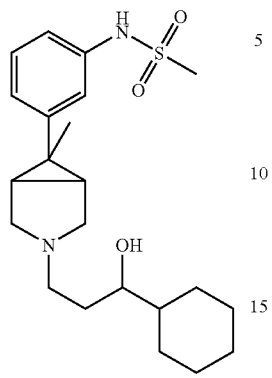

To a solution of the hydrochloride salt of N-[3-(6-methyl-3-azabicyclo[3.1.0]hex-6-yl)phenyl]methanesulfonamide (Preparation 53, 200 mg, 0.66 mmol) in N,N-dimethylformamide (8 ml) was added sodium hydrogen carbonate (3 g, 36 mmol) and (S)-3-cyclohexyl-3-hydroxypropyl 4-bromobenzenesulfonate (J. A. Werner et al, J. Org. Chem., 1996, 61, 587) (0.08 ml, 0.89 mmol) and the reaction mixture was heated at 50° C. for 20 h. After cooling, diethyl ether (15 ml) and water (15 ml) were added and the reaction mixture was stirred vigorously for 5 min. The phases were separated and the aqueous layer was further extracted with diethyl ether (2×15 ml). The combined organic extracts were dried (Na$_2$SO$_4$), filtered and concentrated in vacuo. The residual oil was purified by flash column chromatography using a Sep-Pak™ cartridge packed with silica gel (10 g) eluting with dichloromethane:ethanol:0.88 ammonia solution (200:8:1) to afford the title compound as an oil (90 mg, 25%).

NMR (CDCl$_3$, selected data for the free base): 0.9–1.1 (m, 2H), 1.2–1.4 (m, 6H), 1.5 (m, 2H), 1.6–1.8 (m, 6H), 1.9–2.0 (m, 1H), 2.65–2.95 (m, 4H), 3.0 (s, 2H), 3.0–3.2 (dd, 2H), 3.5 (q, 1H), 3.7 (q, 1H), 7.0 (m, 3H), 7.3 (m, 1H)

MS (thermospray): M/Z (MH$^+$) 407.0 C$_{22}$H$_{34}$N$_2$O$_3$S+H requires 407.2.

EXAMPLE 91

Exo-N-{3-[3-hexyl-6-(hydroxymethyl)-3-azabicyclo[3.1.0]hex-6-yl]phenyl}methanesulfonamide

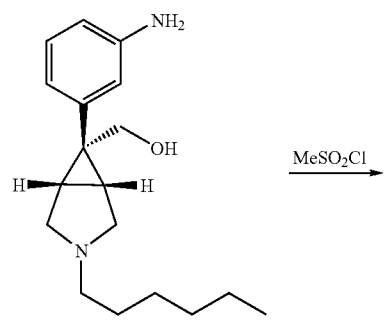

-continued

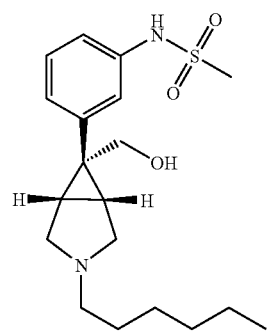

To a solution of [6-(3-aminophenyl)-3-hexyl-3-azabicyclo[3.1.0]hex-6-yl]methanol (Preparation 94, 15 mg, 0.052 mmol) in anhydrous pyridine (0.2 ml) at 0° C. under nitrogen was added methanesulfonyl chloride (4.3 μl, 6.3 mg, 55 μmol) freshly distilled over phosphorous pentoxide. The reaction was stirred for 2 h and gradually allowed to warm to room temperature. The mixture was poured into aqueous sodium hydroxide (1N, 5 ml) and diluted with water (20 ml). The aqueous phase was extracted with ethyl acetate (2×25 ml) and the combined organic layers were washed with brine (25 ml). The combined organic extracts were dried (MgSO$_4$) and then concentrated in vacuo. The crude product was chromatographed on Merck 230–400 mesh silica gel (5 g) eluting with ethyl acetate:2M ammonia in ethanol (98:2) to give the desired compound as a pale yellow oil (5 mg, 26%).

NMR (CDCl$_3$, selected data for the free base): 0.90 (m, 3H), 1.20–1.35 (m, 6H), 1.45 (m, 2H), 1.85 (br s, 2H), 2.50 (t, 2H), 2.65 (br d, 2H), 3.00 (s, 3H), 3.40 (d, 2H), 4.10 (s, 2H), 7.00–7.20 (m, 4H).

MS (Thermospray): M/Z (MH$^+$) 366.9; C$_{19}$H$_{30}$N$_2$O$_3$S+H requires 367.2

EXAMPLE 92

Exo-N-{3-[3-hexyl-6-(methoxymethyl)-3-azabicyclo[3.1.0]hex-6-yl]phenyl}methanesulfonamide

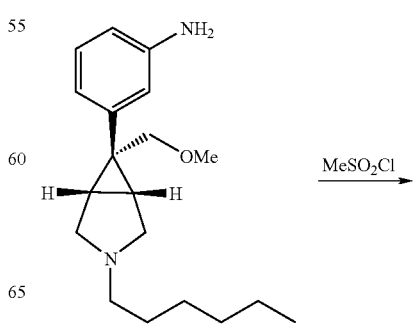

-continued

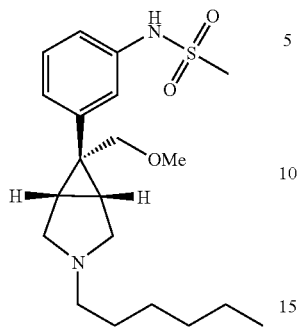

To a solution of 3-[3-hexyl-6-(methoxymethyl)-3-azabicyclo[3.1.0]hex-6-yl]aniline (Preparation 98, 11 mg, 0.036 mmol) in anhydrous pyridine (0.3 ml) at 0° C. under nitrogen was added methanesulfonyl chloride (3.4 µl, 5 mg, 43 µmol) freshly distilled from phosphorous pentoxide. The reaction was stirred for 3 h and quenched by the addition of water (5 ml) and saturated sodium carbonate solution (25 ml). The aqueous layer was extracted with ethyl acetate (2×25 ml) and the organic extracts were washed with brine (25 ml). The organic layers were dried (MgSO$_4$) and then concentrated in vacuo. The crude product was chromatographed on Merck 230–400 mesh silica gel (5 g) eluting with ethyl acetate:2M ammonia in ethanol (99:1) to give the desired product as a pale yellow oil (11 mg, 79%).

NMR (CDCl$_3$, selected data for the free base): 0.90 (m, 3H), 1.15–1.45 (m, 8H), 1.80 (br s, 2H), 2.40 (t, 2H), 2.70 (br d, 2H), 3.00 (s, 3H), 3.20 (d, 2H), 3.30 (s, 3H), 4.10 (s, 2H), 7.00 (d, 1H), 7.10–7.20 (m, 2H), 7.25 (m, 1H).

MS (Thermospray): M/Z (M$^+$) 380.6; C$_{20}$H$_{32}$N$_2$O$_3$S requires 380.6

-continued

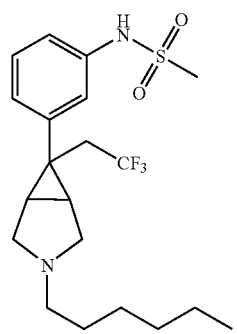

3-[3-Hexyl-6-(2,2,2-trifluoroethyl)-3-azabicyclo[3.1.0]hex-6-yl] aniline (Preparation 101, 143 mg, 0.42 mmol) was dissolved in anhydrous dichloromethane (3 ml) in a dry, nitrogen-flushed flask and cooled to −12° C. in an ice/methanol bath. Pyridine (54 µl, 0.67 mmol) was added dropwise followed by methanesulfonyl chloride (39 µl, 0.50 mmol). The mixture was allowed to slowly warm to room temperature, whereupon its colour changed from yellow to bright amber. After 3 h, the mixture was treated with water (20 ml) and extracted with dichloromethane (3×20 ml). The combined organic extracts were washed with brine (20 ml), dried (MgSO$_4$), filtered and the solvent removed in vacuo. The crude product was purified by chromatography on silica gel (5 g), eluting with hexane:ether (2:1) to give the product as an amber gum (71 mg, 40%).

NMR (CDCl$_3$, selected data for the free base): 0.85–0.95 (m, 3H), 1.20–1.35 (m, 6H), 1.35–1.45 (m, 2H), 1.85 (m, 2H), 2.40 (t, 2H), 2.60 (d, 2H), 2.95 (s, 3H), 3.15 (q, 2H), 2.25 (d, 2H), 7.05, (d, 1H), 7.10 (d, 1H), 7.20 (s, 1H), 7.25 (s, 1H).

MS (Thermospray): (MH$^+$) 419.4, C$_{20}$H$_{29}$F$_3$N$_2$O$_2$S+H requires 419.5.

EXAMPLE 93

N-{3-[3-Hexyl-6-(2,2,2-trifluoroethyl)-3-azabicyclo[3.1.0]hex-6-yl]phenyl}methane sulfonamide

EXAMPLE 94

Exo-N-[3-(6-cyano-3-hexyl-3-azabicyclo[3.1.0]hex-6-yl)phenyl]methanesulfonamide

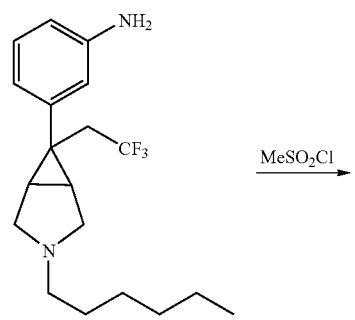 MeSO$_2$Cl →

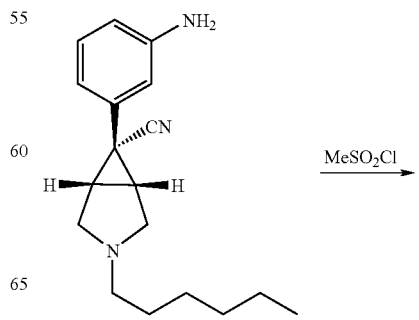 MeSO$_2$Cl →

-continued

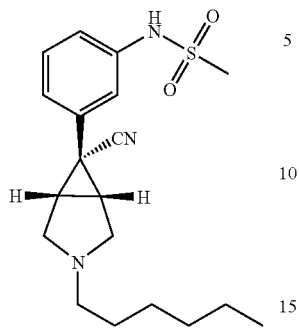

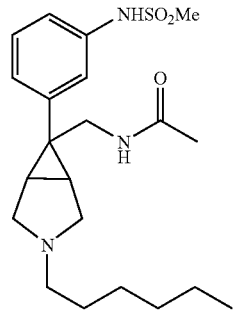

To a solution of 6-(3-aminophenyl)-3-hexyl-3-azabicyclo[3.1.0]hexane-6-carbonitrile (Preparation 105, 1.7 mg, 6.0 μmol) in anhydrous pyridine (0.2 ml) at 0° C. under nitrogen was added methanesulfonyl chloride (0.5 μl, 0.8 mg, 6.6 μmol) which had been freshly distilled over phosphorous pentoxide. The reaction was stirred for 2 h and gradually allowed to warm to room temperature. The mixture was poured into saturated sodium carbonate solution (5 ml) and diluted with water (20 ml). The aqueous phase was extracted with ethyl acetate (2×25 ml) and the organic extracts were washed with brine (25 ml). The combined organic extracts were dried (MgSO$_4$) and then concentrated in vacuo. The crude product was chromatographed on Merck 230–400 mesh silica gel (5 g) eluting with ethyl acetate:hexane:2M ammonia in ethanol (50:49:1) to give the desired compound as a pale yellow oil (2 mg, 92%).

NMR (CDCl$_3$, selected data for the free base): 0.90 (m, 3H), 1.20–1.35 (m, 6H), 1.50 (m, 2H), 2.20 (m, 2H), 2.50 (m, 2H), 2.85 (m, 2H), 3.00 (s, 3H), 3.30 (m, 2H), 7.10–7.30 (m, 4H).

MS (Thermospray): M/Z (MH$^+$) 362.1; C$_{19}$H$_{27}$N$_3$O$_2$S+H requires 362.2

EXAMPLE 95

N-[3-Hexyl-6-{3-[(methylsulphonyl)amino]phenyl}-3-azabicyclo[3.1.0]hex-6-yl)methyl]acetamide A solution of N-{[6-(3-aminophenyl)-3-hexyl-3-azabicyclo[3.1.0]hex-6-yl]methyl}acetamide (Preparation 108, 67 mg, 0.203 mmol) in dry pyridine (0.5 ml) was stirred under nitrogen and cooled in an ice bath. Methanesulfonyl chloride (0.02 ml, 0.258 mmol) was added dropwise and the reaction mixture was allowed to warm to room temperature with stirring over 16 h. The mixture was then diluted with dichloromethane (5 ml) and washed with saturated aqueous sodium hydrogen carbonate solution (5 ml). The aqueous phase was washed with dichloromethane (2×5 ml) and the combined organic phases were dried (Na$_2$SO$_4$) and concentrated in vacuo to give an orange residue (80 mg). Purification was effected by column chromatography on silica gel (4 g) eluting with dichloromethane:ethanol:0.88 ammonia (200:8:1 and then 150:8:1) to give the title compound as a cream foam (65 mg, 78%).

NMR (CDCl$_3$): 0.90 (m, 3H), 1.20–1.35 (m, 6H), 1.45 (m, 2H), 1.85 (m, 2H), 1.90 (s, 3H), 2.45 (m, 2H), 2.75 (m, 2H), 3.00 (s, 3H), 3.20 (m, 2H), 4.00 (m, 2H), 5.65 (m, 1H), 7.00–7.10 (m, 2H), 7.20–7.30 (m, 2H).

MS (thermospray): M/Z (MH$^+$) 408.4; C$_{21}$H$_{33}$N$_3$O$_3$S+H requires 408.2.

EXAMPLE 96

{6-[3-(Acetylamino)phenyl]-3-hexyl-3-azabicyclo[3.1.0]hex-6-yl}methyl acetate

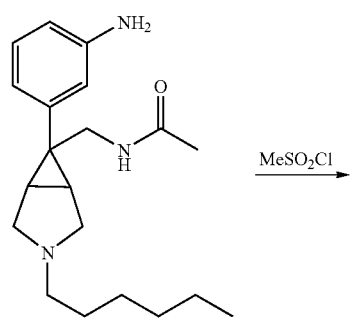 MeSO$_2$Cl →

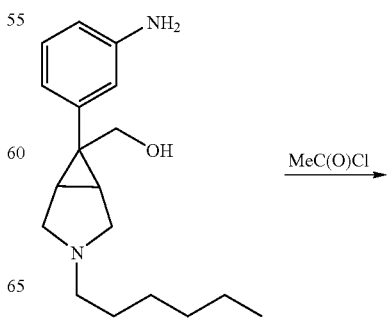 MeC(O)Cl →

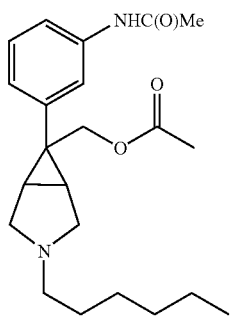

A solution of [6-(3-aminophenyl)-3-hexyl-3-azabicyclo[3.1.0]hex-6-yl]methanol (Preparation 94, 0.03 g, 0.09 mmol) in tetrahydrofuran (2 ml), stirred under nitrogen and cooled to 0° C., was treated with triethylamine (0.03 ml, 0.19 mmol) and acetyl chloride (0.01 ml, 0.17 mmol). The reaction mixture was stirred at room temperature for 3 h, saturated aqueous sodium hydrogen carbonate (50 ml) was added and the product was extracted with ethyl acetate (25 ml×3). The combined organic extracts were dried (Na₂SO₄) and then concentrated in vacuo. The crude residue was purified on a Sep-Pak™ cartridge packed with silica gel (5 g) to give the product as a clear glass, (11 mg, 34%).

NMR (CDCl₃, selected data for the free base): 0.90 (m, 3H), 1.20–1.35 (m, 6H), 1.40 (m, 2H), 1.85 (s, 2H), 1.95 (s, 3H), 2.40 (t, 2H), 2.65 (m, 2H), 3.20 (m, 2H), 4.80 (s, 2H), 7.05 (m, 1H), 7.15–7.30 (m, 2H), 7.45 (s, 1H).

MS (ES): M/Z (MH⁺) 373.3; $C_{22}H_{32}N_2O_3$+H requires 373.2.

EXAMPLE 97

N-(3-{3-[2-(1H-Indol-3-yl)ethyl]-6-methyl-3-azabicyclo[3.1.0]hex-6-yl}phenyl)methanesulfonamide

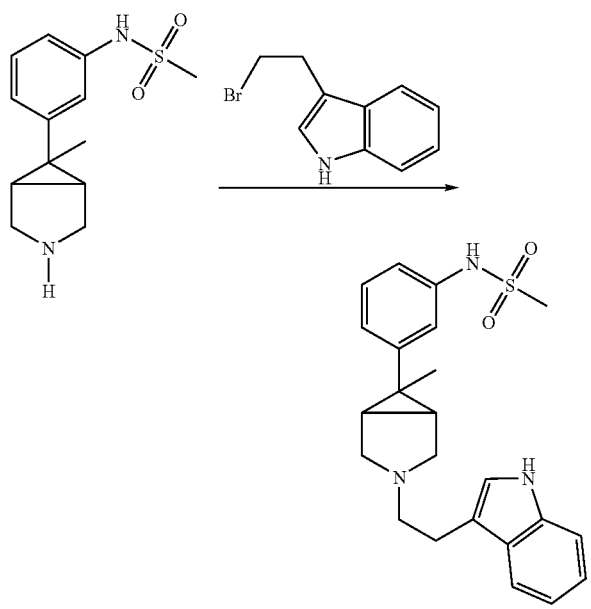

To a solution of the hydrochloride salt of N-[3-(6-methyl-3-azabicyclo[3.1.0]hex-6-yl)phenyl]methanesulfonamide (Preparation 53, 50 mg, 0.165 mmol) in N,N-dimethylformamide (2 ml) was added sodium hydrogen carbonate (35 mg, 0.413 mmol) and 3-(2-bromoethyl)indole (37 mg, 0.165 mmol). The reaction mixture was heated at 55° C. for 48 h, cooled to room temperature and concentrated in vacuo. Water (10 ml) was added and the product was extracted with ethyl acetate (3×10 ml). The combined organic extracts were dried (Na₂SO₄), filtered and concentrated in vacuo to give a brown oil. The crude product was purified by chromatography using a Biotage Flash 12™ cartridge packed with silica gel (8 g), eluting with hexane:ethyl acetate (100:0 and then 0:100). The title compound was obtained as a glass (22 mg, 33%).

NMR (CD₃OD, selected data for the hydrochloride salt): 1.5 (s, 3H), 1.8 (m, 2H), 2.8–3.15 (m, 11H), 7.0–7.3 (m, 7H), 7.4 (d, 1H), 7.8 (d, 1H), 8.0 (br, 1H).

MS (thermospray): M/Z (MH⁺) 410.2; $C_{23}H_{27}N_3O_2S$+H requires 410.2.

EXAMPLE 98

N-(3-{6-Methyl-3-[4-(trifluoromethyl)phenethyl]-3-azabicyclo[3.1.0]hex-6-yl}phenyl)methanesulfonamide

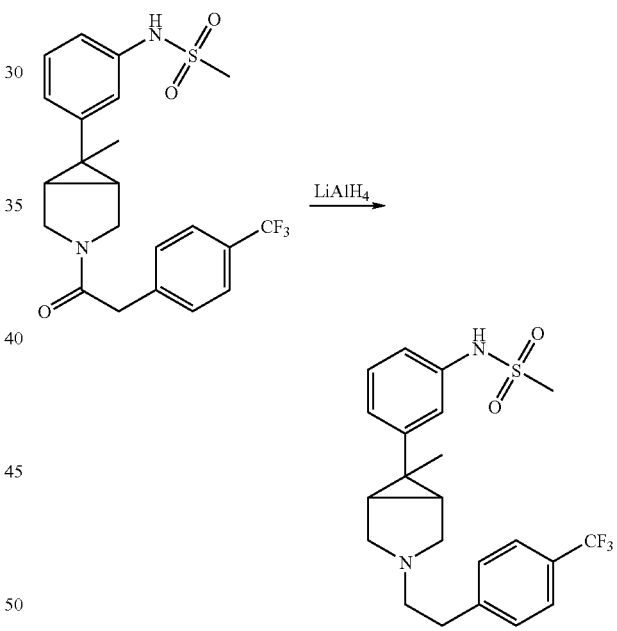

A solution of N-[3-(6-methyl-3-{2-[4-(trifluoromethyl)phenyl]acetyl}-3-azabicyclo[3.1.0]hex-6-yl)phenyl]methanesulfonamide (Preparation 114, 65 mg, 0.144 mmol) in anhydrous tetrahydrofuran (1.0 ml) was stirred under a nitrogen atmosphere and cooled to 0° C. The solution was treated dropwise with lithium aluminium hydride (1.0M solution in tetrahydrofuran, 0.28 ml, 0.28 mmol) and then stirred at room temperature for 18 h. The rapidly stirred reaction mixture was treated with water (0.28 ml), sodium hydrogen carbonate (200 mg) and ethyl acetate (15 ml). After 30 min the reaction mixture was filtered and concentrated in vacuo to afford a colourless oil. The residue was partially purified by chromatography using a Sep-Pak™ cartridge packed with silica gel (10 g) eluting with dichloromethane:ethanol:0.88 ammonia (300:8:1) to afford an off-white solid. This was further purified by preparative HPLC (condition 8) to give the title compound as an off-white solid (22 mg, 35%, m.p. 159–161° C.).

NMR (CD$_3$OD, selected data for the free base): 1.40 (s, 3H), 1.80 (m, 2H), 2.75–2.85 (m, 4H), 2.90 (s, 3H), 2.90–3.00 (m, 4H), 7.02 (m, 2H), 7.10 (br. s, 1H), 7.20 (dd, 1H), 7.40 (d, 2H), 7.75 (d, 2H).

MS (thermospray): M/Z (MH$^+$) 439.3; C$_{22}$H$_{25}$F$_3$N$_2$O$_2$S+H requires 439.2.

EXAMPLE 99

N-{3-[3-(2,3-Dihydro-1H-inden-2-ylmethyl)-6-methyl-3-azabicyclo[3.1.0]hex-6-yl]phenyl}methanesulfonamide

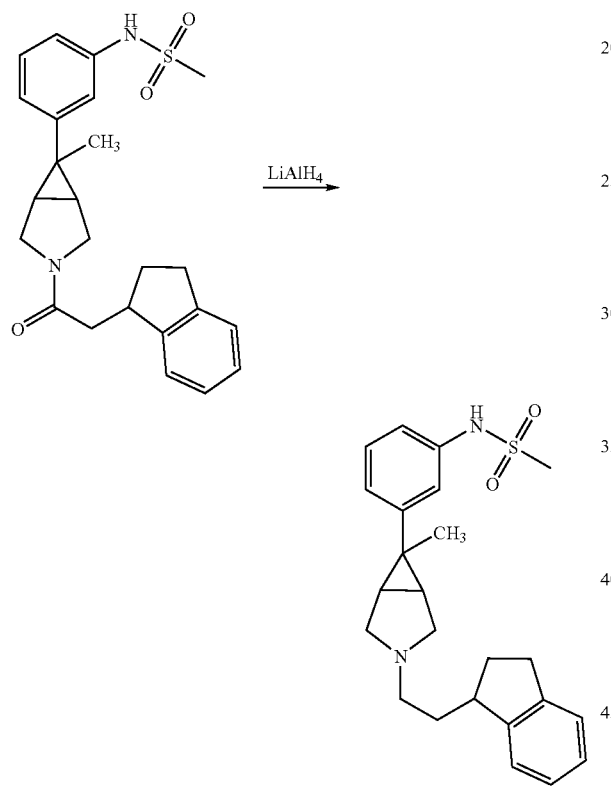

To a solution of N-{3-[3-(2,3-dihydro-1H-inden-2-ylcarbonyl)-6-methyl-3-azabicyclo[3.1.0]hex-6-yl]phenyl}methanesulfonamide (Preparation 115, 94 mg, 0.23 mmol) in anhydrous tetrahydrofuran (2 ml) under a nitrogen atmosphere at 0° C. was added dropwise lithium aluminium hydride (1.0M solution in tetrahydrofuran, 0.40 ml, 0.40 mmol) and the mixture was stirred at room temperature for 3 h. The rapidly stirred reaction mixture was treated sequentially with water (0.40 ml), sodium hydrogen carbonate (400 mg) and ethyl acetate (15 ml). After 30 min the reaction mixture was filtered and concentrated in vacuo to afford a colourless oil. This was purified by preparative HPLC (condition 8) to give a light brown oil which was partitioned between dichloromethane (10 ml) and aqueous potassium carbonate solution (4% w:v, 5 ml). The layers were separated and the organic layer was washed with water (3 ml) and saturated brine (2 ml), dried (Na$_2$SO$_4$), filtered and concentrated in vacuo to afford the title compound as a colourless oil (62 mg, 68%). The free base (55 mg, 0.14 mmol) was dissolved in anhydrous diethyl ether (5 ml) and dichloromethane (1 ml) and the solution was treated with hydrogen chloride (1.0M solution in diethyl ether, 0.153 ml). The heterogeneous suspension was concentrated in vacuo to afford the hydrochloride salt of the title compound as a white solid (50 mg, 83%).

NMR (CD$_3$OD, selected data for the hydrochloride salt): 1.50 (s, 3H), 2.40 (m, 2H), 2.70–2.90 (m, 3H), 2.95 (s, 3H), 3.05–3.30 (m, 4H), 3.40–3.60 (m, 3H), 4.18 (br. d, 1H), 7.00–7.37 (m, 8H).

MS (thermospray): M/Z (MH$^+$) 397.5; C$_{23}$H$_{28}$N$_2$O$_2$S+H requires 397.2.

EXAMPLE 100

N-(3-{3-[2-(1-Benzothioiphene-3-yl)ethyl]-6-methyl-3-azabicyclo[3.1.0]hex-6-yl}phenyl)methanesulfonamide

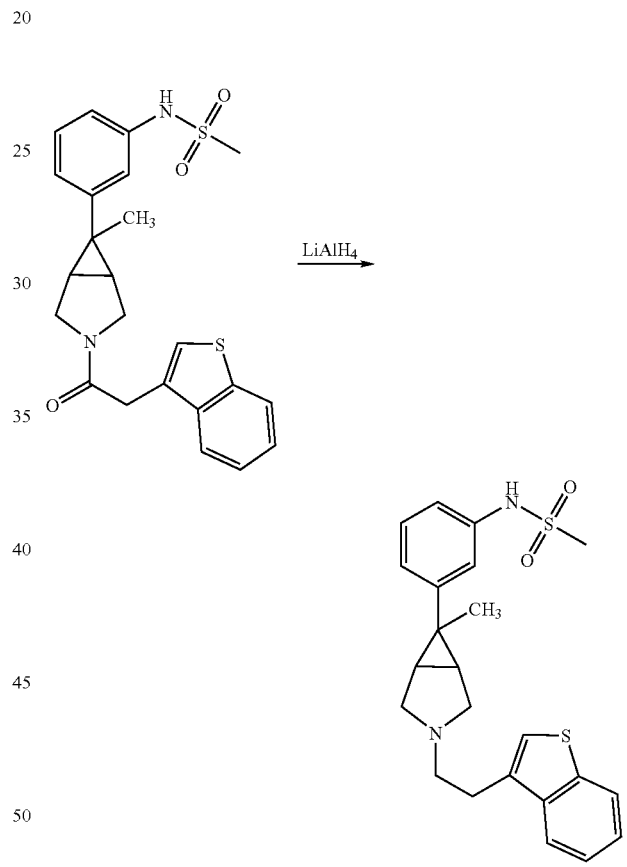

To a solution of N-(3-{3-[2-(1-benzothiophen-3-yl)]-6-methyl-3-azabicyclo[3.1.0]hex-6-yl}phenyl)methanesulfonamide (Preparation 116, 87 mg, 0.2 mmol) in anhydrous tetrahydrofuran (2 ml) under a nitrogen atmosphere at 0° C. was added dropwise lithium aluminium hydride (1.0M solution in tetrahydrofuran, 0.40 ml, 0.40 mmol) and the mixture was stirred at room temperature for 3 h. The rapidly stirred reaction mixture was treated sequentially with water (0.40 ml), sodium hydrogen carbonate (400 mg) and ethyl acetate (15 ml). After 30 min the reaction mixture was filtered and concentrated in vacuo to afford a colourless oil. This was purified by preparative HPLC (condition 8) to give a light brown oil which was partitioned between dichloromethane (10 ml) and aqueous potassium carbonate solution (4% w:v, 5 ml). The layers were separated and the organic layer was washed with water (3 ml), dried ($Na_2SO_4$), filtered and concentrated in vacuo to afford the title compound as a colourless oil (45 mg, 53%).

NMR ($CDCl_3$, selected data): 1.50 (s, 3H), 1.85 (br., 2H), 2.90–3.20 (m, 11H), 7.00–7.15 (m, 3H), 7.15–7.30 (m, 2H), 7.30–7.45 (m, 2H), 7.80 (d, 1H), 7.85 (d, 1H).

MS (thermospray): M/Z ($MH^+$) 427.3; $C_{23}H_{26}N_2O_2S_2$+H requires 427.2.

EXAMPLE 101

N-(3-{6-Methyl-3-[2-(1-methyl-1H-indol-3-yl)ethyl]-3-azabicyclo[3.1.0]hex-6-yl}phenyl)methanesulphonamide

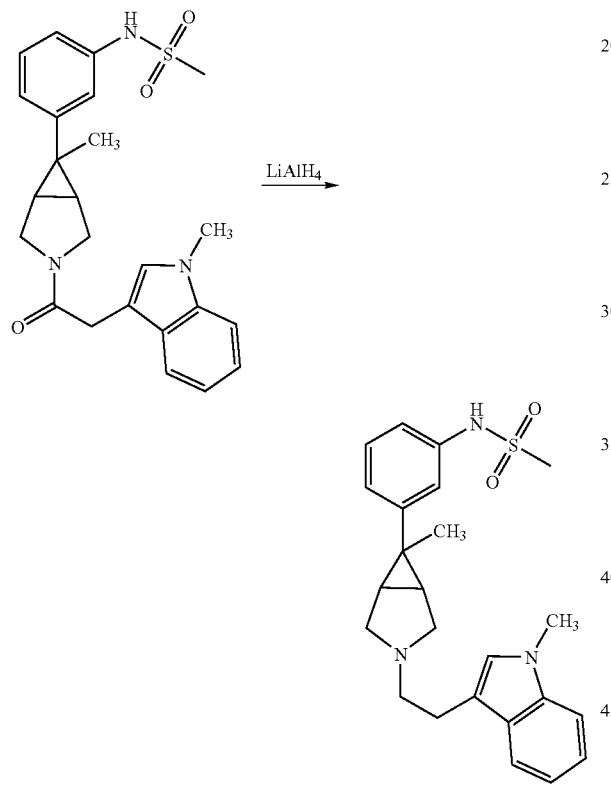

To a solution of N-(3-{6-methyl-3-[2-(1-methyl-1H-indol-3-yl)acetyl]-3-azabicyclo[3.1.0]hex-6-yl}phenyl)methanesulfonamide (Preparation 117, 55 mg, 0.126 mmol) in anhydrous tetrahydrofuran (1 ml) under a nitrogen atmosphere at 0° C. was added dropwise lithium aluminium hydride (1.0M solution in tetrahydrofuran, 0.26 ml, 0.26 mmol) and the reaction mixture was stirred at room temperature for 3 h. The rapidly stirred reaction mixture was treated sequentially with water (0.26 ml), sodium hydrogen carbonate (250 mg) and ethyl acetate (10 ml). After 30 min, the reaction mixture was filtered and concentrated in vacuo to afford a colourless oil. This was purified by preparative HPLC (condition 8) to give a pale yellow oil which was partitioned between dichloromethane (10 ml) and aqueous potassium carbonate solution (4% w:v, 5 ml). The layers were separated and the organic layer was washed with water (3 ml), dried ($Na_2SO_4$), filtered and concentrated in vacuo to afford the title compound as a colourless oil (28 mg, 52%).

NMR ($CDCl_3$, selected data for the free base): 1.50 (br. s, 3H), 1.85 (m, 2H), 2.80–3.20 (m, 11H), 3.75 (s, 3H), 6.90 (s, 1H), 7.00–7.18 (m, 4H), 7.20–7.35 (m, 3H), 7.66 (d, 1H).

MS (thermospray): M/Z ($MH^+$) 424.1; $C_{24}H_{29}N_3O_2S$+H requires 424.2.

EXAMPLE 102

N-(3-{3-[3-(4-Fluorophenyl)propyl]-6-methyl-3-azabicyclo[3.1.0]hex-6-yl}phenyl)methanesulfonamide

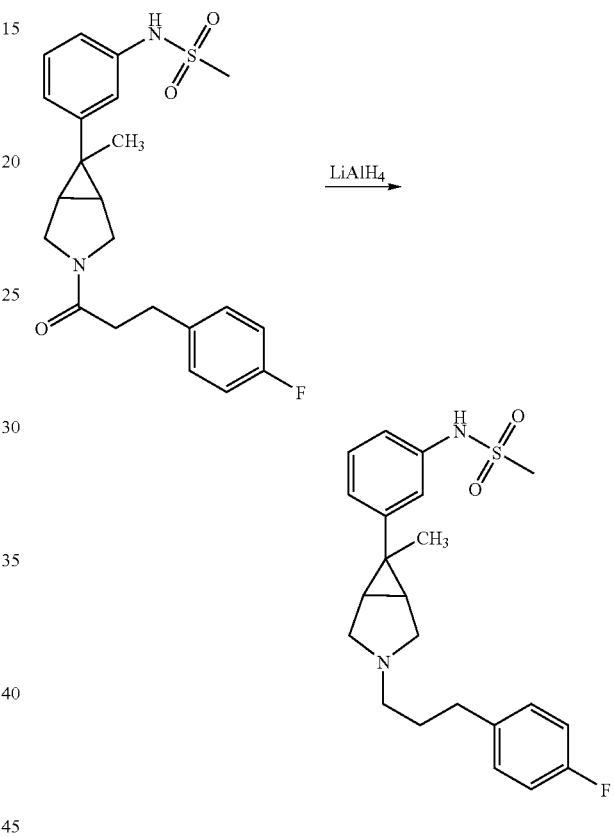

To a solution of N-(3-{3-[3-(4-fluorophenyl)propanoyl]-6-methyl-3-azabicyclo[3.1.0]hex-6-yl}phenyl)methanesulfonamide (Preparation 118, 86 mg, 0.21 mmol) in anhydrous tetrahydrofuran (2 ml) under a nitrogen atmosphere at 0° C. was added dropwise lithium aluminium hydride (1.0M solution in tetrahydrofuran, 0.42 ml, 0.42 mmol) and the mixture was stirred at room temperature for 3 h. The rapidly stirred reaction mixture was treated sequentially with water (0.42 ml), sodium hydrogen carbonate (400 mg) and ethyl acetate (10 ml). After 30 min the reaction mixture was filtered and concentrated in vacuo to afford a colourless oil. The oil was purified by preparative HPLC (condition 8) to give a pale yellow oil which was partitioned between dichloromethane (10 ml) and aqueous potassium carbonate solution (4% w:v, 5 ml). The layers were separated and the organic layer was washed with water (3 ml), dried ($Na_2SO_4$), filtered and concentrated in vacuo to afford the title compound as a colourless oil (52 mg, 62%). The free base (45 mg, 0.112 mmol) was dissolved in anhydrous diethyl ether (5 ml) and dichloromethane (1 ml) and the solution was treated with hydrogen chloride (1.0M solution in diethyl ether, 0.123 ml). The heterogeneous suspension was concentrated in vacuo to afford the hydrochloride salt of the title compound as a white solid (46 mg, 94%).

NMR (CD$_3$OD, selected data for the hydrochloride): 1.45 (s, 3H), 2.00 (m, 2H), 2.35 (m, 2H), 2.70 (m, 2H), 2.95 (s, 3H), 3.00–3.40 (m, 6H), 7.00–7.15 (m, 4H), 7.20–7.35 (m, 4H).

MS (thermospray): M/Z (MH$^+$) 403.3; C$_{22}$H$_{27}$FN$_2$O$_2$S+H requires 403.2.

EXAMPLE 103

N-(3-{3-[3-(3,4-Dichlorophenyl)propyl]-6-methyl-3-azabicyclo[3.1.0]hex-6-yl}phenyl)methanesulfonamide

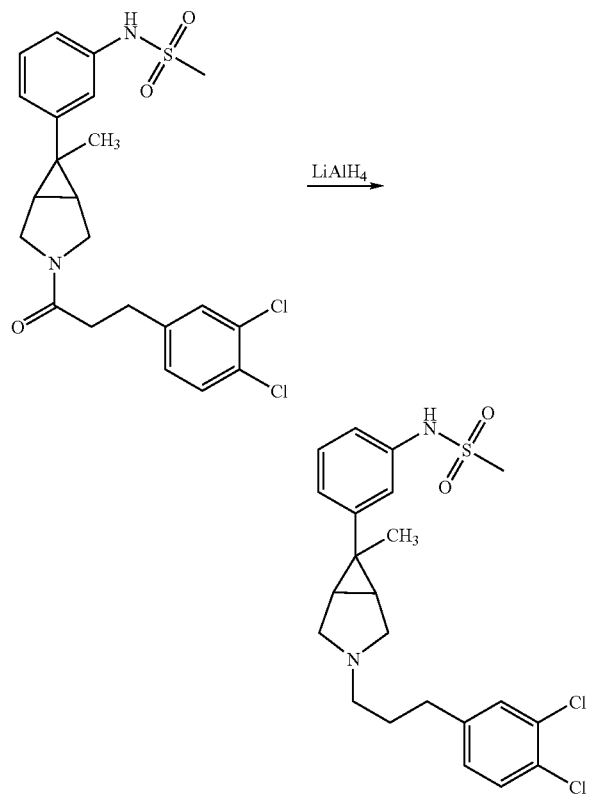

To a solution of N-(3-{3-[3-(3,4-dichlorophenyl)propanoyl]-6-methyl-3-azabicyclo[3.1.0]hex-6-yl}phenyl)methanesulfonamide (Preparation 119, 30 mg, 0.06 mmol) in anhydrous tetrahydrofuran (1 ml) under a nitrogen atmosphere at 0° C. was added dropwise lithium aluminium hydride (1.0M solution in tetrahydrofuran, 0.12 ml, 0.12 mmol) and the mixture was stirred at room temperature for 3 h. The rapidly stirred reaction mixture was treated sequentially with water (0.12 ml), sodium hydrogen carbonate (200 mg) and ethyl acetate (10 ml). After 30 min the reaction mixture was filtered and concentrated in vacuo to give a colourless oil. This was purified by preparative HPLC (condition 8) to afford the title compound as a pale yellow oil (5.2 mg, 19%).

MS (thermospray): M/Z (MH$^+$) 453.1; C$_{22}$H$_{26}$Cl$_2$N$_2$O$_2$S+H requires 453.1.

EXAMPLE 104

N-(3-{3-[3-(1,3-Benzodioxol-5-yl)propyl]-6-methyl-3-azabicyclo[3.1.0]hex-6-yl}phenyl)methanesulfonamide To a solution of N-(3-{3-[3-(1,3-benzodioxol-5-yl)propanoyl]-6-methyl-3-azabicyclo[3.1.0]hex-6-yl}phenyl)methanesulfonamide (Preparation 120, 96 mg, 0.22 mmol) in anhydrous tetrahydrofuran (2 ml) under a nitrogen atmosphere at 0° C. was added dropwise lithium aluminium hydride (1.0M solution in tetrahydrofuran, 0.44 ml, 0.44 mmol) and the mixture was stirred at room temperature for 3 h. The rapidly stirred reaction mixture was treated sequentially with water (0.44 ml), sodium hydrogen carbonate (400 mg) and ethyl acetate (10 ml). After 30 min the reaction mixture was filtered and concentrated in vacuo to afford a colourless oil. This was purified by preparative HPLC (condition 8) to give a pale yellow oil which was partitioned between dichloromethane (10 ml) and aqueous potassium carbonate solution (4% w:v, 5 ml). The layers were separated and the organic layer was washed with water (3 ml), dried (Na$_2$SO$_4$), filtered and concentrated in vacuo to afford the title compound as a colourless oil (32 mg, 34%). The free base (23 mg, 0.054 mmol) was dissolved in anhydrous diethyl ether (5 ml) and dichloromethane (1 ml) and the solution was treated with hydrogen chloride (1.0M solution in diethyl ether, 0.06 ml). The heterogeneous suspension was concentrated in vacuo to afford the hydrochloride salt of the title compound as a white solid (20 mg, 80%).

NMR (CD$_3$OD, selected data for the hydrochloride salt): 1.45 (s, 3H), 1.95 (br., 2H), 2.35 (m, 2H), 2.65 (m, 2H), 2.95 (s, 3H), 3.00–3.40 (m, 6H), 5.90 (m, 2H), 6.65–6.80 (m, 3H), 7.05–7.35 (m, 4H).

MS (thermospray): M/Z (MH$^+$) 429.0; C$_{23}$H$_{28}$N$_2$O$_4$S+H requires 429.2.

EXAMPLE 105

N-(3-{3-[2-(5-Chloro-3-thienyl)ethyl]-6-methyl-3-azabicyclo[3.1.0]hex-6-yl}phenyl)methanesulfonamide

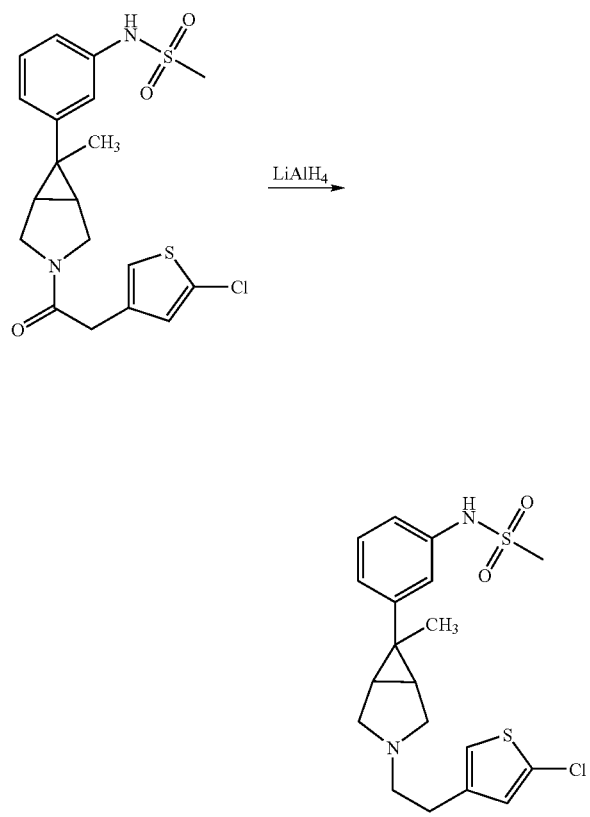

To a solution of N-(3-{3-[2-(5-chloro-3-thienyl)acetyl]-6-methyl-3-azabicyclo[3.1.0]hex-6-yl}phenyl)methanesulfonamide (Preparation 121, 45 mg, 0.11 mmol) in anhydrous tetrahydrofuran (1 ml) under a nitrogen atmosphere at 0° C. was added dropwise lithium aluminium hydride (1.0M solution in tetrahydrofuran, 0.22 ml, 0.22 mmol) and the mixture was stirred at room temperature for 3 h. The rapidly stirred reaction mixture was treated sequentially with water (0.22 ml), sodium hydrogen carbonate (200 mg) and ethyl acetate (10 ml). After 30 min the reaction mixture was filtered and concentrated in vacuo to afford a pale yellow oil. This was purified by preparative HPLC (condition 8) to give a very pale yellow oil which was partitioned between dichloromethane (10 ml) and aqueous potassium carbonate solution (4% w:v, 5 ml). The layers were separated and the organic layer was washed with water (3 ml), dried (Na$_2$SO$_4$), filtered and concentrated in vacuo to afford the title compound as a colourless oil (14 mg, 33%).

NMR (CDCl$_3$, selected data for the free base): 1.25 (s, 3H), 1.80 (m, 2H), 2.75–3.10 (m, 11H), 6.60 (m, 1H), 6.70 (m, 1H), 7.00–7.15 (m, 3H), 7.25 (m, 1H).

MS (electrospray): M/Z (MH$^+$) 411.1; C$_{19}$H$_{23}$ClN$_2$O$_2$S$_2$+H requires 411.1.

EXAMPLE 106

N-{3-[6-Methyl-3-(3-methyl-3-phenylbutyl)-3-azabicyclo[3.1.0]hex-6-yl]phenyl}methanesulfonamide

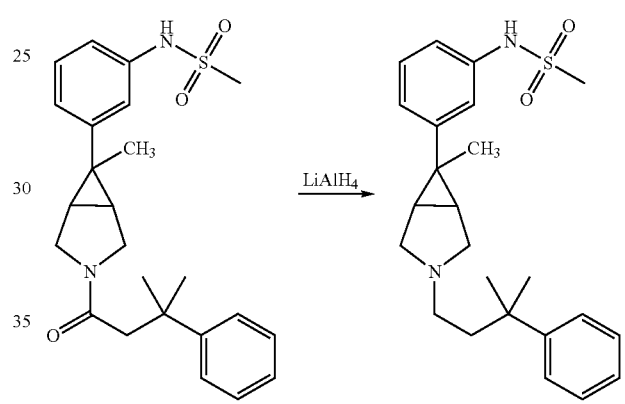

To a solution of N-{3-[6-methyl-3-(3-methyl-3-phenylbutanoyl)-3-azabicyclo[3.1.0]hex-6-yl] phenyl}methanesulfonamide (Preparation 122, 59 mg, 0.138 mmol) in anhydrous tetrahydrofuran (1 ml) under a nitrogen atmosphere at 0° C. was added dropwise lithium aluminium hydride (1.0M solution in tetrahydrofuran, 0.28 ml, 0.28 mmol) and the mixture was stirred at room temperature for 3 h. The rapidly stirred reaction mixture was treated sequentially with water (0.28 ml), sodium hydrogen carbonate (200 mg) and ethyl acetate (10 ml). After 30 min the reaction mixture was filtered and concentrated in vacuo to afford a pale yellow oil. This was purified by preparative HPLC (condition 8) to give a light brown oil which was partitioned between dichloromethane (15 ml) and aqueous potassium carbonate solution (7% w:v, 5 ml). The layers were separated and the organic layer was washed with water (5 ml), dried (MgSO$_4$), filtered and concentrated in vacuo to afford the title compound as a colourless oil (38 mg, 66%).

NMR (CDCl$_3$, selected data for the free base): 1.30 (s, 6H), 1.40 (s, 3H), 1.70–1.90 (m, 4H), 2.35 (m, 2H), 2.80–3.00 (m, 4H), 3.00 (s, 3H), 7.00–7.10 (m, 3H), 7.15–7.40 (m, 6H).

MS (thermospray): M/Z (MH$^+$) 413.2; C$_{24}$H$_{32}$N$_2$O$_2$S+H requires 413.2.

EXAMPLE 107

N-(3-{3-[3-(1H-Indol-3-yl)propyl]-6-methyl-3-azabicyclo[3.1.0]hex-6-yl}phenyl)methanesulfonamide

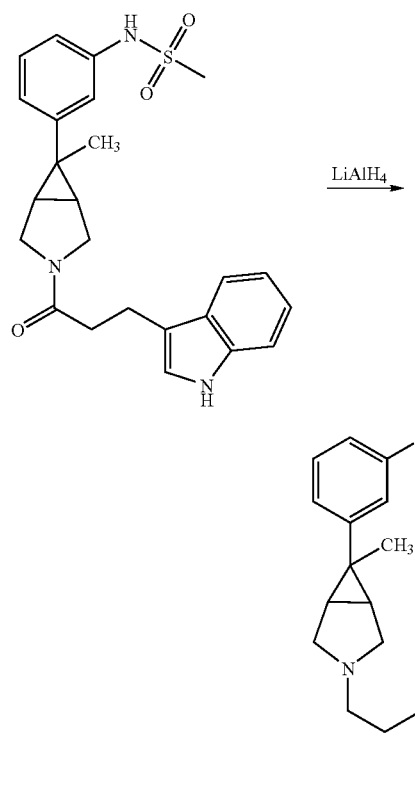

EXAMPLE 108

N-(3-{6-Methyl-3-[3-(4-pyridinyl)propyl]-3-azabicyclo[3.1.0]hex-6-yl}phenyl)methanesulfonamide

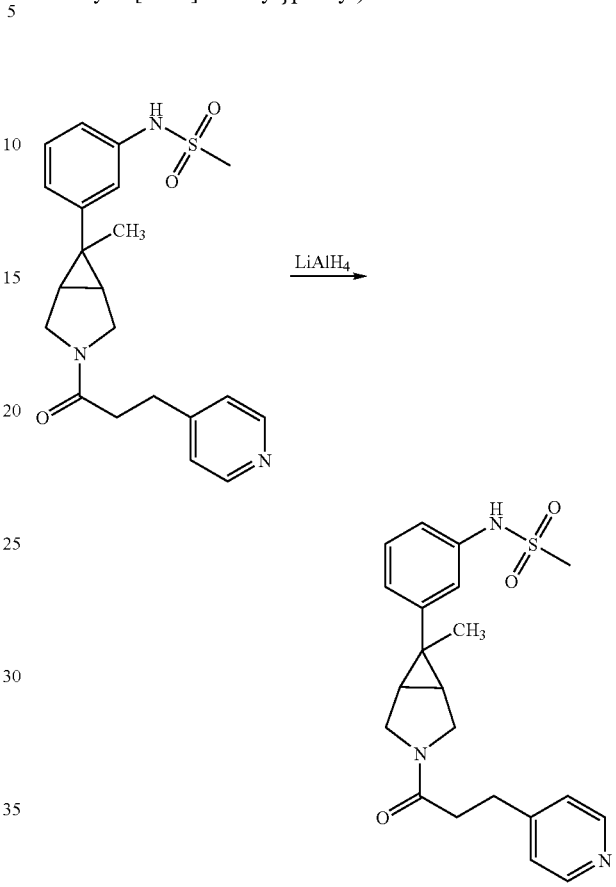

To a solution of N-(3-{3-[3-(1H-indol-3-yl)propanoyl]-6-methyl-3-azabicyclo[3.1.0]hex-6-yl}phenyl)methanesulfonamide (Preparation 123, 135 mg, 0.34 mmol) in anhydrous tetrahydrofuran (2.5 ml) under a nitrogen atmosphere at 0° C. was added dropwise lithium aluminium hydride (1.0M solution in tetrahydrofuran, 0.68 ml, 0.68 mmol) and the mixture was stirred at room temperature for 20 h. The rapidly stirred reaction mixture was treated sequentially with water (0.68 ml), sodium hydrogen carbonate (400 mg) and ethyl acetate (15 ml). After 30 min the reaction mixture was filtered and concentrated in vacuo to afford a glassy oil. This was purified by preparative HPLC (condition 8) to give a light brown oil which was partitioned between dichloromethane (15 ml) and aqueous potassium carbonate solution (7% w:v, 5 ml). The layers were separated and the organic layer was washed with water (5 ml), dried (MgSO$_4$), filtered and concentrated in vacuo to afford the title compound as a colourless oil (69 mg, 50%).

NMR (CDCl$_3$, selected data for the free base): 1.57 (s, 3H), 1.80 (m, 2H), 1.80–2.00 (m, 2H), 2.60 (m, 2H), 2.75–3.10 (m, 9H), 7.00–7.30 (m, 7H), 7.35 (d, 1H), 7.60 (d, 1H), 7.95 (br., 1H).

MS (electrospray): M/Z (MH$^+$) 424.2; C$_{24}$H$_{29}$N$_3$O$_2$S+H requires 424.2.

To a solution of N-(3-{6-methyl-3-[3-(4-pyridinyl)propanoyl]-3-azabicyclo[3.1.0]hex-6-yl}phenyl)methanesulfonamide (Preparation 124, 100 mg, 0.25 mmol) in anhydrous tetrahydrofaran (2.5 ml) under a nitrogen atmosphere at 0° C. was added dropwise lithium aluminium hydride (1.0M solution in tetrahydrofuran, 0.50 ml, 0.50 mmol) and the mixture was stirred at 10° C. for 2 h. The rapidly stirred reaction mixture was treated sequentially with water (0.40 ml), sodium hydrogen carbonate (400 mg) and ethyl acetate (20 ml). After 18 h the reaction mixture was filtered and concentrated in vacuo to afford a colourless oil (70 mg). The free base was dissolved in anhydrous diethyl ether (5 ml) and dichloromethane (1 ml) and the solution was treated with hydrogen chloride (1.0M solution in diethyl ether, 0.18 ml). Excess diethyl ether was decanted from the resulting precipitate and the remaining suspension was concentrated in vacuo to afford the hydrochloride salt of the title compound as a white solid (64 mg, 83%).

NMR (CD$_3$OD, selected data for the hydrochloride salt): 1.45 (br., 3H), 2.10 (m, 2H), 2.38 (m, 2H), 2.82 (m, 2H), 2.95 (m, 3H), 3.08 (m, 1H), 3.22–3.40 (m, 4H), 4.05 (m, 1H), 7.05–7.15 (m, 2H), 7.20 (s, 1H), 7.28 (dd, 1H), 7.50 (d, 2H), 8.55 (d, 2H).

MS (electrospray): M/Z (MH$^+$) 386.2; C$_{21}$H$_{28}$N$_3$O$_2$S+H requires 386.2.

EXAMPLE 109

N-(3-{6-Methyl-3-[2-(2-naphthyl)ethyl]-3-azabicyclo[3.1.0]hex-6-yl}phenyl)methanesulfonamide

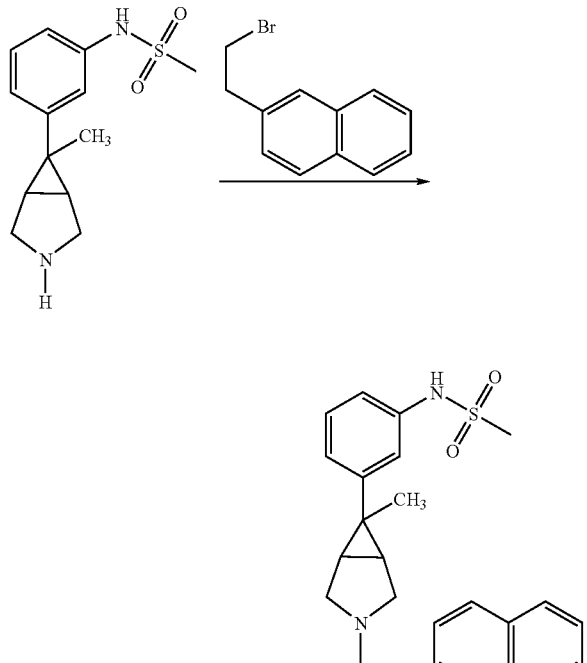

To a solution of the hydrochloride salt of N-[3-(6-methyl-3-azabicyclo[3.1.0]hex-6-yl)phenyl]methanesulfonamide (Preparation 53, 122 mg, 0.404 mmol) in N,N-dimethylformamide (4 ml) was added 2-(2-bromoethyl)naphthalene (A. K. Mitra, R. C. Bannerjee and R. Bhattacharya, J. Ind. Chem. Soc., 1971, 48, 391, 95 mg, 0.404 mmol) and sodium hydrogen carbonate (102 mg 1.212 mmol). The reaction mixture was heated at 80° C. for 6 h before allowing to cool to room temperature. The mixture was partitioned between water (5 ml) and dichloromethane (5 ml), and the aqueous layer was extracted with dichloromethane (2×5 ml). The combined organic extracts were dried ($Na_2SO_4$), filtered and concentrated in vacuo to give a brown oil (130 mg). The residue was purified by chromatography using a Biotage Flash 12™ cartridge packed with silica gel (8 g) eluting with dichloromethane:ethanol:0.88 ammonia (400:8:1) to afford the title compound as a pale yellow oil. The free base was dissolved in anhydrous diethyl ether (2 ml) and dichloromethane (0.5 ml) and the solution was treated with hydrogen chloride (1.0M solution in diethyl ether, 0.15 ml). The resulting suspension was concentrated in vacuo to afford the hydrochloride salt of the title compound as a pale yellow solid (52 mg, 28%).

NMR ($CD_3OD$, for the hydrochloride salt): 1.28 (m, 2H), 1.50 (br., 3H), 2.38 (m, 2H), 2.95 (s, 3H), 3.10–3.25 (m, 3H), 3.55–3.65 (m, 3H), 4.10 (br., 1H), 7.05–7.15 (m, 2H), 7.22–7.35 (m, 2H), 7.45–7.55 (m, 3H), 7.80–7.92 (m, 4H).

MS (electrospray): M/Z (MH$^+$) 421.2; $C_{25}H_{28}N_2O_2S$+H requires 421.2.

EXAMPLE 110

N-[3-(6-methyl-3-{4-[(methylsulfonyl)amino]phenethyl}-3-azabicyclo[3.1.0]hex-6-yl)phenyl]methanesulfonamide

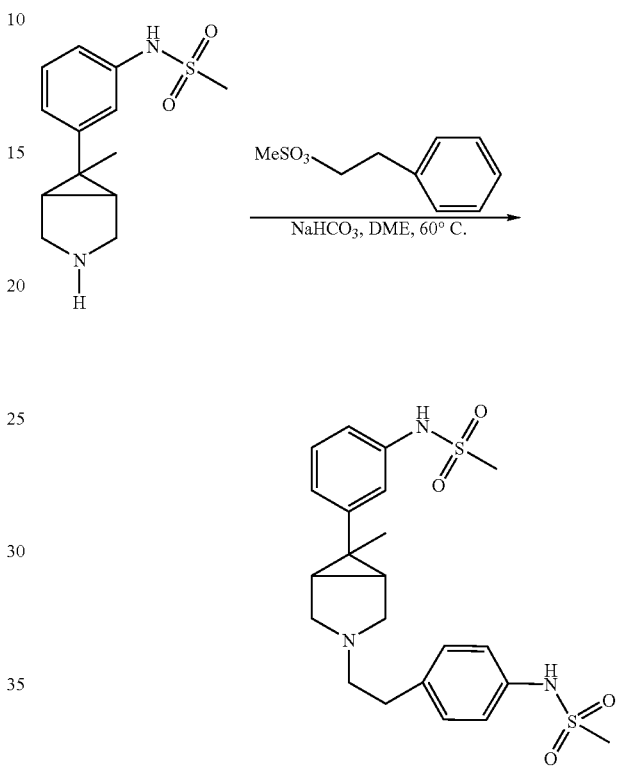

To a solution of N-[3-(6-methyl-3-azabicyclo[3.1.0]hex-6-yl)phenyl]methanesulfonamide hydrochloride salt (Preparation 53, 100 mg, 0.33 mmol) in ethylene glycol dimethyl ether (10 ml) was added sodium hydrogen carbonate (1.5 g, 18 mmol) and 4-[(methylsulfonyl)amino]phenethyl methanesulfonate (P. E. Cross, J. E. Arrowsmith, G. N. Thomas, R. P. Dickinson, DD 281 599 A5, 97 mg, 0.33 mmol) and the reaction mixture was heated at 60° C. for 20 h. After cooling, diethyl ether (15 ml) and water (15 ml) were added and the reaction mixture was stirred vigorously for 5 min. The phases were separated and the aqueous layer was further extracted with diethyl ether (2×10 ml). The combined organic extracts were dried ($Na_2SO_4$), filtered and concentrated in vacuo. The residual oil was purified by flash column chromatography using a Sep-Pak™ cartridge packed with silica gel (10 g) eluting with dichloromethane:ethanol:0.88 ammonia solution (200:8:1) to afford the title compound as an oil. The oil was further purified by preparative HPLC (condition 9) to give the title compound as a colourless glass (11 mg, 7%).

NMR ($CDCl_3$, selected data for the free base): 0.8–1.0 (m, 2H), 1.2 (s, 3H), 1.5 (s, 6H), 1.9 (m, 1H), 2.8 (m, 2H), 3.0 (d, 6H), 3.1 (m, 2H), 7.0–7.3 (m, 8H)

MS (thermospray): M/Z (MH$^+$) 464.0, $C_{22}H_{29}N_3O_4S_2$+H requires 464.1.

EXAMPLE 111

N-[2,4-Dichloro-5-(3-hexyl-6-methyl-3-azabicyclo[3.1.0]hex-6-yl)phenyl]methanesulfonamide

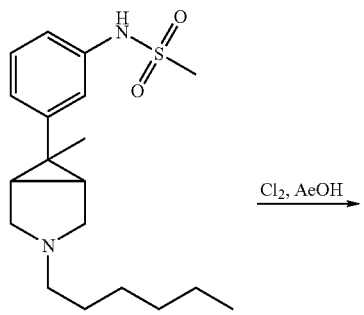

Cl₂, AeOH →

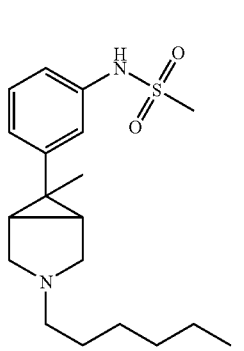

To a solution of N-[3-(3-hexyl-6-methyl-3-azabicyclo[3.1.0]hex-6-yl)phenyl]methanesulfonamide (Example 6, 132 mg, 0.39 mmol) in dichloromethane (12 ml) at 0° C. was added dropwise chlorine (0.132 M solution in acetic acid, 2.94 ml, 0.39 mmol) over 30 min. The mixture was stirred for 3 h, slowly warming to room temperature. The reaction mixture was basified to pH 8 by careful addition of saturated aqueous potassium carbonate solution and the resulting mixture was stirred at room temperature for 15 hours. The layers were separated and the aqueous layer was extracted with dichloromethane (2×15 ml). The combined organic extracts were dried (Na₂SO₄), filtered and concentrated in vacuo. The residual oil was purified by chromatography using a Sep-Pak™ cartridge packed with silica gel (10 g) eluting with dichloromethane:ethanol:0.88 ammonia (100:2:1 then 100:4:1) to give a mixture of two products. The two products were separated by preparative HPLC (condition 10) to afford firstly the title compound as a colourless glass (12 mg, 7%).

NMR (CDCl₃, selected data for the free base): 0.90 (m, 3H), 1.20–1.40 (m, 7H), 1.40–1.50 (m, 4H), 1.75 (m, 2H), 2.40 (m, 2H), 2.80 (m, 2H), 3.00–3.10 (m, 5H), 7.40 (s, 1H), 7.60 (s, 1H).

MS (electrospray): M/Z (MH⁺) 419.0; $C_{19}H_{28}Cl_2N_2O_2S+H$ requires 419.1.

EXAMPLE 112

N-[2,4-Dichloro-3-(3-hexyl-6-methyl-3-azabicyclo[3.1.0]hex-6-yl)phenyl]methanesulfonamide

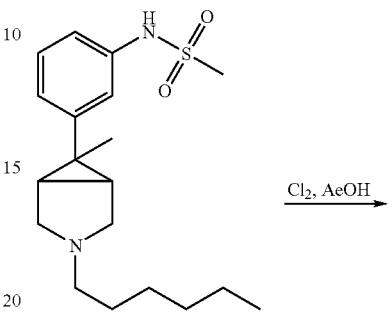

Cl₂, AeOH →

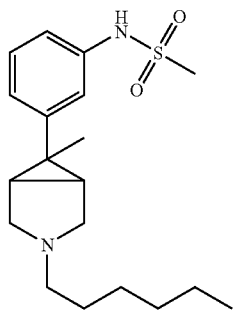

To a solution of N-[3-(3-hexyl-6-methyl-3-azabicyclo[3.1.0]hex-6-yl)phenyl]methanesulfonamide (Example 6, 132 mg, 0.39 mmol) in dichloromethane (12 ml) at 0° C. was added dropwise chlorine (0.132 M solution in acetic acid, 2.94 ml, 0.39 mmol) over 30 min. The mixture was stirred for 3 h, slowly warming to room temperature. The reaction mixture was basified to pH 8 by careful addition of saturated aqueous potassium carbonate solution and the resulting mixture was stirred at room temperature for 15 hours. The layers were separated and the aqueous layer was extracted with dichloromethane (2×15 ml). The combined organic extracts were dried (Na₂SO₄), filtered and concentrated in vacuo. The residual oil was purified by chromatography using a Sep-Pak™ cartridge packed with silica gel (10 g) eluting with dichloromethane:ethanol:0.88 ammonia (100:2:1 then 100:4:1) to give a mixture of two products. The two products were separated by preparative HPLC (condition 10) to afford firstly N-[2,4-Dichloro-5-(3-hexyl-6-methyl-3-azabicyclo[3.1.0]hex-6-yl)phenyl]methanesulfonamide as a colourless glass (Example 111, 12 mg, 7%). Further elution using preparative HPLC (condition 10) afforded the title compound as a colourless glass (11 mg, 7%).

NMR (CDCl₃, selected data for the free base):0.90 (m, 3H), 1.20–1.40 (m, 7H), 1.40–1.50 (m, 4H), 1.75 (m, 1H), 1.85 (m, 1H), 2.45 (m, 2H), 2.80 (m, 2H), 3.00 (m, 3H), 3.10 (m, 2H), 7.25 (d, 1H), 7.45 (d, 1H).

MS (electrospray): M/Z (MH⁺) 419.0; $C_{19}H_{28}Cl_2N_2O_2S+H$ requires 419.1.

EXAMPLE 113

N-(3-{6-Methyl-3-[3-(2-thienyl)propyl]-3-azabicyclo[3.1.0]hex-6-yl}phenyl)methanesulfonamide

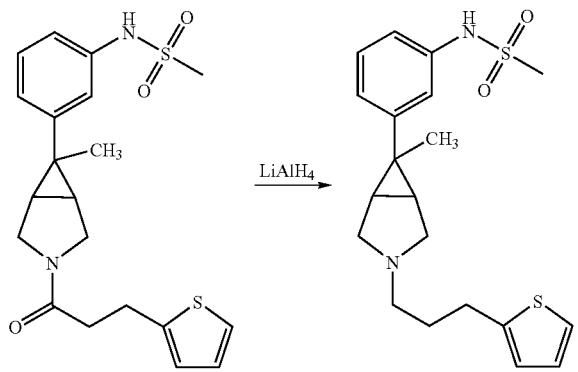

To a solution of N-(3-{6-methyl-3-[3-(2-thienyl)propanoyl]-3-azabicyclo[3.1.0]hex-6-yl}phenyl)methanesulfonamide (Preparation 125, 200 mg, 0.49 mmol) in anhydrous tetrahydrofuran (7.5 ml) under a nitrogen atmosphere at 0° C. was added dropwise lithium aluminium hydride (1.0M solution in tetrahydrofuran, 0.99 ml, 0.99 mmol) and the mixture was stirred at room temperature for 2 h. The rapidly stirred reaction mixture was treated sequentially with water (1.0 ml), sodium hydrogen carbonate (1.0 g) and ethyl acetate (25 ml). After 15 min the reaction mixture was filtered and concentrated in vacuo to afford a light yellow oil. This was purified by chromatography using a Biotage Flash 12™ cartridge packed with silica gel (8 g) eluting with hexane: ethyl acetate (100:0 to 0:100) to afford the title compound as a colourless oil (135 mg, 70%).

NMR (CDCl$_3$, selected data for the free base): 1.55 (s, 3H), 1.75–1.90 (m, 4H), 2.50–2.70 (m, 2H), 2.85–3.10 (m, 9H), 6.80 (m, 1H), 6.95 (m, 1H), 7.00–7.15 (m, 4H), 7.20–7.30 (m, 1H).

MS (electrospray): M/Z (MH$^+$) 391.1; C$_{20}$H$_{26}$N$_2$O$_2$S$_2$+H requires 391.1.

EXAMPLE 114

N-(3-{6-Methyl-3-[3-(3-thienyl)propyl]-3-azabicyclo[3.1.0]hex-6-yl}phenyl)methanesulfonamide

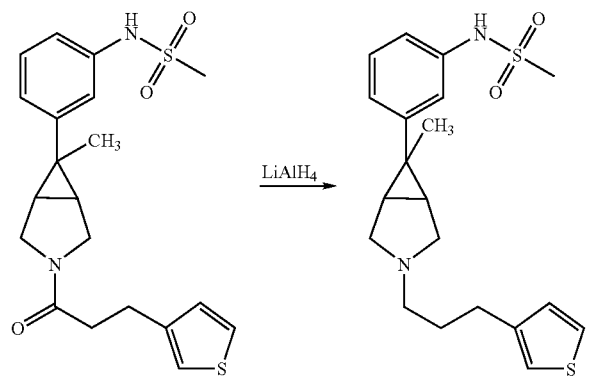

To a solution of N-(3-{6-methyl-3-[3-(3-thienyl)propanoyl]-3-azabicyclo[3.1.0]hex-6-yl}phenyl)methanesulfonamide (Preparation 126, 200 mg, 0.49 mmol) in anhydrous tetrahydrofuran (7.5 ml) under a nitrogen atmosphere at 0° C. was added dropwise lithium aluminium hydride (1.0M solution in tetrahydrofuran, 0.99 ml, 0.99 mmol) and the mixture was stirred at room temperature for 2 h. The rapidly stirred reaction mixture was treated sequentially with water (1 ml), sodium hydrogen carbonate (1.0 g) and ethyl acetate (25 ml). After 15 min the reaction mixture was filtered and concentrated in vacuo to afford a light yellow oil. This was purified by chromatography using a Biotage Flash 12™ cartridge packed with silica gel (8 g) eluting with hexane:ethyl acetate (100:0 to 0:100) to afford the title compound as a colourless oil (108 mg, 56%).

NMR (CDCl$_3$, selected data for the free base): 1.55 (s, 3H), 1.70–1.90 (m, 4H), 2.45–2.60 (m, 2H), 2.70 (m, 2H), 2.80–3.10 (m, 7H), 6.95 (d, 2H), 7.00–7.15 (m, 3H), 7.20–7.30 (m, 2H).

MS (electrospray): M/Z (MH$^+$) 391.1; C$_{20}$H$_{26}$N$_2$O$_2$S$_2$+H requires 391.1.

EXAMPLE 115

(3-Hexyl-6-{3-[(methoxycarbonyl)amino]phenyl}-3-azabicyclo[3.1.0]hex-6-yl)methyl methyl carbonate

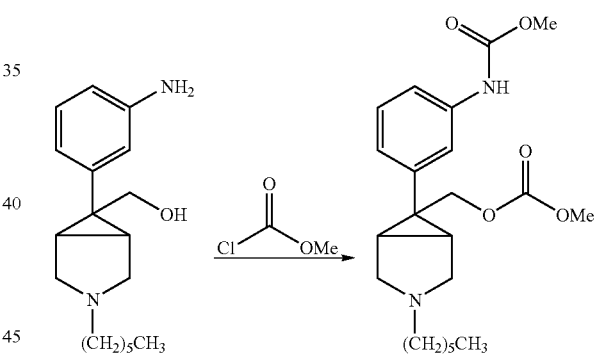

A solution of [6-(3-aminophenyl)-3-hexyl-3-azabicyclo[3.1.0]hex-6-yl]methanol (Preparation 94, 0.03 g, 0.09 mmol) in tetrahydrofuran (1 ml) was stirred at 0° C. under an atmosphere of nitrogen. The reaction mixture was treated with triethylamine (0.03 ml, 0.19 mmol) followed by dropwise addition of methyl chloroformate (0.01 ml, 0.17 mmol). The reaction mixture was allowed to warm to room temperature and stirred for 2 h before pouring onto aqueous saturated sodium hydrogen carbonate (50 ml). The product was extracted with ethyl acetate (3×25 ml) and the combined organic extracts were dried (Na$_2$SO$_4$) and then concentrated in vacuo to give a brown residue. The crude product was purified by preparative HPLC (condition 11) to give a clear glass (6 mg, 15% yield).

NMR (CD$_3$OD, selected data for the free base): 1.55 (m, 2H), 2.10 (m, 1H), 3.55 (m, 2H), 3.70 (s, 3H), 3.75 (s, 3H), 4.0–4.15 (m, 3H), 4.25 (m, 1H), 6.85 (d, 1H), 7.19–7.35 (m, 3H).

EXAMPLE 116

N-{3-[3-(1-Benzofuran-2-ylmethyl)-6-methyl-3-azabicyclo[3.1.0]hex-6-yl]phenyl}methanesulfonamide

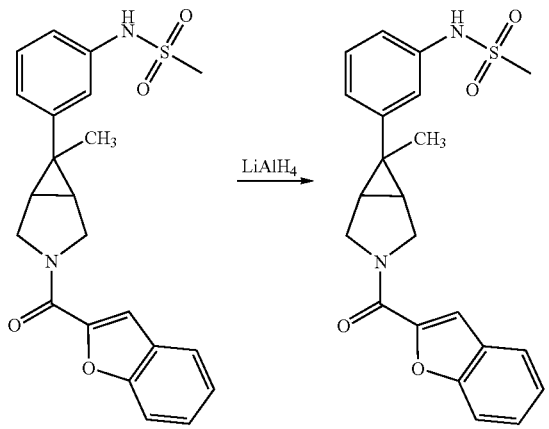

To a suspension of N-{3-[3-(1-benzofuran-2-ylcarbonyl)-6-methyl-3-azabicyclo[3.1.0]hex-6-yl]phenyl}methanesulfonamide (Preparation 127, 200 mg, 0.487 mmol) in anhydrous tetrahydrofuran (5 ml) under a nitrogen atmosphere at 0° C. was added dropwise lithium aluminium hydride (1.0M solution in tetrahydrofuran, 0.97 ml, 0.97 mmol) and the reaction mixture was stirred at room temperature overnight. The rapidly stirred reaction mixture was treated sequentially with water (1.0 ml), sodium hydrogen carbonate (1.0 g) and ethyl acetate (15 ml). After 5 min, the reaction mixture was filtered and concentrated in vacuo to afford 180 mg of a pale yellow oil. This was purified by chromatography using a Biotage Flash 12™ cartridge packed with silica gel (8 g) eluting with hexane:ethyl acetate (100:0 to 0:100 over 30 min) then ethyl acetate:methanol (100:0 to 0:100 over 15 min) to afford the title compound as a white foam (136 mg, 70%).

NMR (CDCl$_3$, selected data for the free base): 1.55 (s, 3H), 1.83 (m, 2H), 3.00 (s, 3H), 3.05–3.20 (m, 4H), 3.88 (m, 2H), 6.40–6.70 (m, 2H), 7.00–7.13 (m, 3H), 7.18–7.35 (m, 2H), 7.45 (d, 1H), 7.55 (d, 1H).

MS (electrospray): M/Z (MH$^+$) 397.4; $C_{22}H_{24}N_2O_3S$+H requires 397.2.

EXAMPLE 117

N-(3-{3-[3-(5-Fluoro-3-methyl-1H-indol-2-yl)propyl]-6-methyl-3-azabicyclo[3.1.0]hex-6-yl}phenyl)methanesulfonamide

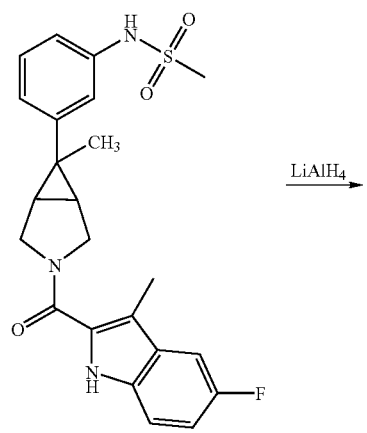

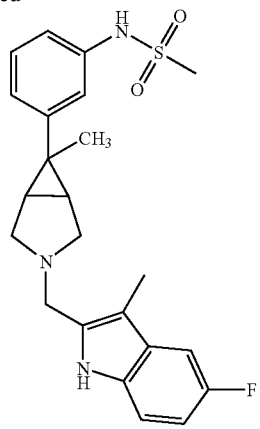

To a solution of N-(3-{3-[3-(5-fluoro-3-methyl-1H-indol-2-yl)propanoyl]-6-methyl-3-azabicyclo[3.1.0]hex-6-yl}phenyl)methanesulfonamide (Preparation 128, 100 mg, 0.213 mmol) in anhydrous tetrahydrofuran (2.5 ml) under a nitrogen atmosphere at 0° C. was added dropwise lithium aluminium hydride (1.0M solution in tetrahydrofuran, 0.42 ml, 0.42 mmol) and the reaction mixture was stirred at room temperature overnight. The rapidly stirred reaction mixture was treated sequentially with water (0.45 ml), sodium hydrogen carbonate (450 mg) and ethyl acetate (10 ml). After 5 min, the reaction mixture was filtered and concentrated in vacuo to afford 95 mg of a colourless oil. This was purified by chromatography using a Biotage Flash 12™ cartridge packed with silica gel (8 g) eluting with hexane:ethyl acetate (100:0 to 0:100 over 30 min) then ethyl acetate:methanol (100:0 to 0:100 over 15 min) to afford the title compound as a white foam (56 mg, 46%).

NMR (CDCl$_3$, selected data for the free base): 1.55 (s, 3H), 1.80–1.93 (m, 4H), 2.20 (s, 3H), 2.59 (t, 2H), 2.83 (t, 2H), 3.00–3.10 (m, 7H), 6.83 (ddd, 1H), 7.00–7.15 (m, 4H), 7.18 (dd, 1H), 7.24 (m, 1H).

MS (electrospray): M/Z (MH$^+$) 456.2; $C_{25}H_{30}FN_3O_2S$+H requires 456.2.

EXAMPLE 118

N-(3-{6-Methyl-3-[3-(2-pyridinyl)propyl]-3-azabicyclo[3.1.0]hex-6-yl}phenyl)methanesulfonamide

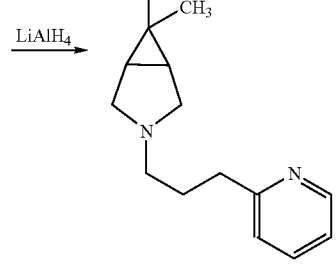

To a solution of N-(3-{6-methyl-3-[3-(2-pyridinyl)propanoyl]-3-azabicyclo[3.1.0]hex-6-yl}phenyl)methanesulfonamide (Preparation 129, 16 mg, 0.04 mmol) in anhydrous tetrahydrofuran (2 ml) under a nitrogen atmosphere at 0° C. was added dropwise lithium aluminium hydride (1.0M solution in tetrahydrofuran, 80 μl, 80 μmol) and the reaction mixture was stirred at room temperature for 5 h. The rapidly stirred reaction mixture was treated sequentially with water (100 μl), sodium carbonate (100 mg) and ethyl acetate (5 ml). After 5 min, the reaction mixture was filtered and concentrated in vacuo to afford 10 mg of a colourless oil. This was purified by chromatography using silica gel (1 g) eluting with dichloromethane:ethanol:0.880 ammonia (200:8:1) to afford the title compound as a colourless oil (3 mg, 19%).

NMR (CDCl$_3$, selected data for the free base): 1.55 (s, 3H), 1.75 (m, 2H), 1.90 (t, 2H), 2.50 (t, 2H), 2.75–2.88 (m, 4H), 3.00 (s, 3H), 3.05 (d, 2H), 7.00 (d, 1H), 7.05–7.30 (m, 5H), 7.60 (d, 1H), 8.55 (d, 1H).

MS (electrospray): M/Z (MH$^+$) 386.2; C$_{21}$H$_{28}$N$_3$O$_2$S+H requires 386.2.

EXAMPLE 119

N-(3-{6-Methyl-3-[3-(3-methyl-2-thienyl)propyl]-3-azabicyclo[3.1.0]hex-6-yl}phenyl)methanesulfonamide

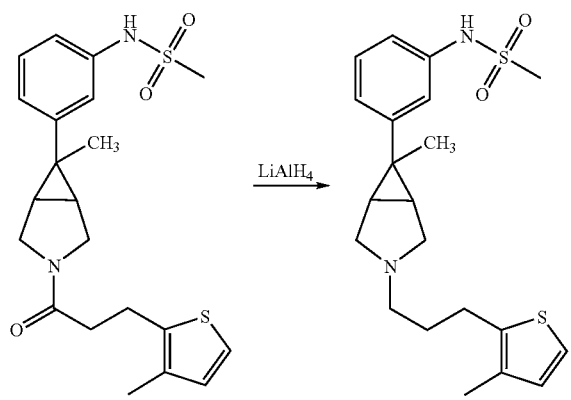

To a solution of N-(3-{6-methyl-3-[3-(3-methyl-2-thienyl)propanoyl]-3-azabicyclo[3.1.0]hex-6-yl}phenyl)methanesulfonamide (Preparation 130, 150 mg, 0.358 mmol) in anhydrous tetrahydrofuran (10 ml) under a nitrogen atmosphere at 0° C. was added dropwise lithium aluminium hydride (1.0M solution in tetrahydrofuran, 0.72 ml, 0.72 mmol) and the reaction mixture was stirred at room temperature overnight. The rapidly stirred reaction mixture was treated sequentially with water (0.75 ml), sodium hydrogen carbonate (750 mg) and ethyl acetate (15 ml). After 15 min, the reaction mixture was filtered and concentrated in vacuo to afford 140 mg of a colourless oil. This was purified by chromatography using a Biotage Flash 12™ cartridge packed with silica gel (8 g) eluting with hexane:ethyl acetate (100:0 to 0:100 over 30 min) and then with ethyl acetate:methanol (100:0 to 0:100 over 5 min) to afford the title compound as a colourless oil (74 mg, 50%).

NMR (CDCl$_3$, selected data for the free base): 1.57 (s, 3H), 1.75–1.90 (m, 4H), 2.18 (s, 3H), 2.58 (m, 2H), 2.79 (t, 2H), 2.82–3.12 (m, 7H), 6.78 (d, 1H), 7.00–7.15 (m, 4H), 7.25 (m, 1H).

MS (electrospray): M/Z (MH$^+$) 405; C$_{21}$H$_{28}$N$_2$O$_2$S$_2$+H requires 405.

EXAMPLE 120

N-(3-{3-[3-(4-methoxyphenyl)propyl]-6-methyl-3-azabicyclo[3.1.0]hex-6-yl}phenyl)methanesulfonamide

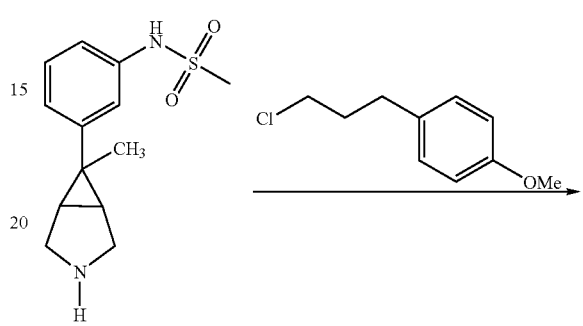

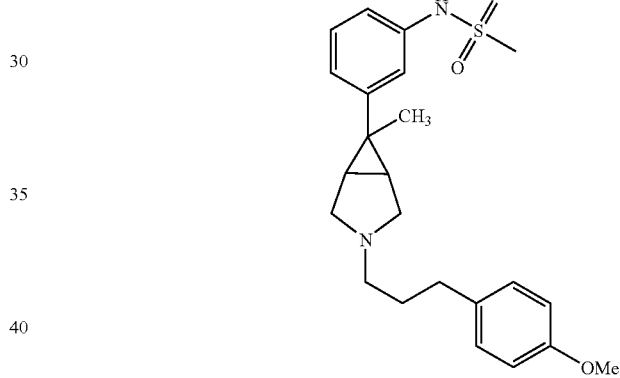

To a solution of the hydrochloride salt of N-[3-(6-methyl-3-azabicyclo[3.1.0]hex-6-yl)phenyl]methanesulfonamide (Preparation 53, 450 mg, 1.50 mmol) in N,N-dimethylformamide (20 ml) was added sodium hydrogen carbonate (375 mg, 4.50 mmol), 1-(3-chloropropyl)-4-methoxybenzene (274 mg, 1.50 mmol) and sodium iodide (35 mg) and the reaction was heated at 55° C. for 3 d. The reaction mixture was concentrated in vacuo and the residue was treated with water (15 ml) and extracted with ethyl acetate (2×20 ml). The combined organic extracts were washed with water (15 ml), dried (MgSO$_4$), filtered and concentrated in vacuo to afford 570 mg of a brown gum. This was purified by chromatography using a Biotage Flash 12™ cartridge packed with silica gel (8 g) eluting with dichloromethane:ethanol:0.880 ammonia (250:8:1) to afford the title compound as a colourless oil (37 mg, 6%).

NMR (CDCl$_3$, selected data for the free base): 1.55 (s, 3H), 1.70–1.85 (m, 4H), 2.52 (t, 2H), 2.60 (t, 2H), 2.83–3.08 (m, 7H), 3.80 (s, 3H), 6.82 (d, 2H), 7.00–7.15 (m, 5H), 7.24 (dd, 1H).

MS (thermospray): M/Z (MH$^+$) 415; C$_{23}$H$_{30}$N$_2$O$_3$S+H requires 415.

EXAMPLE 121

N-(3-{3-[3-(2-Chlorophenyl)propyl]-6-methyl-3-azabicyclo[3.1.0]hex-6-yl}phenyl)methanesulfonamide

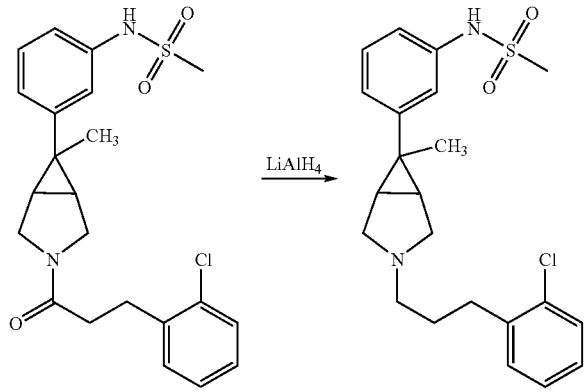

To a solution of N-(3-{3-[3-(2-chlorophenyl)propanoyl]-6-methyl-3-azabicyclo[3.1.0]hex-6-yl}phenyl)methanesulfonamide (Preparation 131, 100 mg, 0.231 mmol) in anhydrous tetrahydrofuran (2.5 ml) under a nitrogen atmosphere at 0° C. was added dropwise lithium aluminium hydride (1.0M solution in tetrahydrofuran, 0.25 ml, 0.25 mmol) and the reaction mixture was stirred at room temperature for 7 h. The rapidly stirred reaction mixture was treated sequentially with water (0.25 ml), sodium carbonate (250 mg) and ethyl acetate (2.5 ml). The reaction mixture was left to stir overnight and then was filtered and concentrated in vacuo. This was purified by chromatography using silica gel (2 g) eluting with ethyl acetate:hexane:0.880 ammonia (60:40:1) to afford the title compound as a colourless oil (77 mg, 80%).

NMR (CDCl$_3$, selected data): 1.58 (s, 3H), 1.70–1.80 (m, 4H), 2.52 (t, 2H), 2.65–2.82 (m, 4H), 3.00 (s, 3H), 3.03 (d, 2H), 7.00–7.38 (m, 8H).

MS (electrospray): M/Z (M+H$^+$) 419.2; C$_{22}$H$_{27}$ClN$_2$O$_2$S+H requires 419.2.

IR ?$_{max}$ (polyethylene card)/cm$^{-1}$: 1607 (w), 1472 (w), 1325 (m), 1156 (s).

EXAMPLE 122

N-(3-{6-Methyl-3-[(E)-3-(3-thienyl)-2-propenyl]-3-azabicyclo[3.1.0]hex-6-yl}phenyl)methanesulfonamide

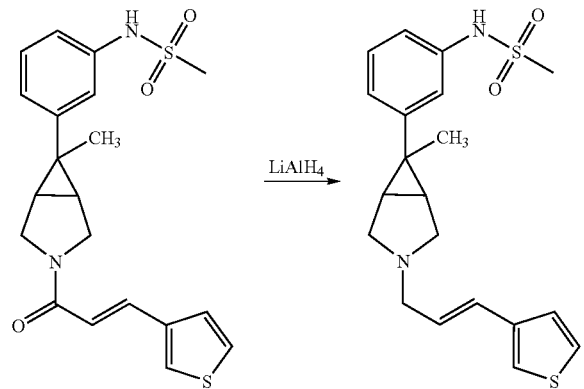

To a solution of N-(3-{6-methyl-3-[(E)-3-(3-thienyl)-2-propenoyl]-3-azabicyclo[3.1.0]hex-6-yl}phenyl)methanesulfonamide (Preparation 132, 100 mg, 0.248 mmol) in anhydrous tetrahydrofuran (2.5 ml) under a nitrogen atmosphere at 0° C. was added dropwise lithium aluminium hydride (1.0M solution in tetrahydrofuran, 0.25 ml, 0.25 mmol) and the reaction mixture was stirred at room temperature for 7 h. The rapidly stirred reaction mixture was treated sequentially with water (0.25 ml), sodium carbonate (250 mg) and ethyl acetate (2.5 ml). The reaction mixture was left to stir overnight and then was filtered and concentrated in vacuo. This was purified by chromatography using silica gel (2 g) eluting with ethyl acetate:hexane:0.880 ammonia (60:40:1) to afford the title compound as a colourless oil (32 mg, 33%).

NMR (CDCl$_3$, selected data): 1.58 (s, 3H), 1.78 (m, 2H), 2.42–2.95 (m, 2H), 3.00–3.10 (m, 5H), 3.25 (d, 2H), 6.05 (dt, 1H), 6.55 (d, 1H), 6.92–7.15 (m, 5H), 7.20–7.30 (m, 2H).

MS (electrospray): M/Z (MH$^+$) 389.1; C$_{20}$H$_{24}$N$_2$O$_2$S$_2$+H requires 389.1.

IR ?$_{max}$ (polyethylene card)/cm$^{-1}$: 1607 (w), 1472 (w), 1325 (m), 1155 (s), 971 (m).

EXAMPLE 123

N-(3-{6-Methyl-3-[(E)-3-(2-thienyl)-2-propenyl]-3-azabicyclo[3.1.0]hex-6-yl}phenyl)methanesulfonamide

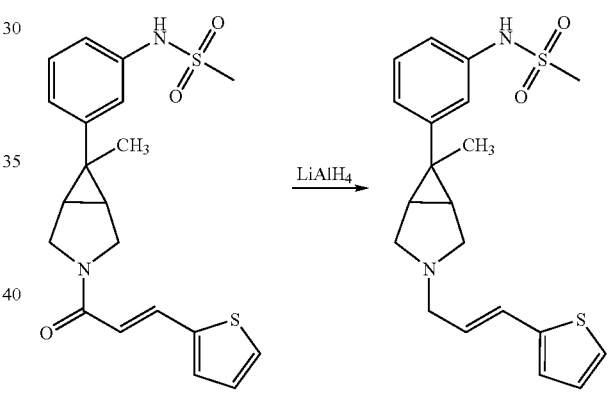

To a solution of N-(3-{6-methyl-3-[(E)-3-(2-thienyl)-2-propenoyl]-3-azabicyclo[3.1.0]hex-6-yl}phenyl)methanesulfonamide (Preparation 133, 100 mg, 0.248 mmol) in anhydrous tetrahydrofuran (2.5 ml) under a nitrogen atmosphere at 0° C. was added dropwise lithium aluminium hydride (1.0M solution in tetrahydrofuran, 0.25 ml, 0.25 mmol) and the reaction mixture was stirred at room temperature for 7 h. The rapidly stirred reaction mixture was treated sequentially with water (0.25 ml), sodium carbonate (250 mg) and ethyl acetate (2.5 ml). The reaction mixture was left to stir overnight and then was filtered and concentrated in vacuo. This was purified by chromatography using silica gel (2 g) eluting with ethyl acetate:hexane:0.880 ammonia (60:40:1) to afford the title compound as a pale yellow oil (67 mg, 69%).

NMR (CDCl$_3$, selected data): 1.58 (s, 3H), 1.80 (m, 2H), 2.95 (m, 2H), 3.00 (s, 3H), 3.04 (d, 2H), 3.23 (d, 2H), 6.10 (dt, 1H), 6.65 (d, 1H), 6.92–6.98 (m, 2H), 7.00–7.15 (m, 4H), 7.23 (m, 1H).

MS (electrospray): M/Z (M+H$^+$) 389.1; C$_{20}$H$_{24}$N$_2$O$_2$S$_2$+H requires 389.1.

IR ?$_{max}$ (polyethylene card)/cm$^{-1}$: 1607 (w), 1472 (w), 1325 (m), 1155 (s), 974 (m).

EXAMPLE 124

N-(3-{6-Methyl-3-[(E)-3-(3-methyl-2-thienyl)-2-propenyl]-3-azabicyclo[3.1.0]hex-6-yl}phenyl)methanesulfonamide

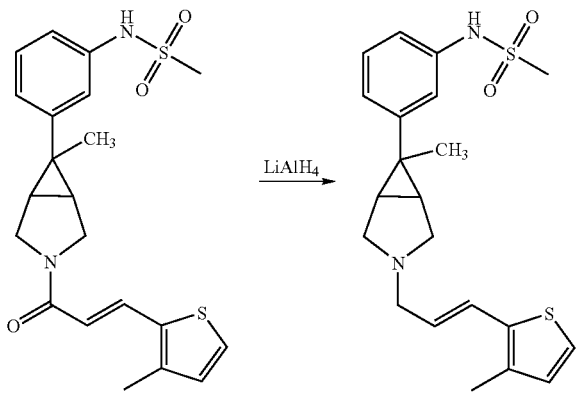

To a solution of N-(3-{6-methyl-3-[(E)-3-(3-methyl-2-thienyl)-2-propenoyl]-3-azabicyclo[3.1.0]hex-6-yl}phenyl)methanesulfonamide (Preparation 134, 100 mg, 0.240 mmol) in anhydrous tetrahydrofuran (2.5 ml) under a nitrogen atmosphere at 0° C. was added dropwise lithium aluminium hydride (1.0M solution in tetrahydrofuran, 0.25 ml, 0.25 mmol) and the reaction mixture was stirred at room temperature for 7 h. The rapidly stirred reaction mixture was treated sequentially with water (0.25 ml), sodium carbonate (250 mg) and ethyl acetate (2.5 ml). The reaction mixture was left to stir overnight and then was filtered and concentrated in vacuo. This was purified by chromatography using silica gel (2 g) eluting with ethyl acetate:hexane:0.880 ammonia (60:40:1) to afford the title compound as a very pale yellow oil (60 mg, 62%).

NMR (CDCl$_3$, selected data): 1.58 (s, 3H), 1.78 (m, 2H), 2.02 (s, 3H), 2.90 (m, 2H), 3.00 (s, 3H), 3.05 (d, 2H), 3.27 (d, 2H), 6.00 (dt,1H), 6.65 (d, 1H), 6.78 (d, 1H), 7.00–7.05 (m, 2H), 7.05–7.10 (m, 2H), 7.25 (m, 1H).

MS (electrospray): M/Z (M+H$^+$) 403.2; C$_{21}$H$_{26}$N$_2$O$_2$S$_2$+H requires 403.2.

IR ?$_{max}$ (polyethylene card)/cm$^{-1}$: 2360 (m), 1607 (w), 1472 (w), 1325 (m), 1155 (s), 975 (m).

EXAMPLE 125

N-(2-{3-Hexyl-6-methyl-3-azabicyclo[3.1.0]hex-6-yl}phenyl)methanesulfonamide

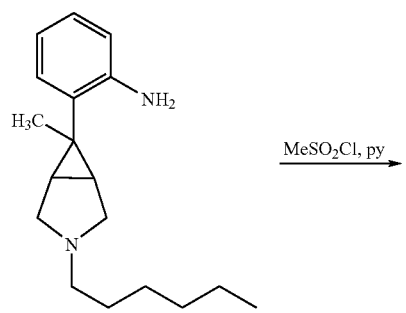

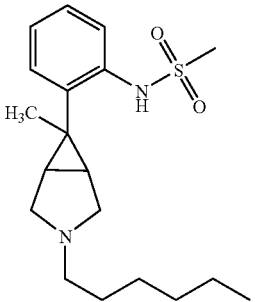

To a solution of 2-[3-hexyl-6-methyl-3-azabicyclo[3.1.0]hex-6-yl]phenylamine (Preparation 140, 30 mg, 0.11 mmol) in pyridine (1.0 ml) under a nitrogen atmosphere at room temperature was added dropwise methane sulfonyl chloride (13 μl, 0.16 mmol), and the reaction mixture was stirred at room temperature for 2 d. Ice (2 g) and dichloromethane (5 ml) were added, the layers were separated and the aqueous layer was further extracted with dichloromethane (5 ml). The combined extracts were dried (Na$_2$SO$_4$), filtered and concentrated in vacuo. This was purified by chromatography using silica gel (1.5 g) eluting with dichloromethane:ethanol:0.880 ammonia (200:8:1) to afford the title compound as a very pale yellow oil (5.2 mg, 14%).

NMR (CDCl$_3$, selected data): 0.88 (m, 3H), 1.20–1.40 (m, 6H), 2.18 (d, 1H), 2.40 (d, 1H), 3.15–3.30 (m, 4H), 3.38 (m, 1H), 7.14 (dd, 1H), 7.23 (s, 1H), 7.32 (dd, 1H), 7.55 (d, 1H).

EXAMPLE 126

N-(3-{6-Methyl-3-(3-phenylpropyl)-3-azabicyclo[3.1.0]hex-6-yl}phenyl)methanesulfonamide hydrochloride salt

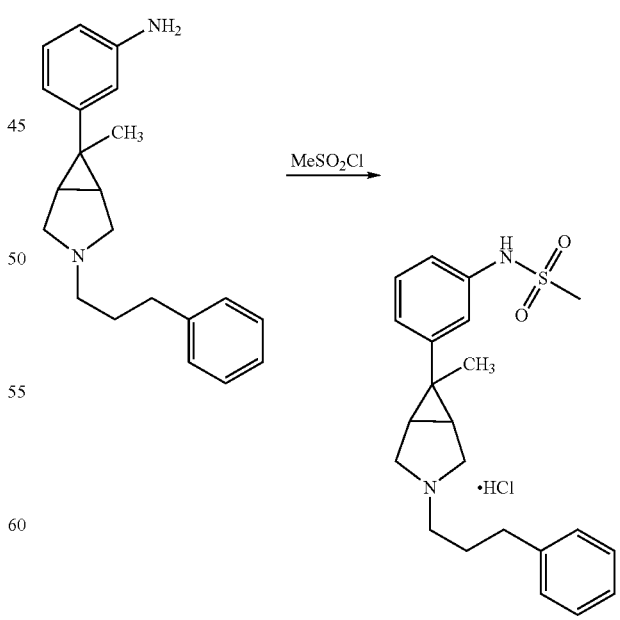

To a solution of 3-[6-methyl-3-(3-phenylpropyl)-3-azabicyclo[3.1.0]hex-6-yl]phenylamine (Preparation 8, 1.00 g, 3.26 mmol) in acetone (5 ml) at 0° C. was added methanesulfonyl chloride (0.28 ml, 3.58 mmol) and the reaction mixture was stirred at room temperature overnight. The resulting precipitate was collected by filtration to afford the title compound as a white crystalline solid (1.19 g, 87%).

Melting point 212–214° C.

MS (APCI): M/Z (MH⁺) 385.8; $C_{22}H_{28}N_2O_2S+H$ requires 385.2.

EXAMPLE 127

N-(3-{6-Methyl-3-(3-phenylpropyl)-3-azabicyclo[3.1.0]hex-6-yl}phenyl)methanesulfonamide benzenesulfonate salt

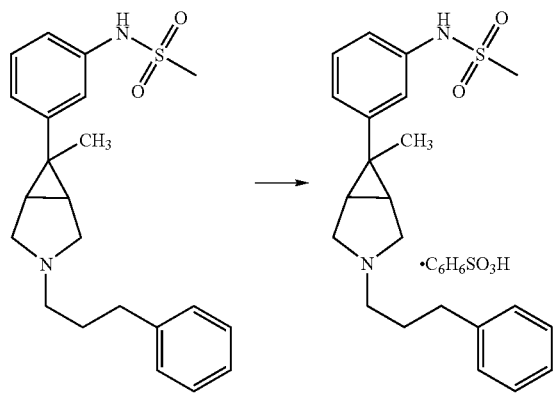

A solution of N-(3-{6-methyl-3-(3-phenylpropyl)-3-azabicyclo[3.1.0]hex-6-yl}phenyl)methanesulfonamide (Example 1, 53.88 g, 0.14 mol) in 2-butanone (480 ml) was heated under reflux. To the solution was added a solution of benzenesulfonic acid (22.17 g, 0.14 mol) in 2-butanone (50 ml) and the reaction mixture was heated under reflux for 30 min before cooling to 10° C. over a 2 h period. The resulting precipitate was collected by filtration to afford the title compound as a beige crystalline solid (73.55 g, 97%).

Melting point 166–168° C.

MS (APCI): M/Z (MH⁺) 385.7; $C_{22}H_{28}N_2O_2S+H$ requires 385.2.

EXAMPLE 128

N-(3-{6-Methyl-3-(3-phenylpropyl)-3-azabicyclo[3.1.0]hex-6-yl}phenyl)methanesulfonamide para-toluenesulfonate salt

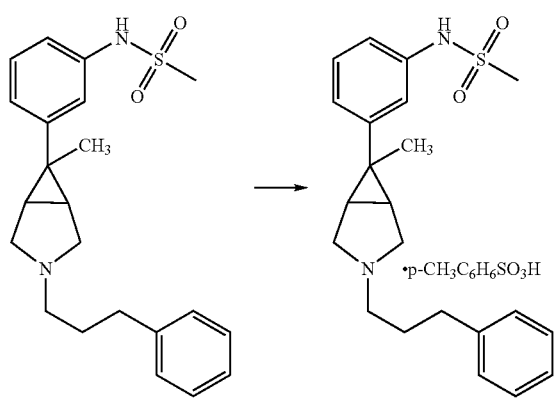

A solution of N-(3-{6-methyl-3-(3-phenylpropyl)-3-azabicyclo[3.1.0]hex-6-yl}phenyl)methanesulfonamide (Example 1, 25.00 g, 65 mmol) in ethyl acetate (250 ml) was heated under reflux. To the solution was added para-tolu-enesulfonic acid (12.36 g, 72 mmol) and the reaction mixture was heated under reflux for 60 min before cooling to 10° C. over a 2 h period. The resulting precipitate was collected by filtration to afford the title compound as a white solid (35.46 g, 95%).

Melting point 182–184° C.

MS (APCI): M/Z (MH⁺) 385.3; $C_{22}H_{28}N_2O_2S+H$ requires 385.2.

EXAMPLE 129

N-(3-{6-Methyl-3-(3-phenylpropyl)-3-azabicyclo[3.1.0]hex-6-yl}phenyl)methanesulfonamide L-tartrate salt

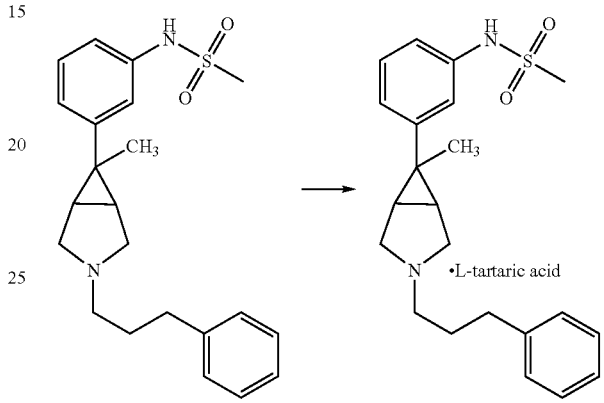

A solution of N-(3-{6-methyl-3-(3-phenylpropyl)-3-azabicyclo[3.1.0]hex-6-yl}phenyl)methanesulfonamide (Example 1, 2.00 g, 5.2 mmol) in Industrial Methylated Spirits (20 ml) was heated under reflux. To the solution was added L-tartaric acid (0.86 g, 5.8 mmol) and the reaction mixture was heated under reflux for 30 min before cooling to 10° C. over a 2 h period. The resulting precipitate was collected by filtration to afford the title compound as a white solid (1.40 g, 50%).

Melting point 162–164° C.

MS (APCI): M/Z (MH⁺) 385.5; $C_{22}H_{28}N_2O_2S+H$ requires 385.2.

EXAMPLE 130

N-(3-{6-Methyl-3-(3-phenylpropyl)-3-azabicyclo[3.1.0]hex-6-yl}phenyl)methanesulfonamide succinate salt

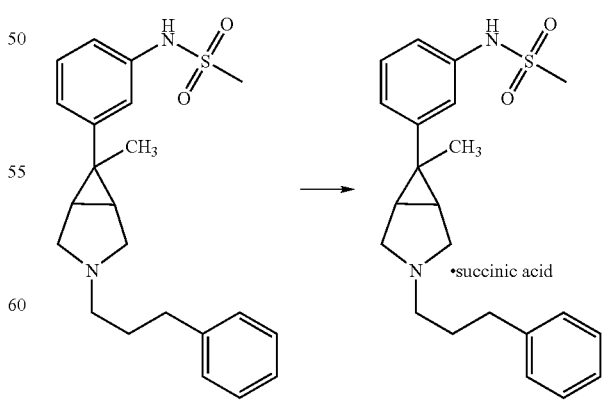

A solution of N-(3-{6-methyl-3-(3-phenylpropyl)-3-azabicyclo[3.1.0]hex-6-yl}phenyl)methanesulfonamide (Example 1, 2.00 g, 5.2 mmol) in Industrial Methylated Spirits (20 ml) was heated under reflux. To the solution was added succinic acid (0.68 g, 5.8 mmol) and the reaction mixture was heated under reflux for 30 min before cooling to 10° C. over a 2 h period. The resulting precipitate was collected by filtration to afford the title compound as a white solid (1.42 g, 54%).

Melting point 162–164° C.

MS (APCI): M/Z (MH$^+$) 385.4; $C_{22}H_{28}N_2O_2S$+H requires 385.2.

EXAMPLE 131

Formulation of N-(3-{6-methyl-3-(3-phenylpropyl)-3-azabicyclo[3.1.0]hex-6-yl}phenyl)methanesulfonamide A composition suitable for intravenous administration is as follows:

| | |
|---|---|
| N-(3-{6-Methyl-3-(3-phenylpropyl)-3-azabicyclo[3.1.0]hex-6-yl}phenyl)methanesulfonamide acetate salt (Example 2) | 45 mg |
| Dimethylsulfoxide | 2.02 ml |
| 0.9% w:v Aqueous sodium chloride solution | 42.98 ml |

EXAMPLE 132

Formulation of N-(3-{6-methyl-3-(3-phenylpropyl)-3-azabicyclo[3.1.0]hex-6-yl}phenyl)methanesulfonamide A composition suitable for oral capsule administration is as follows:

| | |
|---|---|
| N-(3-{6-Methyl-3-(3-phenylpropyl)-3-azabicyclo[3.1.0]hex-6-yl}phenyl)methanesulfonamide hydrochloride salt (Example 126) | 59.4 mg |
| Tetragylcol | 2.715 ml |
| Polyethyleneglycol 400 | 2.715 ml |

A suspension of N-(3-{6-methyl-3-(3-phenylpropyl)-3-azabicyclo[3.1.0]hex-6-yl}phenyl)methanesulfonamide hydrochloride salt (Example 126) in 50:50 tetragylcol:polyethylene glycol 400 was placed on a Denley Spiromix 5™ overnight to afford a solution. The solution was placed in a hard gelatin capsule shell, size 0, and the capsule lid was placed on the capsule body and sealed tight.

EXAMPLE 133

Formulation of N-(3-{6-methyl-3-(3-phenylpropyl)-3-azabicyclo[3.1.0]hex-6-yl}phenyl)methanesulfonamide A composition suitable for oral gavage administration is as follows:

| | |
|---|---|
| N-(3-{6-Methyl-3-(3-phenylpropyl)-3-azabicyclo[3.1.0]hex-6-yl}phenyl)methanesulfonamide para-toluenesulfonate salt (Example 128) | 140 mg |
| Propylene glycol | 70 ml |

EXAMPLE 134

Formulation of N-(3-{3-hexyl-6-methyl-3-azabicyclo[3.1.0]hex-6-yl}phenyl)methanesulfonamide

| | |
|---|---|
| N-(3-{3-Hexyl-6-methyl-3-azabicyclo[3.1.0]hex-6-yl}phenyl)methanesulfonamide hydrochloride salt (Example 6) | 80 mg |
| Propylene glycol | 40 ml |

EXAMPLE 135

Formulation of N-(3-{3-(3-cyclohexylpropyl)-6-methyl-3-azabicyclo[3.1.0]hex-6-yl}phenyl)ethanesulfonamide

| | |
|---|---|
| N-(3-{3-(3-Cyclohexylpropyl)-6-methyl-3-azabicyclo[3.1.0]hex-6-yl}phenyl)ethanesulfonamide hydrochloride salt (Example 5) | 70 mg |
| Water | 35 ml |

EXAMPLE 136

N-(3-{6-Methyl-3-[(E)-3-(2-pyridinyl)-2-prolpenyl]-3-azabicyclo[3.1.0]hex-6-yl}phenyl)methanesulfonamide

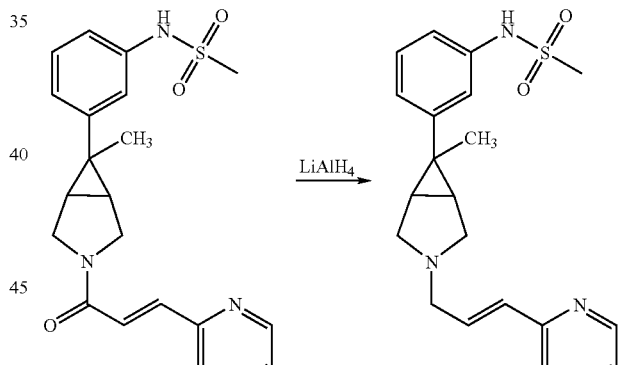

To a solution of N-(3-{6-methyl-3-[(E)-3-(2-pyridinyl)-2-propenoyl]-3-azabicyclo[3.1.0]hex-6-yl}phenyl)methanesulfonamide (Preparation 141, 172 mg, 0.43 mmol) in anhydrous tetrahydrofuran (2.5 ml) under a nitrogen atmosphere at room temperature was added dropwise lithium aluminium hydride (1.0M solution in tetrahydrofuran, 0.50 ml, 0.50 mmol) and the reaction mixture was stirred at room temperature for 2 h. The rapidly stirred reaction mixture was treated sequentially with water (0.5 ml), sodium carbonate (0.5 g) and ethyl acetate (5 ml). The reaction mixture was left to stir for 1 h 30 min, filtered, solid washed with methanol (5 ml) and combined filtrate concentrated using a stream of nitrogen to afford 215 mg of a pale brown oil. This was purified by chromatography using a Biotage Flash 40S™ cartridge packed with silica gel (40 g) eluting with dichloromethane:ethanol:0.880 ammonia (300:8:1) to afford the title compound as a pale brown oil (78 mg, 47%).

NMR (CDCl₃, selected data): 1.58 (s, 3H), 1.78 (br. s, 2H), 2.90 (br. d, 2H), 3.00 (s, 3H), 3.12 (d, 2H), 3.37 (d, 2H), 6.60–6.70 (m, 2H), 7.00 (d, 1H), 7.05–7.15 (m, 3H), 7.20–7.35 (m, 2H), 7.62 (dd, 1H), 8.57 (d, 1H).

MS (electrospray): M/Z (MH$^+$) 384.3; $C_{21}H_{25}N_3O_2S$+H requires 384.2.

EXAMPLE 137

N-(3-{6-Methyl-3-[(E)-3-(2-quinolinyl)-2-propenyl]-3-azabicyclo[3.1.0]hex-6-yl}phenyl)methanesulfonamide

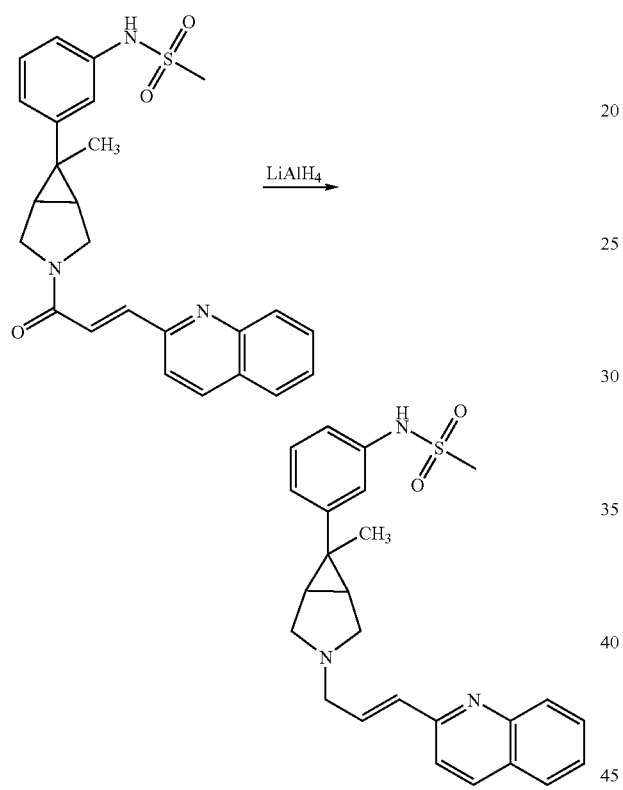

To a solution of N-(3-{6-methyl-3-[(E)-3-(2-quinolinyl)-2-propenoyl]-3-azabicyclo[3.1.0]hex-6-yl}phenyl)methanesulfonamide (Preparation 142, 206 mg, 0.46 mmol) in anhydrous tetrahydrofuran (2.5 ml) under a nitrogen atmosphere at room temperature was added dropwise lithium aluminium hydride (1.0M solution in tetrahydrofuran, 0.50 ml, 0.50 mmol) and the reaction mixture was stirred at room temperature for 2 h. The rapidly stirred reaction mixture was treated sequentially with water (0.5 ml), sodium carbonate (0.5 g) and ethyl acetate (5 ml). The reaction mixture was left to stir for 1 h 30 min, filtered, solid washed with methanol (5 ml) and combined filtrate concentrated using a stream of nitrogen to afford 221 mg of a pale brown oil. This was purified by chromatography using a Biotage Flash 40S™ cartridge packed with silica gel (40 g) eluting with dichloromethane:ethanol:0.880 ammonia (300:8:1) to afford the title compound as a dark yellow oil (84 mg, 42%).

NMR (CDCl₃, selected data): 1.58 (s, 3H), 1.79 (br. s, 2H), 2.92 (d, 2H), 3.00 (s, 3H), 3.13 (d, 2H), 3.42 (d, 2H), 6.80–6.88 (m, 2H), 7.00 (d, 1H), 7.05–7.10 (m, 2H), 7.23 (m, 1H), 7.47 (dd, 1H), 7.56 (d, 1H), 7.68 (dd, 1H), 7.75 (d, 1H), 8.05 (d, 1H), 8.10 (d, 1H).

MS (electrospray): M/Z (MH$^+$) 434.3; $C_{25}H_{27}N_3O_2S$+H requires 434.2.

EXAMPLE 138

N-(3-{3-[3-(1,3-Benzothiazol-2-yl)propyl]-6-methyl-3-azabicyclo[3.1.0]hex-6-yl}phenyl)methanesulfonamide

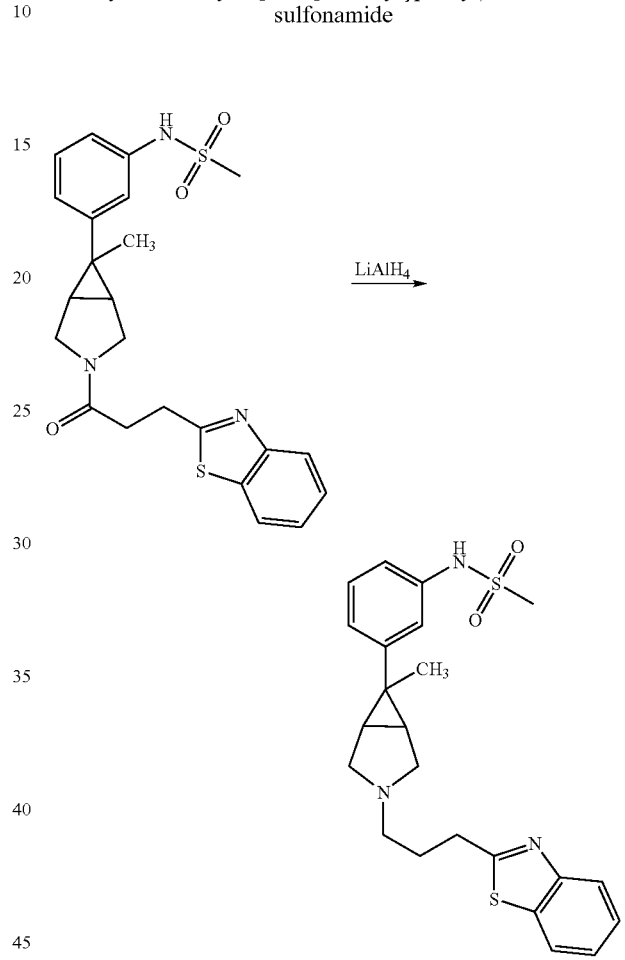

To a solution of N-(3-{3-[3-(1,3-benzothiazol-2-yl)propanoyl]-6-methyl-3-azabicyclo[3.1.0]hex-6-yl}phenyl)methanesulfonamide (Preparation 143, 228 mg, 0.50 mmol) in anhydrous tetrahydrofuran (2.5 ml) under a nitrogen atmosphere at room temperature was added dropwise lithium aluminium hydride (1.0M solution in tetrahydrofuran, 0.50 ml, 0.50 mmol) and the reaction mixture was stirred at room temperature for 2 h. The rapidly stirred reaction mixture was treated sequentially with water (0.5 ml), sodium carbonate (0.5 g) and ethyl acetate (5 ml). The reaction mixture was left to stir for 1 h 30 min, filtered, solid washed with methanol (5 ml) and combined filtrate concentrated using a stream of nitrogen to afford 650 mg of a pale brown oil. This was purified by chromatography using a Biotage Flash 40S™ cartridge packed with silica gel (40 g) eluting with dichloromethane:ethanol:0.880 ammonia (300:8:1) to afford the title compound as a yellow oil (198 mg, 90%).

NMR (CDCl₃, selected data): 1.58 (s, 3H), 1.76 (m, 2H), 2.02 (dd, 2H), 2.60 (dd, 2H), 2.80 (br. d, 2H), 3.00 (s, 3H), 3.10 (d, 2H), 3.16 (dd, 2H), 7.00 (d, 1H), 7.05–7.10 (m, 2H), 7.23 (m, 1H), 7.35 (dd, 1H), 7.45 (dd, 1H), 7.83 (d, 1H), 7.96 (d, 1H).

MS (electrospray): M/Z (MH$^+$) 442.3; $C_{23}H_{27}N_3O_2S$+H requires 442.2.

EXAMPLE 139

N-(3-{6-Methyl-3-[(E)-3-(6-methyl-2-pyridinyl)-2-propenyl]-3-azabicyclo[3.1.0]hex-6-yl}phenyl)methanesulfonamide

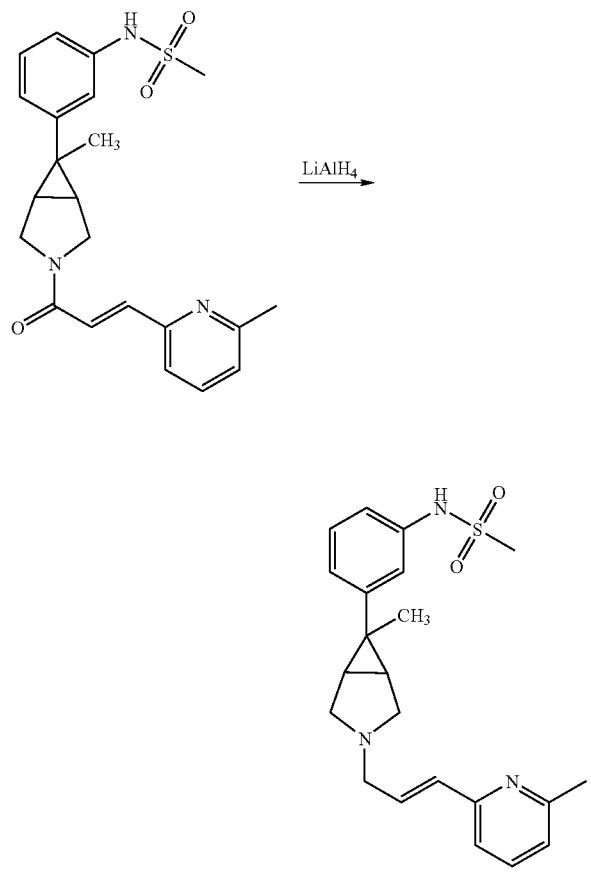

To a solution of N-(3-{6-methyl-3-[(E)-3-(6-methyl-2-pyridinyl)-2-propenoyl]-3-azabicyclo[3.1.0]hex-6-yl}phenyl)methanesulfonamide (Preparation 144, 191 mg, 0.46 mmol) in anhydrous tetrahydrofuran (2.5 ml) under a nitrogen atmosphere at room temperature was added dropwise lithium aluminium hydride (1.0M solution in tetrahydrofuran, 0.50 ml, 0.50 mmol) and the reaction mixture was stirred at room temperature for 2 h. The rapidly stirred reaction mixture was treated sequentially with water (0.5 ml), sodium carbonate (0.5 g) and ethyl acetate (5 ml). The reaction mixture was left to stir for 1 h 30 min, filtered, solid washed with methanol (5 ml) and combined filtrate concentrated using a stream of nitrogen to afford 221 mg of a dark yellow oil. This was purified by chromatography using a Biotage Flash 40S™ cartridge packed with silica gel (40 g) eluting with dichloromethane:ethanol:0.880 ammonia (300:8:1) to afford the title compound as a pale brown oil (102 mg, 56%).

NMR (CDCl$_3$, selected data): 1.58 (s, 3H), 1.78 (br. s, 2H), 2.55 (s, 3H), 2.90 (d, 2H), 3.00 (s, 3H), 3.08 (d, 2H), 3.35 (d, 2H), 6.63–6.69 (m, 2H), 6.97–7.03 (m, 2H), 7.05–7.10 (m, 2H), 7.15 (d, 1H), 7.23 (m, 1H), 7.53 (dd, 1H).

MS (electrospray): M/Z (MH$^+$) 398.3; $C_{22}H_{27}N_3O_2S$+H requires 398.2.

EXAMPLE 140

N-[3-(6-Methyl-3-{(E)-3-[2-(trifluoromethyl)phenyl]-2-propenyl}-3-azabicyclo[3.1.0]hex-6-yl)phenyl]methanesulfonamide

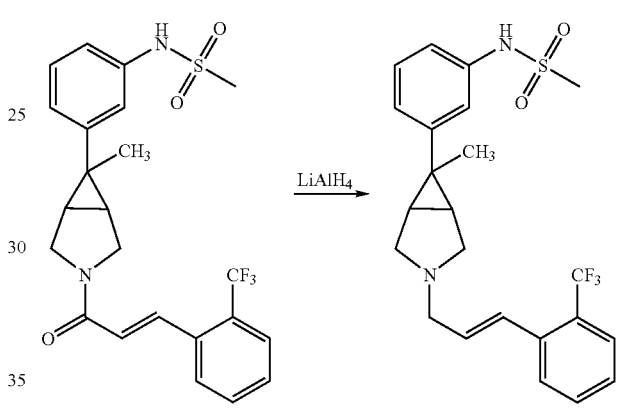

To a solution of N-[3-(6-methyl-3-{(E)-3-[2-(trifluoromethyl)phenyl]-2-propenoyl}-3-azabicyclo[3.1.0]hex-6-yl)phenyl]methanesulfonamide (Preparation 145, 240 mg, 0.52 mmol) in anhydrous tetrahydrofuran (2.5 ml) under a nitrogen atmosphere at room temperature was added dropwise lithium aluminium hydride (1.0M solution in tetrahydrofuran, 0.55 ml, 0.55 mmol) and the reaction mixture was stirred at room temperature for 5 h. A further addition of lithium aluminium hydride (1.0M solution in tetrahydrofuran, 0.50 ml, 0.50 mmol) was made dropwise and the reaction mixture was left a further 30 min. The rapidly stirred reaction mixture was treated sequentially with water (1.0 ml), sodium carbonate (1.0 g) and ethyl acetate (5 ml). The reaction mixture was left to stir for 1 h 30 min, filtered, solid washed with methanol (5 ml) and combined filtrate concentrated using a stream of nitrogen to afford 689 mg of a pale yellow oil. This was purified by chromatography using a Biotage Flash 40S™ cartridge packed with silica gel (40 g) eluting with dichloromethane:ethanol:0.880 ammonia (600:8:1) to afford the title compound as a pale yellow oil (77 mg, 33%).

NMR (CDCl$_3$, selected data): 1.58 (s, 3H), 1.76 (m, 2H), 2.55 (dd, 1H), 2.80 (dd, 1H), 2.88 (d, 1H), 3.00 (s, 3H), 3.07–3.13 (m, 2H), 3.33 (d, 1H), 6.22 (ddd, 1H), 6.95 (d, 1H), 7.02 (d, 1H), 7.05–7.12 (m, 2H), 7.24–7.28 (m, 2H), 7.33 (dd, 1H), 7.49 (dd, 1H), 7.62 (d, 1H).

MS (electrospray): M/Z (MH$^+$) 451.4; $C_{23}H_{25}{}^{19}F_3N_2O_2S$+H requires 451.2.

EXAMPLE 141

N-(3-{3-[3-(2,6-Dichlorophenyl)propyl]-6-methyl-3-azabicyclo[3.1.0]hex-6-yl}phenyl)methanesulfonamide

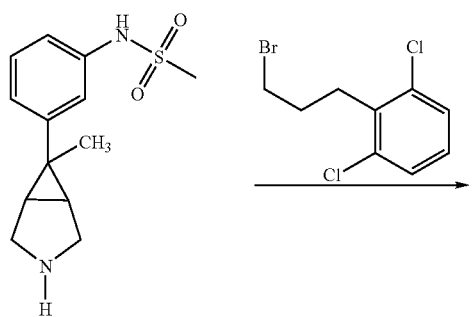

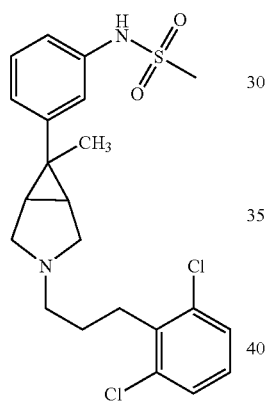

To a solution of the hydrochloride salt of N-[3-(6-methyl-3-azabicyclo[3.1.0]hex-6-yl)phenyl]methanesulfonamide (Preparation 53, 226 mg, 0.746 mmol) in N,N-dimethylformamide (10 ml) was added 2-(3-bromopropyl)-1,3-dichlorobenzene (J. Augstein et al., J. Med. Chem., 1967, 10, 391; 200 mg, 0.746 mmol) and sodium hydrogen carbonate (187 mg 2.238 mmol). The reaction mixture was heated at 80° C. for overnight before allowing to cool to room temperature. The mixture was concentrated in vacuo and the residue was partitioned between water (10 ml) and ethyl acetate (15 ml). The organic extract was dried (Na$_2$SO$_4$), filtered and concentrated in vacuo to give a brown oil (325 mg). The residue was purified by silica (5 g) gel chromatography eluting with dichloromethane:ethanol:0.880 ammonia (250:8:1) to afford the title compound as a pale yellow oil (42 mg, 13%).

NMR (CDCl$_3$, selected data for the free base): 1.58 (s, 3H), 1.65–1.80 (m, 4H), 2.60 (t, 2H), 2.85 (br. m, 2H), 2.97 (d, 2H), 3.00 (s, 3H), 3.15 (d, 2H), 7.00–7.15 (m, 4H), 7.22–7.30 (m, 3H).

MS (electrospray): M/Z (MH$^+$) 453; C$_{22}$H$_{26}$Cl$_2$N$_2$O$_2$S+H requires 453.

EXAMPLE 142

N-{3-[6-Methyl-3-(4-phenylbutyl)-3-azabicyclo[3.1.0]hex-6-yl]phenyl}methanesulfonamide

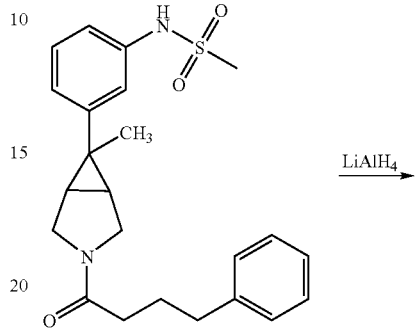

To a solution of N-{3-[6-methyl-3-(4-phenylbutanoyl)-3-azabicyclo[3.1.0]hex-6-yl]phenyl}methanesulfonamide (Preparation 146, 100 mg, 0.24 mmol) in anhydrous tetrahydrofuran (2.5 ml) under a nitrogen atmosphere at 0° C. was added dropwise lithium aluminium hydride (1.0M solution in tetrahydrofuran, 0.48 ml, 0.48 mmol) and the reaction mixture was stirred at room temperature overnight. The rapidly stirred reaction mixture was treated sequentially with water (0.48 ml), sodium carbonate (500 mg) and ethyl acetate (10 ml). The reaction mixture was left to stir for 15 min filtered, solid washed with ethyl acetate (10 ml) and combined filtrate concentrated in vacuo to afford 102 mg of a pale yellow oil. The residue was purified by silica (4 g) gel chromatography eluting with dichloromethane:ethanol: 0.880 ammonia (250:8:1) to afford the title compound as a pale yellow oil (80 mg, 84%).

NMR (CDCl$_3$, selected data): 1.45–1.58 (m, 5H), 1.66 (dd, 2H), 1.75 (m, 2H), 2.48 (t, 2H), 2.63 (t, 2H), 2.80 (br. d, 2H), 2.95–3.00 (m, 5H), 7.00–7.12 (m, 3H), 7.15–7.32 (m, 6H).

MS (electrospray): M/Z (MH$^+$) 398.8; C$_{23}$H$_{30}$N$_2$O$_2$S+H requires 399.2.

EXAMPLE 143

N-(3-{3-[3-(2-Methoxyphenyl)propyl]-6-methyl-3-azabicyclo[3.1.0]hex-6-yl}phenyl)methanesulfonamide

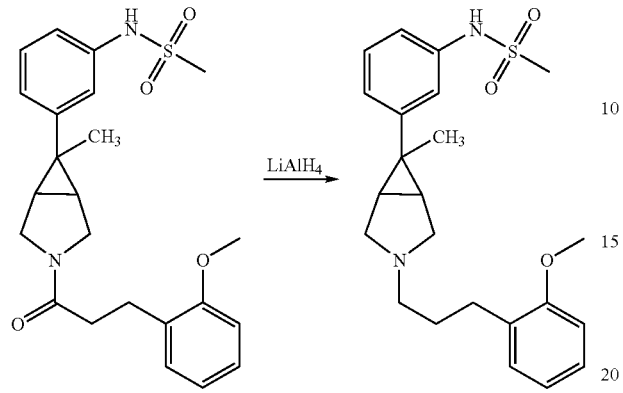

To a solution of N-(3-{3-[3-(2-methoxyphenyl)propanoyl]-6-methyl-3-azabicyclo[3.1.0]hex-6-yl}phenyl) methanesulfonamide (Preparation 147, 100 mg, 0.234 mmol) in anhydrous tetrahydrofuran (2.5 ml) under a nitrogen atmosphere at 0° C. was added dropwise lithium aluminium hydride (1.0M solution in tetrahydrofuran, 0.47 ml, 0.47 mmol) and the reaction mixture was stirred at room temperature overnight. The rapidly stirred reaction mixture was treated sequentially with water (0.47 ml), sodium carbonate (500 mg) and ethyl acetate (10 ml). The reaction mixture was left to stir for 15 min, filtered, solid washed with ethyl acetate (10 ml) and combined filtrate concentrated in vacuo to afford 103 mg of a pale yellow oil. The residue was purified by silica (4 g) gel chromatography eluting with dichloromethane:ethanol:0.880 ammonia (250:8:1) to afford the title compound as a colourless oil (86 mg, 89%).

NMR (CDCl$_3$, selected data): 1.55 (s, 3H), 1.70–1.85 (m, 4H), 2.50 (t, 2H), 2.65 (t, 2H), 2.80 (m, 2H), 3.00–3.10 (m, 5H), 3.80 (s, 3H), 6.80–6.95 (m, 2H), 7.00–7.30 (m, 6H).

MS (thermospray): M/Z (MH$^+$) 415.1; $C_{23}H_{30}N_2O_3S$+H requires 415.2.

EXAMPLE 144

N-{3-[3-(1-Benzothiophen-2-ylmethyl)-6-methyl-3-azabicyclo[3.1.0]hex-6-yl]phenyl}methanesulfonamide

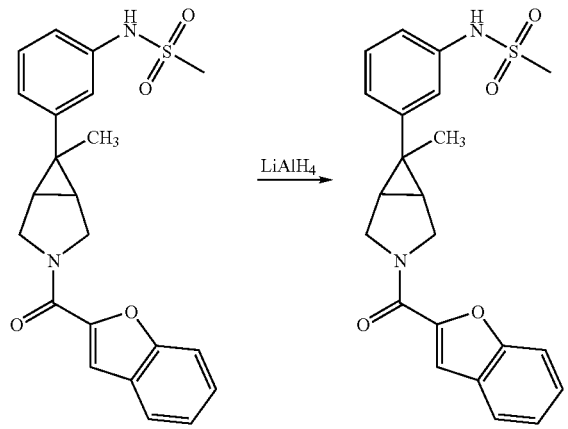

To a solution of N-{3-[3-(1-benzothiophen-2-ylcarbonyl)-6-methyl-3-azabicyclo[3.1.0]hex-6-yl]phenyl}methanesulfonamide (Preparation 148, 100 mg, 0.235 mmol) in anhydrous tetrahydrofuran (2.5 ml) under a nitrogen atmosphere at 0° C. was added dropwise lithium aluminium hydride (1.0M solution in tetrahydrofuran, 0.47 ml, 0.47 mmol) and the reaction mixture was stirred at room temperature overnight. The rapidly stirred reaction mixture was treated sequentially with water (0.47 ml), sodium carbonate (500 mg) and ethyl acetate (10 ml). The reaction mixture was left to stir for 15 min, filtered, solid washed with ethyl acetate (10 ml) and combined filtrate concentrated in vacuo to afford 104 mg of a light yellow oil. The residue was purified by silica (4 g) gel chromatography eluting with hexane:ethyl acetate:0.880 ammonia (50:50:1) to afford the title compound as a colourless oil (74 mg, 76%).

NMR (CDCl$_3$, selected data): 1.60 (s, 3H), 1.80 (br. s, 2H), 2.88 (m, 2H), 3.00 (s, 3H), 3.98 (br. s, 2H), 7.00–7.20 (m, 3H), 7.25–7.40 (m, 4H), 7.70 (d, 1H), 7.80 (d, 1H).

MS (electrospray): M/Z (MH$^+$) 413.2; $C_{22}H_{24}N_2O_2S_2$+H requires 413.1.

PREPARATION 1

Ethyl (E)-3-(3-nitrophenyl)-2-butenoate

To a solution of sodium hydride (60% dispersion in oil, 20 g, 0.5 mol) in tetrahydrofuran (1 l) stirred at –10° C. under nitrogen was added dropwise over 30 minutes triethylphosphonoacetate (112 g, 0.5 mol). A further portion of sodium hydride (60% dispersion in oil, 20 g, 0.5 mol) and tetrahydrofuran (1 l) was added followed by dropwise addition of triethylphosphonoacetate (112 g, 0.5 mol) over 30 minutes. 3-Nitroacetophenone (165 g, 1 mol) was added portionwise such that the temperature was maintained below 10° C. The mixture was allowed to warm to room temperature and was stirred for 1 h. Water (2 l) was added, and the mixture was extracted with diethyl ether (2×1 l). The combined extracts were washed with water (1 l), dried (MgSO$_4$), filtered and concentrated in vacuo. The residue was recrystallised from isopropanol to give a first crop of the title compound as a white solid (90 g, 38%).

mp 43–44° C.

NMR (CDCl$_3$) δ: 1.34 (t, 3H), 2.60 (s, 3H), 4.25 (q, 2H), 6.20 (s, 1H), 7.56 (t, 1H), 7.80 (d, 1H), 8.22 (d, 1H), 8.33 (s, 1H)

MS (thermospray): M/Z [MNH$_4^+$] 253.1; $C_{12}H_{13}NO_4$+NH$_4$ requires 253.1

PREPARATION 2

(E)-3-(3-Nitrophenyl)-2-buten-1-ol

To a solution of ethyl (E)-3-(3-nitrophenyl)-2-butenoate (Preparation 1, 102 g, 0.43 mol) in toluene (1400 ml) at –10° C. under nitrogen was added dropwise over 3 h diisobutylaluminium hydride (1.0 M in toluene, 1 l), then the mixture was stirred at 0° C. for 1 h. Water (400 ml) was carefully added, followed by sodium hydrogen carbonate (300 g). The resulting slurry was vigorously stirred for 10 min, then ethyl acetate (2 l) was added, and the mixture stirred for 1 h. The mixture was dried (MgSO$_4$), filtered and concentrated in vacuo to give the title compound as a pale brown oil (81 g, 97%).

NMR (CDCl$_3$) δ: 2.11 (s, 3H), 4.41 (d, 2H), 6.08 (t, 1H), 7.48 (t, 1H), 7.72 (d, 1H), 8.10 (d, 1H), 8.25 (s, 1H).

MS (thermospray): M/Z [MH$^+$] 194.1; $C_{10}H_{11}NO_3$+H requires 194.1

PREPARATION 3

1-[(E)-3-Chloro-1-methyl-1-propenyl]-3-nitrobenzene

To a solution of N-chlorosuccinimide (52.3 g, 0.39 mol) in dichloromethane (800 ml) at 0° C. was added dropwise over 1 h dimethylsulfide (27.9 ml, 0.38 mol). To the mixture was added dropwise over 30 min at 0° C. a solution of (E)-3-(3-nitrophenyl)-2-buten-1-ol (Preparation 2, 72 g, 0.373 mol) in dichloromethane (200 ml). The mixture was warmed to room temperature over 1 h, then poured onto brine (500 ml). The layers were separated, and the aqueous layer extracted with ether (500 ml). The organic extracts were combined, dried ($MgSO_4$), filtered and concentrated in vacuo. The residue was purified by silica column chromatography, eluting with 10:1 hexane/ethyl acetate, then as a gradient up to 4:1 hexane/ethyl acetate. Appropriate fractions were combined and concentrated in vacuo to give the title compound as a very pale yellow solid (69 g, 88%).
mp 46–47° C.
NMR ($CDCl_3$) δ: 2.20 (s, 3H), 4.27 (d, 2H) 6.10 (t, 1H), 7.52 (t, 1H), 7.73 (d, 1H), 8.13 (d, 1H), 8.26 (s, 1H).

PREPARATION 4

1-[(E)-3-Bromo-1-methyl-1-propenyl]-3-nitrobenzene

To a solution of triphenylphosphine (5.15 g, 19.7 mmol) in acetonitrile (140 ml) was added dropwise over 5 minutes a solution of bromine (3.15 g, 19.7 mmol) in acetonitrile (5 ml) at a rate such that the temperature did not exceed −10° C. The mixture was allowed to warm to room temperature, then to this was added a solution of (E)-3-(3-nitrophenyl)-2-buten-1-ol (Preparation 2, 4 g, 20.7 mmol) in acetonitrile (5 ml). The mixture was warmed gently to 65° C. for 1 h, cooled to room temperature and then poured onto diethyl ether (50 ml). The mixture was concentrated in vacuo, then diethyl ether (200 ml) was added. The mixture was filtered, concentrated again in vacuo and the residue purified by silica column (300 g) chromatography, eluting with 3:1 hexane/dichloromethane then 1:1 hexane/dichloromethane. Appropriate fractions were combined and concentrated in vacuo to give the title compound as a very pale yellow oil (4 g, 75%).
NMR ($CDCl_3$) δ: 2.20 (s, 3H), 4.20 (d, 2H) 6.20 (t, 1H), 7.51 (t, 1H), 7.73 (d, 1H), 8.13 (d, 1H), 8.26 (s, 1H).

PREPARATION 5

Ethyl 3-(chloromethyl)-2-methyl-2-(3-nitrophenyl) cyclopropanecarboxylate

To a solution of 1-[(E)-3-chloro-1-methyl-1-propenyl]-3-nitrobenzene (Preparation 3, 36 g, 0.17 mol) in dichloromethane (50 ml) was added rhodium (II) acetate dimer (1 g, 2.3 mmol). To the mixture was added dropwise at room temperature over 8 h a solution of ethyl diazoacetate (50 ml, 54.25 g, 0.475 mol) in dichloromethane (50 ml), then the mixture was stirred at room temperature for 16 h. To the mixture was added dropwise at room temperature over 7 h a further solution of ethyl diazoacetate (50 ml, 54.25 g, 0.475 mol) in dichloromethane (50 ml), then the mixture was stirred at room temperature for a further 16 h. The mixture was concentrated in vacuo and the residue purified by silica column (1 kg) chromatography, eluting with 1:1 hexane/dichloromethane then dichloromethane. Product-containing fractions were combined and concentrated in vacuo, then concentrated under a stream of nitrogen for 16 h. The residue was purified further by silica column (2 kg) chromatography, eluting with 1:1 hexane/dichloromethane then dichloromethane. Product containing fractions were combined and concentrated in vacuo, to give the title compound as a very pale yellow oil (14.2 g, 29%).
NMR ($CDCl_3$) δ: 1.34 (t, 3H), 1.60 (s, 3H), 2.01 (m, 1H), 2.20 (d, 1H), 4.03 (dd, 11H), 4.15–4.27 (m, 3H), 7.50 (t, 1H), 7.69 (d, 1H), 8.10 (d, 1H), 8.19 (s, 1H)

PREPARATION 6

Ethyl 3-(bromomethyl)-2-methyl-2-(3-nitrophenyl) cyclopropane carboxulate

To a solution of 1-[(E)-3-bromo-1-methyl-1-propenyl]-3-nitrobenzene (Preparation 4, 4 g, 15.6 mmol) in dichloromethane (5 ml) was added rhodium (II) acetate dimer (100 mg, 0.22 mmol). To the mixture was added dropwise at room temperature over 4.5 h a solution of ethyl diazoacetate (3.1 ml, 2.84 g, 25 mmol) in dichloromethane (15 ml). The mixture was filtered, concentrated in vacuo, and the residue purified by silica column (100 g) chromatography, eluting with 2:1 hexane/dichloromethane then dichloromethane. Product-containing fractions were combined and concentrated in vacuo, then purified further by preparative HPLC (Condition 1). Combination and evaporation of appropriate fractions gave the title compound as a colourless oil (0.5 g, 11%).
NMR ($CDCl_3$) δ: 1.34 (t, 3H), 1.60 (s, 3H), 2.10 (m, 1H), 2.22 (d, 1H), 3.88 (dd, 1H), 4.06 (t, 1H), 4.23 (m, 2H), 7.50 (t, 11H), 7.72 (d, 1H), 8.12 (d, 1H), 8.22 (s, 1H).

PREPARATION 7

6-Methyl-6-(3-nitrophenyl)-3-(3-phenylpropyl)-3-azabicyclo[3.1.0]hexan-2-one To a solution of ethyl 3-(chloromethyl)-2-methyl-2-(3-nitrophenyl)cyclopropane carboxylate (Preparation 5, 14.4 g, 48.6 mmol), in N,N-dimethylformamide (120 ml) was added sodium hydrogen carbonate (12 g, 143 mmol) and 3-phenylpropylamine (38.8 g, 41 ml, 290 mmol). The mixture was heated to 150° C. for 7 h, then cooled to room temperature and poured onto water (1000 ml). The mixture was extracted with diethyl ether (2×500 ml), and the combined extracts were washed with water (2×250 ml), dried ($Na_2SO_4$), filtered and concentrated in vacuo. The residue was purified by silica (1000 g) column chromatography eluting with dichloromethane then dichloromethane/ethyl acetate 4:1. Product-containing fractions were combined and concentrated in vacuo to give the title compound as a very pale yellow oil (6.2 g, 36%).
NMR ($CDCl_3$) δ: 1.37 (s, 3H), 1.88 (p, 2H), 2.16 (t, 1H), 2.36 (d,1H), 2.66 (t, 2H), 3.23 (m, 1H), 3.38 (m, 2H), 3.70 (m, 1H), 7.20 (m, 3H), 7.27 (m, 2H), 7.48 (t, 1H), 7.64 (d, 1H), 8.07 (d, 1H), 8.16 (s, 1H)
MS (thermospray): M/Z [$MH^+$] 351.1; $C_{21}H_{22}N_2O_3$+H requires 351.2

PREPARATION 8

3-[6-Methyl-3-(3-phenylpropyl)-3-azabicyclo[3.1.0]hex-6-yl]phenylamine

Method A: To a solution of 6-methyl-6-(3-nitrophenyl)-3-(3-phenylpropyl)-3-azabicyclo[3.1.0]hexan-2-one (Preparation 7, 6.2 g, 17.71 mmol) in anhydrous tetrahydrofuran (200 ml) at room temperature under nitrogen, was added dropwise a solution of lithium aluminium hydride (1.0M in tetrahydrofuran, 100 ml, 100 mmol), then the mixture was gently refluxed for 4 h. The mixture was cooled, then quenched by the careful addition of water (200 ml). The pH of the mixture was adjusted to 4 by the addition of dilute hydrochloric acid, then adjusted to pH 10 by the addition of dilute sodium hydroxide solution. The mixture was extracted with ethyl acetate (2×200 ml), and the combined extracts were washed with water (100 ml), dried ($Na_2SO_4$), filtered and concentrated in vacuo to give 5.2 g of a yellow oil. This was dissolved in ethanol (200 ml), Raney nickel (300 mg) was added and the mixture was placed under an atmosphere of hydrogen (2 atm, 203 kPa) and stirred at 60° C. for 18 h. The mixture was cooled, filtered through Arbocel™, and concentrated in vacuo to give the title compound as a very pale yellow oil (4.6 g, 85%).

Or Method B: (i) To a stirred solution of 6-methyl-6-(3-nitrophenyl)-3-(3-phenylpropyl)azabicyclo[3.1.0]hexane-2,4-dione (Preparation 136, 15.0 g, 41.2 mmol) in tetrahydrofuran (60 ml) under nitrogen was added sodium borohydride (3.27 g, 86.4 mmol) and the reaction mixture was stirred at room temperature for 1 h. The reaction mixture was cooled to between 0° C. and 5° C. and borontrifluoride diethyletherate (16.36 g, 115 mmol) was added. The reaction mixture was allowed to warm to room temperature over 2 h before being heated under reflux for a further 2 h. The reaction mixture was cooled to between 0° C. and 5° C. and an aqueous solution of piperazine (20.92 g in 120 ml) was added. The reaction mixture was then heated under reflux for 18 h. The tetrahydrofuran was removed by distillation and the reaction mixture was allowed to cool to 50° C. Ethyl acetate (90 ml) was added and the resulting biphasic mixture was allowed to cool to room temperature. The phases were separated and the organic extract was washed water (3×60 ml) to afford a solution of 6-(3-nitrophenyl)-6-methyl-3-(2-phenylpropyl)azabicyclo[3.1.0]hexane in ethyl acetate. (ii) To the reaction mixture was added 5% palladium on charcoal (Johnsson Matthey type 87, 1.5 g) and the reaction mixture was placed under an atmosphere of hydrogen (60 psi) at 25° C. for 16 h. The catalyst was removed by filtration through Celite™ and the filtrate was concentrated in vacuo to afford the title compound as a yellow oil which crystallised on standing (11.09 g, 88%).

NMR ($CDCl_3$, selected data for the free base): 1.52 (s, 3H), 1.71–1.78 (m, 4H), 2.47 (t, 2H), 2.66 (t, 2H), 2.79 (d, 2H), 2.99 (d, 2H), 3.59 (s, 2H), 6.49 (d, 1H), 6.60 (s, 1H), 6.65 (d, 1H), 7.06 (t, 1H), 7.15–7.20 (m, 2H), 7.20–7.30 (m, 3H).

MS (APCI): M/Z [MH$^+$] 307.3; $C_{21}H_{26}N_2$+H requires 307.2

PREPARATION 9

3-(3-Cyclohexylpropyl)-6-methyl-6-(3-nitrophenyl)-3-azabicyclo[3.1.0]hexan-2-one A solution of ethyl 3-(chloromethyl)-2-methyl-2-(3-nitrophenyl)cyclopropane carboxylate (Preparation 5, 1 g, 3.36 mmol) in 3-cyclohexylpropylamine ([Preparation—Eur. J. Med. Chem. (1992), 27, 321–330], 2.9 g, 20.5 mmol) was heated to 160° C. for 16 h. The mixture was cooled, 2N hydrochloric acid solution (20 ml) was added and the mixture was extracted with dichloromethane (3×20 ml). The combined extracts were dried ($Na_2SO_4$), filtered and concentrated in vacuo. The residue was purified by silica (200 g) column chromatography eluting with dichloromethane then diethyl ether. Appropriate fractions were combined and concentrated in vacuo to give the title compound as an amber oil (870 mg, 73%).

NMR ($CDCl_3$) δ: 0.90 (m, 2H), 1.22 (m, 6H), 1.38 (s, 3H), 1.47–1.60 (m, 2H), 1.60–1.75 (m, 5H), 2.14 (t, 1H), 2.37 (d, 1H), 3.08–3.30 (m, 2H), 3.36 (d, 1H), 3.73 (dd, 1H), 7.48 (t, 1H), 7.64 (d, 1H), 8.08 (d, 1H), 8.16 (s, 1H)

MS (thermospray): M/Z [MH$^+$] 357.1; $C_{21}H_{28}N_2O_3$+H requires 357.2

PREPARATION 10

3-[3-(3-Cyclohexylpropyl)-6-methyl-3-azabicyclo[3.1.0]hex-6-yl]aniline

To a solution of 3-(3-cyclohexylpropyl)-6-methyl-6-(3-nitrophenyl)-3-azabicyclo[3.1.0]hexan-2-one (Preparation 9, 56 mg, 0.16 mmol) in anhydrous tetrahydrofuran (2.5 ml) at room temperature under nitrogen was added dropwise a solution of lithium aluminium hydride (1.0M in tetrahydrofuran, 0.8 ml, 0.8 mmol), then the mixture was gently refluxed for 4.5 h. The mixture was cooled, then quenched by the careful addition of water (30 ml). The pH of the mixture was adjusted to 1 by the addition of dilute hydrochloric acid, then adjusted to pH 10 by the addition of dilute sodium hydroxide solution. The mixture was extracted with ethyl acetate (40 ml) and the organic extract was washed with water (10 ml), dried ($Na_2SO_4$), filtered and concentrated in vacuo to give 50 mg of a yellow oil. This was dissolved in ethanol (6 ml), and Raney nickel (50 mg) was added and the mixture was placed under an atmosphere of hydrogen (2 atm, 203 kPa) and stirred at 60° C. for 7 h. The mixture was cooled, filtered through Arbocel™, and concentrated in vacuo, to give the title compound as a very pale yellow oil (50 mg, 99%).

NMR ($CDCl_3$) δ: 0.90 (m, 2H), 1.06–1.31 (m, 6H), 1.43 (s, 3H), 1.58–1.76 (m, 7H), 2.02 (s, 2H), 2.70 (t, 2H), 2.97 (d, 2H), 3.42 (m, 2H), 6.40–6.63 (m, 3H), 7.08 (m, 1H)

MS (thermospray): M/Z [MH$^+$] 313.4; $C_{21}H_{32}N_2$+H requires 313.3

PREPARATION 11

3-Hexyl-6-methyl-6-(3-nitrophenyl)-3-azabicyclo[3.1.0]hexan-2-one

To a solution of ethyl 3-(chloromethyl)-2-methyl-2-(3-nitrophenyl)cyclopropane carboxylate (Preparation 5, 20 g, 67.2 mmol) in hexylamine (36 ml, 270 mmol) was added sodium hydrogen carbonate (5.64 g, 67.2 mmol), and the mixture was heated at 100° C. for 16 h. The mixture was cooled, diluted with water (80 ml) and extracted with dichloromethane (3×150 ml). The combined extracts were dried ($MgSO_4$), filtered and concentrated in vacuo. The residue was purified by silica column chromatography, eluting with a gradient of 2:1 to 1:2 hexane/ethyl acetate. Appropriate fractions were combined and concentrated in vacuo to give the title compound as a very pale yellow oil (14.2 g, 67%).

NMR (CDCl$_3$) δ: 0.90 (t, 3H), 1.23–1.38 (m, 6H), 1.38 (s, 3H), 1.46–1.60 (m, 2H), 2.17 (t, 1H), 2.37 (d, 1H), 3.11–3.40 (m, 3H), 3.71 (dd, 1H), 7.49 (t, 1H), 7.65 (m, 1H), 8.08 (d, 1H), 8.15 (s, 1H)

MS (APCI): M/Z [MH$^+$] 317.5; C$_{18}$H$_{24}$N$_2$O$_3$+H requires 317.2

PREPARATION 12

3-(3-Hexyl-6-methyl-3-azabicyclo[3.1.0]hex-6-yl) phenylamine

To a solution of 3-hexyl-6-methyl-6-(3-nitrophenyl)-3-azabicyclo[3.1.0]hexan-2-one (Preparation 11, 10.7 g, 33.86 mmol) in tetrahydrofuran (500 ml) under nitrogen, was added dropwise over 1 h at room temperature a 1.0 M solution of lithium aluminium hydride in tetrahydrofuran (100 ml, 100 mmol). The mixture was heated to 50° C. for 2 h, then cooled to room temperature. Water (50 ml) was carefully added, and the mixture was stirred for 1 h, before the tetrahydrofuran was removed in vacuo. The aqueous residue was acidified by the addition of 2N hydrochloric acid (20 ml) and then basified with the addition of 2N sodium hydroxide solution (25 ml). The mixture was extracted with ethyl acetate (3×250 ml). The combined extracts were dried (MgSO$_4$), filtered and concentrated in vacuo. The residue was dissolved in ethanol (450 ml), Raney nickel (500 mg) was added, and the mixture was placed under an atmosphere of hydrogen (2 atm, 203 kPa) and stirred at 50° C. for 24 hours. The mixture was filtered through Celite™, and concentrated in vacuo. The residue was purified by silica column chromatography, eluting with 80:20:2 ethyl acetate/methanol/ammonia solution (0.880). Product-containing fractions were combined and concentrated in vacuo to give the title compound as a colourless oil (3.3 g, 36%).

NMR (CDCl$_3$) δ: 0.90 (t, 3H), 1.30 (m, 6H), 1.42 (m, 2H), 1.46 (s, 3H), 1.74 (s, 2H), 2.43 (t, 2H), 2.82 (d, 2H), 2.93 (d, 2H), 6.48 (d, 1H), 6.59 (s, 1H), 6.65 (d, 1H), 7.05 (t, 1H)

MS (thermospray): M/Z [MH$^+$] 273.4; C$_{18}$H$_{28}$N$_2$+H requires 273.2

PREPARATION 13

Ethyl (E)-3-(3-nitrophenyl)-2-pentenoate

To a solution of sodium hydride (60% dispersion in oil, 40 g, 1.0 mol) in tetrahydrofuran (2 l) stirred at −10° C. under nitrogen was added dropwise over 30 minutes triethylphosphonoacetate (224 g, 1.0 mol). 3-Nitropropiophenone (180 g, 1 mol) was added portionwise such that the temperature was maintained below 10° C. The mixture was allowed to warm to room temperature and was stirred for 18 h. Water (1.5 l) was added, and the mixture was extracted with diethyl ether (2×1 l). The combined extracts were washed with water (1 l), dried (MgSO$_4$), filtered and concentrated in vacuo and the residue was purified by silica column (4×2 kg) chromatography eluting with 12:1 hexane/diethyl ether. Appropriate fractions were combined and concentrated in vacuo to give the title compound as a very pale yellow oil (105 g, 42%).

NMR (CDCl$_3$) δ: 1.08 (t, 3H), 1.33 (t, 3H), 3.13 (q, 2H), 4.22 (q, 2H), 6.05 (s, 1H), 7.56 (t, 1H), 7.76 (d, 1H), 8.21 (d, 1H), 8.30 (s, 1H)

MS (thermospray): m/z [MH$^+$] 250.0; C$_{13}$H$_{15}$NO$_4$+H requires 250.1

PREPARATION 14

(E)-3-(3-Nitrophenyl)-2-penten-1-ol

To a solution of ethyl (E)-3-(3-nitrophenyl)-2-pentenoate (Preparation 13, 105 g, 0.43 mol) in toluene (1400 ml) at −10° C. under nitrogen was added dropwise over 3 h diisobutylaluminium hydride (1.0 M in toluene, 1 l, 1.0 mol), then the mixture was stirred at 0° C. for 1 hour. Water (400 ml) was carefully added, followed by sodium hydrogen carbonate (700 g). The resulting slurry was vigorously stirred for 10 minutes, then ethyl acetate (2 l) was added, and the mixture stirred for 1 h. The mixture was dried (MgSO$_4$), filtered and concentrated in vacuo to give the title compound as a pale brown oil (80 g, 90%).

NMR (CDCl$_3$) δ: 0.99 (t, 3H), 2.60 (q, 2H), 4.39 (d, 2H), 5.91 (t, 1H), 7.47 (t, 1H), 7.67 (d, 1H), 8.09 (d, 1H), 8.20 (s, 1H)

PREPARATION 15

1-[(E)-3-Chloro-1-ethyl-1-propenyl]-3-nitrobenzene

To a solution of N-chlorosuccinimide (52.3 g, 0.39 mol) in dichloromethane (1.2 l) at 0° C. was added dropwise over 20 minutes dimethylsulfide (27.9 ml, 0.38 mol). To the mixture was added dropwise over 20 minutes at 0° C. a solution of (E)-3-(3-nitrophenyl)-2-penten-1-ol (Preparation 14, 80 g, 0.39 mol) in dichloromethane (300 ml). The mixture was warmed to room temperature over 1 h, stirred at room temperature for 16 h, then partitioned between water (2 l) and dichloromethane (1 l). The layers were separated and the organic layer was dried (MgSO$_4$), filtered and concentrated in vacuo. The residue was purified by silica column chromatography (2 kg), eluting with 10:1 hexane/diethyl ether. Appropriate fractions were combined and concentrated in vacuo to give the title compound as a very pale yellow oil (54 g, 62%).

NMR (CDCl$_3$) δ: 1.33 (t, 3H), 2.63 (q, 2H), 4.27 (d, 2H), 5.94 (t, 1H), 7.52 (t, 1H), 7.69 (d, 1H), 8.15 (d, 1H), 8.23 (s, 1H).

PREPARATION 16

Ethyl 3-(chloromethyl)-2-ethyl-2-(3-nitrophenyl) cyclopropanecarboxylate

To a solution of 1-[(E)-3-chloro-1-ethyl-1-propenyl]-3-nitrobenzene (Preparation 15, 50 g, 0.22 mol) in dichloromethane (40 ml) was added rhodium (II) acetate dimer (2.0 g, 4.6 mmol). To the mixture was added dropwise at room temperature over 6 hours a solution of ethyl diazoacetate (50 ml, 54.25 g, 0.475 mol) in dichloromethane (50 ml), then the mixture stirred at room temperature for 16 hours. To the mixture was added dropwise at room temperature over 7 hours a solution of ethyl diazoacetate (20 ml, 21.70 g, 0.190 mol) in dichloromethane (20 ml), then the mixture was stirred at room temperature for 16 h. The mixture was concentrated in vacuo and the residue purified by silica column (1 kg) chromatography, eluting with 1:1 hexane/dichloromethane. Product-containing fractions were combined and concentrated in vacuo to give the title compound as a pale orange oil (10.5 g, 15%).

NMR (CDCl$_3$) δ: 0.79 (t, 3H), 1.33 (t, 3H), 1.93–2.11 (m, 3H), 2.20 (d, 1H), 4.04 (dd, 1H), 4.23 (m, 3H), 7.51 (t, 1H), 7.68 (d, 1H), 8.13 (d, 1H), 8.17 (s, 1H)

PREPARATION 17

6-Ethyl-6-(3-nitrophenyl)-3-(3-phenylpropyl)-3-azabicyclo[3.1.0]hexan-2-one

To a solution of ethyl 3-(chloromethyl)-2-ethyl-2-(3-nitrophenyl)cyclopropane carboxylate (Preparation 16, 3.5 g, 11.2 mmol), in N,N-dimethylformamide (33 ml) was added sodium hydrogen carbonate (3.3 g, 39 mmol) and 3-phenylpropylamine (10.6 g, 11.2 ml, 79.2 mmol). The mixture was heated to 150° C. for 12 h, then cooled to room temperature and partitioned between water (500 ml) and diethyl ether (500 ml). The organic layer was washed successively with water (4×250 ml). The aqueous layers were combined and extracted with diethyl ether (250 ml). The combined organic extracts were dried (MgSO$_4$), filtered and concentrated in vacuo. The residue was purified by silica (200 g) column chromatography eluting with dichloromethane. Product-containing fractions were combined and concentrated in vacuo to give the title compound as a very pale yellow oil (1.8 g, 43%).

NMR (CDCl$_3$) δ: 0.87 (t, 3H), 1.64 (m, 2H), 1.86 (m, 2H), 2.15 (t, 1H), 2.37 (d, 1H), 2.65 (t, 2H), 3.26 (m, 1H), 3.37 (m, 2H), 3.67 (dd, 1H), 7.20 (m, 3H), 7.27 (m, 2H), 7.48 (t, 1H), 7.67 (d, 1H), 8.08 (d, 1H), 8.17 (s, 1H)

PREPARATION 18

3-[6-Ethyl-3-(3-phenylpropyl)-3-azabicyclo[3.1.0]hex-6-yl]phenylamine

To a solution of 6-ethyl-6-(3-nitrophenyl)-3-(3-phenylpropyl)-3-azabicyclo[3.1.0]hexan-2-one (Preparation 17, 1.8 g, 4.9 mmol) in anhydrous tetrahydrofuran (60 ml) at room temperature under nitrogen, was added dropwise a solution of lithium aluminium hydride (1.0M in tetrahydrofuran, 32 ml, 32 mmol) and the mixture was gently refluxed for 6 h. The mixture was cooled, then quenched by carefully pouring into ice cold hydrochloric acid (1N, 400 ml). The acidic layer was extracted with diethyl ether (300 ml). The pH of the aqueous layer was adjusted to 10 by the addition of potassium carbonate and extracted with diethyl ether (300 ml). The organic layers were combined, dried (MgSO$_4$), filtered and concentrated in vacuo to give a yellow oil (1.2 g). This was dissolved in ethanol (60 ml), Raney nickel (120 mg) was added and the mixture was placed under an atmosphere of hydrogen (2 atm, 203 kPa) and stirred at 60° C. for 40 h. The mixture was cooled, filtered through Arbocel™, and concentrated in vacuo to give the title compound as a very pale yellow oil (1.3 g, 82%).

NMR (CDCl$_3$) δ: 0.86 (m, 3H), 1.88 (m, 6H), 2.64 (m, 4H), 2.96 (m, 2H), 3.09 (m, 2H), 6.46–6.75 (m, 4H), 7.06 (m, 1H), 7.13–7.35 (m, 4H)

MS (electrospray): m/z [MH$^+$] 321.1; C$_{22}$H$_{28}$N$_2$+H requires 321.2

PREPARATION 19

6-Ethyl-3-hexyl-6-(3-nitrophenyl)-3-azabicyclo[3.1.0]hexan-2-one

To a solution of ethyl 3-(chloromethyl)-2-ethyl-2-(3-nitrophenyl)cyclopropane carboxylate (Preparation 16, 4.0 g, 12.8 mmol), was added sodium hydrogen carbonate (1.3 g, 15.4 mmol) and hexylamine (15.3 g, 20 ml, 151 mmol). The mixture was heated to 150° C. for 12 h, then cooled to room temperature and partitioned between hydrochloric acid (2N, 500 ml) and ethyl acetate (2×500 ml). The combined organic layers were washed with water (500 ml), dried (MgSO$_4$), filtered and concentrated in vacuo. The residue was purified by silica (200 g) column chromatography eluting with a gradient of dichloromethane/ethyl acetate 100:0 to 90:10. Product-containing fractions were combined and concentrated in vacuo to give the title compound as an orange oil (1.4 g, 32%).

NMR (CDCl$_3$) δ: 0.93 (m, 6H), 1.30 (m, 6H), 1.52 (m, 2H), 1.62 (m, 2H), 2.17 (m, 1H), 2.38 (d, 1H), 3.25 (m, 2H), 3.38 (d, 1H), 3.69 (dd, 1H), 7.50 (t, 1H), 7.68 (d, 1H), 8.10 (d, 1H), 8.18 (s, 1H)

MS (electrospray): m/z [MH$^+$] 331.1; C$_{19}$H$_{26}$N$_2$O$_3$+H requires 331.2

PREPARATION 20

3-(6-Ethyl-3-hexyl-3-azabicyclo[3.1.0]hex-6-yl)phenylamine

To a solution of 6-ethyl-3-hexyl-6-(3-nitrophenyl)-3-azabicyclo[3.1.0]hexan-2-one (Preparation 19, 1.4 g, 4.2 mmol) in anhydrous tetrahydrofuran (42 ml) at room temperature under nitrogen, was added dropwise a solution of lithium aluminium hydride (1.0 M in tetrahydrofuran, 23 ml, 23 mmol), then the mixture was gently heated under reflux for 18 h. The mixture was cooled, then quenched by carefully pouring onto ice cold hydrochloric acid (1N, 400 ml). The acidic layer was extracted with diethyl ether (2×200 ml). The pH of the aqueous layer was adjusted to 10 by the addition of potassium carbonate and then was extracted with diethyl ether (300 ml). The organic extract was dried (MgSO$_4$), filtered and concentrated in vacuo to give a yellow oil (1.2 g). This was dissolved in ethanol (50 ml), Raney nickel (100 mg) was added, then the mixture was placed under an atmosphere of hydrogen (2 atm, 203 kPa) and stirred at 60° C. for 40 h. The mixture was cooled, filtered through Arbocel™, and concentrated in vacuo to give the title compound as a very pale yellow oil (1.1 g, 77%).

NMR (CDCl$_3$) δ: 0.85 (m, 6H), 1.27 (m, 6H), 1.44 (m, 2H), 1.87 (m, 4H), 2.48 (m, 2H), 2.93 (m, 4H), 6.46–6.73 (m, 3H), 7.04 (m, 1H)

MS (electrospray): m/z [MH$^+$] 287.1; C$_{19}$H$_{30}$N$_2$+H requires 287.2

PREPARATION 21

(E)-3-(3-Nitrophenyl)-2-propen-1-ol

To a solution of ethyl (E)-3-(3-nitrophenyl)-2-propenoate (8.04 g, 36 mmol) in dichloromethane at 0° C. under nitrogen was added dropwise over 5 minutes diisobutylaluminium hydride (1.0 M solution in dichloromethane, 80 ml, 80 mmol). The mixture was stirred at 0° C. for 10 minutes, then allowed to warm to room temperature over 30 minutes. Hydrochloric acid (1N, 500 ml) was added, the layers were separated and the aqueous layer was extracted with dichloromethane (2×250 ml). The organic layers were combined, washed with brine (2×100 ml), filtered and concentrated in vacuo to give the title compound as a red oil.

NMR (CDCl$_3$) δ: 4.40 (d, 2H), 6.50 (dt, 1H), 6.70 (d, 1H), 7.48 (t, 1H), 7.67 (d, 1H), 8.09 (d, 1H), 8.23 (s,1H).

PREPARATION 22

1-[(E)-3-Bromo-1-propenyl]-3-nitrobenzene

To a solution of triphenylphosphine (1.47 g, 5.6 mmol) in acetonitrile (35 ml) at 0° C. was added dropwise over 5 minutes a solution of bromine (0.88 g, 5.6 mmol) in acetonitrile (5 ml) at a rate such that the temperature was kept between 5° C. and 10° C. The mixture was then allowed to warm to room temperature, then to this was added dropwise a solution of (E)-3-(3-nitrophenyl)-2-propen-1-ol (Preparation 21, 1 g, 5.6 mmol) in acetonitrile (5 ml). The mixture was warmed to 65° C. for 40 min, cooled to room temperature, and poured onto diethyl ether (150 ml). The mixture was concentrated in vacuo. The residue was purified by silica (10 g) column chromatography eluting with hexane then dichloromethane. Product-containing fractions were combined and concentrated in vacuo, and the residue recrystallised from cyclohexane to give the title compound as a very pale yellow solid (0.82 g, 61%).

NMR (CDCl$_3$) δ: 4.18 (d, 2H), 6.48–6.60 (m, 1H), 6.72 (d, 1H), 7.52 (t, 1H), 7.68 (d, 1H), 8.12 (d, 1H), 8.24 (s,1H).

PREPARATION 23

Ethyl 2-(bromomethyl)-3-(3-nitrophenyl)cyclopropane carboxylate

To a solution of 1-[(E)-3-bromo-1-propenyl]-3-nitrobenzene (Preparation 22, 820 mg, 3.23 mmol) in dichloromethane (3 ml) was added rhodium (II) acetate dimer (20 mg, 0.046 mmol). To the mixture was added dropwise at room temperature over 3 h a solution of ethyl diazoacetate (0.47 ml, 510 mg, 4.47 mmol) in dichloromethane (3 ml), then the mixture was stirred at room temperature for 66 h. The mixture was purified by silica (100 g) column chromatography eluting with hexane:dichloromethane 100:0 to 50:50. Product containing fractions were combined and concentrated in vacuo to afford the title compound as a colourless oil (65 mg, 7%).

NMR (CDCl$_3$) δ: 1.33 (t, 3H), 2.20 (m, 1H), 2.35 (m, 1H), 2.80 (m, 1H), 3.74 (t, 1H), 3.90 (m, 1H), 4.25 (m, 2H), 7.58 (m, 2H), 7.98 (s, 1H), 8.09 (m, 1H)

PREPARATION 24

6-(3-Nitrophenyl)-3-(3-phenylpropyl)-3-azabicyclo[3.1.0]hexan-2-one

To a solution of ethyl 2-(bromomethyl)-3-(3-nitrophenyl) cyclopropane carboxylate (Preparation 23, 60 mg, 0.18 mmol) in N,N-dimethylformamide (2 ml) was added sodium hydrogen carbonate (30 mg, 0.36 mmol) and 3-phenylpropylamine (30 mg, 31 μl, 0.22 mmol). The mixture was heated to 150° C. for 1 hour, then cooled to room temperature and stirred for 16 hours. Water (30 ml) was added and the mixture was extracted with diethyl ether (2×50 ml). The combined extracts were concentrated in vacuo and the residue was purified by silica (5 g) column chromatography eluting with dichloromethane then 4:1 dichloromethane: ethyl acetate. Product-containing fractions were combined and concentrated in vacuo to give the title compound as a colourless glassy solid (55 mg, 90%).

NMR (CDCl$_3$) δ: 1.85 (m, 2H), 2.02 (m, 1H), 2.20 (m, 1H), 2.32 (m, 1H), 2.64 (t, 2H), 3.20–3.40 (m, 2H), 3.49 (d, 1H), 3.65 (dd, 1H), 7.14–7.49 (m, 7H), 7.87 (s, 1H), 8.05 (d, 1H)

MS (APCI): m/z [MH$^+$] 337.2; C$_{20}$H$_{20}$N$_2$O$_3$+H requires 337.2

PREPARATION 25

3-[3-(3-Phenylpropyl)-3-azabicyclo[3.1.0]hex-6-yl] phenyl amine

To a solution of 6-(3-nitrophenyl)-3-(3-phenylpropyl)-3-azabicyclo[3.1.0]hexan-2-one (Preparation 24, 55 mg, 0.16 mmol) in tetrahydrofuran (3 ml) under nitrogen, was added dropwise at room temperature a 1.0 M solution of lithium aluminium hydride in tetrahydrofuran (0.81 ml, 0.81 mmol). The mixture was heated to 60° C. for 4 h. Further lithium aluminium hydride in tetrahydrofuran (1.0M, 0.3 ml, 0.3 mmol) was added, and the mixture was heated at 60° C. for 20 minutes, then cooled to room temperature. Water (30 ml) was carefully added, then the residue was acidified by the addition of 2N hydrochloric acid (5 ml), and then basified with 2N sodium hydroxide solution (6 ml). The mixture was extracted with ethyl acetate (3×50 ml). The combined extracts were dried (Na$_2$SO$_4$), filtered and concentrated in vacuo. The residue was dissolved in ethanol (5 ml), Raney nickel (50 mg) was added, and the mixture was placed under an atmosphere of hydrogen (2 atm, 203 kPa) and stirred at 60° C. for 16 h. The mixture was filtered through Celite™ and concentrated in vacuo to give the title compound as a pale yellow oil (35 mg, 75%).

NMR (CDCl$_3$) δ: 1.74 (m, 2H), 1.95 (m, 2H), 2.39 (br.s, 1H), 2.65 (m, 6H), 3.38 (br.d, 2H), 6.28–6.50 (m, 3H), 7.05 (m, 1H), 7.15–7.34 (m, 5H).

MS (thermospray): M/Z [MH$^+$] 293.3; C$_{20}$H$_{24}$N$_2$+H requires 293.2

PREPARATION 26

Ethyl 2-(bromomethyl)-3-phenylcyclopropanecarboxylate

To a solution of [(E)-3-bromo-1-propenyl]benzene (705 mg, 3.58 mmol) in dichloromethane (1 ml) was added rhodium (II) acetate dimer (20 mg, 0.05 mmol). To the mixture was added dropwise at room temperature over 4 h a solution of ethyl diazoacetate (0.43 ml, 0.47 g, 4.15 mmol) in dichloromethane (2.5 ml). The mixture was stirred at room temperature for 60 h. The mixture was purified by silica column (40 g) chromatography eluting with 1:1 hexane:dichloromethane then dichloromethane. Product-containing fractions were purified further by silica column (10 g) chromatography eluting with 9:1 hexane:dichloromethane then dichloromethane. Product-containing fractions were combined and concentrated in vacuo to give the title compound as a colourless oil (75 mg, 8%).

NMR (CDCl$_3$) δ: 1.32 (t, 3H), 2.16 (m, 1H), 2.27 (dd, 1H), 2.70 (t, 1H), 3.76 (t, 1H), 3.90 (dd,1H), 4.23 (m, 2H), 7.12 (d, 2H), 7.17–7.36 (m, 3H)

PREPARATION 27

3-Hexyl-6-phenyl-3-azabicyclo[3.1.0]hexan-2-one

To a solution of ethyl 2-(bromomethyl)-3-phenylcyclopropanecarboxylate (Preparation 26, 65 mg, 0.22 mmol) in N,N-dimethylformamide (2 ml) was added sodium hydrogen carbonate (30 mg, 0.36 mmol) and hexylamine (33 μl, 26 mg, 0.26 mmol), and the mixture was heated to 150° C. for 3 h. The mixture was cooled, water (30 ml) was added, and the mixture was extracted with diethyl ether (2×30 ml). The extracts were combined, dried (Na$_2$SO$_4$), filtered and concentrated in vacuo. The mixture was purified by silica column (5 g) chromatography eluting with 4:1 dichloromethane:ethyl acetate. Product-containing fractions were combined and concentrated in vacuo to give the title compound as a colourless oil (45 mg, 76%).

NMR (CDCl$_3$) δ: 0.89 (t, 3H), 1.28 (m, 6H), 1.48 (m, 2H), 2.00 (m, 1H), 2.12 (m, 1H), 2.22 (m, 1H), 3.08–3.31 (m, 2H), 3.47 (d, 1H), 3.63 (m, 1H), 7.03 (d, 2H), 7.12–7.33 (m, 3H)

MS (APCI): M/Z [MH$^+$] 258.1; C$_{17}$H$_{23}$NO+H requires 258.2

PREPARATION 28

3-Benzyl-6-methyl-6-(3-nitrophenyl)-3-azabicyclo[3.1.0]hexan-2-one

A solution of ethyl 3-(chloromethyl)-2-methyl-2-(3-nitrophenyl)cyclopropane carboxylate (Preparation 5, 10 g, 33.6 mmol) in benzylamine (21.6 g, 201.6 mmol) was heated to 160° C. for 16 h. The mixture was cooled, 2N hydrochloric acid was added (200 ml), and the mixture was extracted with dichloromethane (3×250 ml). The combined extracts were dried (Na$_2$SO$_4$), filtered and concentrated in vacuo. The residue was purified by silica (600 g) column chromatography eluting with dichloromethane, then a gradient of dichloromethane:ethyl acetate ending with pure ethyl acetate. Appropriate fractions were combined and concentrated in vacuo to give the title compound as an amber oil (6 g, 55%).

NMR (CDCl$_3$) δ: 1.27 (s, 3H), 2.13 (t, 1H), 2.42 (d, 1H), 3.25 (d, 1H), 3.62 (dd, 1H), 4.31 (d, 1H), 4.57 (d, 1H), 7.33 (m, 5H), 7.49 (t, 1H), 7.63 (d, 1H), 8.08 (d, 1H), 8.13 (s, 1H)

MS (electrospray): M/Z [MH$^+$] 323.1; C$_{19}$H$_{18}$N$_2$O$_3$+H requires 323.1

PREPARATION 29

6-(3-Aminophenyl)-3-benzyl-6-methyl-3-azabicyclo[3.1.0]hexan-2-one

To a solution of 3-benzyl-6-methyl-6-(3-nitrophenyl)-3-azabicyclo[3.1.0]hexan-2-one (Preparation 28, 2 g, 6.2 mmol) in absolute ethanol (170 ml) was added water (30 ml), calcium chloride (344 mg, 3.1 mmol) and iron powder (3.02 g, 53.8 mmol). The mixture was heated to reflux under nitrogen for 4 h, then cooled. The solution was filtered through silica (10 g) eluting with methanol, then concentrated in vacuo to give the title compound as a white solid (1.73 g, 95%).

mp 150–151° C.

NMR (CDCl$_3$) δ: 1.22 (s, 3H), 2.03 (t, 1H), 2.33 (d, 1H), 3.15 (d, 1H), 3.53 (dd, 1H), 4.23 (d, 1H), 4.54 (d, 1H), 6.53 (d, 1H), 6.66 (m, 2H), 7.05 (t, 1H), 7.30 (m, 5H)

MS (electrospray): M/Z [MH$^+$] 293.1; C$_{19}$H$_{20}$N$_2$O+H requires 293.2

PREPARATION 30

3-(3-Benzyl-6-methyl-3-azabicyclo[3.1.0]hex-6-yl)phenylamine

Lithium aluminium hydride (1M in tetrahydrofuran, 11.84 ml, 11.84 mmol) was added dropwise to dry tetrahydrofuran (60 ml) under nitrogen. 6-(3-Aminophenyl)-3-benzyl-6-methyl-3-azabicyclo[3.1.0]hexan-2-one (Preparation 29, 1.73 g, 5.90 mmol) was suspended in dry tetrahydrofuran (100 ml) and added slowly to the lithium aluminium hydride solution by cannula. The reaction was then heated at 50° C. for 2 hours. After cooling, water (20 ml) was cautiously added to the solution, the pH of the aqueous layer was adjusted to 4 by the addition of 2N hydrochloric acid and then adjusted to 10 using dilute sodium hydroxide solution. The mixture was extracted with ethyl acetate (3×200 ml), and the combined extracts were washed with water (100 ml), dried (Na$_2$SO$_4$) and concentrated in vacuo to give the title compound as a yellow oil (1.58 g, 96%).

NMR (CDCl$_3$) δ: 1.60 (s, 3H), 1.78 (s, 2H), 2.83 (d, 2H), 3.02 (d, 2H), 3.67 (s, 2H), 6.48 (d, 1H), 6.60 (s, 1H), 6.67 (d, 1H), 7.05 (t, 1H), 7.33 (m, 5H).

MS (electrospray): M/Z [MH$^+$] 279.1; C$_{19}$H$_{22}$N$_2$+H requires 279.2

PREPARATION 31

Ethyl (E)-3-(3-cyanophenyl)-2-butenoate

To a solution of sodium hydride 60% dispersion in oil (8.28 g, 0.19 mol) in tetrahydrofuran (300 ml) stirred at 0° C. under nitrogen was added dropwise over 45 minutes triethyl phosphonoacetate (46.2 g, 0.21 mol). The mixture was then stirred at room temperature for 30 minutes. 3-Cyanoacetophenone (25.1 g, 0.172 mol) in tetrahydrofuran (200 ml) was added via a cannula at room temperature and the brown reaction mixture was stirred for 1 h. Saturated ammonium chloride solution (150 ml) was added, and the mixture was concentrated in vacuo. The aqueous layer was extracted with ethyl acetate (3×150 ml). The combined extracts were dried (MgSO$_4$), filtered and concentrated in vacuo. The residue was purified by silica column chromatography eluting with a gradient of hexane:ethyl acetate 100:0 to 70:30 to afford the title compound as a mixture of the E and Z isomers (ratio 5:1) as a colourless oil which solidified on standing. This was taken on without further purification.

NMR (CDCl$_3$) for the E isomer δ: 1.34 (t, 3H), 2.58 (s, 3H), 4.25 (q, 2H), 6.15 (s, 1H), 7.50 (t, 1H), 7.62–7.70 (m, 2H), 7.77 (s, 1H)

PREPARATION 32

(E)-3-(3-Cyanophenyl)-2-butenoic acid

To a mixture of lithium hydroxide monohydrate (10.8 g, 0.26 mol) in tetrahydrofuran (100 ml) and water (100 ml) was added crude ethyl (E)-3-(3-cyanophenyl)-2-butenoate (Preparation 31) in tetrahydrofuran (150 ml). The resultant mixture was made homogeneous by-the addition of methanol (approx. 50 ml), and then stirred at room temperature for 16 h. The mixture was concentrated in vacuo and acidified with 2N hydrochloric acid, following which a solid precipitated. The solid was collected by suction filtration, washing with cold water. The solid was then dried and recrystallised from acetonitrile.

From the first crop, 15.8 g (49% over 2 steps) of the pure E-isomer was isolated.

NMR (CDCl$_3$) δ: 2.58 (s, 3H), 6.18 (s, 1H), 7.58 (t, 1H), 7.72 (d, 1H), 7.81 (d, 1H), 7.90 (s, 1H)

PREPARATION 33

3-[(E)-3-Hydroxy-1-methyl-1-propenyl]benzonitrile

To a solution of (E)-3-(3-cyanophenyl)-2-butenoic acid (Preparation 32, 15.83 g, 84.6 mmol) and triethylamine (8.99 g, 88.8 mmol) in tetrahydrofuran (150 ml) at 0° C. was added over 10 minutes ethyl chloroformate (9.65 g, 88.8 mmol). The mixture was then stirred at 0° C. for 30 minutes and at room temperature for a further 30 minutes. The resulting precipitate was collected by filtration and the solid was washed with cold tetrahydrofuran (2×30 ml). The preformed mixed anhydride in tetrahydrofuran was then added over 30 minutes via cannula to sodium borohydride (11.2 g, 0.30 mol) in a mixture of tetrahydrofuran/water (4:1, 100 ml) at 0° C. The resultant mixture was stirred at 0° C. for 1 h, at room temperature for 3 h and then cooled to 0° C. 2N Hydrochloric acid was added cautiously until effervescence had ceased. The mixture was concentrated in vacuo and 1N hydrochloric acid (100 ml) was added. The aqueous solution was extracted with ethyl acetate (3×150 ml) and the combined extracts were dried ($MgSO_4$), filtered and concentrated in vacuo. The crude oil was purified by silica column chromatography eluting with a gradient of ethyl acetate:hexane (1:1 to 100:0). An impurity, unreacted starting carboxylic acid, was removed by a basic wash with 2N sodium hydroxide solution (150 ml) and the pure product was extracted with dichloromethane (3×100 ml). The combined extracts were dried ($MgSO_4$), filtered and concentrated in vacuo to give the title compound as a colourless oil (11.9 g, 82%).

NMR ($CDCl_3$) δ: 1.4 (t, 1H), 2.05 (br. s, 3H), 4.40 (t, 2H), 6.01 (m, 1H), 7.42 (t, 1H), 7.57 (d, 1H), 7.62 (d, 1H), 7.68 (s, 1H)

PREPARATION 34

3-[(E)-3-Chloro-1-methyl-1-propenyl]benzonitrile

To a solution of N-chlorosuccinimide (9.8 g, 73.1 mmol) in dichloromethane (25 ml) at −10° C. was added dropwise over 15 minutes dimethylsulfide (5.4 ml, 73.1 mmol). The mixture was stirred at −10° C. for 30 min, then a solution of 3-[(E)-3-hydroxy-1-methyl-1-propenyl]benzonitrile (from Preparation 33, 11.9 g, 69.6 mmol) in dichloromethane (20 ml) was added dropwise over 15 minutes at −10° C. The mixture was stirred at 0° C. for 1 h, and was then poured onto saturated brine (50 ml). The layers were separated, and the aqueous layer was extracted with diethyl ether (2×50 ml). The extracts were combined, washed with water (50 ml), dried ($MgSO_4$), filtered and concentrated in vacuo. The crude pale yellow oil (13.1 g, 100%) was used directly in the next step.

NMR ($CDCl_3$) δ: 2.16 (s, 3H), 4.27 (d, 2H) 6.04 (t, 1H), 7.42 (t, 1H), 7.59 (d, 1H), 7.63 (d, 1H), 7.68 (s, 1H)

PREPARATION 35

Ethyl 3-(chloromethyl)-2-(3-cyanophenyl)-2-methylcyclopropane carboxylate

To a solution of 3-[(E)-3-chloro-1-methyl-1-propenyl] benzonitrile (Preparation 34, 13.1 g, 69.6 mmol) in dichloromethane (20 ml) was added rhodium (II) acetate dimer (0.46 g, 1.0 mmol). To the mixture was added dropwise at room temperature over 8 h (via a syringe pump) a solution of ethyl diazoacetate (14.6 ml, 0.14 mol) in dichloromethane (20 ml). The solvent was removed in vacuo and the crude residue was then partially purified by silica column chromatography eluting with dichloromethane:hexane (80:20). This material was then dissolved in dichloromethane (20 ml) containing rhodium (II) acetate dimer (0.46 g, 1.0 mmol). To this mixture was added dropwise a solution of ethyl diazoacetate (14.6 ml, 0.14 mol) in dichloromethane (20 ml) at room temperature over 8 h. The mixture was concentrated in vacuo and the residue purified by silica column chromatography eluting with hexane:dichloromethane (80:20) and then hexane:diethyl ether (80:20) to give the title compound as a colourless oil which solidified on standing (5.82 g, 30%).

NMR ($CDCl_3$) δ: 1.30 (t, 3H), 1.58 (s, 3H), 1.95 (m, 1H), 2.15 (m, 1H), 4.00 (dd, 1H), 4.17–4.27 (m, 3H), 7.43 (t, 1H), 7.56 (d, 1H), 7.58 (d, 1H), 7.62 (s, 1H)

PREPARATION 36

3-(3-Hexyl-6-methyl-2-oxo-3-azabicyclo[3.1.0]hex-6-yl)benzonitrile

To a solution of ethyl 3-(chloromethyl)-2-(3-cyanophenyl)-2-methylcyclopropanecarboxylate (Preparation 35, 5.82 g, 21.1 mmol) in N,N-dimethylformamide (20 ml) at room temperature was added sodium hydrogen carbonate (1.77 g, 21.1 mmol) followed by hexylamine (16.7 ml, 0.13 mol). The mixture was then heated under reflux for 16 h, cooled to room temperature and poured onto ice. After warming to room temperature, the mixture was partitioned against diethyl ether (50 ml). The two layers were separated and the aqueous layer was extracted with diethyl ether (2×30 ml). The ethereal extracts were washed with water (50 ml), dried ($MgSO_4$), filtered and concentrated in vacuo. The crude oil was purified by silica column chromatography eluting with a gradient of hexane:ethyl acetate (5:1 to 0:100) to afford the title compound (2.2 g, 35%) as a colourless oil.

NMR ($CDCl_3$) δ: 0.82–0.91 (m, 3H), 1.20–1.40 (m, 9H), 1.47–1.58 (m, 2H), 2.10 (m, 1H), 2.30 (m, 1H), 3.10–3.38 (m, 3H), 3.70 (dd, 1H), 7.41 (t, 1H), 7.56 (m, 2H), 7.59 (s, 1H).

PREPARATION 37

3-[6-Methyl-2-oxo-3-(3-phenylpropyl)-3-azabicyclo[3.1.0]hex-6-yl]-benzonitrile To a solution of ethyl 3-(chloromethyl)-2-(3-cyanophenyl)-2-methylcyclopropanecarboxylate (Preparation 35, 170 mg, 0.62 mmol) in N,N-dimethylformamide (6.0 ml) at room temperature was added sodium hydrogen carbonate (52 mg, 0.62 mmol) followed by 3-phenylpropylamine (0.35 ml, 2.47 mmol). The mixture was heated at 100° C. for 6 h and under reflux for 5 h. After the mixture had cooled to room temperature, water (4 ml) was added and the aqueous layer was extracted with diethyl ether (3×4 ml). The combined ethereal extracts were dried ($MgSO_4$), filtered and concentrated in vacuo. The crude oil was purified by silica column chromatography eluting with a gradient of hexane: ethyl acetate (50:50 to 0:100) to afford the title compound (80 mg, 40%) as a colourless oil.

NMR ($CDCl_3$) δ: 1.35 (s, 3H), 1.87 (m, 2H), 2.10 (t, 1H), 2.30 (d, 1H), 2.64 (m, 2H), 3.16–3.40 (m, 3H), 3.70 (dd, 1H), 7.17–7.60 (m, 9H)

PREPARATION 38

6-Methyl-3-(3-phenylpropyl)-6-{3-[5-(trimethylsilyl)-1H-1,2,3-triazol-5-yl]phenyl}-3-azabicyclo[3.1.0]hexan-2-one To a solution of (trimethylsilyl)diazomethane (0.36 ml, 0.74 mmol) in tetrahydrofuran (4 ml) at 0° C. was added n-butyllithium (0.40 ml, 0.64 mmol) dropwise over a few minutes. The mixture was then stirred at 0° C. for 30 minutes. To this mixture was added 3-[6-methyl-2-oxo-3-(3-phenylpropyl)-3-azabicyclo[3.1.0]hex-6-yl]benzonitrile (Preparation 37, 78.0 mg, 0.24 mmol) in tetrahydrofuran (2 ml) at 0° C. via a cannula. The mixture was then allowed to warm to room temperature and stirred for 16 h. Further reaction was quenched by the addition of saturated ammonium chloride solution (5 ml) and the aqueous layer was extracted with ethyl acetate (3×5 ml). The combined extracts were dried (MgSO$_4$), filtered and concentrated in vacuo. The crude oil was purified by silica column chromatography eluting with a gradient of hexane:ethyl acetate (50:50 to 0:100) to afford the title compound (58 mg, 55%) as a colourless oil.

NMR (CDCl$_3$) δ: 0.37 (s, 9H), 1.38 (s, 3H), 1.85 (m, 2H), 2.09 (t, 1H), 2.40 (d, 1H), 2.64 (m, 2H), 3.16–3.44 (m, 3H), 3.65 (dd, 1H), 7.17–7.45 (m, 8H), 7.64 (s, 1H)

PREPARATION 39

3-Hexyl-6-methyl-6-{3-[5-(trimethylsilyl)-1H-1,2,3-triazol-5-yl]phenyl}-3-azabicyclo[3.1.0]hexan-2-one To a solution of (trimethylsilyl)diazomethane (4.32 ml, 8.64 mmol) in tetrahydrofuran (10 ml) at 0° C. was added n-butyllithium (3.46 ml, 8.64 mmol) dropwise over 10 minutes. The mixture was then stirred at 0° C. for 30 minutes. To this mixture was added 3-(3-hexyl-6-methyl-2-oxo-3-azabicyclo[3.1.0]hex-6-yl)benzonitrile (Preparation 36, 852 mg, 2.88 mmol) in tetrahydrofuran (12 ml) at 0° C. via cannula. The mixture was then allowed to warm to room temperature and stirred for 48 h. Further reaction was quenched by the addition of saturated ammonium chloride solution (25 ml), and the tetrahydrofuran was removed in vacuo. The aqueous solution was extracted with ethyl acetate (3×20 ml). The combined extracts were dried (MgSO$_4$), filtered and concentrated in vacuo. The crude oil was purified by silica column chromatography, eluting with a gradient of hexane:ethyl acetate (66:33 to 0:100) to afford the title compound (1.2 g, 100%) as a colourless oil.

NMR (CDCl$_3$) δ: 0.38 (s, 9H), 0.82–0.95 (m, 3H), 1.30–1.40 (m, 9H), 1.47–1.58 (m, 2H), 2.08 (t, 1H), 2.40 (d, 1H), 3.10–3.38 (m, 3H), 3.67 (dd, 1H), 7.30–7.45 (m, 3H), 7.63 (s, 1H).

PREPARATION 40

3-Hexyl-6-methyl-6-[3-(1H-1,2,3-triazol-5-yl)phenyl]-3-azabicyclo[3.1.0]hexan-2-one To a solution of 3-hexyl-6-methyl-6-{3-[5-(trimethylsilyl)-1H-1,2,3-triazol-4-yl]phenyl}-3-azabicyclo[3.1.0]hexan-2-one (Preparation 39, 1.2 g, 2.88 mmol) in ethanol (15 ml) was added potassium fluoride (183 mg, 3.17 mmol) and a few drops of concentrated hydrochloric acid. The mixture was heated at reflux for 1.5 hours and then cooled to room temperature. The solvent was removed in vacuo and the crude residue was dissolved in dichloromethane (40 ml) and washed with 10% potassium carbonate solution. The extract was dried (MgSO$_4$), filtered and concentrated in vacuo to give the crude product which was used directly in the next step.

NMR (CDCl$_3$) δ: 0.80–0.98 (m, 3H), 1.25–1.40 (m, 9H), 1.43–1.58 (m, 2H), 2.10 (t, 1H), 2.43 (d, 1H), 3.13–3.40 (m, 3H), 3.65–3.76 (m, 1H), 7.25–7.38 (m, 2H), 7.63 (d, 1H), 7.86 (s, 1H), 7.99 (s, 1H)

PREPARATION 41

6-Methyl-3-(3-phenylpropyl)-6-[3-(1H-1,2,3-triazol-5-yl)phenyl]-3-azabicyclo[3.1.0]hexan-2-one To a solution of 6-methyl-3-(3-phenylpropyl)-6-{3-[5-(trimethylsilyl)-1H-1,2,3-triazol-4-yl]phenyl}-3-azabicyclo[3.1.0]hexan-2-one (Preparation 38, 58.0 mg, 0.13 mmol) in ethanol (2 ml) was added potassium fluoride (8.3 mg, 0.14 mmol) and a drop of concentrated sulphuric acid. The mixture was heated at reflux for 4 hours and then stirred at room temperature for 16 hours. The solvent was removed in vacuo and the crude residue was absorbed onto silica. This material was then purified by silica column chromatography eluting first with hexane:ethyl acetate (1:1) and then increasing gradually to neat ethyl acetate. The desired title compound (32 mg, 66%) was isolated as a colourless oil.

NMR (CDCl$_3$) δ: 1.38 (s, 3H), 1.85 (p, 2H), 2.09 (t, 1H), 2.45 (d, 1H), 2.65 (m, 2H), 3.19–3.48 (m, 3H), 3.70 (dd, 1H), 7.17–7.40 (m, 7H), 7.66 (d, 1H), 7.86 (br. s, 1H), 7.99 (s, 1H)

MS (thermospray): m/z [MH$^+$] 373.5; $C_{23}H_{24}N_4O$+H requires 373.2

PREPARATION 42

Ethyl 3-(3-hexyl-6-methyl-2-oxo-3-azabicyclo[3.1.0]hex-6-yl)benzene carboximidoate Hydrogen chloride gas was bubbled through a solution of 3-(3-hexyl-6-methyl-2-oxo-3-azabicyclo[3.1.0]hex-6-yl)benzonitrile (Preparation 36, 0.55 g, 1.86 mmol) in ethanol (8 ml) at 0° C. for 1 h. The reaction vessel was then sealed and left standing in the fridge for 48 h. The mixture was allowed to warm to room temperature and the solvent was removed in vacuo (to afford the title compound as its hydrochloride salt). The residue was dissolved in dichloromethane (20 ml) and washed with 10% w/v potassium carbonate solution (2×10 ml). The organic layer was dried (MgSO$_4$), filtered and concentrated in vacuo. The crude title compound (700 mg) was isolated as a colourless oil which was taken on without further purification.

NMR (CDCl$_3$) δ: 0.82–0.91 (m, 3H), 1.20–1.38 (m, 9H), 1.42 (t, 3H), 1.44–1.58 (m, 2H), 2.10 (m, 1H), 2.35 (m, 1H), 3.10–3.38 (m, 3H), 3.68 (dd, 1H), 4.38 (t, 2H), 7.30–7.44 (m, 2H), 7.60 (m, 1H), 7.68 (s, 1H).

PREPARATION 43

3-Hexyl-6-methyl-6-[3-(4H-1,2,4-triazol-3-yl)phenyl]-3-azabicyclo[3.1.0]hexan-2-one To a solution of crude ethyl 3-(3-hexyl-6-methyl-2-oxo-3-azabicyclo[3.1.0]hex-6-yl)benzenecarboximidoate (Preparation 42, 700 mg, 1.86 mmol) in methanol (5 ml) was added formic acid hydrazide (123 mg, 2.05 mmol) and the mixture was heated under reflux for 90 min. After cooling to room temperature, the solvent was removed in vacuo and the residue was heated to 150° C. for 12 h. The mixture was cooled and purified directly by silica column chromatography eluting with ethyl acetate:methanol (95:5) to afford the title compound (400 mg, 64%) as a colourless gum.

NMR (CDCl$_3$) δ: 0.83–0.94 (m, 3H), 1.22–1.38 (m, 9H),1.44–1.58 (m, 2H), 2.17 (t, 1H), 2.41 (m, 1H), 3.10–3.38 (m, 3H), 3.68 (dd, 1H), 7.36–7.43 (m, 2H), 7.92–7.99 (m, 2H), 8.20 (s, 1H)

PREPARATION 44

3-Hexyl-6-[3-(1H-imidazol-2-yl)phenyl]-6-methyl-3-azabicyclo[3.1.0]hexan-2-one To a solution of ethyl 3-(3-hexyl-6-methyl-2-oxo-3-azabicyclo[3.1.0]hex-6-yl)benzenecarboximidoate hydrochloride (Preparation 42, 528 mg, 1.45 mmol) in methanol (6 ml) at room temperature was added aminoacetaldehyde dimethylacetal (0.16 g, 1.52 mmol). The mixture was heated under reflux for 90 min, cooled to room temperature and the solvent was removed in vacuo. The crude residue was dissolved in 6N hydrochloric acid (8 ml) and the mixture was heated to 80° C. for 30 min and then left at room temperature for 2 h. The mixture was diluted with water (5 ml), the pH was adjusted to 9 using 5N sodium hydroxide solution and the aqueous solution was extracted with ethyl acetate (3×20 ml). The combined extracts were dried (MgSO$_4$), filtered and concentrated in vacuo. The crude residue was purified by silica column chromatography eluting with ethyl acetate:methanol:ammonia solution (0.880) (90:10:1) to afford the title compound (190 mg, 39%) as a colourless oil.

NMR (CDCl$_3$) δ: 0.82–0.91 (m, 3H), 1.18 (s, 3H), 1.24–1.38 (m, 6H), 1.44–1.58 (m, 2H), 2.0 (m, 1H), 2.18 (m, 1H), 3.08–3.38 (m, 3H), 3.62 (dd, 1H), 7.12–7.35 (m, 4H), 7.58 (s, 1H), 7.82 (d, 1H).

PREPARATION 45

N-[3-(3-Hexyl-6-methyl-3-azabicyclo[3.1.0]hex-6-yl)phenyl]acetamide

To a solution of 3-(3-hexyl-6-methyl-3-azabicyclo[3.1.0]hex-6-yl)phenylamine (Preparation 12, 1.30 g, 4.8 mmol) and triethylamine (3.34 ml, 24.0 mmol) in dichloromethane (30 ml) at room temperature was slowly added acetyl chloride (0.48 ml, 6.72 mmol). The mixture was stirred at room temperature overnight and then saturated ammonium chloride solution (50 ml) was added. The two layers were separated and the aqueous layer was extracted with dichloromethane (3×20 ml). The combined extracts were dried (MgSO$_4$), filtered and concentrated in vacuo. The crude residue was purified by silica column chromatography eluting with ethyl acetate:methanol:ammonia solution (0.880) (90:10:1) to afford the title compound (1.5 g, 100%) as a colourless gum.

NMR (CDCl$_3$) δ: 0.82–0.95 (m, 3H), 1.25–1.38 (m, 6H), 1.38–1.43 (m, 2H), 1.50 (s, 3H), 1.76 (m, 2H), 2.18 (s, 3H), 2.42 (m, 2H), 2.78 (m, 2H), 2.98 (m, 2H), 7.00 (d, 1H), 7.10–7.30 (m, 3H), 7.38 (s, 1H).

PREPARATION 46

N-[5-(3-Hexyl-6-methyl-3-azabicyclo[3.1.0]hex-6-yl)-2-nitrophenyl]-acetamide To a solution of N-[3-(3-hexyl-6-methyl-3-azabicyclo[3.1.0]hex-6-yl)phenyl]acetamide (Preparation 45, 1.5 g, 4.78 mmol) in acetonitrile (20 ml) at 0° C. was added nitronium tetrafluoroborate (1.0 g, 7.53 mmol) in several portions over 5 minutes. The mixture was stirred at 0° C. for 30 minutes and then saturated sodium hydrogen carbonate solution (30 ml) was added. The aqueous mixture was extracted with ethyl acetate (3×15 ml) and the combined extracts were dried (MgSO$_4$), filtered and concentrated in vacuo. The crude residue was purified by silica column chromatography eluting with ethyl acetate:hexane (50:50) to afford the title compound (534 mg, 32%) as pale yellow platelets.

NMR (CDCl$_3$) δ: 0.82–0.92 (m, 3H), 1.25–1.45 (m, 8H), 1.58 (s, 3H), 1.80 (m, 2H), 2.28 (s, 3H), 2.40 (t, 2H), 2.78 (m, 2H), 3.02 (m, 2H), 7.00 (d, 1H), 8.09 (d, 1H), 8.64 (s, 1H), 10.4 (broad s, 1H)

MS (thermospray): m/z [MH$^+$] 360.2; C$_{20}$H$_{29}$N$_3$O$_3$+H requires 360.2

PREPARATION 47

5-(3-Hexyl-6-methyl-3-azabicyclo[3.1.0]hex-6-yl)-2-nitrophenylamine

To a solution of potassium hydroxide (100 mg, 1.79 mmol) in methanol (5.0 ml) and water 2.0 ml) was added N-[5-(3-hexyl-6-methyl-3-azabicyclo[3.1.0]hex-6-yl)-2-nitrophenyl]acetamide (Preparation 46, 534 mg, 1.49 mmol) in methanol (5 ml). The mixture was heated under reflux for 30 minutes and then was allowed to cool. The solvent was removed in vacuo, water (5 ml) was added and the aqueous solution was extracted with ethyl acetate (3×5 ml). The combined extracts were dried (MgSO$_4$), filtered and concentrated in vacuo to afford the title compound (360 mg, 76%) as a crude oil which was used without further purification.

NMR (CDCl$_3$) δ: 0.82–0.95 (m, 3H), 1.25–1.45 (m, 8H), 1.56 (s, 3H), 1.79 (m, 2H), 2.42 (t, 2H), 2.80 (m, 2H), 3.00 (m, 2H), 6.00 (broad s, 2H), 6.53 (d, 1H), 6.63 (s, 1H), 7.99 (d, 1H)

PREPARATION 48

2-Amino-4-(3-hexyl-6-methyl-3-azabicyclo[3.1.0]hex-6-yl) phenylamine

To a solution of 5-(3-hexyl-6-methyl-3-azabicyclo[3.1.0]hex-6-yl)-2-nitrophenylamine (Preparation 47, 360 mg, 1.14 mmol) in ethanol (15 ml) was added 10% palladium on carbon (50 mg). The mixture was placed under an atmosphere of hydrogen (50 psi, 345 kPa) and heated at 50° C. for 16 hours. The mixture was then cooled and filtered through Celite™, washing with ethanol. The filtrate was concentrated in vacuo to give the crude title compound (328 mg, 100%) as a yellow oil which was used without further purification.

NMR (CDCl$_3$) δ: 0.82–0.92 (m, 3H), 1.25–1.38 (m, 6H), 1.42–1.60 (m, 5H), 1.80 (m, 2H), 2.45–2.60 (m, 2H), 2.80–3.10 (m, 4H), 3.35 (broad s, 4H), 6.57–6.62 (m, 3H)

MS (thermospray): m/z [MH$^+$] 288.4; C$_{18}$H$_{29}$N$_3$+H requires 288.2

PREPARATION 49

2-[(Chlorosulfonyl)amino]propane

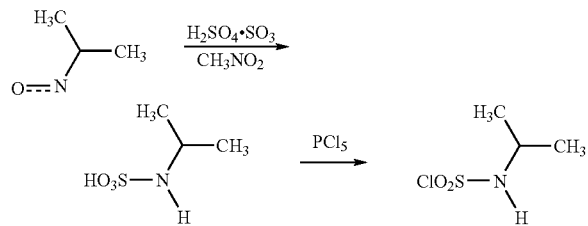

To sulfuric acid oleum (6 ml) in nitromethane (15 ml) was added dropwise over 30 min isopropyl isocyanate at 0° C. The reaction mixture was heated under reflux for 30 min and then cooled to room temperature, the solid was collected by suction filtration and washed with diethyl ether. The solid was dissolved in toluene (6 ml) and phosphorus pentachloride (7.58 g, 36.4 mmol) was added. The reaction mixture was heated under reflux for 2.5 h and the solvent was removed in vacuo. The crude product was distilled to give the title compound as an oil (b.p.80° C. at 0.5 mmHg).

NMR (CDCl$_3$): 1.35 (d, 6H), 3.9 (m, 1H), 5.4 (br, 1H).

PREPARATION 50

3-Allyl-6-methyl-6-(3-nitrophenyl)-3-azabicyclo[3.1.0]hexan-2-one

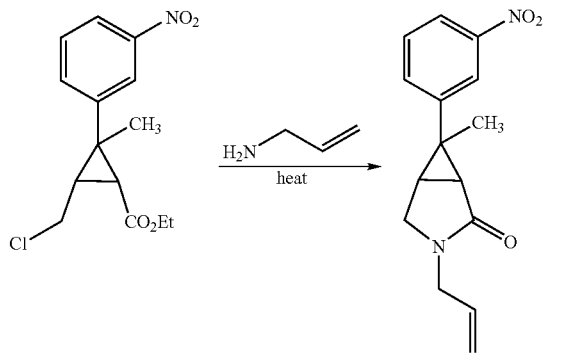

Ethyl 3-(chloromethyl)-2-methyl-2-(3-nitrophenyl)cyclopropanecarboxylate (Preparation 5, 1 g, 3.36 mmol) in allylamine (1.15 g, 20.1 mmol) was heated in a sealed tube at 150° C. for 16 h. After cooling the reaction mixture was concentrated in vacuo. The residue was dissolved in dichloromethane and washed with saturated aqueous sodium hydrogen carbonate solution. The organic extracts were dried (Na$_2$SO$_4$) and concentrated in vacuo to give the crude product as a yellow oil (0.92 g, 100%).

NMR (CDCl$_3$, selected data for the free base): 1.4 (s, 3H), 2.1 (m, 1H), 2.4 (m, 1H), 3.35 (m, 1H), 3.7 (m, 1H), 3.8–4.0 (m, 2H), 5.2–5.3 (m, 2H), 5.75 (m, 1H), 7.5 (t, 1H), 7.65 (d, 1H), 8.05 (d, 1H), 8.15 (s, 1H).

MS (ES): M/Z (MH$^+$) 273.0; C$_{15}$H$_{16}$N$_2$O$_3$+H requires 273.1.

PREPARATION 51

3-Allyl-6-(3-aminophenyl)-6-methyl-3-azabicyclo[3.1.0]hexan-2-one

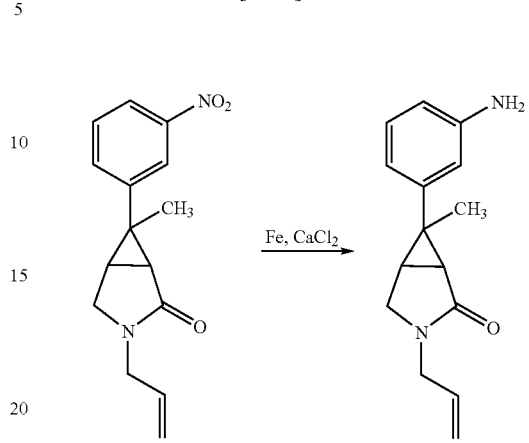

To a solution of 3-allyl-6-methyl-6-(3-nitrophenyl)-3-azabicyclo[3.1.0]hexan-2-one (Preparation 50, 10.2 g, 37.5 mmol) in ethanol (850 ml) and water (150 ml) was added iron powder (18.9 g, 337.5 mmol) and calcium chloride (2.1 g, 18.7 mmol). The reaction mixture was refluxed for 5 h, and then filtered to remove the iron powder. The reaction mixture was concentrated in vacuo and the residue was dissolved in dichloromethane:methanol (85:15), filtered and then concentrated in vacuo, dissolved in tetrahydrofuran, filtered and then concentrated in vacuo to give the title compound as a pale yellow foam (9 g, 99%).

NMR (CDCl$_3$, selected data for the free base): 1.2 (s, 3H), 2.05 (m, 1H), 2.2 (m, 1H), 3.2 (m, 1H), 3.6 (m, 1H), 3.7–3.8 (m, 2H), 5.1–5.2 (m, 2H), 5.7 (m, 1H), 6.5 (d, 1H), 6.6–6.7 (m, 2H), 7.0 (t, 1H).

PREPARATION 52

3-(3-Allyl-6-methyl-3-azabicyclo[3.1.0]hex-6-yl)aniline

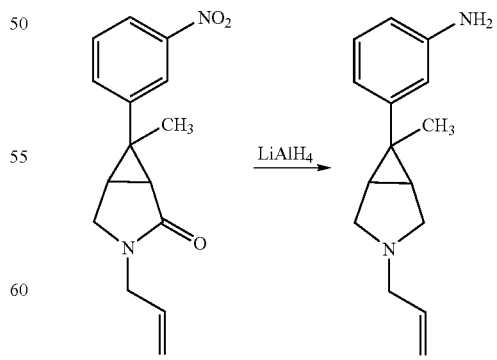

To dry tetrahydrofuran (300 ml) under nitrogen was added dropwise lithium aluminium hydride (1M in tetrahydrofuran, 75 ml, 75 mmol). To this solution, 3-allyl-6-(3-aminophenyl)-6-methyl-3-azabicyclo[3.1.0]hexan-2-one (Preparation 51, 9.0 g, 37.1 mmol) dissolved in tetrahydrofuran (200 ml), was added dropwise at 0° C. The reaction mixture was stirred for 1 h and then heated to 50° C. for 3 h. The reaction mixture was quenched with water (150 ml) and solid sodium hydrogen carbonate was added. The slurry was extracted with ethyl acetate and then dichloromethane. The organic extracts were combined and dried (Na₂SO₄) and then concentrated in vacuo to give the title compound as a thick yellow oil (8.5 g, 100%).

NMR (CDCl₃, selected data for the free base): 1.5 (s, 3H), 1.8 (m, 2H), 2.85 (m, 2H), 2.95 (m, 2H), 3.2 (m, 2H), 5.0–5.3 (m, 2H), 5.9 (m, 1H), 6.5 (d, 1H), 6.6 (s, 1H), 6.65 (d, 1H), 7.1 (t, 1H).

PREPARATION 53

N-[3-(6-Methyl-3-azabicyclo[3.1.0]hex-6-yl)phenyl]methanesulfonamide

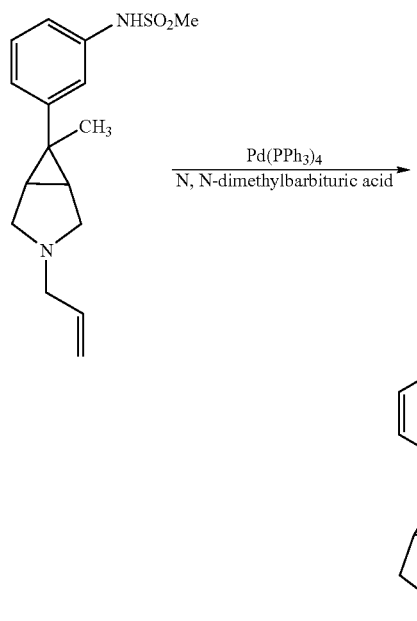

A stirred mixture of N-[3-(3-allyl-6-methyl-3-azabicyclo[3.1.0]hex-6-yl)phenyl]methanesulfonamide (Example 56, 1.90 g, 6.19 mmol), tetrakis(triphenylphosphine)palladium (0) (71.8 mg, 62.1 µmol) and N,N-dimethylbarbituric acid (2.91 g, 18.6 mmol) in dichloromethane (15 ml) was degassed and then heated to 35° C. under nitrogen for 3 h. The solution was rapidly stirred with aqueous hydrochloric acid solution (2M, 40 ml) and the aqueous portion was separated, this process was repeated. The combined aqueous layers were washed with dichloromethane (7×50 ml), and then concentrated in vacuo to give the hydrochloride salt of the title compound as an off white solid (1.40 g, 74%).

NMR (d₆-DMSO, selected data for the hydrochloride salt): 1.25 (s, 3H), 2.15 (m, 2H), 2.95 (s, 3H), 3.2 (m, 2H), 3.6 (m, 2H), 6.95–7.05 (m, 2H), 7.1 (s, 1H), 7.2 (t, 1H), 9.6 (br, 1H).

MS (ES): M/Z (MH⁺) 267.1; $C_{13}H_{18}N_2O_2S$+H requires 267.1.

PREPARATION 54

4-(Hexylamino)-4-oxo-2-butenoic acid

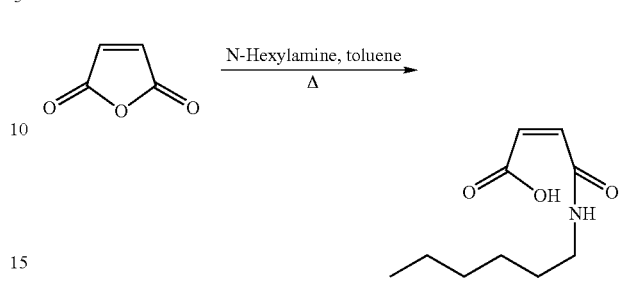

Maleic anhydride (39.4 g, 0.40 mol) was partly dissolved in toluene (1 l) to form a milky suspension. N-hexylamine (53 ml, 0.40 mol) was diluted with toluene (500 ml) and added dropwise over a period of 1.5 h. After 2 h, the reaction mixture was filtered and the title compound was obtained as a white solid (76.4 g, 96%) after drying for 16 h in a vacuum oven at 40° C.

NMR (CDCl₃, selected data for the free base) 0.8 (m, 3H), 1.2–1.4 (m, 6H), 1.6 (m, 2H), 3.3 (m, 2H) 6.25 (d, 1H), 6.45 (d, 1H), 7.8 (br, 1H).

PREPARATION 55

2-Methyl-1-(3-nitrophenyl)-1-propanone

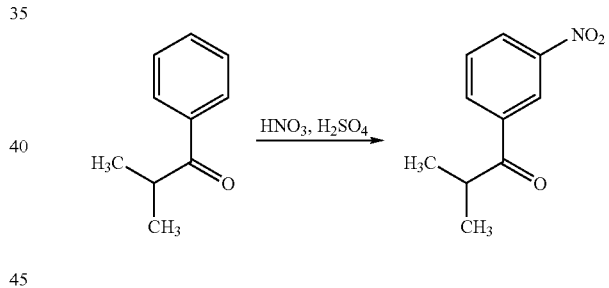

Concentrated nitric acid (20 ml) was added cautiously with cooling to concentrated sulphuric acid (50 ml) maintaining a temperature of –5° C. Another solution of 2-methyl-1-phenyl-1-propanone (29.6 g, 0.2 mol) in concentrated sulphuric acid (70 ml) was made up with shaking, keeping the temperature at –5° C. The former nitric acid/sulphuric acid solution was added portionwise over 30 min to the latter solution of ketone in sulphuric acid keeping the temperature at –10° C.+/–5° C. during the addition and for a subsequent 30 min. The reaction mixture was poured onto crushed ice (1 l) and then extracted with diethyl ether (3×100 ml). The organic extracts were washed with water (300 ml) and then brine (300 ml), dried (Na₂SO₄) and then concentrated in vacuo. The crude product was obtained as an orange oil (40 g) which was purified by chromatography on silica gel (450 g) eluting with hexane: diethyl ether (9:1) to give the title compound as a pale yellow solid (16.3 g, 42%), m.p.33–35° C.

NMR (CDCl₃, selected data for the free base): 1.25 (d, 6H), 3.6 (m, 1H), 7.65 (t, 1H), 8.25 (d, 1H), 8.4 (d, 1H), 8.9 (s, 1H).

PREPARATION 56

1-Hexyl-1H-pyrrole-2,5-dione

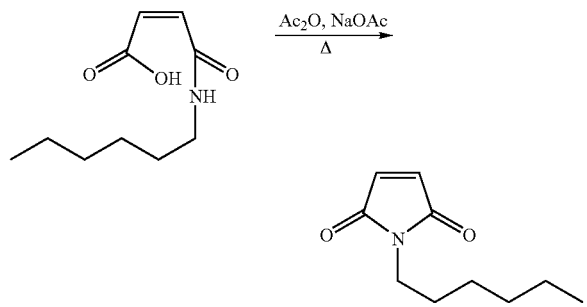

4-(Hexylamino)-4-oxo-2-butenoic acid (Preparation 54, 75.8 g, 0.38 mol) was partially dissolved in acetic anhydride (1.5 l) and sodium acetate (125.6 g, 0.19 mol) was added in one portion. The reaction mixture was gradually heated to 110° C. for 4 h. Acetic anhydride was removed in vacuo and the title compound was obtained by vacuum distillation of the crude residue to give a colourless oil (49.8 g, 72%) which partially crystallised upon standing.

NMR (CDCl$_3$, selected data for the free base): 0.85 (m, 3H), 1.2–1.4 (m, 6H), 1.6 (m, 2H), 3.5 (m, 2H), 6.7 (s, 2H).

PREPARATION 57

2-Methyl-1-(3-nitrophenyl)-1-propanone hydrazone

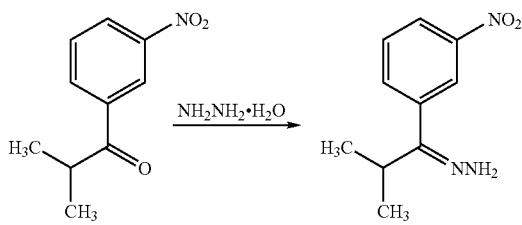

To a partially dissolved solution of 2-methyl-1-(3-nitrophenyl)-1-propanone (Preparation 55, 1.0 g, 5.2 mmol) in industrial methylated spirits (6 ml) was added dropwise hydrazine hydrate monohydrate (0.5 ml, 10.4 mmol). The reaction mixture was refluxed for 16 h, before cooling to room temperature and pouring into ice and water (50:50, 15 ml) giving a very fine white precipitate in a yellow solution. The mixture was extracted with diethyl ether (2×50 ml), the combined organic extracts were washed with brine and dried (MgSO$_4$), before concentrating to give an amber oil. The crude product was purified by chromatography on silica gel eluting with dichloromethane:ethyl acetate (19:1) to give the title compound as a mixture of cis and trans hydazones (0.54 g, 50%).

NMR (CDCl$_3$, selected data for the free base, 2:1 mixture of isomers): 1.1 (d, 4H), 1.25 (d, 2H), 2.75 (m, 0.6), 3.2 (m, 0.4), 4.95 (br, 1.2), 5.6 (br, 0.8), 7.45–8.3 (m, 4H).

MS (ES): M/Z (MH$^+$) 208.2; C$_{10}$H$_{13}$N$_3$O$_2$+H requires 208.1.

PREPARATION 58

5-Hexyl-3-isopropyl-3(3-nitrophenyl)-3a,6a-dihydropyrrolo(3,4-c)pyrazole-4,6(3H,5H)-dione

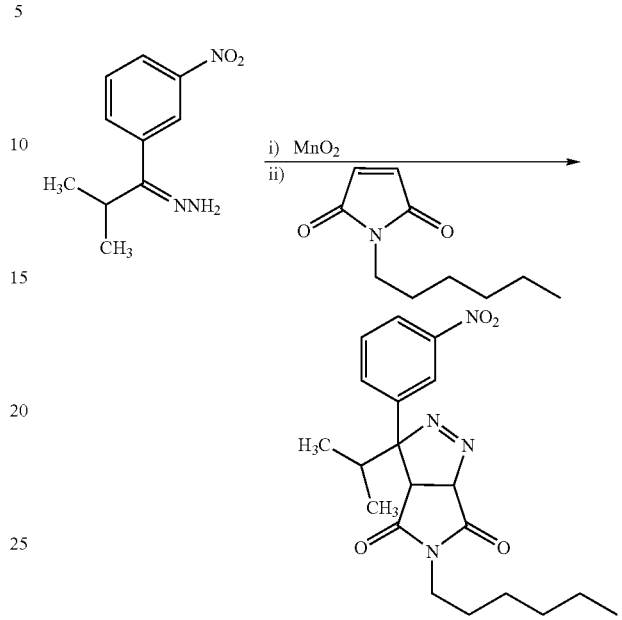

2-Methyl-1-(3-nitrophenyl)-1-propanone hydrazone (Preparation 57, 0.52 g, 2.5 mmol) was dissolved in dioxan (10 ml) and manganese dioxide (grade CMD-1 from Sumitomo, 5.2 g, 60.0 mmol) was added portionwise and the reaction mixture was stirred at room temperature for 20 minutes. This solution was filtered over a pad of Celite® dropwise, directly into a solution of 1-hexyl-1H-pyrrole-2,5-dione (Preparation 56, 0.54 g, 3.0 mmol) in dioxan (10 ml). The Celite® pad was washed with dioxan (40 ml) to ensure complete addition of the reactants and then the reaction mixture was stoppered and stirred for 72 h. The reaction mixture was purified by chromatography using a Biotage Flash 40S™ cartridge packed with silica gel (40 g), eluting with petroleum ether:ethyl acetate (4:1). The title compound was obtained as a yellow solid (0.65 g, 67%).

NMR (CDCl$_3$, selected data for the free base): 0.8–1.4 (m, 15H), 1.8 (m, 2H), 2.7 (m, 1H), 3.1–3.25 (m, 3H), 5.85 (d, 1H), 7.6 (m, 2H), 8.2 (m, 2H).

PREPARATION 59

3-Hexyl-6-isopropyl-6-(3-nitrophenyl)-3-azabicyclo [3.1.0]hexane-2,4-dione

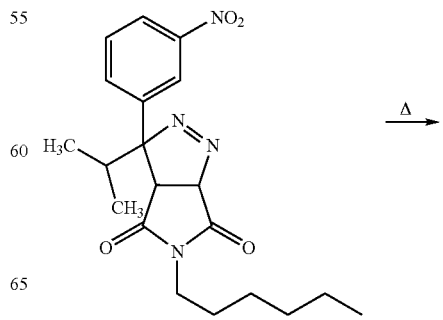

-continued

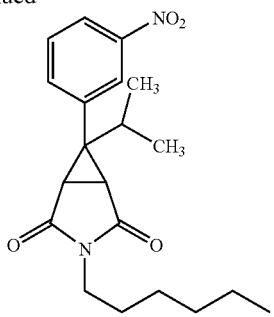

5-Hexyl-3-isopropyl-3(3-nitrophenyl)-3a,6a-dihydropyrrolo(3,4-c)pyrazole-4,6(3H,5H)-dione (Preparation 58, 0.65 g, 1.6 mmol) was dissolved in dioxan (25 ml) and heated under reflux for 3 h. The solvent was removed in vacuo and the oily residue dried in vacuum for 16 h at room temperature to give the crude product as a yellow solid. The crude product was purified by chromatography on a Biotage Flash 12™ cartridge packed with silica gel (8 g), eluting with hexane:ethyl acetate (9:1) to give the title compound (0.60 g, 100%).

NMR (CDCl$_3$, selected data for the free base): 0.85 (m, 3H), 0.95 (d, 6H), 1.2–1.4 (m, 6H), 1.55 (m, 2H), 1.7 (m, 1H), 2.8 (s, 2H), 3.45 (m, 2H), 7.5 (t, 1H), 7.65 (d, 1H), 8.2 (m, 2H).

MS (TSP): M/Z (MNH$_4^+$) 376.4; C$_{20}$H$_{26}$N$_2$O$_4$+NH$_4^+$ requires 376.2.

PREPARATION 60

3-Hexyl-6-isopropyl-6-(3-nitrophenyl)-3-azabicyclo[3.1.0]hexane

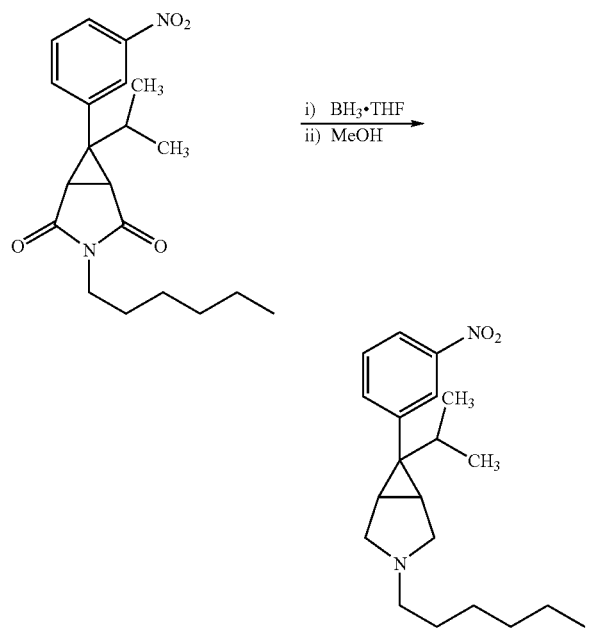

To a stirred solution of 3-hexyl-6-isopropyl-6-(3-nitrophenyl)-3-azabicyclo[3.1.0]hexane-2,4-dione (Preparation 59, 0.57 g, 1.6 mmol) in tetrahydrofuran (6 ml), under nitrogen, was added borane tetrahydrofuran complex (1M in tetrahydrofuran, 3.0 ml, 3.0 mmol) and the reaction mixture was heated under reflux for 2 h. The reaction mixture was cooled to room temperature before the addition of further borane tetrahydrofuran complex (1M in tetrahydrofuran, 3.0 ml, 3.0 mmol). After 20 min, the reaction mixture was cooled to room temperature and methanol (8 ml) was added and then the reaction mixture was once more heated under reflux for 6 h. The reaction mixture was concentrated in vacuo and the residue was dried under vacuum at room temperature. The residue was treated with dichloromethane (4 ml), filtered and purified by chromatography on a Biotage Flash40S™ cartridge packed with silica gel (40 g) eluting with hexane:ethyl acetate (6:1). The title compound was obtained initially as a yellow oil which crystallised upon standing (0.2 g, 40%).

NMR (CDCl$_3$, selected data for the free base): 0.8–1.0 (m, 9H), 1.25–1.4 (m, 6H), 1.4 (m, 2H), 1.8 (m, 2H), 2.45 (m, 2H), 2.6 (m, 1H), 2.85 (m, 2H), 3.05 (m, 2H), 7.4 (t, 1H), 7.6 (d, 1H), 8.0–8.15 (m, 2H).

PREPARATION 61

3-(3-Hexyl-6-isopropyl-3-azabicyclo[3.1.0]hex-6-yl)aniline

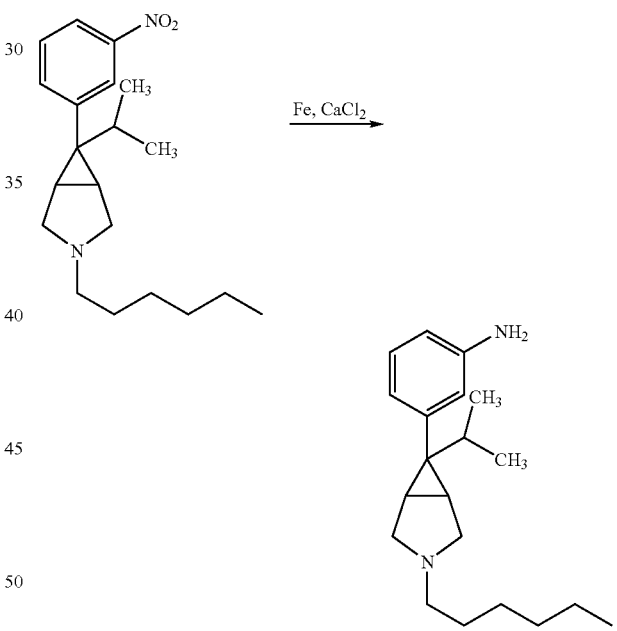

To a stirred suspension of 3-hexyl-6-isopropyl-6-(3-nitrophenyl)-3-azabicyclo[3.1.0]hexane (Preparation 60, 0.18 g, 0.54 mmol), ethanol (15 ml) and iron powder (0.27 g, 4.88 mmol) was added calcium chloride (0.06 gm 0.54 mmol) in water (3 ml). The reaction mixture was heated under reflux for 3 h and then filtered through a pad of Celite®, the mother liquors were concentrated in vacuo. The residue was dissolved in dichloromethane and filtered again through a Sep-Pak® Plus cartridge containing silica (1.5 g), (Water Division Millipore), to remove any residual iron salts and then concentrated to give the crude title compound as a yellow solid (0.17 g, 100%).

NMR (CDCl$_3$, selected data for the free base): 0.75–0.85 (m, 9H), 1.2–1.4 (m, 6H), 6.4–6.6 (m, 3H), 7.0 (t, 1H).

MS (APCI): M/Z (MH⁺) 301.1; $C_{20}H_{32}N_2$+H⁺ requires 301.3.

PREPARATION 62

1-(3-Nitrophenyl)-1-butanone

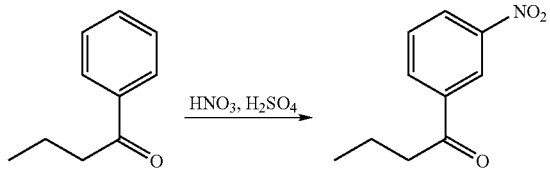

Concentrated nitric acid (40 ml) was added cautiously with cooling to concentrated sulphuric acid (100 ml) maintaining a temperature of −5° C. Another solution of butyrophenone (59.2 g, 0.47 mol) in concentrated sulphuric acid (140 ml) was made up with shaking, keeping the temperature at −5° C. (+/−5° C.). The former nitric acid/sulphuric acid solution was added portionwise over 45 min to the latter solution of ketone in sulphuric acid keeping the temperature at −10° C.(+/−5° C. during the addition and for a subsequent 30 min. The reaction mixture was poured onto crushed ice (1.5 l) and then extracted with diethyl ether (200 ml and then 3×100 ml). The combined organic extracts were washed with water and then aqueous saturated sodium hydrogen carbonate solution and dried ($MgSO_4$) before concentrating in vacuo. The crude yellow oil crystallised after 16 h and was then purified by chromatography on silica gel (1 kg) eluting with hexane:diethyl ether (9:1) to give the title compound as a white solid (9.1 g, 10%).

NMR (CDCl₃, selected data for the free base): 1.05 (t, 3H), 1.8 (m, 2H), 3.0 (t, 2H), 7.65 (t, 1H), 8.25 (d, 1H), 8.4 (d, 1H), 8.9 (s, 1H).

PREPARATION 63

1-(3-Nitrophenyl)-1-butanone hydrazone

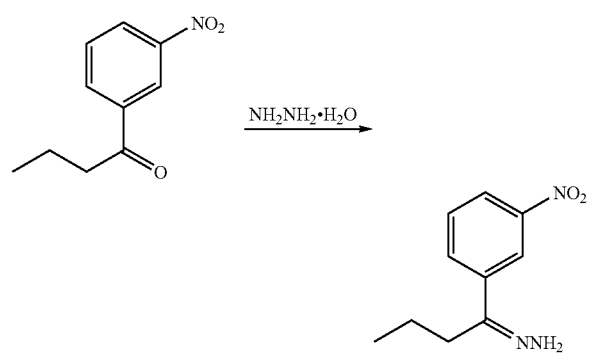

To a partially dissolved solution of 1-(3-nitrophenyl)-1-butanone (Preparation 62, 9.0 g, 46.6 mmol) in industrial methylated spirits (60 ml) was added dropwise hydrazine hydrate monohydrate (4.5 ml, 93.2 mmol). The reaction mixture was refluxed for 6 h, before cooling to 0° C. and adding water (60 ml) dropwise with stirring. The mixture was cooled in a refrigerator for 16 h and the orange crystals (7.5 g) so formed were removed by filtration. The filtrate was diluted with water (350 ml) and extracted with dichloromethane (3×150 ml), the combined organic extracts were dried ($Na_2SO_4$), and concentrated to give an orange oil (1.8 g). Both the crystals and oil were combined to give the desired title compound (9.3 g, 96%).

NMR (CDCl₃, selected data for the free base): 1.1 (m, 3H), 1.6 (m, 2H), 2.6 (m, 2H), 7.5 (t, 1H), 8.0 (d, 1H), 8.1 (d, 1H), 8.5 (s, 1H).

MS (TSP): M/Z (MH⁺) 207.9; $C_{10}H_{13}N_3O_2$+H requires 208.1.

PREPARATION 64

3-Hexyl-6-(3-nitrophenyl)-6-propyl-3-azabicyclo [3.1.0]hexane-2,4-dione

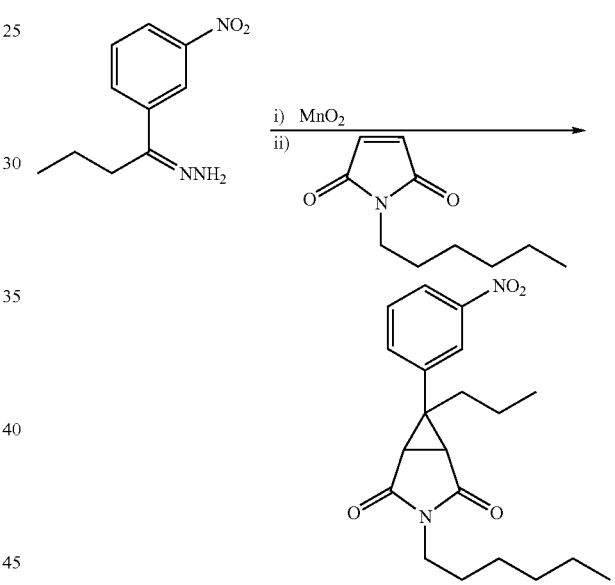

1-(3-Nitrophenyl)-1-butanone hydrazone (Preparation 63, 1.0 g, 4.8 mmol) was dissolved in dioxan (20 ml) and cooled to 10° C., manganese dioxide (grade CMD-1 from Sumitomo, 10 g, 117 mmol) was added portionwise. After the addition was complete, the reaction mixture was stirred at room temperature for 30 minutes. This suspension was filtered over a pad of Celite® directly into a solution of 1-hexyl-1H-pyrrole-2,5-dione (Preparation 56, 0.88 g, 4.5 mmol) in dioxan (20 ml). The Celite® pad was washed with dioxan (125 ml) and then stirred at room temperature for 20 h. The reaction mixture was concentrated in vacuo to give a crude orange oil. Methanol (8 ml) was added and the mixture was cooled to 0° C. and upon scratching a white solid precipitated. The solid was filtered off and washed with cold methanol to give the pure product, the mother liquors were concentrated in vacuo and treated again with methanol under the procedure described above to give further product. The title compound was obtained as a white solid (0.28 g, 16%).

NMR (CDCl₃, selected data for the free base): 0.8 (m, 3H), 0.9 (m, 3H), 1.2–1.4 (m, 8H), 1.6 (m, 2H), 1.7 (m, 2H), 2.8 (m, 2H), 3.5 (m, 2H), 7.5 (t, 1H), 7.65 (d, 1H), 8.1 (d, 1H), 8.2 (s, 1H).

PREPARATION 65

3-Hexyl-6-(3-nitrophenyl)-6-propyl-3-azabicyclo[3.1.0]hexane

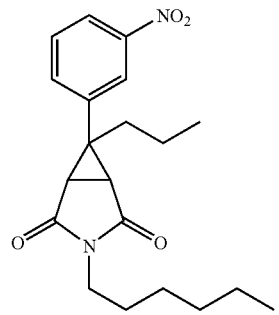

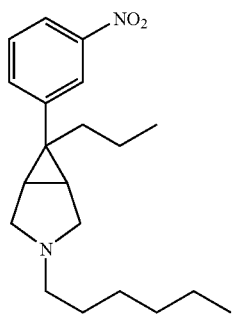

To a stirred solution of 3-hexyl-6-(3-nitrophenyl)-6-propyl-3-azabicyclo[3.1.0]hexane-2,4-dione (Preparation 64, 0.28 g, 0.78 mmol) in tetrahydrofuran (3 ml), under nitrogen, was added borane tetrahydrofuran complex (1M in tetrahydrofuran, 1.7 ml, 1.7 mmol) and the reaction mixture was heated under reflux for 2 h. The reaction mixture was cooled to room temperature, methanol (1.5 ml) was added and then the reaction mixture was heated under reflux for 16 h. The reaction mixture was concentrated in vacuo and the residue was dissolved in methanol (14 ml) and refluxed for 5 h. The reaction mixture was concentrated in vacuo, methanol (14 ml) was added and the reaction mixture was refluxed for a further 3 h before concentrating in vacuo. The crude residue was purified by chromatography on a Biotage Flash12™ cartridge packed with silica gel (8 g), eluting with hexane:ethyl acetate (4:1) to give the title compound as a yellow oil (0.2 g, 79%).

NMR (CDCl₃, selected data for the free base): 0.8–1.0 (m, 6H), 1.15–1.5 (m, 10H), 1.8 (m, 2H), 2.0 (m, 2H), 2.4 (m, 2H), 2.8 (m, 2H), 3.0 (m, 2H), 7.4 (t, 1H), 7.6 (d, 1H), 8.0 (d, 1H), 8.1 (s, 1H).

MS (ES): M/Z (MH⁺) 331.1; $C_{20}H_{30}N_2O_2$+H requires 331.2.

PREPARATION 66

3-(3-Hexyl-6-propyl-3-azabicyclo[3.1.0]hex-6-yl)aniline

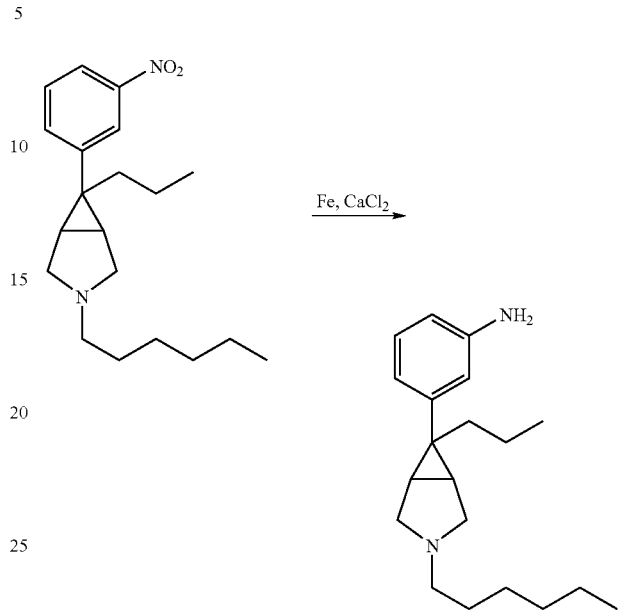

To a stirred suspension of 3-hexyl-6-(3-nitrophenyl)-6-propyl-3-azabicyclo[3.1.0]hexane (Preparation 65, 2.60 g, 7.2 mmol), ethanol (150 ml) and iron powder (0.41 g, 73.2 mmol) was added calcium chloride (1.5 g 13.0 mmol) in water (50 ml). The reaction mixture was heated under reflux for 16 h. The reaction mixture was cooled to room temperature, filtered through a pad of Celite®, and the mother liquors were concentrated in vacuo. The residue was dissolved in dichloromethane and filtered through a pad of sodium sulphate to give upon concentration the title compound as a yellow oil (2.17 g, 100%).

NMR (CDCl₃, selected data for the free base): 0.8–1.0 (m, 6H), 1.2–1.4 (m, 10H), 1.6–1.8 (m, 4H), 2.0 (m, 2H), 2.8 (m, 2H), 3.6 (m, 2H), 6.45–6.55 (m, 2H), 6.6 (d, 1H), 7.0 (m, 1H).

MS (ES): M/Z (MH⁺) 301.2; $C_{20}H_{32}N_2$+H⁺ requires 301.3.

PREPARATION 67

3-Hexyl-6-(3-iodophenyl)-6-methyl-3-azabicyclo[3.1.0]hexan-2-one

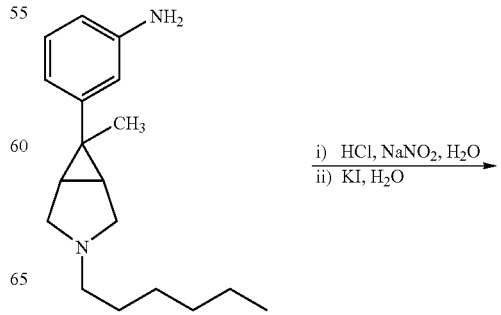

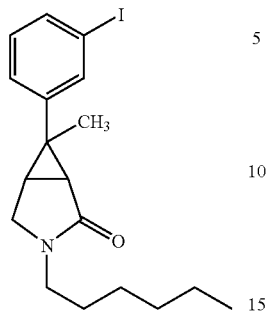

A solution of sodium nitrite (0.25 g, 3.6 mmol) dissolved in water (4 ml) was added to 3-(3-hexyl-6-methyl-3-azabicyclo[3.1.0]hex-6-yl)phenylamine (Preparation 12, 0.43 g, 1.6 mmol) dissolved in aqueous hydrochloric acid (2.0 M, 4 ml) at 0° C. After 15 min at 0° C., the reaction mixture was added to potassium iodide (0.61 g, 3.69 mmol) in water (4 ml) at 0° C. with rapid stirring. The reaction mixture was stirred for 30 min at room temperature and was then heated to 90° C. for 5 min. The reaction mixture was cooled to room temperature and then poured cautiously onto solid sodium hydrogen carbonate with cooling. After 12 h, the reaction mixture was extracted with diethyl ether and then ethyl acetate and the combined organic extracts were washed with aqueous sodium thiosulphate solution, dried (MgSO$_4$) and then concentrated in vacuo. The crude residue was purified by chromatography on silica gel eluting with hexane: ethyl acetate (10:1 and then 3:1) to give the title compound (0.18 g, 24%).

NMR (CDCl$_3$, selected data for the free base): 0.85 (m, 3H), 1.2–1.4 (m, 9H), 1.5 (m, 2H), 2.05 (m, 1H), 2.25 (m, 1H), 3.05–3.3 (m, 3H), 3.65 (m, 1H), 7.0 (t, 1H), 7.2 (d, 1H), 7.5 (d, 1H), 7.65 (s, 1H).

MS (TSP): M/Z (MH$^+$) 398.1; C$_{18}$H$_{24}$$^{129}$INO+H$^+$ requires 398.1.

PREPARATION 68

3-Hexyl-6-methyl-6-[3-(2-pyridinyl)phenyl]-3-azabicyclo[3.1.0]hexan-2-one

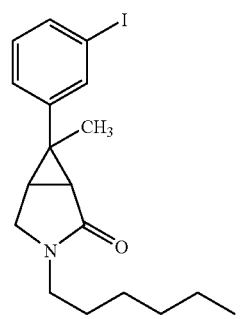 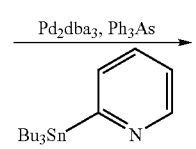

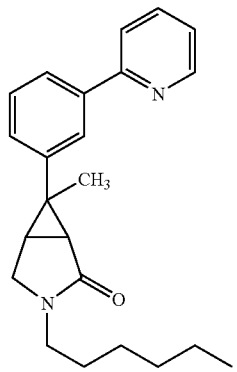

To tris(dibenzylideneacetone)dipalladium (0) (4.4 mg, 4.80 µmol) in tetrahydrofuran (1 ml) at room temperature was added triphenylarsine (5.9 mg, 19.2 µmol). After 5 min, 2-(tributylstannyl)pyridine (0.10 g, 0.29 mmol) in tetrahydrofuran (1 ml) was added followed by 3-hexyl-6-(3-iodophenyl)-6-methyl-3-azabicyclo[3.1.0]hexan-2-one (Preparation 67, 77 mg, 0.19 mmol) in tetrahydrofuran (1 ml). The reaction mixture was stirred at room temperature for 16 h and then refluxed for 2 h. The cooled reaction mixture was concentrated in vacuo and chromatographed on silica gel eluting with hexane:ethyl acetate (1:1 then 0:1) to give the title compound as a colourless oil (67 mg, 100%).

NMR (CDCl$_3$, selected data for the free base): 0.9 (m, 3H), 1.2–1.4 (m, 6H), 1.5–1.7 (m, 5H), 2.1 (m, 1H), 2.4 (m, 1H), 3.1–3.4 (m, 3H), 3.7 (m, 1H), 7.2–7.3 (m, 2H), 7.35–7.45 (m, 2H), 7.65–7.85 (m, 2H), 8.0 (m, 1H), 8.7 (m, 1H).

MS (TSP): M/Z (MH$^+$) 348.9; C$_{23}$H$_{28}$N$_2$O+H requires 349.2.

PREPARATION 69

3-Hexyl-6-methyl-6-[3-(2-thienyl phenyl]-3-azabicyclo[3.1.0]hexan-2-one

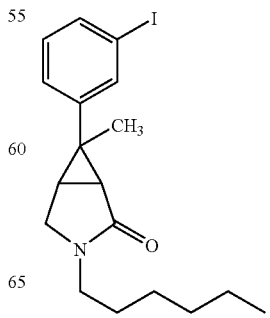 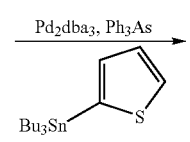

-continued

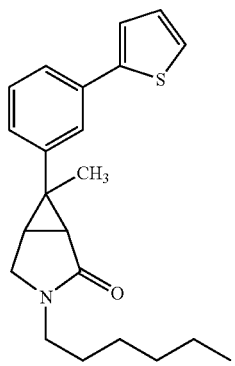

To tris(dibenzylideneacetone)dipalladium (0) (4.5 mg, 4.91 μmol) in tetrahydrofuran (1 ml) at room temperature was added triphenylarsine (5.9 mg, 19.2 μmol). After 5 min, 2-(tributylstannyl)thiophene (0.10 g, 0.27 mmol) in tetrahydrofuran (1 ml) was added followed by 3-hexyl-6-(3-iodophenyl)-6-methyl-3-azabicyclo[3.1.0]hexan-2-one (Preparation 67, 78 mg, 0.19 mmol) in tetrahydrofuran (1 ml). The reaction mixture was stirred at room temperature for 16 h and then refluxed for 2 h. The cooled reaction mixture was concentrated in vacuo and chromatographed on silica gel eluting with hexane: ethyl acetate (2:1) to give the title compound as a colourless oil (68 mg, 98%).

NMR (CDCl$_3$, selected data for the free base): 0.9 (m, 3H), 1.2–1.4 (m, 9H), 1.5 (m, 2H), 2.15 (m, 1H), 2.4 (m, 1H), 3.1–3.4 (m, 3H), 3.7 (m, 1H), 7.05 (m, 1H), 7.2–7.35 (m, 4H), 7.45 (d, 1H), 7.55 (s, 1H).

MS (TSP): M/Z (MH$^+$) 354.2; C$_{22}$H$_{27}$NOS+H requires 354.2.

PREPARATION 70

4,5-Diiodo-1H-imidazole

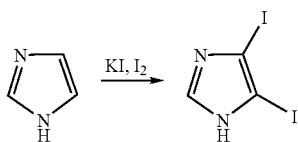

A solution of iodine (22.5 g, 88 mmol) in 20% aqueous potassium iodide (150 ml) was added dropwise to a stirred solution of imidazole (3.4 g, 49 mmol) in aqueous sodium hydroxide solution (1M, 300 ml) at room temperature. After stirring for 16 h, acetic acid was added to neutralise the reaction mixture. The white precipitate formed was filtered off and washed with water before dissolving in ethanol and concentrating in vacuo to give the title compound (7.7 g, 54%).

NMR (d$_6$-DMSO, selected data for the free base: 7.8 (br, 1H), 12.75 (br, 1H).

MS (TSP): M/Z (MH$^+$) 320.8; C$_3$H$_2$$^{129}$I$_2$N$_2$+H requires 320.8.

PREPARATION 71

4-Iodo-1H-imidazole

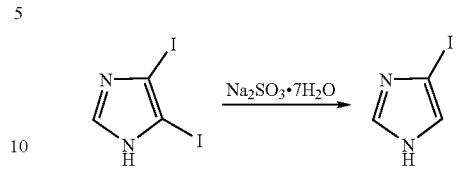

To a solution of 4,5-diiodo-1H-imidazole (Preparation 70, 7.7 g, 24 mmol) in ethanol (80 ml) and water (20 ml) was added solid sodium sulfite heptahydrate (20 g, 79 mmol). The reaction mixture was heated at reflux for 16 h, cooled, and the solid by-products were removed by filtration. The filtrate was then concentrated in vacuo and the resultant solid was dried by suction. The crude residue was recrystallised from dichloromethane to give the title compound as a white solid (4.6 g, 64%).

NMR (CDCl$_3$, selected data for the free base: 7.0 (s, 1H), 7.5 (s, 1H).

MS (TSP): M/Z (MH$^+$): 195.2; C$_3$H$_3$$^{129}$IN$_2$+H requires 194.9.

PREPARATION 72

4-Iodo-1-triphenylmethyl-1H-imidazole

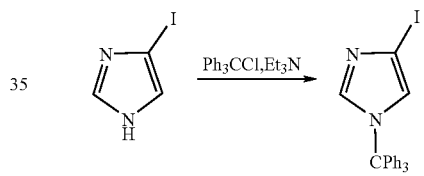

To 4-iodo-1H-imidazole (Preparation 71, 3.0 g, 15.3 mmol) in N,N-dimethylformamide (25 ml) was added triphenylmethyl chloride (4.72 g, 16.9 mmol) and then triethylamine (2.5 ml, 18.4 mmol). After stirring at room temperature for 2.5 h, water (200 ml) was added and the reaction mixture was filtered and washed with water. The crude solid was chromatographed on silica gel eluting with hexane:ethyl acetate (5:1 and then 2:1). The material was then recrystallised from hexane and dichloromethane to give the title compound as a white solid (4.0 g, 59%).

NMR (CDCl$_3$, selected data for the free base: 6.9 (m, 1H), 7.0–7.2 (m, 6H), 7.25–7.4 (m, 10H).

MS (TSP): M/Z (MH$^+$): 436.3; C$_{22}$H$_{17}$$^{129}$IN$_2$+H requires 437.1.

PREPARATION 73

4-(tributylstannyl)-1-triphenylmethyl-1H-imidazole

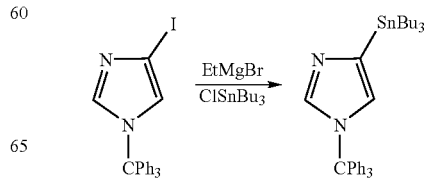

To 4-iodo-1-triphenylmethyl-1H-imidazole (Preparation 72, 0.44 g, 0.10 mmol) in dichloromethane (8.0 ml) at room temperature was added slowly ethyl magnesium bromide (3.0 M in diethyl ether, 0.35 ml, 1.0 mmol). After 30 min, tributyltin chloride (0.3 ml, 1.1 mmol) was added and the reaction mixture was stirred at room temperature for 2 h. The reaction mixture was quenched with saturated aqueous ammonium chloride solution (10 ml) and the product was extracted with dichloromethane (3×10 ml). The combined organic layers were dried ($Na_2SO_4$) and concentrated in vacuo. The residue was purified by flash chromatography on silica gel eluting with hexane:ethyl acetate (10:1 and then 5:1) to give the title compound (59 mg, 98%).

NMR ($CDCl_3$, selected data for the free base: 0.8–1.0 (m, 9H), 1.2–1.7 (m, 18H), 6.75 (m, 1H), 7.1–7.2 (m, 6H), 7.25–7.4 (m, 9H), 7.6 (s, 1H).

PREPARATION 74

3-Hexyl-6-methyl-6-[3-(1-triphenylmethyl-1H-imidazol-5-yl)phenyl]-3-azabicyclo[3.1.0]hexan-2-one

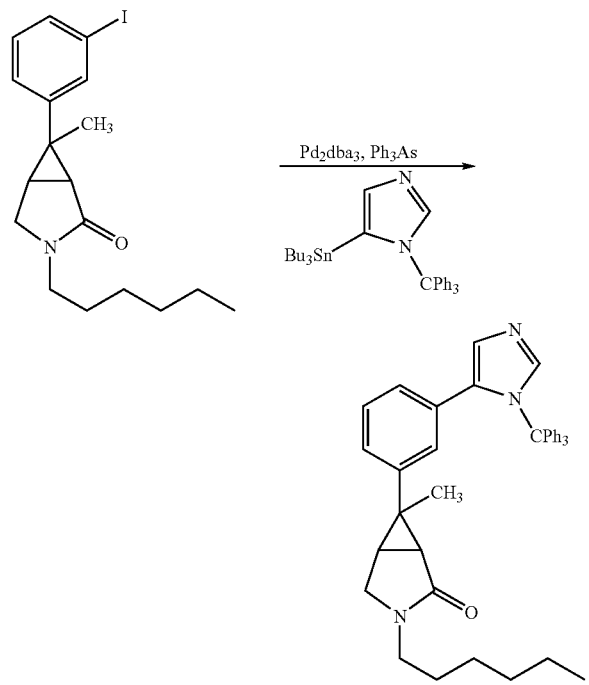

To tris(dibenzylideneacetone)dipalladium (0) (8.7 mg, 9.5 µmol) in tetrahydrofuran (2.5 ml) at room temperature was added triphenylarsine (12 mg, 39.2 µmol). After 10 min, a solution of 3-hexyl-6-(3-iodophenyl)-6-methyl-3-azabicyclo[3.1.0]hexan-2-one (Preparation 67, 0.15 g, 3.8 mmol) in tetrahydrofuran (2.5 ml) was added. A minute later, 4-(tributylstannyl)-1-triphenylmethyl-1H-imidazole (Preparation 73, 0.332 g, 0.55 mmol) in tetrahydrofuran (3 ml) was added. The reaction mixture was stirred at room temperature for 30 min and then refluxed for 3.5 h. The cooled reaction mixture was concentrated in vacuo and chromatographed on silica gel eluting with hexane:ethyl acetate (1:1 then 0:1) to give the title compound (55 mg, 25%).

NMR ($CDCl_3$, selected data for the free base: 0.9 (m, 3H), 1.2–1.4 (m, 9H), 1.5 (m, 2H), 2.15 (m, 1H), 0.35 (m, 1H), 3.05–3.4 (m, 3H), 3.65 (m, 1H), 7.1–7.4 (m, 18H), 7.5–7.6 (m, 2H), 7.75 (m, 1H).

MS (ES): M/Z (MH$^+$) 580.4; $C_{40}H_{41}N_3O+H$ requires 580.3.

PREPARATION 75

3-Hexyl-6-[3-(1H-imidazol-5-yl)phenyl]-6-methyl-3-azabicyclo[3.1.0]hexan-2-one

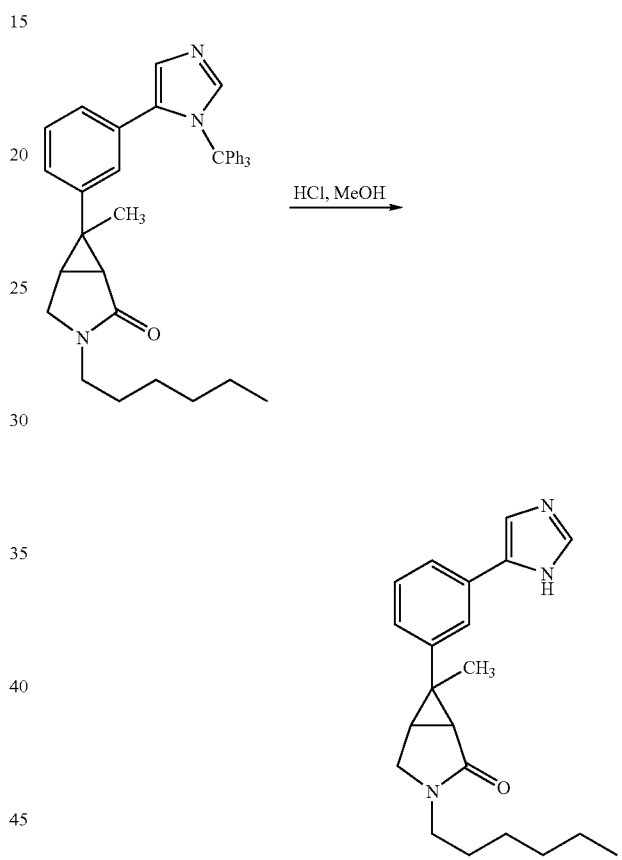

To a solution of 3-hexyl-6-methyl-6-[3-(1-triphenylmethyl-1H-imidazol-5-yl)phenyl]-3-azabicyclo[3.1.0]hexan-2-one (Preparation 74, 55 mg, 0.95 mmol) in methanol (1.5 ml) was added aqueous hydrochloric acid (2M, 0.5 ml) and the mixture was heated under reflux for 16 h. The reaction mixture was then cooled to room temperature and poured onto solid sodium hydrogen carbonate. Dichloromethane was added, the layers were separated and the organic extracts were dried ($MgSO_4$) and concentrated in vacuo. The crude residue was chromatographed on silica gel eluting with ethyl acetate to give the title compound as a clear oil (21 mg, 66%).

NMR ($CDCl_3$, selected data for the free base: 0.9 (m, 3H), 1.2–1.4 (m, 9H), 1.5 (m, 2H), 2.15 (m, 1H), 2.35 (m, 1H), 3.1–3.4 (m, 3H), 3.7 (m, 1H), 7.2 (d, 1H), 7.3 (t, 1H), 7.35 (s, 1H), 7.55 (d, 1H), 7.65 (s, 1H), 7.75 (s, 1H).

MS (ES): M/Z (MH$^+$) 338.3; $C_{21}H_{27}N_3O+H$ requires 338.2.

PREPARATION 76

1-(3-Pyridinyl)-1-ethanone hydrazone

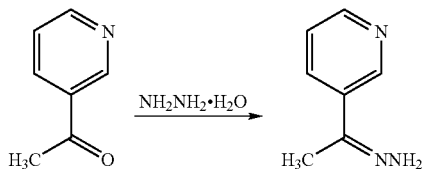

To 3-acetylpyridine (6.1 g, 52 mmol) in industrial methylated spirits (50 ml) was added dropwise hydrazine hydrate monohydrate (3.11 ml, 0.1 mol). The reaction mixture was refluxed for 4 h, before cooling to room temperature and stirring for 16 h. Water (25 ml) was added and the volatile organics were removed in vacuo. The predominantly aqueous residual liquor was extracted with ethyl acetate, and the combined organic extracts were dried ($Na_2SO_4$) and concentrated to give a yellow oil (5.4 g, 80%) which was taken forward without further purification.

NMR ($CDCl_3$, selected data for the free base): 2.1 (s, 3H), 5.5 (br, 2H), 7.2 (m, 1H), 7.9 (m, 1H), 8.45 (m, 1H), 8.8 (s, 1H).

MS (ES): M/Z ($2M+H^+$) 270.7; $C_{14}H_{19}N_6+H$ requires 271.2.

PREPARATION 77

3-Benzyl-6-methyl-6-(3-pyridinyl)-3-azabicyclo[3.1.0]hexane-2,4-dione

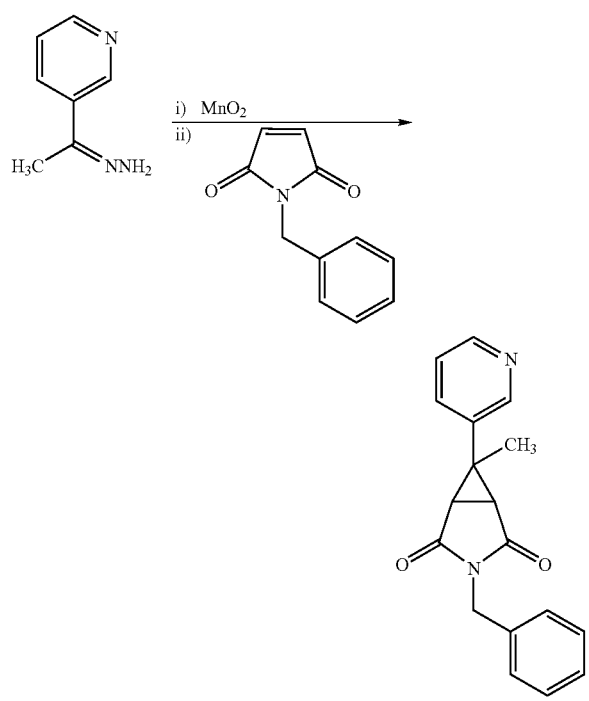

1-(3-Pyridinyl)-1-ethanone hydrazone (Preparation 76, 5.0 g, 40.0 mmol) was dissolved in dioxan (250 ml) and manganese dioxide (6.4 g, 40.0 mmol) was added portionwise followed by a saturated solution of potassium hydroxide in ethanol (2 ml). The reaction mixture was stirred at room temperature for 4 h and then filtered through a pad of Celite®. The filtrate was added to 1-benzyl-1H-pyrrole-2,5-dione (7.5 g, 40.0 mmol) and the reaction mixture was stirred for 16 h at room temperature and was then refluxed for 72 h. The reaction mixture was concentrated in vacuo and the residue was suspended in methanol and filtered to give the title compound as a white solid (3 g, 25%).

NMR ($CDCl_3$, selected data for the free base): 1.2 (s, 3H), 2.8 (s, 2H), 4.6 (s, 2H), 7.1–7.6 (m, 7H), 8.4–8.6 (m, 2H).

MS (TSP): M/Z ($MH^+$) 293.0; $C_{18}H_{16}N_2O_2+H$ requires 293.1.

PREPARATION 78

3-Hexyl-6-methyl-6-(3-pyridinyl)-3-azabicyclo[3.1.0]hexane-2,4-dione

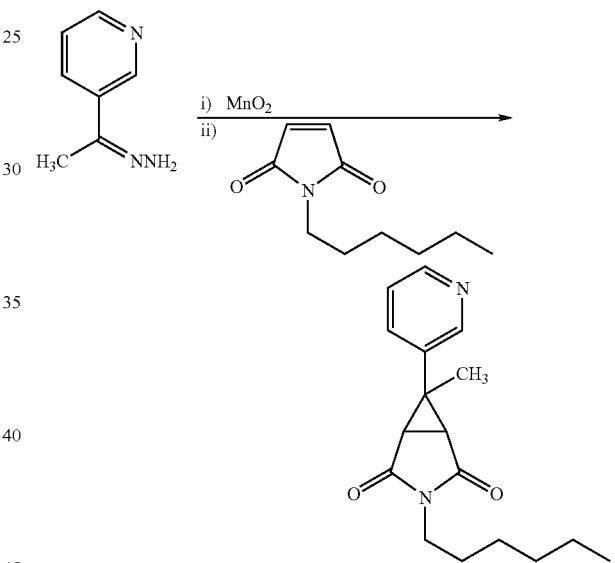

1-(3-Pyridinyl)-1-ethanone hydrazone (Preparation 76, 0.69 g, 5.3 mmol) was dissolved in dioxan (30 ml) and manganese dioxide (0.85 g, 5.3 mmol) was added portionwise followed by a saturated solution of potassium hydroxide in ethanol (0.5 ml). The reaction mixture was stirred at room temperature for 1.5 h and then filtered through a pad of Celite®. To half of the filtrate was added 1-hexyl-1H-pyrrole-2,5-dione (Preparation 56, 0.48 g, 2.6 mmol) and the reaction mixture was heated to 90° C. for 7 h and then cooled to room temperature for 16 h. The reaction mixture was heated under reflux for 16 h and then stirred at room temperature for 72 h before concentrating in vacuo. The reaction mixture was purified by chromatography using silica gel (30 g) eluting with dichloromethane:0.880 ammonia (99:1) and then dichloromethane:methanol:0.880 ammonia (97:2:1) to afford the title compound (0.22 g, 29%).

NMR ($CDCl_3$, selected data for the free base): 0.8 (m, 3H), 1.2–1.4 (m, 6H), 1.5 (s, 3H), 1.6 (m, 2H), 2.8 (m, 2H), 3.45 (m, 2H), 7.3 (m, 1H), 7.65 (m, 1H), 8.5 (m, 1H), 8.6 (m, 1H).

PREPARATION 79

6-Methyl-3-(3-phenylpropyl)-6-(3-pyridinyl)-3-azabicyclo[3.1.0]hexane-2,4-dione

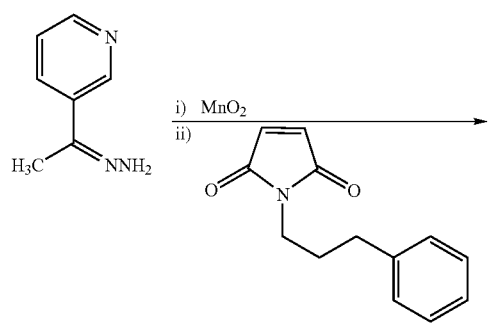

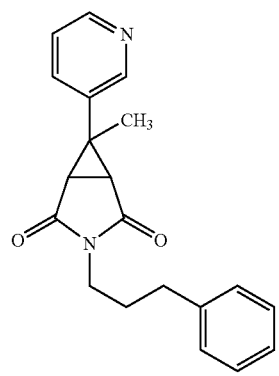

1-(3-Pyridinyl)-1-ethanone hydrazone (Preparation 76, 0.69 g, 5.3 mmol) was dissolved in dioxan (30 ml) and manganese dioxide (0.85 g, 5.3 mmol) was added portionwise followed by a saturated solution of potassium hydroxide in ethanol (0.5 ml). The reaction mixture was stirred at room temperature for 1.5 h and then filtered through a pad of Celite®. To half of the filtrate was added 1-(3-phenylpropyl)-1H-pyrrole-2,5-dione (Preparation 80, 0.57 g, 2.6 mmol) and the reaction mixture was heated to 90° C. for 7 h and then cooled to room temperature for 16 h. The reaction mixture was heated under reflux for 16 h and then cooled to room temperature for 72 h before concentrating in vacuo. The reaction mixture was purified by chromatography using silica gel (30 g) eluting with dichloromethane:0.880 ammonia (99:1) and then dichloromethane:methanol:0.880 ammonia (97:2:1) to afford the title compound as an oil (230 mg, 28%).

NMR (CDCl$_3$, selected data for the free base): 1.5 (s, 3H), 1.9 (m, 2H), 2.6 (m, 2H), 2.75 (s, 2H), 3.5 (m, 2H), 7.1–7.4 (m, 6H), 7.65 (m, 1H), 8.5–8.65 (m, 2H).

PREPARATION 80

1-(3-Phenylpropyl)-1H-pyrrole-2,5-dione

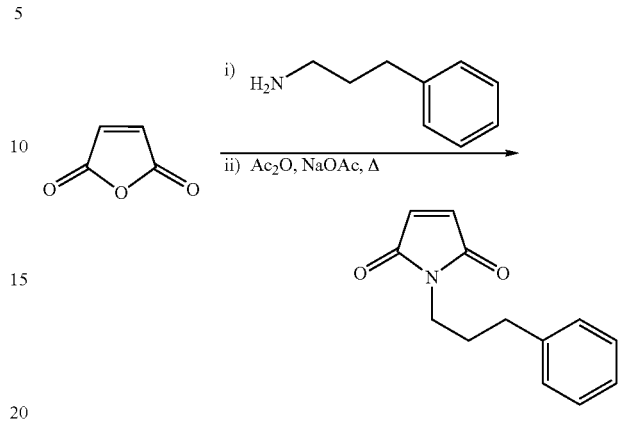

To stirred maleic anhydride (54.4 g, 0.55 mol) in toluene (1.5 l) was added dropwise, over 1 h, 3-phenylpropylamine (79.0 ml, 0.55 mol) in toluene (500 ml) to give a pale milky solution. After 2 h, the reaction mixture was filtered and the white solid obtained was dried for 16 h in vacuo at 40° C. The solid was dissolved in acetic anhydride (2.0 l) with stirring and heated in a steam bath. After 10 min, sodium acetate (23 g, 0.27 mol) was added. After 4 h, the acetic anhydride was removed in vacuo, and the residual black solid was treated with unsaturated brine (400 ml) and extracted with ethyl acetate (3×). The combined organic phase was washed with saturated aqueous sodium hydrogen carbonate solution, followed by brine. The organic layer was dried (Na$_2$SO$_4$), filtered and concentrated in vacuo to a dark solid. The crude residue was dissolved in dichloromethane and passed through a large plug of silica gel eluting with dichloromethane to give a peach coloured solid. This solid was then recrystallised from diisopropyl ether, filtered and dried in vacuo at 40° C. to give the title compound as a beige solid (69.6 g, 59%).

NMR (CDCl$_3$, selected data for the free base): 1.95 (m, 2H), 2.65 (t, 2H), 3.55 (m, 2H), 6.65 (s, 2H), 7.1–7.2 (m, 3H), 7.25–7.35 (m, 2H).

MS (ES): M/Z (MH$^+$) 216; C$_{13}$H$_{13}$NO$_2$+H requires 216.

PREPARATION 81

6-[3-(1H-Benzimidazol-2-yl)phenyl]-3-hexyl-6-methyl-3-azabicyclo[3.1.0]hexan-2-one

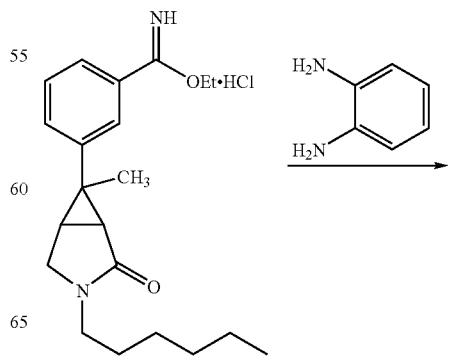

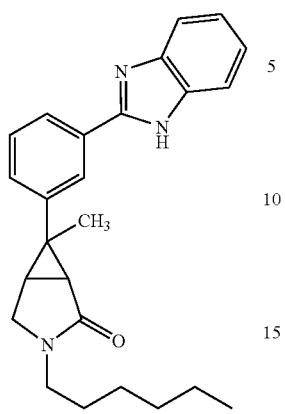

To ethyl 3-(3-hexyl-6-methyl-2-oxo-3-azabicyclo[3.1.0]hex-6-yl)benzenecarboximidoate (Preparation 42, 0.13 g, 0.34 mmol) in methanol (4 ml) at room temperature was added 1,2-diaminobenzene (37 mg, 0.34 mmol) and the mixture was heated under reflux for 1 h and then cooled and concentrated in vacuo. The residue was dissolved in dichloromethane (10 ml) and washed with 10% aqueous potassium carbonate solution (10 ml). The aqueous layer was then reextracted with dichloromethane (2×8 ml). The combined organic layers were dried (MgSO$_4$) and then concentrated in vacuo. The crude residue was purified by chromatography on silica gel eluting with hexane:ethyl acetate (1:1 and then 1:2) to give the title compound as a white foam (61 mg, 47%).

NMR (CDCl$_3$, selected data for the free base): 0.85 (m, 3H), 1.0 (s, 3H), 1.2–1.4 (m, 6H), 1.5 (m, 2H), 1.8 (m, 2H), 2.1 (m, 1H), 3.05–3.2 (m, 2H), 3.35 (m, 1H), 3.5 (m, 1H), 7.15–7.35 (m, 4H), 7.6–7.8 (m, 3H), 8.0 (d, 1H).

MS (ES): M/Z (MH$^+$) 388.1 C$_{25}$H$_{29}$N$_3$O+H requires 388.2.

PREPARATION 82

2-(1,3-Dioxo-1,3-dihydro-2H-isoindol-2-yl)-1-ethanesulfonyl chloride

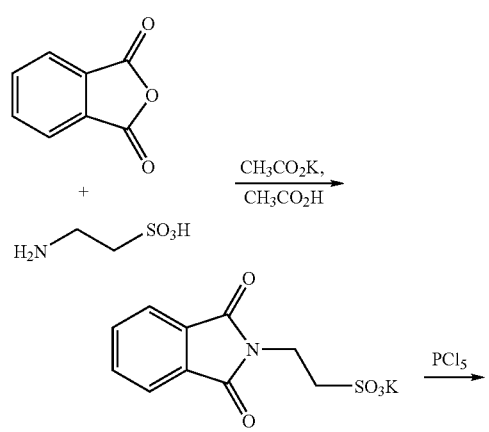

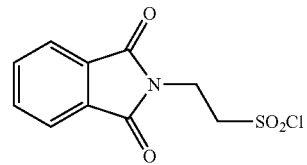

A suspension of taurine (8.0 g, 63.9 mmol) and potassium acetate (6.7 g, 68.3 mmol) in acetic acid was refluxed for 15 min. Phthalic anhydride (10.1 g, 68.4 mmol) was added and the solution was refluxed for 3 h. The reaction was cooled to room temperature and the solid was filtered off, washed with cold acetic acid and dried under vacuum at 100° C. to give a white solid. The solid (14.3 g, 54.7 mmol) was suspended in toluene (50 ml) and phosphorus pentachloride (8.12 g, 39.0 mmol) was added under nitrogen. The reaction mixture was heated under reflux for 1 h. Further phosphorus pentachloride (8.12 g, 39.0 mmol) was added and the reaction mixture was refluxed for 2.5 h. The brownish solution was decanted from the small amount of solid formed and then concentrated in vacuo, the residue was poured onto ice:water (50:50, 100 ml) and filtered. The solid was dried for 16 h in vacuo at 45° C. to give a pale brown solid (6.4 g, 34%).

PREPARATION 83

[(tert-Butoxycarbonyl)amino](chloro)dioxo-λ$^6$-sulfane

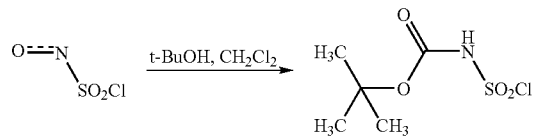

To a solution of chlorosulphonyl isocyanate (2.4 g, 17.0 mmol) in dry dichloromethane (10 ml) stirred under nitrogen at 0° C., was added tert-butanol (2.2 g, 34.0 mmol). The reaction mixture was allowed to warm to room temperature and stirred for 16 h before the solvent was removed in vacuo to give a fluffy white solid.

PREPARATION 84

6-(3-Aminophenyl)-3-hexyl-6-methyl-3-azabicyclo[3.1.0]hexan-2-one

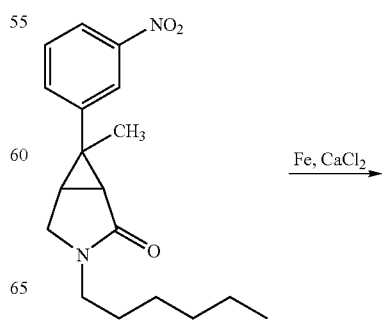

-continued

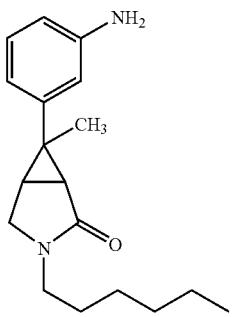

3-Hexyl-6-methyl-6-(3-nitrophenyl)-3-azabicyclo[3.1.0]hexan-2-one (Preparation 11, 6.3 g, 19.9 mmol) was dissolved in ethanol (250 ml), and iron powder (8.5 g, 0.15 mol), calcium chloride (0.95 g, 8.6 mmol) and water (50 ml) was added. The reaction mixture was refluxed for 2 h. The reaction mixture was cooled to room temperature and calcium chloride (0.95 g, 8.6 mmol) was added, the reaction mixture was refluxed for a further 16 h. The reaction mixture was cooled and filtered and then concentrated in vacuo, the residue was partitioned between dichloromethane and water and the organic layer separated, the aqueous layer was extracted with dichloromethane (3×) and the combined extracts were dried (Na$_2$SO$_4$) and concentrated in vacuo. The title compound was obtained as an orange solid (5.72 g, 100%).

NMR (CDCl$_3$, selected data for the free base): 0.85 (m, 3H), 1.2–1.4 (m, 9H), 1.4–1.6 (m, 2H), 2.05 (m, 1H), 2.3 (m, 1H), 3.1–3.3 (m, 3H), 3.6–3.7 (m, 2H), 6.5 (d, 1H), 6.6–6.7 (m, 2H), 7.05 (t, 1H).

MS (ES): M/Z (MH$^+$) 287.1 C$_{18}$H$_{26}$N$_2$O+H requires 287.2

PREPARATION 85

3-Hexyl-6-(3-hydroxyphenyl)-6-methyl-3-azabicyclo[3.1.0]hexan-2-one

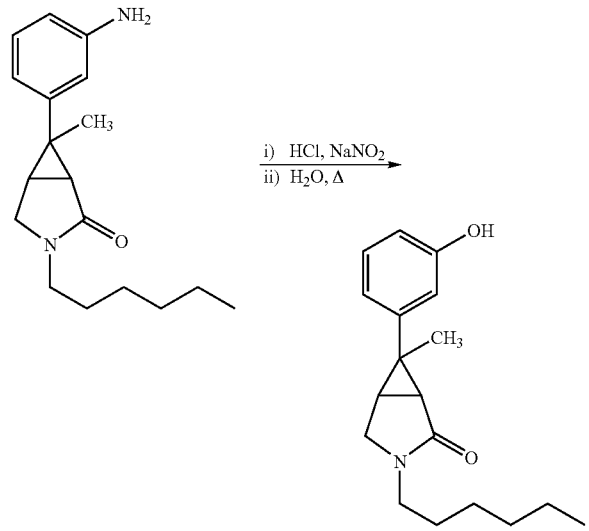

6-(3-Aminophenyl)-3-hexyl-6-methyl-3-azabicyclo[3.1.0]hexan-2-one (Preparation 84, 1.0 g, 3.5 mmol) was dissolved in aqueous hydrochloric acid (2.5 M, 3.5 ml) and cooled to 0° C. Sodium nitrite (0.25 g, 3.6 mmol) dissolved in water (1 ml) was added to the reaction mixture and stirred for 30 min. The reaction mixture was neutralised with solid sodium carbonate and then diluted with water (5 ml). The reaction mixture was heated to 60° C. for 1 h during which time a dark brown oil formed on top of the aqueous layer. The product was extracted with dichloromethane (50 ml), and the organic extracts were dried (Na$_2$SO$_4$) and concentrated in vacuo to give a brown oil. The crude product was purified by chromatography on silica gel (20 g) eluting with ethyl acetate:hexane (1:1) to give the title compound (0.34 g, 34%).

NMR (CDCl$_3$, selected data for the free base): 0.85 (m, 3H), 1.2–1.4 (m, 9H), 1.4–1.6 (m, 2H), 2.1 (m, 1H), 2.4 (m, 1H), 3.1–3.4 (m, 3H), 3.65 (m, 1H), 6.7–6.8 (m, 2H), 6.9 (s, 1H), 7.15 (t, 1H).

MS (ES): M/Z (MH$^+$) 288.2; C$_{18}$H$_{25}$NO$_2$+H requires 288.2.

PREPARATION 86

2-Cyclohexyloxyethyl 4-bromobenzenesulfonate

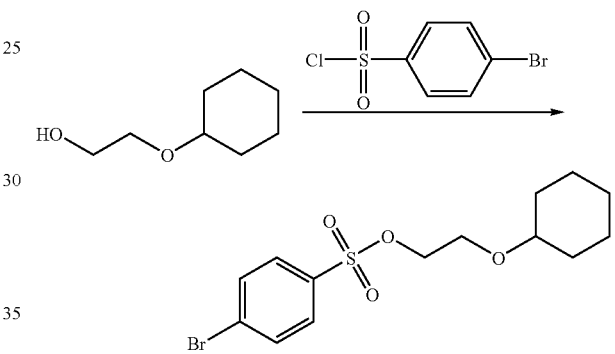

To a solution of 2-cyclohexyloxy-1-propanol (4.0 g, 28 mmol) in triethylanine (5.8 ml) and dichloromethane (250 ml) was added 4-bromobenzenesulfonyl chloride (7.87 g, 31 mmol) at 0° C. under nitrogen, and the resulting mixture was stirred for 16 h at room temperature. The reaction mixture was washed with saturated aqueous sodium hydrogen carbonate solution, water and brine (100 ml each), dried (MgSO$_4$) and concentrated in vacuo to give the crude product. This was purified by silica (200 g) column chromatography using a gradient elution of hexane:ethyl acetate (6:1 to 1:1) to give the title compound as a white crystalline solid (8.0 g, 80%).

NMR (CDCl$_3$): 1.1–1.8 (m, 14H), 3.2 (m, 2H), 3.65 (t, 2H), 4.15 (t, 2H), 7.6–7.9 (m, 4H).

MS (thermospray): M/Z [MH$^+$] 362.9; C$_{14}$H$_{19}$$^{79}$BrO$_4$S+H requires 363.0.

PREPARATION 87

2-Cyclohexyloxy-1-iodoethane

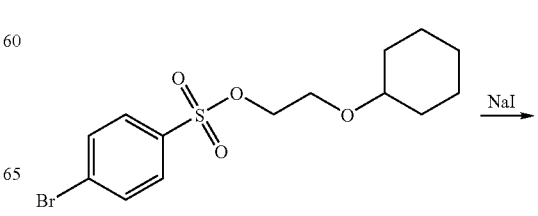

-continued

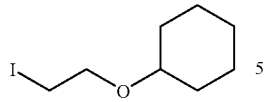

To a solution of 2-cyclohexyloxyethyl 4-bromobenzenesulfonate (Preparation 86, 120 mg, 0.3 mmol) in acetone (5 ml) was added sodium iodide (90 mg, 0.6 mmol) and the reaction mixture was left to stir at room temperature for 18 h. A further equivalent of sodium iodide was added and the reaction mixture was stirred at room temperature for a further 18 h after which time the reaction mixture was heated to 80° C. for 5 h. The resulting precipitate was filtered and the filtrate was diluted with water (100 ml) and extracted with dichloromethane (100 ml). The extract was washed with brine (100 ml), dried (MgSO$_4$) and concentrated in vacuo to give the title compound as a colourless oil (50 mg, 60%).

NMR (CDCl$_3$): 1.1–1.9 (m, 11H), 3.1 (t, 2H), 3.7 (t, 2H).

PREPARATION 88

1-[(E)-3-bromo-1-propenyl]cyclohexane

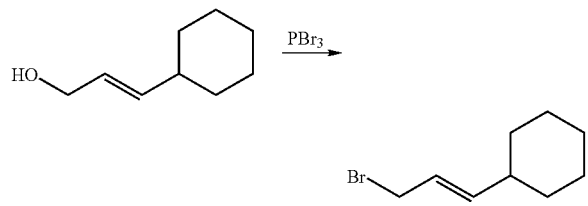

To a stirred solution of (E)-3-cyclohexyl-2-propen-1-ol (A. G. M. Barrett et al, Tetrahedron, 1996, 52, 15325), (1.47 g, 10.5 mmol) in diethyl ether (20 ml) and pyridine (1 ml) was added phosphorus tribromide (1.40 ml, 15 mmol) dropwise at room temperature under an atmosphere of nitrogen. After 16 h, the reaction mixture was carefully poured onto ice water (100 ml) and extracted with diethyl ether (100 ml). The extract was washed with saturated aqueous sodium hydrogen carbonate solution (100 ml), dried (MgSO$_4$) and concentrated in vacuo to give the crude product. This was purified by silica (20 g) column chromatography eluting with hexane:ethyl acetate (4:1) to give the title compound as a colourless oil (1.3 g, 61%).

NMR (CDCl$_3$): 0.8–1.4 (m, 6H), 1.6–1.8 (m, 4H), 2.0 (m, 1H), 3.95 (d, 2H), 5.6–5.8 (m, 2H).

MS (thermospray): M/Z [MH$^+$] 203.3; C$_9$H$_{15}$$^{79}$Br+H requires 203.0.

PREPARATION 89

(Benzyloxy)ethyl 4-bromobenzenesulfonate

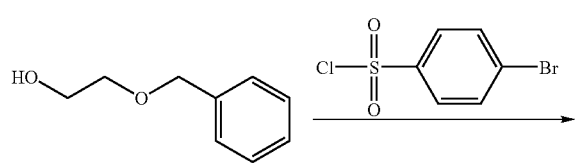

-continued

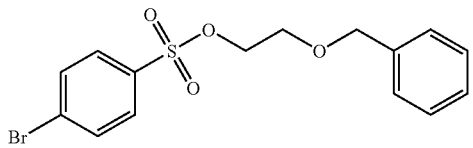

A solution of 4-bromobenzenesulfonyl chloride (5.5 g, 21.7 mmol) dissolved in dichloromethane (15 ml) was added dropwise to a solution of 2-benzyloxyethanol (3.0 g, 19.7 mmol) in triethylamine (3 g, 29.6 mmol) at 0° C. under nitrogen. The resultant mixture was stirred for 16 h at room temperature. To the reaction mixture was added water (3 ml) and then the combined mixture was poured onto water (100 ml) and the product was extracted with dichloromethane. The organic layer was washed repeatedly with water and then saturated aqueous sodium hydrogen carbonate solution, before drying (Na$_2$SO$_4$) and concentrating in vacuo to give the title compound as a white solid (6.9 g, 94%).

NMR (CDCl$_3$): 3.65 (m, 2H), 4.2 (m, 2H), 4.45 (s, 2H), 7.2 (m, 2H), 7.25–7.35 (m, 3H), 7.6 (d, 2H), 7.8 (d, 2H).

PREPARATION 90

1-[(2-iodoethoxy)methyl]benzene

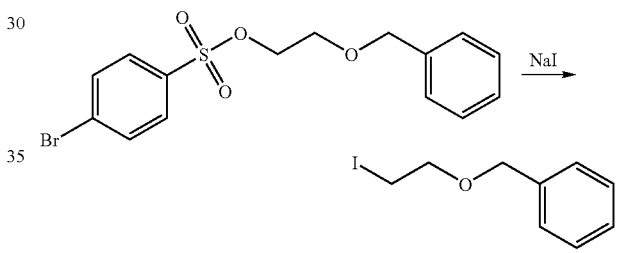

To a solution of (benzyloxy)ethyl 4-bromobenzenesulfonate (Preparation 89, 6.92 g, 19.5 mmol) in acetone (60 ml) was added sodium iodide (5.84 g, 39.0 mmol) and the reaction mixture was left to stir at room temperature for 16 h. The resulting precipitate was filtered and the filtrate was concentrated in vacuo. The crude residue was dissolved in dichloromethane and washed with aqueous sodium thiosulphate solution and then with water (2×60 ml). The organic layer was dried (Na$_2$SO$_4$) and concentrated in vacuo to give the title compound as a pale brown oil (4.5 g, 88%).

NMR (CDCl$_3$): 3.25 (t, 2H), 3.75 (t, 2H), 4.6 (s, 2H).

PREPARATION 91

3-Cyclohexyl-3-oxopropyl 4-bromobenzenesulfonate

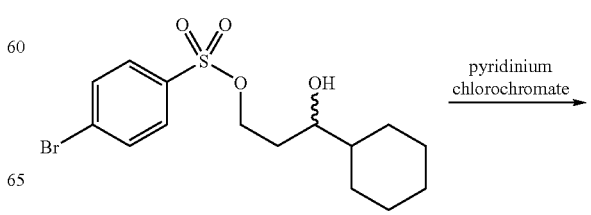

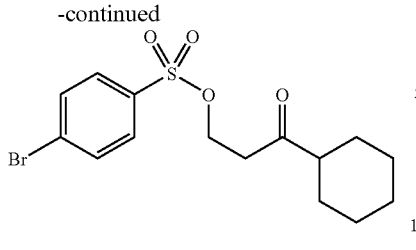

To a solution of (S)-3-cyclohexyl-3-hydroxypropyl 4-bromobenzenesulfonate (J. A. Werner et al, J. Org. Chem., 1996, 61, 587), (40 mg, 0.106 mmol) in dichloromethane (3 ml) was added silica (50 mg) and pyridinium chlorochromate (20 mg, 0.09 mmol), and the reaction mixture was left to stir at room temperature for 16 h. The reaction mixture was subjected to direct silica (5 g) column chromatography eluting with dichloromethane:hexane (4:1) to afford the title compound as a yellow solid (38 mg, 96%).

NMR (CDCl$_3$): 1.1–1.9 (m, 10H), 2.3 (m, 1H), 2.85 (m, 2H), 4.3 (m, 2H), 7.7–7.85 (m, 4H).

PREPARATION 92

2-Adamantylethyl 4-bromobenzenesulfonate

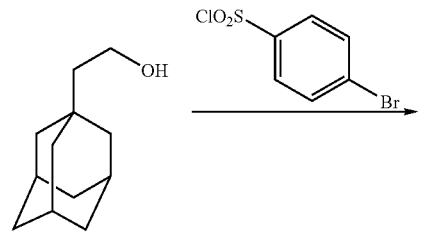

To a solution of 1-adamantylethanol (5.8 g, 32 mmol) in triethylamine (6.7 ml) and dichloromethane (50 ml) was added 4-bromobenzenesulphonyl chloride (8.9 g, 35 mmol) at room temperature. The solution was stirred for 16 h, diluted with aqueous hydrochloric acid (2M, 100 ml) and extracted with dichloromethane (100 ml). The extract was washed with saturated aqueous sodium hydrogen carbonate solution (100 ml) and brine (100 ml), dried (MgSO$_4$), and concentrated in vacuo to give the title compound as a white crystalline solid (11.2 g, 88%).

NMR (CDCl$_3$): 1.4–1.6 (m, 11H), 1.65 (d, 3H), 2.0 (2, 3H), 4.1 (t, 2H), 7.6–7.8 (m, 4H).

MS (thermospray): M/Z [MH$^+$] 416.3; C$_{18}$H$_{23}$$^{79}$BrO$_3$S+ NH$_4$ requires 416.1.

PREPARATION 93

1-Adamantyl-2-iodoethane

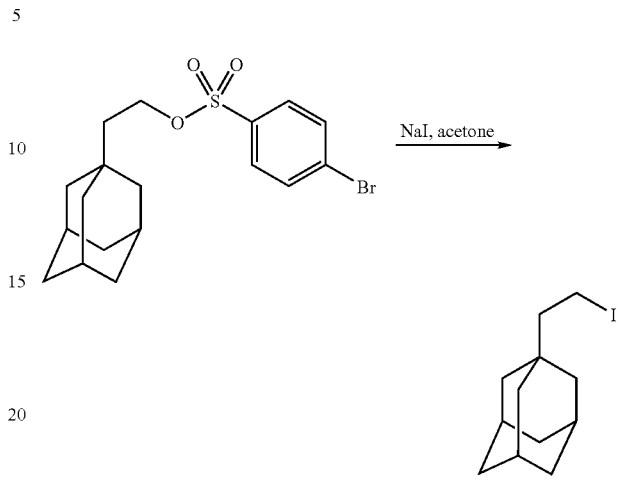

To a solution of 2-adamantylethyl 4-bromobenzenesulfonate (Preparation 92, 1.0 g, 2.5 mmol) in acetone (25 ml) was added sodium iodide (0.75 g, 5 mmol) and the reaction mixture was left to stir at room temperature for 72 h. The resulting precipitate was filtered and the filtrate was diluted with water (100 ml) and extracted with dichloromethane (100 ml). The extract was washed with brine (100 ml), dried (MgSO$_4$) and concentrated in vacuo to give the title compound as a white crystalline solid (0.54 g, 75%).

NMR (CDCl$_3$): 1.4–1.8 (m, 155H), 1.95 (t, 2H), 3.1 (t, 2H).

PREPARATION 94

Exo-[6-(3-Aminophenyl)-3-hexyl-3-azabicyclo [3.1.0]hex-6-yl]methanol

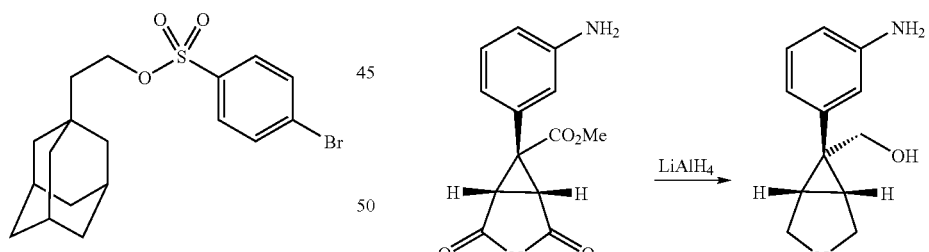

To a solution of methyl 6-(3-aminophenyl)-3-hexyl-2,4-dioxo-3-azabicyclo[3.1.0]hexane-6-carboxylate (Preparation 95, 25 mg, 0.0726 mmol) in anyhydrous tetrahydrofiran (1 ml) at −10° C. under nitrogen was added lithium aluminium hydride (1M solution in tetrahydrofuran, 218 µl, 0.218 mmol) dropwise over 10 min. The reaction was left to warm to room temperature then heated under reflux for 18 h. The cooled reaction was poured into hydrochloric acid (2M, 5 ml) then basified with aqueous sodium hydroxide (2M, 10 ml). The mixture was extracted with ethyl acetate (2×25 ml) and the organic layers washed with brine (25 ml), combined then dried (MgSO$_4$). The organic extracts were concentrated in vacuo then chromatographed on Merck 230–400 silica gel (7 g) eluting with ethyl acetate:2M ammonia in ethanol (197:3) to give the desired product as a colourless oil (15 mg, 71%).

NMR (CDCl$_3$, selected data for the free base): 0.90 (m, 3H), 1.20–1.40 (m, 6H), 1.50 (m, 2H), 1.85 (br s, 2H), 2.50 (t, 2H), 2.60 (br d, 2H), 3.40 (d, 2H), 4.10 (s, 2H), 6.50 (d, 1H), 6.60 (br s, 1H), 6.65 (d, 1H), 7.05 (dd, 1H).

MS (Thermospray): M/Z (MH$^+$) 289.1; C$_{18}$H$_{28}$N$_2$O+H requires 289.4

PREPARATION 95

Exo Methyl 6-(3-aminophenyl)-3-hexyl-2,4-dioxo-3-azabicyclo[3.1.0]hexane-6-carboxylate

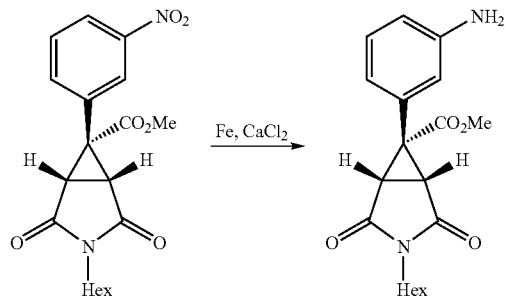

To a solution of methyl 3-hexyl-6-(3-nitrophenyl)-2,4-dioxo-3-azabicyclo[3.1.0]hexane-6-carboxylate (Preparation 96, 50 mg, 0.134 mmol) in ethanol (4.3 ml) and water (0.8 ml) was added iron powder (68 mg, 1.21 mmol) then calcium chloride (8 mg, 0.067 mmol). The reaction was heated under reflux for 6 h, cooled then filtered through Celite™ washing with ethyl acetate (50 ml). The filtrate was concentrated and the chromatographed on Merck 230–400 silica gel (10 g) eluting with ethyl acetate:hexane (40:60) to give the desired product as a pale yellow semi-solid (26 mg, 56%).

NMR (CDCl$_3$, selected data for the free base): 0.90 (m, 3H), 1.25–1.35 (m, 6H), 1.45 (m, 2H), 2.90 (s, 2H), 3.35 (t, 2H), 3.60 (s, 3H), 6.65 (br d, 1H), 6.75 (br s, 1H), 6.80 (d, 1H), 7.10 (dd, 1H).

MS (Thermospray): M/Z (MH$^+$) 345.1; C$_{19}$H$_{24}$N$_2$O$_4$+H requires 345.4

PREPARATION 96

Exo and Endo Methyl 3-hexyl-6-(3-nitrophenyl)-2,4-dioxo-3-azabicyclo[3.1.0]hexane-6-carboxylate

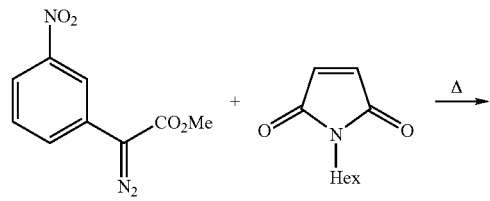

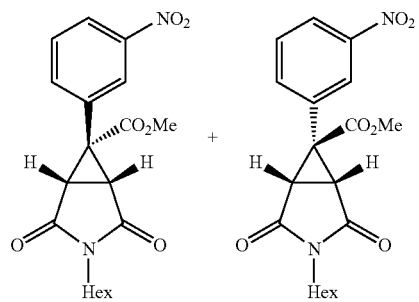

To a stirred solution of 1-hexyl-1H-pyrrole-2,5-dione (Preparation 56, 123 mg, 0.678 mmol) in 1,4-dioxane (2 ml) under nitrogen was added methyl 2-diazo-2-(3-nitrophenyl)acetate (Preparation 97, 100 mg, 0.452 mmol) and the reaction mixture was heated under reflux for 48 h. The cooled mixture was concentrated in vacuo and the residue chromatographed on Merck 230–400 silica gel (20 g) eluting with ethyl acetate:hexane (15:85 and then 30:70) to give a mixture of two isomeric cyclopropanes (140 mg). These were separated by preparative HPLC (Condition 2), which gave in order of elution the endo isomer as a white solid (30 mg, 12%) some mixed fractions (40 mg, 16%) followed by the exo isomer as a white solid (60 mg, 24%).

NMR (CDCl$_3$, selected data for the free base endo isomer): 0.50 (tt, 2H), 0.80 (t, 3H), 0.85–1.15 (m, 6H), 2.90 (t, 2H), 3.30 (s, 2H), 3.70 (s, 3H), 7.50 (dd, 1H), 7.65 (d, 1H), 8.20 (br s, 2H).

MS (electrospray): M/Z (MH$^+$) 375; C$_{19}$H$_{22}$N$_2$O$_6$+H requires 375

NMR (CDCl$_3$, selected data for the free base exo isomer): 0.90 (m, 3H), 1.25–1.35 (m, 6H), 1.50 (m, 2H), 3.00 (s, 2H), 3.40 (t, 2H), 3.70 (s, 3H), 7.60 (dd, 1H), 7.80 (d, 1H), 8.20 (br d, 1H), 8.30 (br s, 1H).

MS (Electrospray): M/Z (MH$^+$) 375; C$_{19}$H$_{22}$N$_2$O$_6$+H requires 375

PREPARATION 97

Methyl 2-diazo-2-(3-nitrophenyl)acetate

UK-385510

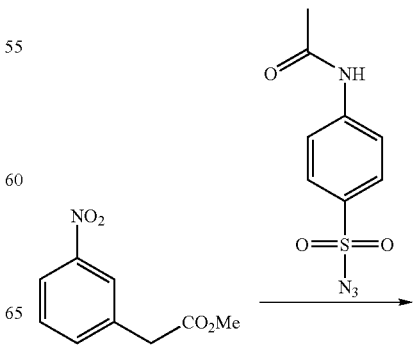

-continued

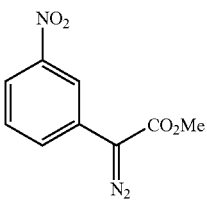

To a solution of methyl 2-(3-nitrophenyl)acetate (C. Abell et al, J. Chem. Soc., Perkin Trans. 1, 1994, 1997; 3.13 g, 16.0 mmol) and 1,8-diazabicyclo[5.4.0]undec-7-ene (7.18 ml, 7.31 g, 48.0 mmol) in anhydrous acetonitrile (35 ml), was added a solution of 4-acetamidobenzenesulphonyl azide (4.81 g, 20.0 mmol) in anhydrous acetonitrile (5 ml) in one portion. The reaction mixture was stirred for 48 h at room temperature under nitrogen before pouring into water (300 ml). The resultant precipitate was collected by filtration and washed with water (50 ml) and cold methanol (50 ml) to give the desired product as an orange/yellow solid (2.60 g, 74%).

NMR (CDCl$_3$, selected data for the free base): 3.90 (s, 3H), 7.60 (dd, 1H), 7.85 (br d, 1H), 8.00 (br d, 1H), 8.40 (br s, 1H).

PREPARATION 98

Exo-3-[3-Hexyl-6-(methoxymethyl)-3-azabicyclo [3.1.0]hex-6-yl]aniline

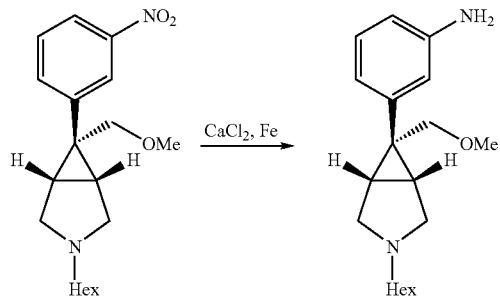

To a solution of [3-hexyl-6-(3-nitrophenyl)-3-azabicyclo [3.1.0]hex-6-yl]methyl methyl ether (Preparation 99, 16 mg, 0.048 mmol) in ethanol (1.5 ml) and water (0.3 ml) was added iron powder (25 mg, 0.435 mmol) then calcium chloride (3 mg, 0.24 mmol). The reaction mixture was heated under reflux for 6 hours, cooled then filtered through Celite™ washing with ethyl acetate. The filtrate was concentrated in vacuo and chromatographed on Merck 230–400 mesh silica gel (7 g) eluting with ethyl acetate:hexane: 2M ammonia in hexane (50:49:1 and then 99:0:1) to give the desired product as a pale yellow oil (11 mg, 76%).

NMR (CDCl$_3$, selected data for the free base): 0.90 (m, 3H), 1.20–1.50 (m, 8H), 1.85 (br s, 2H), 2.45 (t, 2H), 2.70 (br d, 2H), 3.20 (d, 2H), 3.30 (s, 3H), 4.05 (s, 2H), 6.50 (br d, 1H), 6.70 (br s, 1H), 6.75 (d, 1H), 7.05 (dd, 1H).

MS (Thermospray): M/Z (MH$^+$) 303; $C_{19}H_{30}N_2O$+H requires 303

PREPARATION 99

Exo-[3-hexyl-6-(3-nitrophenyl)-3-azabicyclo[3.1.0] hex-6-yl]methyl methyl ether

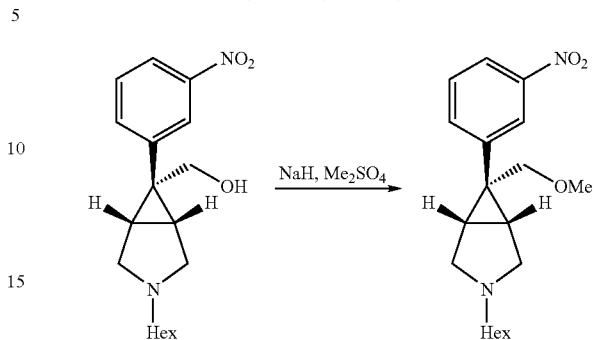

To sodium hydride (60% oil dispersion washed with anhydrous pentane, 13 mg, 0.320 mmol) under nitrogen was added a solution of [3-hexyl-6-(3-nitrophenyl)-3-azabicyclo [3.1.0]hex-6-yl]methanol (Preparation 100, 51 mg, 0.160 mmol) in anhydrous tetrahydrofuran (1 ml) dropwise over 10 minutes. The reaction was stirred for 1 h at room temperature, cooled in an ice-water bath and dimethylsulphate (18 μl, 24 mg, 0.192 mmol) added. The reaction mixture was allowed to warm to room temperature slowly and then stirred at room temperature for 16 h, before quenching by dropwise addition of water (5 ml). The reaction mixture was partitioned between ethyl acetate (25 ml) and sodium carbonate (25 ml). The separated aqueous layer was extracted with ethyl acetate (25 ml) and the organic extracts were washed with brine (25 ml). The combined organic extracts were dried (MgSO$_4$) and then concentrated in vacuo. The residue was chromatographed on Merck 230–400 mesh silica gel eluting with ethyl acetate:hexane: 2M ammonia in ethanol (20:79:1 and then 40:49:1) to give the desired product as a pale yellow oil (16 mg, 30%).

NMR (CDCl$_3$, selected data for the free base): 0.90 (m, 3H), 1.25–1.45 (m, 8H), 1.90 (br s, 2H), 2.45 (t, 2H), 2.70 (br d, 2H), 3.20 (d, 2H), 3.30 (s, 3H), 4.15 (s, 2H), 7.40 (dd, 1H), 7.65 (d, 1H), 8.05 (br d, 1H), 8.15 (br s, 1H).

MS (thermospray): M/Z (MH$^+$) 333; $C_{19}H_{28}N_2O_3$+H requires 333

PREPARATION 100

Exo-[3-hexyl-6-(3-nitrophenyl)-3-azabicyclo[3.1.0] hex-6-yl]methanol

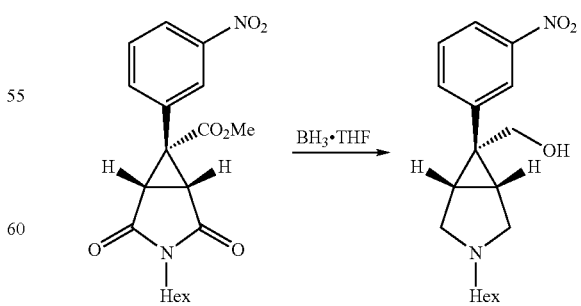

To a solution of methyl 3-hexyl-6-(3-nitrophenyl)-2,4-dioxo-3-azabicyclo[3.1.0]hexane-6-carboxylate (Preparation 96, 200 mg, 0.534 mmol) in anhydrous tetrahydrofuran (1 ml) cooled in an ice-water bath under nitrogen was added borane (1M solution in tetrahydrofuran, 2.14 ml, 2.14 mmol) dropwise over 30 minutes. The reaction mixture was allowed to warm to room temperature and was then heated under reflux for 1 h. The mixture was quenched by the careful addition of methanol and was then heated under reflux for 16 h. The reaction was cooled and the solvent removed in vacuo. More methanol was added and the mixture heated under reflux for 16 h. The solvent was again removed in vacuo and this process was repeated twice more. The residue was chromatographed on Merck 230–400 mesh silica gel (25 g) eluting with ethyl acetate:hexane:2M ammonia in ethanol (40:59:1) to give the desired product as a pale yellow solid (113 mg, 66%).

NMR (CDCl$_3$, selected data for the free base): 0.90 (m, 3H), 1.20–1.40 (m, 6H), 1.50 (m, 2H), 1.90 (br s, 2H), 2.50 (t, 2H), 2.65 (br d, 2H), 3.45 (d, 2H), 4.20 (s, 2H), 7.45 (dd, 1H), 7.65 (d, 1H), 8.05 (br d, 1H), 8.15 (br s, 1H).

MS (thermospray): M/Z (MH$^+$) 319; C$_{18}$H$_{26}$N$_2$O$_3$+H requires 319

PREPARATION 101

3-[3-Hexyl-6-(2,2,2-trifluoroethyl)-3-azabicyclo[3.1.0]hex-6-yl] aniline

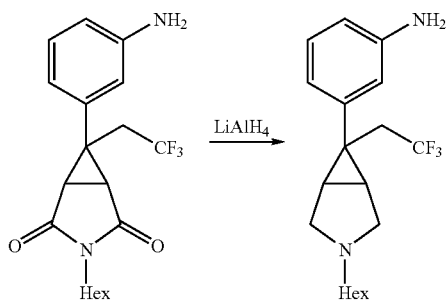

3-Hexyl-6-(3-aminophenyl)-6-(2,2,2-trifluoroethyl)-3-azabicyclo[3.1.0]hexane-2,4-dione (Preparation 102, 170 mg, 0.46 mmol) was dissolved in anhydrous tetrahydrofuran (5 ml) in a dry, nitrogen-flushed flask fitted with a thermometer and reflux condenser. The pale orange solution was cooled to −12° C. in an ice/methanol bath and lithium aluminium hydride (1M solution in tetrahydrofuran, 0.9 ml, 0.9 mmol) was added dropwise maintaining the internal temperature below −10° C. Once the addition was completed, the red-orange mixture was allowed to warm to room temperature before heating under reflux for 1.5 h. The mixture was cooled to room temperature and the residual lithium aluminium hydride quenched by the careful addition of aqueous hydrochloric acid (2M) until hydrogen evolution had ceased. The mixture was then neutralised with saturated sodium hydrogen carbonate solution and extracted with ethyl acetate (2×20 ml). The combined organic extracts were washed with brine (10 ml), dried (MgSO$_4$), filtered and the solvents removed in vacuo to give the product as a pale brown gum (145 mg, 93%).

NMR (CDCl$_3$, selected data for the free base): 0.80–0.95 (m, 3H), 1.20–1.45 (m, 8H), 1.45–1.60 (m, 2H), 2.40 (t, 2H), 2.60 (d, 2H), 3.10 (q, 2H), 3.20 (d, 2H), 3.60 (br, 2H), 6.50 (d, 1H), 6.60 (s, 1H), 6.65 (d, 1H), 7.05 (t, 1H).

MS (electrospray): M/Z (MH$^+$) 341.4; C$_{19}$H$_{27}$F$_3$N$_2$+H requires 341.4.

PREPARATION 102

3-Hexyl-6-(3-aminophenyl)-6-(2,2,2-trifluoroethyl)-3-azabicyclo[3.1.0]hexane-2,4-dione

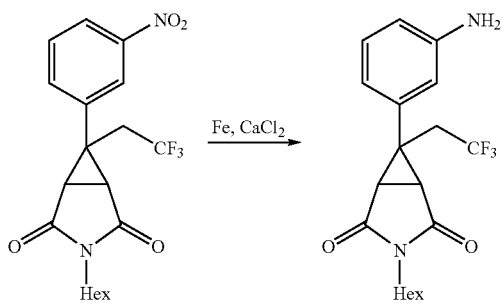

3-Hexyl-6-(3-nitrophenyl)-6-(2,2,2-trifluoroethyl)-3-azabicyclo[3.1.0]hexane-2,4-dione (Preparation 103, 178 mg, 0.45 mmol) was dissolved in ethanol (15 ml). Iron powder (225 mg, 4.0 mmol) was added at room temperature followed by calcium chloride (50 mg, 0.45 mmol), dissolved in water (2 ml). The vigorously stirred mixture was heated under reflux for 2 h then cooled to room temperature and filtered through a pad of silica. The solvent was removed in vacuo and the filtrate was dissolved in dichloromethane and filtered through a Whatman anotop 10 plus™ cartridge. The organic mixture was concentrated in vacuo to give the product as a brown gum (170 mg, 100%).

NMR (CDCl$_3$, selected data for the free base): 0.80–0.95 (m, 3H), 1.20–1.35 (m, 6H), 1.45–1,60 (m, 2H), 2.55 (q, 2H), 2.80 (s, 2H), 3.45 (t, 2H), 2.75 (broad s, 2H), 6.55 (d, 1H), 6.65 (s, 1H), 6.70 (d, 1H), 7.10 (t, 1H).

MS (thermospray): M/Z (MNH$_4^+$) 386.5; C$_{19}$H$_{23}$F$_3$N$_2$O$_2$+NH$_4$ requires 386.4

PREPARATION 103

3-Hexyl-6-(3-nitrophenyl)-6-(2,2,2-trifluoroethyl)-3-azabicyclo[3.1.0]hexane-2,4-dione

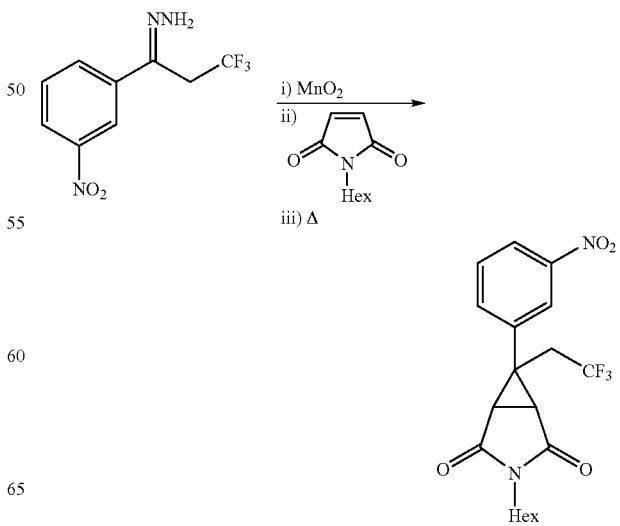

3,3,3-Trifluoro-1-(3-nitrophenyl)-1-propanone hydrazone (Preparation 104, 150 mg, 0.6 mmol) was dissolved in dioxan (10 ml) and manganese dioxide (600 mg, 7.1 mmol) was added in one portion at room temperature. After stirring for 30 min, the reaction mixture was filtered through a pad of Arbocel™ directly into a flask containing a stirred solution of 1-hexyl-1H-pyrrole-2,5-dione (Preparation 56, 44 mg, 0.2 mmol) in dioxan (10 ml). The filter pad was washed further with dioxan (40 ml), and was also added to the reaction mixture. The resulting amber-yellow solution was stirred for 16 h at room temperature. The colourless mixture was then heated under reflux for 1 h before cooling to room temperature and concentrating in vacuo. The residue was purified by chromatography on silica gel (10 g), eluting with hexane:ether (2:1) to give the product as a white solid (178 mg, 74%).

NMR (selected data): 0.85–0.95 (m, 3H), 1.25–1.35 (m, 6H), 1.50–1.65 (m, 2H), 2.60 (q, 2H), 2.90 (s, 2H), 3.40–3.55 (t, 2H), 7.60 (t, 1H), 7.75 (d, 1H), 8.20 (d, 1H), 8.30 (s, 1H).

MS (APCI): M/Z (M–H+) 397.0: $C_{19}H_{21}F_3N_2O_4$–H requires 397.4.

PREPARATION 104

3,3,3-Trifluoro-1-(3-nitrophenyl)-1-propanone hydrazone

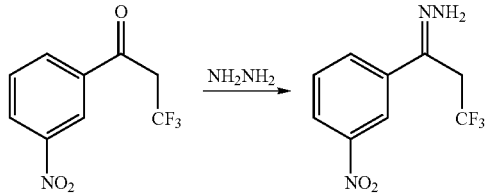

3,3,3-Trifluoro-1-(3-nitrophenyl)-1-propanone (Sov. Prog. Chem. (Engl.Transl.), 1966, 32, 745, 1.8 g, 7.72 mmol) was dissolved in tetrahydrofuran (10 ml) and hydrazine monohydrate (0.56 ml, 11.58 mmol) was added dropwise at room temperature. The reaction mixture was stirred for 1 h at room temperature then heated under reflux for 40 min. The reaction mixture was concentrated in vacuo and the residue treated with water (10 ml) and extracted with dichloromethane (4×10 ml). The organic extracts were concentrated in vacuo and the residue was purified by chromatography on silica gel (100 g), eluting with dichloromethane:hexane (1:1 and then 2:1). The product was obtained as an amber gum (159 mg, 8%).

NMR (CDCl$_3$, selected data for the free base): 3.55 (q, 2H), 5.95 (br s, 2H), 7.55 (t, 1H), 8.00 (d, 1H), 8.15 (d, 1H), 8.55 (s, 1H).

MS (electrospray): M/Z (M–H$^+$) 246.1 $C_9H_8F_3N_3O_2$–H requires 246.2.

PREPARATION 105

Exo-6-(3-aminophenyl)-3-hexyl-3-azabicyclo[3.1.0] hexane-6-carbonitrile

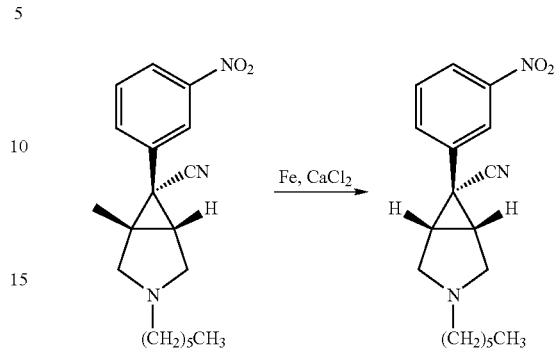

To a solution of 3-hexyl-6-(3-nitrophenyl)-3-azabicyclo[3.1.0]hexane-6-carbonitrile (Preparation 106, 3 mg, 0.0096 mmol) in ethanol (1 ml) and water (0.2 ml) was added iron powder (6 mg, 0.096 mmol) then calcium chloride (0.6 mg, 0.0048 mmol). The reaction was heated under reflux for 6 h, cooled then filtered through Celite™ washing with ethyl acetate (50 ml). The filtrate was concentrated in vacuo to give the desired product as a pale yellow oil (1.7 mg, 63%).

NMR (CDCl$_3$, selected data for the free base): 0.90 (m, 3H), 1.25–1.35 (m, 6H), 1.45 (m, 2H), 2.20 (m, 2H), 2.45 (m, 2H), 2.85 (m, 2H), 3.20 (m, 2H), 6.50–6.60 (m, 2H), 6.70 (br s, 1H), 7.10 (dd, 1H).

MS (thermospray): M/Z (M+) 283.2; $C_{18}H_{25}N_3$ requires 283.2

PREPARATION 106

Exo-3-hexyl-6-(3-nitrophenyl)-3-azabicyclo[3.1.0]hexane-6-carbonitrile

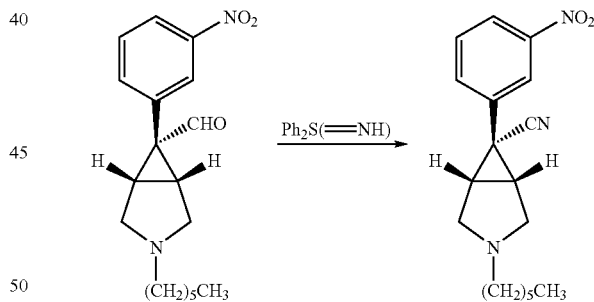

A solution of 3-hexyl-6-(3-nitrophenyl)-3-azabicyclo[3.1.0]hexane-6-carbaldehyde (Preparation 107, 9 mg, 0.028 mmol) and diphenylsulphilimine monohydrate (12.5 mg, 0.057 mmol) in anhydrous benzene (1 ml) was heated under reflux under nitrogen for 24 hours. The solvent was removed in vacuo and the residue chromatographed on Merck 230–400 mesh silica gel (5 g) eluting with ethyl acetate:hexane (30:70 and then 50:50) to give the desired product as a pale yellow oil (3 mg, 34%).

NMR (CDCl$_3$, selected data for the free base): 0.90 (m, 3H), 1.20–1.45 (m, 6H), 1.50 (m, 2H), 2.25 (m, 2H), 2.55 (m, 2H), 2.80 (m, 2H), 3.35 (m, 2H), 7.5 (dd, 1H), 7.80 (d, 1H), 8.05 (br s, 1H), 8.15 (br d, 1H).

MS (thermospray): M/Z (MH$^+$) 314.2; $C_{18}H_{23}N_3O_2$+H requires 314.2

PREPARATION 107

Exo-3-hexyl-6-(3-nitrophenyl)-3-azabicyclo[3.1.0]hexane-6-carbaldehyde

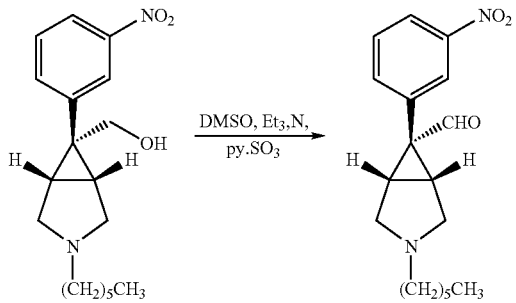

To a solution of [3-hexyl-6-(3-nitrophenyl)-3-azabicyclo[3.1.0]hex-6-yl]methanol (Preparation 100, 50 mg, 0.157 mmol) in anhydrous dimethylsulphoxide (1 ml) was added anhydrous triethylamine (131 μl, 0.941 mmol) followed by a solution of sulphur trioxide-pyridine complex (75 mg, 0.471 mmol) in anhydrous dimethyl sulphoxide (0.7 ml). The reaction mixture was stirred at room temperature for 40 h under nitrogen, before pouring into dichloromethane (25 ml) and basifying with aqueous saturated sodium bicarbonate solution (20 ml). The separated aqueous layer was extracted with dichloromethane (20 ml) and the combined organic extracts were dried (MgSO$_4$) and then concentrated in vacuo to give the desired product as a pale yellow oil (9 mg, 18%).

NMR (CDCl$_3$, selected data for the free base): 0.90 (m, 3H), 1.20–1.40 (m, 6H), 1.50 (m, 2H), 2.05 (br s, 2H), 2.55–2.60 (m, 4H), 3.15 (d, 2H), 7.45 (dd, 1H), 7.70 (d, 1H), 8.05 (br d, 1H), 8.15 (br s, 1H), 9.40 (s, 1H).

PREPARATION 108

N-{[6-(3-Aminophenyl)-3-hexyl-3-azabicyclo[3.1.0]hex-6-yl]methyl}acetamide

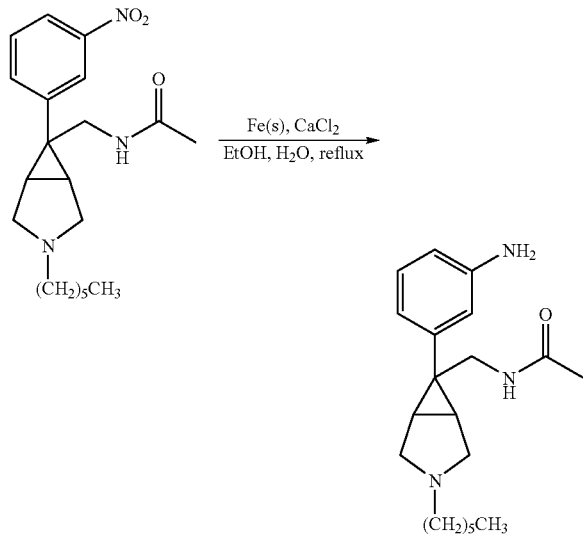

To a solution of N-{3-hexyl-6-(3-nitrophenyl)-3-azabicyclo[3.1.0]hex-6-yl]methyl}acetamide (Preparation 109, 84 mg, 0.234 mmol) in ethanol (4 ml) and water (1 ml) was added iron powder (120 mg, 2.15 mmol) and calcium chloride (16 mg, 0.14 mmol). The mixture was stirred and heated under reflux for 1¼ h, before allowing to cool and filtering through Celite™, washing with hot ethanol. The filtrate was concentrated in vacuo to give a brown residue which was partitioned between dichloromethane (5 ml) and water (5 ml), leaving some insoluble material at the interface. The phases were separated and the aqueous layer was re-extracted with dichloromethane (2×5 ml). The combined organic extracts were dried (Na$_2$SO$_4$) and concentrated in vacuo to give the title compound as a golden oil (68 mg, 77%).

NMR (CDCl$_3$): 0.90 (m, 3H), 1.23–1.40 (m, 6H), 1.45 (m, 2H), 1.80–1.90 (m, 5H), 2.50 (m, 2H), 2.80 (m, 2H), 3.10 (m, 2H), 3.65 (m, 2H), 3.95 (m, 2H), 5.45 (m, 1H), 6.5 (m, 1H), 6.55–6.65 (m, 2H), 7.05 (t, 1H).

MS (thermospray): M/Z (MH$^+$) 330.3; C$_{20}$H$_{31}$N$_3$O+H requires 330.3.

PREPARATION 109

N-{3-Hexyl-6-(3-nitrophenyl)-3-azabicyclo[3.1.0]hex-6-yl]methyl}acetamide

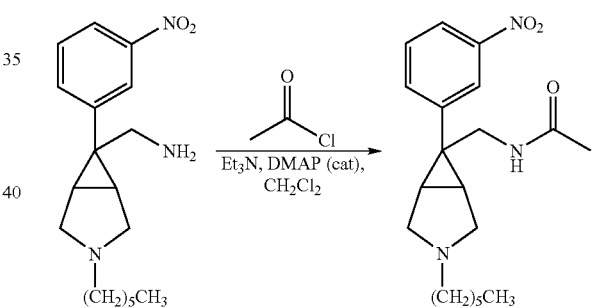

A solution of [3-hexyl-6-(3-nitrophenyl)-3-azabicyclo[3.1.0]hex-6-yl]methylamine (Preparation 110, 80 mg, 0.234 mmol) and triethylamine (0.16 ml, 0.35 mmol) in anhydrous dichloromethane (2 ml) was stirred under nitrogen and treated with acetyl chloride (0.025 ml, 0.35 mmol) followed by 4-dimethylaminopyridine (a few crystals). The reaction mixture was stirred for 18 h at room temperature, then concentrated in vacuo to give a yellow solid (205 mg). The crude solid was purified by column chromatography on silica gel (10 g) eluting with dichloromethane:ethanol:0.88 ammonia (300:8:1 and then 50:8:1) to give the title compound as a yellow solid (84 mg, 100%).

NMR (CDCl$_3$): 0.90 (m, 3H), 1.22–1.35 (m, 6H), 1.50 (m, 2H), 1.80–1.95 (m, 5H), 2.50 (m, 2H), 2.75 (m, 2H), 3.25 (m, 2H), 4.25 (m, 2H), 5.55 (m, 1H), 7.45 (m, 1H), 7.65 (d, 1H), 8.00–8.10 (m, 2H).

MS (thermospray): M/Z (MH$^+$) 360.2; C$_{20}$H$_{29}$N$_3$O$_3$+H requires 360.2.

PREPARATION 110

[3-Hexyl-6-(3-nitrophenyl)-3-azabicyclo[3.1.0]hex-6-yl]methylamine

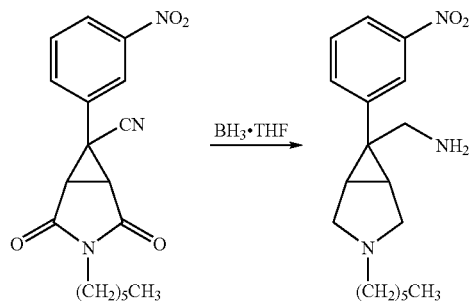

To a solution of 3-hexyl-6-(3-nitrophenyl)-2,4-dioxo-3-azabicyclo[3.1.0]hexane-6-carbonitrile (Preparation 111, 250 mg, 0.732 mmol) in anhydrous tetrahydrofuran (3 ml) stirred under nitrogen was added dropwise borane-tetrahydrofuran complex (1.0M in tetrahydrofuran, 2.9 ml, 2.9 mmol). The reaction mixture was heated at reflux for 2 h, before cooling and quenching with dry methanol (2 ml). The solution in methanol was heated under reflux for 18 h before concentrating in vacuo. The residue was again dissolved in methanol (ca 5 ml) and heated at reflux for 3 hours, followed by evaporation to dryness in vacuo. This process was repeated once more and extensive drying gave a brown oil (270 mg) which was purified by column chromatography on silica gel (13 g) eluting with dichloromethane:ethanol:0.88 ammonia (150:8:1). This gave the title compound as an orange oil (124 mg, 53%).

NMR (CDCl$_3$): 0.90 (t, 3H), 1.20–1.35 (m, 6H), 1.45 (m, 2H), 1.85 (m, 2H), 2.45 (t, 2H), 2.75 (m, 2H), 3.20 (m, 2H), 3.42 (s, 2H), 7.45 (t, 1H), 7.65 (d, 1H), 8.05 (d, 1H), 8.17 (s, 1H).

MS (thermospray): M/Z (MH$^+$) 318.2; C$_{20}$H$_{29}$N$_3$O$_3$+H requires 318.2.

PREPARATION 111

3-Hexyl-6-(3-nitrophenyl)-2,4-dioxo-3-azabicyclo[3.1.0]hexane-6-carbonitrile

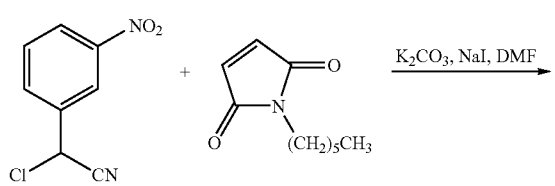

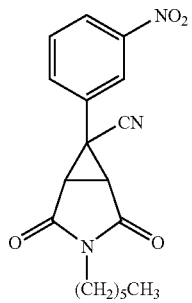

A solution of 2-chloro-2-(3-nitrophenyl)acetonitrile (Preparation 112, 103 mg, 0.524 mmol) and 1-hexyl-1H-pyrrole-2,5-dione (Preparation 56, 79 mg, 0.436 mmol) in N,N-dimethylformamide (2 ml) was added dropwise over 30 min to a stirred slurry of potassium carbonate (120 mg, 0.868 mmol) and sodium iodide (33 mg, 0.22 mmol) in N,N-dimethylformamide (4 ml) and water (0.1 ml) at 0° C. The reaction mixture was stirred for 30 min at 0° C. and then allowed to warm to room temperature. After stirring at room temperature for 2 h the mixture was diluted with water (10 ml) and extracted with ethyl acetate (3×5 ml). The combined organic phases were dried (MgSO$_4$) and concentrated in vacuo to give a residue which was purified by column chromatography on silica gel eluting with hexane:ethyl acetate (5:1 and then 3:1). This gave the title compound as brown needles (47 mg, 32%).

NMR (CDCl$_3$): 0.90 (m, 3H), 1.20–1.40 (m, 6H), 1.63 (m, 2H), 3.21 (s, 2H), 3.56 (m, 2H), 7.68 (t, 1H), 7.80 (m, 1H), 8.12 (s, 1H), 8.30 (d, 1H).

PREPARATION 112

2-Chloro-2-(3-nitrophenyl)acetonitrile

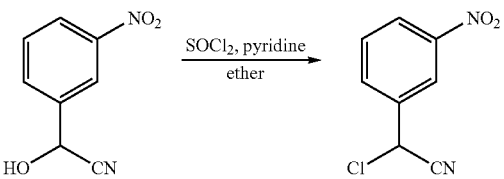

A solution of 2-hydroxy-2-(3-nitrophenyl)acetonitrile (Preparation 113, 1.0 g, 5.62 mmol) in diethyl ether (10 ml) was stirred at room temperature and treated with pyridine (0.1 ml, 1.24 mmol) followed by thionyl chloride (0.82 ml, 11.2 mmol) dropwise over 5 minutes. The mixture was gently heated under reflux and after 30 min the solvent was removed by evaporation to give a pale yellow solid. This was purified by column chromatography on silica gel eluting with hexane:ethyl acetate (3:1 and then 2:1) to give the title compound as a white crystalline solid (980 mg, 89%).

NMR (CDCl$_3$): 5.68 (s, 1H), 7.70 (t, 1H), 7.95 (d, 1H), 8.35 (d, 1H), 8.42 (s, 1H).

MS (electrospray): M/Z (M+) 195.6; $C_8H_5ClN_2O_2$ requires 196.0.

PREPARATION 113

2-Hydroxy-2-(3-nitrophenyl)acetonitrile

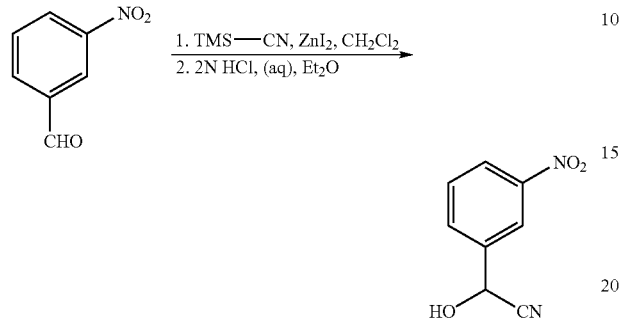

To a stirred solution of 3-nitrobenzaldehyde (5.0 g, 33.1 mmol) in dichloromethane (30 ml) at 0° C. was added trimethylsilyl cyanide (4.63 ml, 34.7 mmol). After stirring for 6 h at room temperature, zinc iodide (210 mg, 0.66 mmol) was added which caused the reaction mixture to warm and gently reflux. After 30 min, the reaction mixture was treated with hydrochloric acid (2M, 100 ml) and diethyl ether (150 ml) and stirred vigorously for 16 h. The phases were separated and the aqueous phase was further extracted with diethyl ether (3×100 ml). The combined organic extracts were dried (MgSO$_4$) and concentrated in vacuo to give a residue which was purified by column chromatography on silica gel eluting with hexane:ethyl acetate (3:1 and then 1:1). This gave the title compound as a clear oil (5.0 g, 85%).

NMR (CDCl$_3$): 3.42 (br s, 1H), 5.70 (s, 1H), 7.65 (t, 1H), 7.92 (d, 1H), 8.32 (m, 1H), 8.42 (s, 1H).

MS (electrospray): M/Z (M–H+) 177.0; $C_8H_6N_2O_3$–H requires 177.0.

PREPARATION 114

N-[3-(6-Methyl-3-{2-[4-(trifluoromethyl)phenyl]acetyl}-3-azabicyclo[3.1.0]hex-6-yl)phenyl]methanesulfonamide

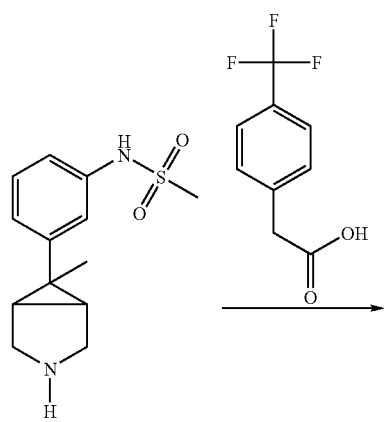

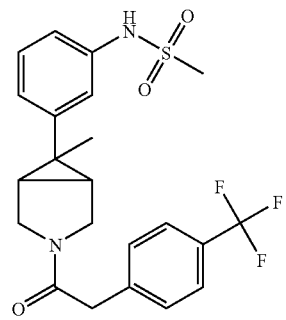

To a solution of 4-(trifluoromethyl)phenyl acetic acid (63 mg, 0.31 mmol) in N,N-dimethylformamide (6.5 ml) was added 1-hydroxybenzotriazole monohydrate (50 mg, 0.33 mmol) and 1-(3-dimethylaminopropyl)-3-ethylcarbodiimide hydrochloride (85 mg, 0.44 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 100 mg, 0.33 mmol) and sodium hydrogen carbonate (28 mg, 0.34 mmol). The reaction mixture was stirred at room temperature for 18 h before concentrating in vacuo. Water (10 ml) was added and the reaction mixture was extracted with ethyl acetate (2×15 ml). The combined organic extracts were dried (Na$_2$SO$_4$), filtered and concentrated in vacuo to give a light brown oil. The residue was purified by chromatography using a Sep-Pak™ cartridge packed with silica gel (5 g) eluting with dichloromethane:ethanol:0.88 ammonia (200:8:1) to afford the title compound as a glassy oil (70 mg, 47%).

NMR (CDCl$_3$): 1.15 (s, 3H), 1.95 (m, 2H), 3.00 (s, 3H), 3.55–3.90 (m, 6H), 6.45 (br. s, 1H), 7.00–7.15 (m, 3H), 7.25 (m, 1H), 7.40 (d, 2H), 7.60 (d, 2H).

MS (thermospray): M/Z (MH+) 452.8; $C_{22}H_{23}F_3N_2O_3S$+H requires 453.1.

PREPARATION 115

N-{3-[3-(2,3-Dihydro-1H-inden-2-ylcarbonyl)-6-methyl-3-azabicyclo[3.1.0]hex-6-yl]phenyl}methanesulfonamide

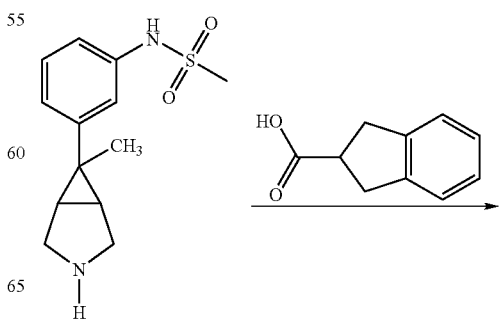

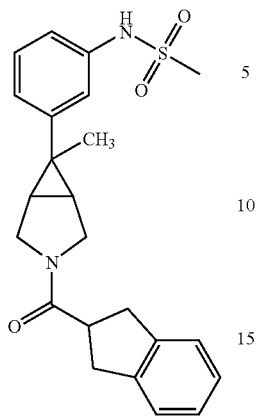

To a solution of 2-indane carboxylic acid (E. D. Bergmann and E. Hoffmann, J. Org. Chem., 1961, 26, 3555, 100 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (117 mg, 43%).

NMR ($CDCl_3$, selected data): 1.30 (s, 3H), 2.00 (m, 2H), 3.00 (s, 3H), 3.05–3.45 (m, 5H), 3.70–3.80 (m, 3H), 3.95 (m, 1H), 6.50 (br., 1H), 7.00–7.35 (m, 8H).

MS (thermospray): M/Z (MH$^+$) 411.2; $C_{23}H_{26}N_2O_3S$+H requires 411.2.

PREPARATION 116

N-(3-{3-[2-(1-Benzothiophene-3-yl)acetyl]-6-methyl-3-azabicyclo[3.1.0]hex-6-yl}phenyl)methanesulfonamide

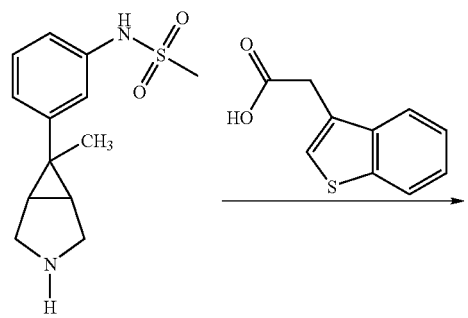

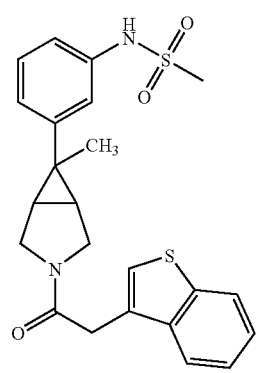

To a solution of 2-(1-benzothiophen-3-yl)acetic acid (118 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (99 mg, 34%).

NMR ($CDCl_3$): 1.15 (s, 3H), 1.95 (m, 2H), 3.00 (s, 3H), 3.60 (d, 1H), 3.75–3.90 (m, 5H), 6.5 (br., 1H), 7.00–7.10 (m, 3H), 7.20–7.35 (m, 2H), 7.35–7.45 (m, 2H), 7.85 (m, 2H).

MS (thermospray): M/Z (MH$^+$) 441.1; $C_{23}H_{24}N_2O_3S_2$+H requires 441.1.

PREPARATION 117

N-(3-{6-Methyl-3-[2-(1-methyl-1H-indol-3-yl)acetyl]-3-azabicyclo[3.1.0]hex-6-yl}phenyl)methanesulfonamide

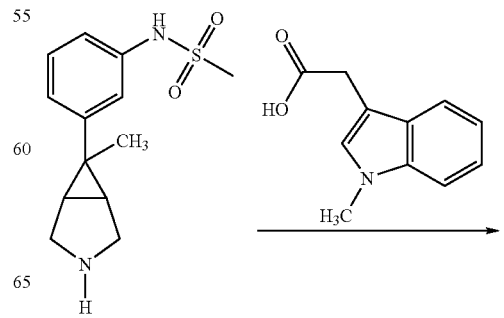

-continued

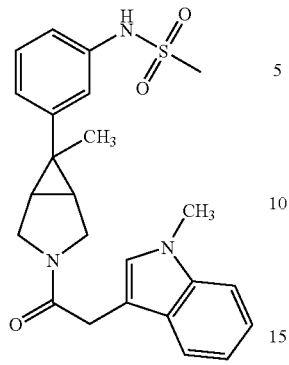

To a solution of 2-(6-methyl-3H-indol-3-yl)acetic acid (117 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodi-imide hydrochloride hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (58 mg, 20%).

NMR ($CDCl_3$, selected data): 1.15 (s, 3H), 1.90 (br. s, 2H), 3.00 (s, 3H), 3.60–3.90 (m, 9H), 6.55 (br., 1H), 7.00–7.35 (m, 8H), 7.60 (d, 1H).

MS (thermospray): M/Z (MH$^+$) 438.2; $C_{24}H_{27}N_3O_3S$+H requires 438.2

PREPARATION 118

N-(3-{3-[3-(4-Fluorophenyl)propanoyl]-6-methyl-3-azabicyclo[3.1.0]hex-6-yl}phenyl)methanesulfonamide

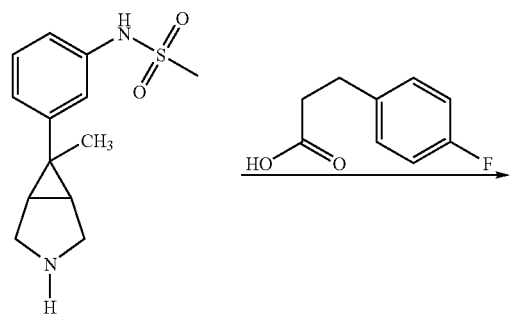

-continued

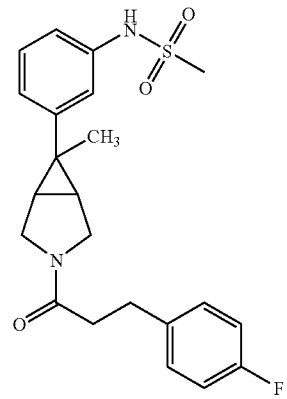

To a solution of 3-(4-fluorophenyl)propanoic acid (104 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (100 mg, 36%).

NMR ($CDCl_3$): 1.15 (s, 3H), 1.95 (m, 2H), 2.55 (m, 2H), 2.95 (m, 2H), 3.00 (s, 3H), 3.50 (d, 1H), 3.60–3.80 (m, 3H), 6.55 (br., 1H), 6.90–7.30 (m, 8H)

MS (thermospray): M/Z (MH$^+$) 417.3; $C_{22}H_{25}FN_2O_3S$+H requires 417.2.

PREPARATION 119

N-(3-{3-[3-(3,4-Dichlorophenyl)propanoyl]-6-methyl-3-azabicyclo[3.1.0]hex-6-yl}phenyl)methanesulfonamide

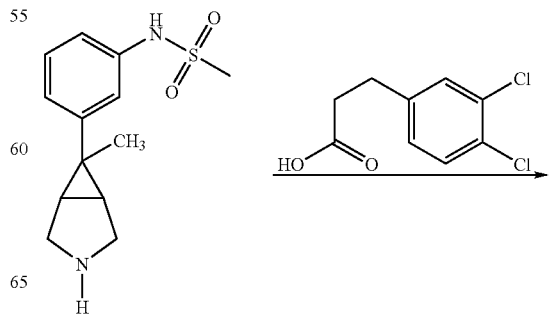

-continued

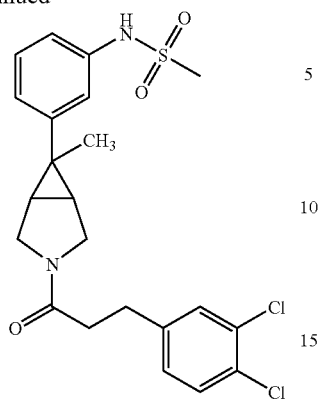

To a solution of 3-(3,4-dichlorophenyl)propanoic acid (35 mg, 0.16 mmol) in N,N-dimethylformamide (4 ml) was added 1-hydroxybenzotriazole monohydrate (26 mg, 0.17 mmol) and 1-(3-dimethylaminopropyl)-3-ethylcarbodiimide hydrochloride (44 mg, 0.23 mmol). After stirring at room temperature for 5 min the mixture was treated with the hydrochloride salt of N-[3-(6-methyl-3-azabicyclo[3.1.0] hex-6-yl)phenyl]methanesulfonamide (Preparation 53, 52 mg, 0.17 mmol) and triethylamine (33 mg, 0.33 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (38 mg, 51%).

NMR ($CDCl_3$): 1.20 (s, 3H), 1.95 (m, 2H), 2.55 (m, 2H), 2.95 (m, 2H), 3.00 (s, 3H), 3.50 (m, 1H), 3.70–3.80 (m, 3H), 6.50 (br., 1H), 7.00–7.15 (m, 4H), 7.20–7.40 (m, 3H).

MS (thermospray): M/Z ($MH^+$) 466.8; $C_{22}H_{24}Cl_2N_2O_3S+H$ requires 467.1.

PREPARATION 120

N-(3-{3-[3-(1,3-Benzodioxol-5-yl)propanoyl]-6-methyl-3-azabicyclo[3.1.0]hex-6-yl}phenyl)methanesulfonamide

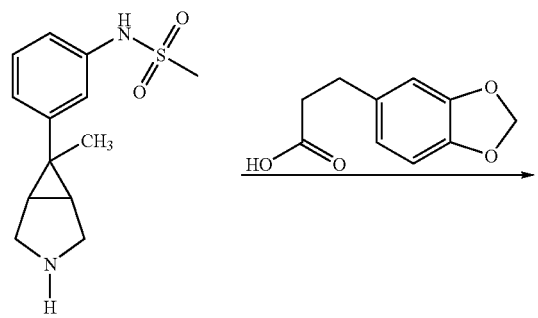

-continued

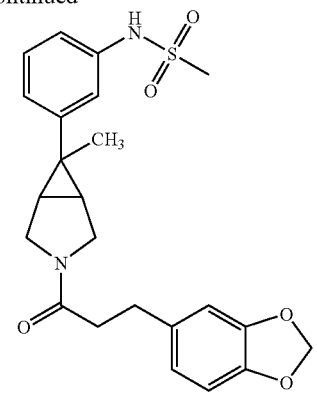

To a solution of 3-(1,3-benzodioxol-5-yl)propanoic acid (120 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride (170 mg, 0.88 mmol). After stirring at room temperature for 5 min the mixture was treated with the hydrochloride salt of N-[3-(6-methyl-3-azabicyclo[3.1.0] hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried ($Na_2SO_4$), filtered and concentrated in vacuo to give a light brown oil. The residue was purified by chromatography using a Sep-Pak™ cartridge packed with silica gel (10 g) eluting with dichloromethane:ethanol:0.88 ammonia (300:8:1) to afford the title compound as a white foam (107 mg, 38%).

NMR ($CDCl_3$):1.20 (s, 3H), 1.95 (br., 2H), 2.55 (m, 2H), 2.95 (m, 2H), 3.00 (s, 3H), 3.50 (m, 1H), 3.65–3.80 (m, 3H), 5.90 (s, 2H), 6.55 (br., 1H), 6.65-6.75 (m, 3H), 7.00–7.15 (m, 3H), 7.15–7.20 (m, 1H).

MS (thermospray): M/Z ($MH^+$) 443.2; $C_{23}H_{26}N_2O_5S+H$ requires 443.2.

PREPARATION 121

N-(3-{3-[2-(5-Chloro-3-thienyl)acetyl]-6-methyl-3-azabicyclo[3.1.0]hex-6-yl}phenyl)methanesulfonamide

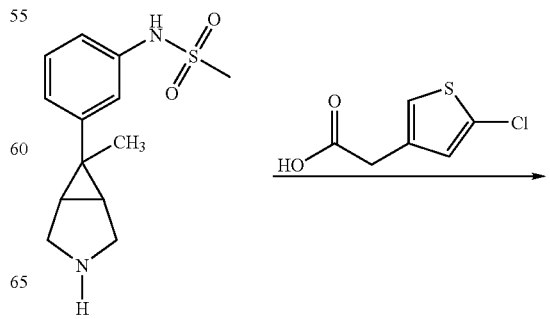

-continued

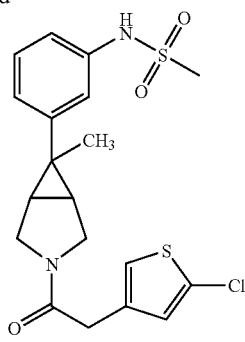

To a solution of 2-(5-chloro-3-thienyl)acetic acid (T. L. Cairns and B. C. McKusick, J. Org. Chem., 1950, 15, 790; 109 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried (Na$_2$SO$_4$), filtered and concentrated in vacuo to give a light brown oil. The residue was purified by chromatography using a Biotage Flash 12™ cartridge packed with silica gel (8 g) eluting with dichloromethane:ethanol:0.88 ammonia (250:8:1) to afford a crude product which was further purified using a Sep-Pak™ cartridge packed with silica gel (10 g) eluting with dichloromethane:ethanol:0.88 ammonia (300:8:1) to afford the title compound as a white foam (51 mg, 19%).

NMR (CDCl$_3$, selected data): 1.20 (s, 3H), 2.00 (m, 2H), 3.00 (s, 3H), 3.60–3.95 (m, 6H), 6.50 (br., 1H), 6.70–6.80 (m, 2H), 7.00–7.15 (m, 3H), 7.25 (m, 1H).

MS (thermospray): M/Z (MH$^+$) 425.2; C$_{19}$H$_{21}$ClN$_2$O$_3$S$_2$+H requires 425.1.

PREPARATION 122

N-{3-[6-Methyl-3-(3-methyl-3-phenylbutanoyl)-3-azabicaclo[3.1.0]hex-6-yl]phenyl}methanesulfonamide

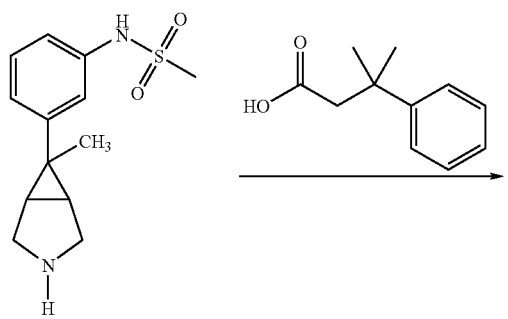

-continued

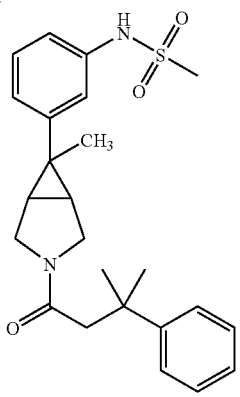

To a solution of 3-methyl-3-phenylbutanoic acid (F. C. Whitmore, C. A. Weisgerber and A. C. Shabica Jr., J. Am. Chem. Soc.,1943, 65, 1469; 110 mg, 0.62 mmol) in N,N-dimethylformamide (13 ml) was added 1-hydroxybenzotriazole monohydrate (100 mg, 0.66 mmol) and 1-(3-dimethylaminopropyl)-3-ethylcarbodiimide hydrochloride (170 mg, 0.88 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 200 mg, 0.66 mmol) and triethylamine (133 mg, 1.32 mmol). The reaction mixture was stirred at room temperature for 72 h before concentrating in vacuo. Water (10 ml) was added and the reaction mixture was extracted with ethyl acetate (2×15 ml). The combined organic extracts were washed with water (10 ml) and saturated brine (10 ml), dried (Na$_2$SO$_4$), filtered and concentrated in vacuo to give a light brown oil. The residue was purified by chromatography using a Biotage Flash 12™ cartridge packed with silica gel (8 g) eluting with dichloromethane:ethanol:0.88 ammonia (250:8:1) to afford a pale yellow oil which was further purified using a Sep-Pak™ cartridge packed with silica gel (10 g) eluting with dichloromethane:ethanol: 0.88 ammonia (300:8:1) to afford the title compound as a white foam (70 mg, 26%).

NMR (CDCl$_3$): 1.05 (s, 3H), 1.55 (m, 6H), 1.85 (m, 2H), 2.55 (m, 2H), 3.00 (s, 3H), 3.30–3.50 (m, 2H), 3.50–3.70 (m, 2H), 6.50 (br., 1H), 6.95–7.10 (m, 3H), 7.10–7.50 (m, 6H).

MS (thermospray): M/Z (MH$^+$) 427.4; C$_{24}$H$_{30}$N$_2$O$_3$S+H requires 427.2.

PREPARATION 123

N-(3-{3-[3-(1H-Indol-3-yl)propanoyl]-6-methyl-3-azabicyclo[3.1.0]hex-6-yl}phenyl)methanesulfonamide

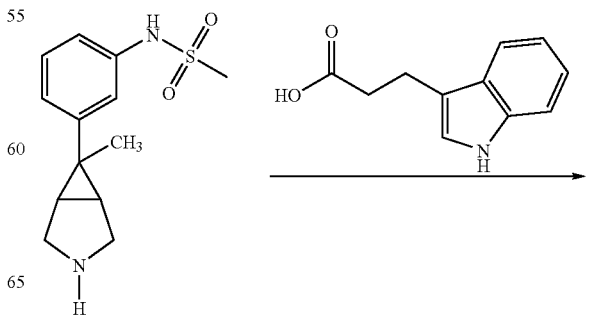

-continued

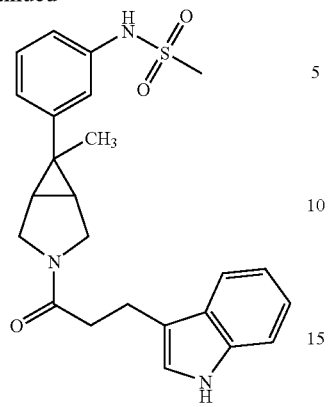

To a solution of 3-(1H-indol-3-yl)propanoic acid (235 mg, 1.2 mmol) in N,N-dimethylformamide (13 ml) was added 1-hydroxybenzotriazole monohydrate (200 mg, 1.31 mmol) and 1-(3-dimethylaminopropyl)-3-ethylcarbodiimide hydrochloride (340 mg, 1.77 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 400 mg, 1.3 mmol) and sodium hydrogen carbonate (220 mg, 2.6 mmol). The reaction mixture was stirred at room temperature for 72 h before concentrating in vacuo. Water (20 ml) was added and the reaction mixture was extracted with ethyl acetate (2×30 ml). The combined organic extracts were washed with water (20 ml) and saturated brine (20 ml), dried ($MgSO_4$), filtered and concentrated in vacuo to give a pale yellow solid. The crude product was purified by shaking with dichloromethane (10 ml) and after filtration the filtrate was concentrated in vacuo to afford a pale yellow solid which was further purified by chromatography using a Sep-Pak™ cartridge packed with silica gel (10 g) eluting with dichloromethane:ethanol:0.88 ammonia (300:8:1) to afford the title compound as a white solid (235 mg, 43%).

NMR ($CDCl_3$): 1.05 (s, 3H), 1.90 (m, 2H), 2.70 (m, 2H), 3.00 (s, 3H), 3.20 (m, 2H), 3.45 (m, 1H), 3.60–3.80 (m, 3H), 6.40 (br., 1H), 7.00–7.30 (m, 7H), 7.37 (d, 1H), 7.60 (d, 1H), 7.95 (br., 1H).

MS (thermospray): M/Z (MH$^+$) 438.1; $C_{24}H_{27}N_3O_3S$+H requires 438.2.

PREPARATION 124

N-(3-{6-Methyl-3-[3-(4-pyridinyl)propanoyl]-3-azabicyclo[3.1.0]hex-6-yl}phenyl)methanesulfonamide

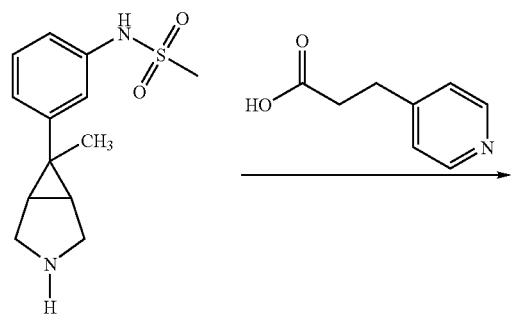

To a solution of 3-(4-pyridinyl)propanoic acid (E. A. Hallinan et al., J. Med. Chem., 1996, 39, 609, 96 mg, 0.635 mmol) in N,N-dimethylformamide (6 ml) was added 1-hydroxybenzotriazole monohydrate (96 mg, 0.627 mmol) and 1-(3-dimethylaminopropyl)-3-ethylcarbodiimide hydrochloride (122 mg, 0.636 mmol). After stirring at room temperature for 5 min the mixture was treated with the hydrochloride salt of N-[3-(6-methyl-3-azabicyclo[3.1.0]hex-6-yl)phenyl]methanesulfonamide (Preparation 53, 193 mg, 0.635 mmol) and sodium hydrogen carbonate (160 mg, 1.907 mmol). The reaction mixture was stirred at room temperature for 5 d before partitioning between water (5 ml) and dichloromethane (5 ml). The layers were separated and the aqueous layer was extracted with dichloromethane (2×5 ml). The combined organic extracts were dried ($Na_2SO_4$), filtered and concentrated in vacuo to give a brown oil (260 mg). The residue was purified by chromatography using a Biotage Flash 12™ cartridge packed with silica gel (8 g) eluting with dichloromethane:ethanol:0.88 ammonia (300:8:1) to afford the title compound as a pink foam (100 mg, 62%).

NMR ($CDCl_3$): 1.18 (s, 3H), 1.95 (m, 2H), 2.60 (m, 2H), 2.95–3.05 (m, 4H), 3.52 (m, 2H), 3.70–3.80 (m, 4H), 7.00–7.10 (m, 2H), 7.10–7.20 (m, 2H), 7.20–7.30 (m, 2H), 8.50 (d, 2H).

MS (electrospray): M/Z (MH$^+$) 400.2; $C_{21}H_{25}N_3O_3S$+H requires 400.2.

IR ?$_{max}$ (polyethylene card)/cm$^{-1}$: 1328 (w), 1447 (w), 1606 (m), 1622 (m), 2915 (m).

PREPARATION 125

N-(3-{6-Methyl-3-[3-(2-thienyl)propanoyl]-3-azabicyclo[3.1.0]hex-6-yl}phenyl)methanesulfonamide

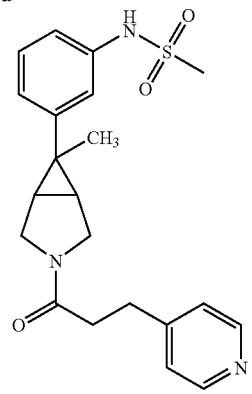

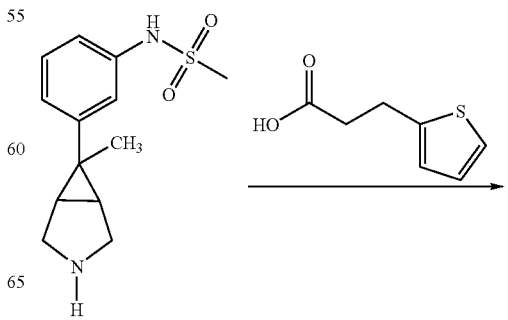

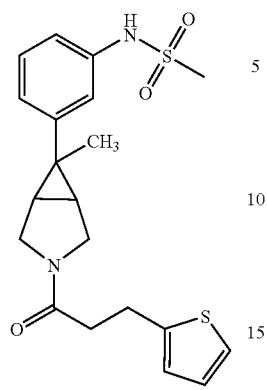

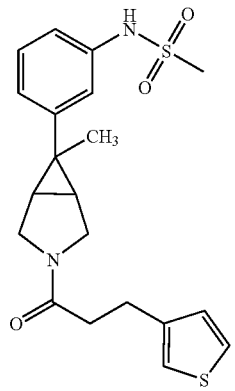

To a solution of 3-(2-thienyl)propanoic acid (200 mg, 1.2 mmol) in N,N-dimethylformamide (25 ml) was added 1-hydroxybenzotriazole monohydrate (200 mg, 1.31 mmol) and 1-(3-dimethylaminopropyl)-3-ethylcarbodiimide hydrochloride (340 mg, 1.77 mmol). After stirring at room temperature for 10 min the mixture was treated with the hydrochloride salt of N-[3-(6-methyl-3-azabicyclo[3.1.0]hex-6-yl)phenyl]methanesulfonamide (Preparation 53, 400 mg, 1.3 mmol) and sodium hydrogen carbonate (220 mg, 2.6 mmol). The reaction mixture was stirred at room temperature for 3 h before concentrating in vacuo. Water (15 ml) was added and the reaction mixture was extracted with ethyl acetate (1×30 ml and 2×15 ml). The combined organic extracts were washed with water (15 ml) and saturated brine (15 ml), dried ($MgSO_4$), and concentrated in vacuo to give a buff solid. The crude product was sonicated in methanol (5 ml) to afford the title compound as an off-white solid (350 mg, 66%, m.p. 184.5° C.).

NMR ($CDCl_3$, selected data): 1.20 (s, 3H), 1.95 (m, 2H), 2.60 (m, 2H), 3.00 (s, 3H), 3.25 (m, 2H), 3.55 (d, 1H), 3.70–3.85 (m, 3H), 6.62 (br., 1H), 6.85 (m, 1H), 6.95 (m, 1H), 7.00–7.20 (m, 4H), 7.22–7.35 (m, 1H).

MS (electrospray): M/Z ($MH^+$) 405.1; $C_{20}H_{24}N_2O_3S_2$+H requires 405.1.

To s solution 3-(3-thienyl propanoic acid (200 mg, 1.2 mmol) in N,N-dimethylformamide (25 ml) was added 1-hydroxybenzotriazole monohydrate (200 mg, 1.31 mmol) and 1-(3-dimethylaminopropyl)-3-ethylcarbodiimide hydrochloride (340 mg, 1.77 mmol). After stirring at room temperature for 10 min the mixture was treated with the hydrochloride salt of N-[3-(6-methyl-3-azabicyclo[3.1.0]hex-6-yl)phenyl]methanesulfonamide (Preparation 53, 400 mg, 1.3 mmol) and sodium hydrogen carbonate (220 mg, 2.6 mmol). The reaction mixture was stirred at room temperature for 72 h before concentrating in vacuo. Water (15 ml) was added and the reaction mixture was extracted with ethyl acetate (1×20 ml and 2×15 ml). The combined organic extracts were washed with water (15 ml) and saturated brine (15 ml), dried ($MgSO_4$), and concentrated in vacuo to give a buff solid. The crude product was sonicated in methanol (5 ml) to afford the title compound as an off-white solid (330 mg, 63%, m.p. 179.7° C.).

NMR ($CDCl_3$, selected data): 1.20 (s, 3H), 1.95 (m, 2H), 2.55 (m, 2H), 2.90–3.10 (m, 5H), 3.50 (m, 1H), 3.60–3.80 (m, 3H), 6.60 (br., 1H), 6.95–7.15 (m, 5H), 7.20–7.30 (m, 2H).

MS (electrospray): M/Z ($MH^+$) 405.1; $C_{20}H_{24}N_2O_3S_2$+H requires 405.1.

PREPARATION 126

N-(3-{6-Methyl-3-[3-(3-thienyl)propanoyl]-3-azabicyclo[3.1.0]hex-6-yl}phenyl)methanesulfonamide

PREPARATION 127

N-{3-[3-(1-Benzofuran-2-ylcarbonyl)-6-methyl-3-azabicyclo[3.1.0]hex-6-yl]phenyl}methanesulfonamide

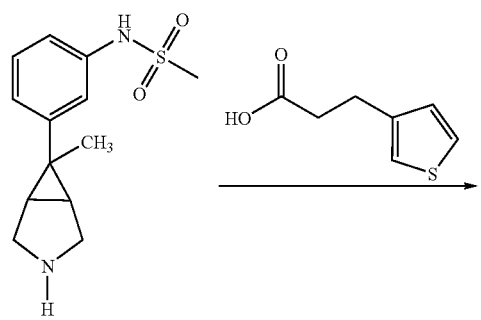

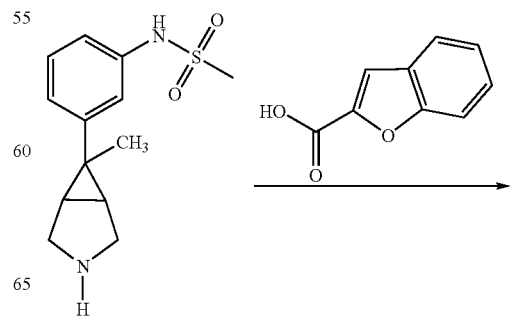

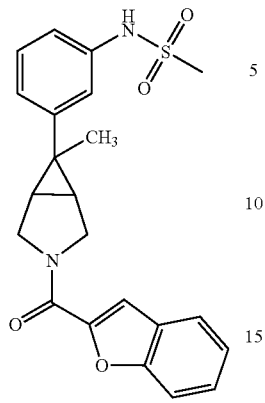

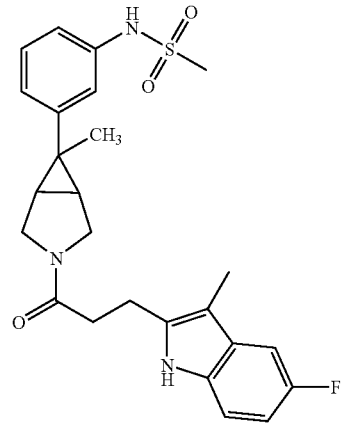

To a solution of 1-benzofuran-2-carboxylic acid (201 mg, 1.24 mmol) in N,N-dimethylformamide (25 ml) was added 1-hydroxybenzotriazole monohydrate (200 mg, 1.31 mmol) and 1-(3-dimethylaminopropyl)-3-ethylcarbodiimide hydrochloride (340 mg, 1.77 mmol). After stirring at room temperature for 10 min the mixture was treated with the hydrochloride salt of N-[3-(6-methyl-3-azabicyclo[3.1.0]hex-6-yl)phenyl]methanesulfonamide (Preparation 53, 400 mg, 1.3 mmol) and sodium hydrogen carbonate (220 mg, 2.6 mmol). The reaction mixture was stirred at room temperature overnight before concentrating in vacuo. Water (15 ml) was added and the reaction mixture was extracted with ethyl acetate (2×20 ml). The combined organic extracts were treated with water (15 ml) upon which a buff solid precipitated. The biphasic mixture was filtered to afford 380 mg of a buff solid. The biphasic filtrate was separated and the organic layer was dried (MgSO$_4$), and concentrated in vacuo to afford a further 80 mg of buff solid. The combined buff solid was warmed to 60° C. in methanol and allowed to slowly cool to room temperature upon which the title compound was collected by filtration as an off-white solid (340 mg, 63%).

NMR (DMSO, selected data): 1.20 (s, 3H), 2.02 (m, 2H), 2.95 (s, 3H), 3.75–3.90 (m, 2H), 4.02 (m, 1H), 4.25 (m, 1H), 7.00–7.08 (m, 2H), 7.15.(s, 1H), 7.2–7.35 (m, 2H), 7.45 (dd, 1H), 7.55 (s, 1H), 7.68 (d, 1H), 7.78 (d, 1H).

MS (electrospray): M/Z (MH$^+$) 411.1; $C_{22}H_{22}N_2O_4S$+H requires 411.1.

PREPARATION 128

N-(3-{3-[3-(5-Fluoro-3-methyl-1H-indol-2-yl)propanoyl]-6-methyl-3-azabicyclo[3.1.0]hex-6-yl}phenyl)methanesulfonamide To a solution of 3-(5-fluoro-3-methyl-1H-indol-2-yl)propanoic acid (prepared according to the method described in EP 510398 A2, 200 mg, 0.90 mmol) in N,N-dimethylformamide (20 ml) was added 1-hydroxybenzotriazole monohydrate (154 mg, 1.00 mmol) and 1-(3-dimethylaminopropyl)-3-ethylcarbodiimide hydrochloride (262 mg, 1.36 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 308 mg, 0.90 mmol) and sodium hydrogen carbonate (150 mg, 1.80 mmol). The reaction mixture was stirred at room temperature overnight before concentrating in vacuo. Water (15 ml) was added and the reaction mixture was extracted with ethyl acetate (2×20 ml). The combined organic extracts were washed with water (15 ml), dried (MgSO$_4$), and concentrated in vacuo to afford 350 mg of a brown viscous oil which was not purified further.

NMR (CDCl$_3$, selected data): 1.15 (s, 3H), 1.95 (m, 2H), 2.20 (s, 3H), 2.50 (m, 2H), 3.00 (s, 3H), 3.18 (m, 2H), 3.50 (m, 1H), 3.60–3.80 (m, 3H), 6.60 (br. s, 1H), 6.82 (dd, 1H), 7.00–7.15 (m, 4H), 7.18 (m, 1H), 7.25 (m, 1H).

MS (electrospray): M/Z (MH$^+$) 470.2; $C_{25}H_{28}FN_3O_3S$+H requires 470.2.

PREPARATION 129

N-(3-{6-Methyl-3-[3-(2-pyridinyl)propanoyl]-3-azabicyclo[3.1.0]hex-6-yl}phenyl)methanesulfonamide

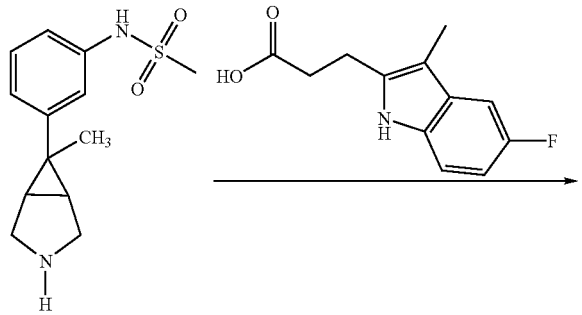

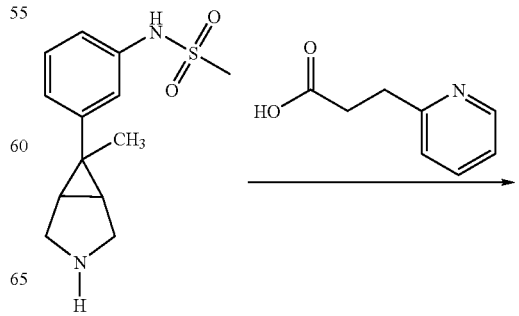

-continued

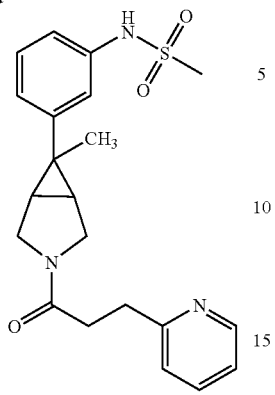

To a solution of 3-(2-pyridinyl)propanoic acid (prepared according to the method described in WO 9730045 A1, 32 mg, 0.212 mmol) in N,N-dimethylformamide (2 ml) was added 1-hydroxybenzotriazole monohydrate (32 mg, 0.209 mmol) and 1-(3-dimethylaminopropyl)-3-ethylcarbodiimide hydrochloride (41 mg, 0.214 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 64 mg, 0.212 mmol) and sodium hydrogen carbonate (36 mg, 0.424 mmol). The reaction mixture was stirred at room temperature for 5 d. Water (5 ml) was added and the reaction mixture was extracted with dichloromethane (3×5 ml). The combined organic extracts were dried (MgSO$_4$), and concentrated in vacuo to afford 70 mg of a brown oil. This was purified by chromatography using a Biotage Flash 12™ cartridge packed with silica gel (8 g) eluting with dichloromethane:ethanol:0.880 ammonia (400:8:1 then 300:8:1) to afford the title compound as a colourless oil (17 mg, 20%).

NMR (CDCl$_3$, selected data): 1.18 (s, 3H), 1.95 (m, 2H), 2.75 (m, 2H), 3.00 (s, 3H), 3.20 (dd, 2H), 3.60 (m, 1H), 3.70 (m, 2H), 3.80 (dd, 1H), 7.00–7.18 (m, 4H), 7.20–7.30 (m, 2H), 7.45 (br. s, 1H), 7.58 (m, 1H), 8.50 (d, 1H).

MS (electrospray): M/Z (M+H$^+$) 400.2; $C_{21}H_{25}N_3O_3S$+H requires 400.2.

M/Z (MNa$^+$) 422.2; $C_{21}H_{25}N_3O_3S$+Na requires 422.2.

IR ?$_{max}$ (polyethylene card)/cm$^{-1}$: 2360 (s), 2341 (m), 1624 (m), 1437 (w), 1238 (w), 1154 (w).

PREPARATION 130

N-(3-{6-Methyl-3-[3-(3-methyl-2-thienyl)propanoyl]-3-azabicyclo[3.1.0]hex-6-yl}phenyl)methanesulfonamide

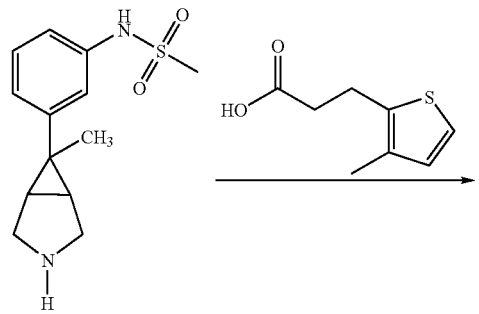

-continued

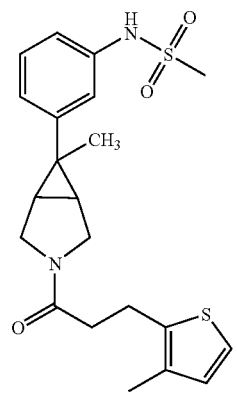

To a solution of 3-(3-methyl-2-thienyl)propanoic acid (J. W. McFarland et al., J. Med. Chem., 1970, 13, 113, 200 mg, 1.17 mmol) in N,N-dimethylformamide (25 ml) was added 1-hydroxybenzotriazole monohydrate (200 mg, 1.31 mmol) and 1-(3-dimethylaminopropyl)-3-ethylcarbodiimide hydrochloride (340 mg, 1.77 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 400 mg, 1.32 mmol) and sodium hydrogen carbonate (200 mg, 2.38 mmol). The reaction mixture was stirred at room temperature overnight and then concentrated in vacuo. Water (10 ml) was added and the reaction mixture was extracted with ethyl acetate (2×15 ml). The combined organic extracts were washed with water (10 ml), dried (MgSO$_4$), and concentrated in vacuo to afford 620 mg of a brown oil. This was purified by chromatography using a Biotage Flash 12™ cartridge packed with silica gel (8 g) eluting with hexane:ethyl acetate (100:0 to 0:100 over 30 min) and then with ethyl acetate:methanol (100:0 to 0:100 over 5 min) to afford the title compound as a colourless oil (244 mg, 50%).

NMR (CDCl$_3$, selected data): 1.19 (s, 3H), 1.95 (m, 2H), 2.20 (s, 3H), 2.48 (m, 2H), 3.00 (s, 3H), 3.15 (dd, 2H), 3.55 (m, 1H), 3.70–3.80 (m, 1H), 6.65 (br. s 1H), 6.78 (d, 1H), 7.00–7.15 (m, 4H), 7.25 (m, 1H).

MS (electrospray): M/Z (MH$^+$) 419.1; $C_{21}H_{26}N_2O_3S_2$+H requires 419.1.

M/Z (MNa$^+$) 441.1; $C_{21}H_{25}N_3O_3S$+Na requires 441.1.

PREPARATION 131

N-(3-{3-[3-(2-Chlorophenyl)propanoyl]-6-methyl-3-azabicyclo[3.1.0]hex-6-yl}phenyl)methanesulfonamide

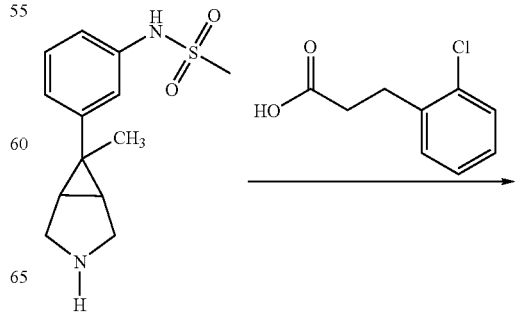

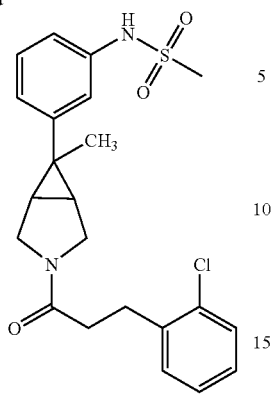

To a solution of 3-(2-chlorophenyl)propanoic acid (200 mg, 1.08 mmol) in N,N-dimethylformamide (20 ml) was added 1-hydroxybenzotriazole monohydrate (187 mg, 1.22 mmol) and 1-(3-dimethylaminopropyl)-3-ethylcarbodiimide hydrochloride (318 mg, 1.66 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 400 mg, 1.32 mmol) and sodium hydrogen carbonate (200 mg, 2.38 mmol). The reaction mixture was stirred at room temperature for 3 d and then concentrated in vacuo. Water (15 ml) was added and the reaction mixture was extracted with ethyl acetate (2×20 ml). The combined organic extracts were washed with water (10 ml), dried (MgSO$_4$), and concentrated in vacuo to afford 510 mg of a light brown oil. Sonication for 5 min at room temperature in dichloromethane (5 ml) followed by filtration afforded the title compound as an off-white solid (124 mg, 27%).

NMR (CDCl$_3$, selected data): 1.18 (s, 3H), 1.95 (m, 2H), 2.60 (t, 2H), 3.00 (s, 3H), 3.12 (dd, 2H), 3.55 (m, 1H), 3.70–3.80 (m, 3H), 6.55 (br. s 1H), 7.00–7.20 (m, 4H), 7.25–7.40 (m, 4H).

MS (thermospray): M/Z (MH$^+$) 433.1; C$_{22}$H$_{25}$ClN$_2$O$_3$S+H requires 433.1.

PREPARATION 132

N-(3-{6-Methyl-3-[(E)-3-(3-thienyl)-2-propenoyl]-3-azabicyclo[3.1.0]hex-6-yl}phenyl)methanesulfonamide

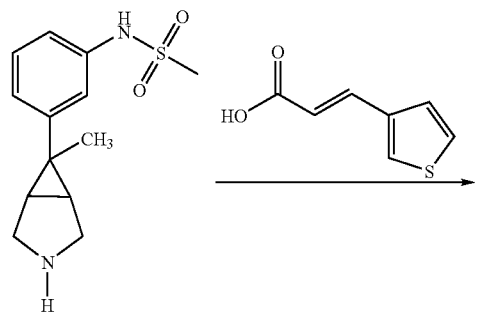

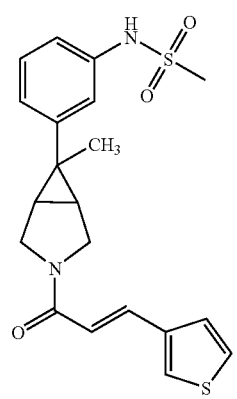

To a solution of (E)-3-(3-thienyl-2-propenoic acid (200 mg, 1.08 mmol) in N,N-dimethylformamide (20 ml) was added 1-hydroxybenzotriazole monohydrate (225 mg, 1.47 mmol) and 1-(3-dimethylaminopropyl)-3-ethylcarbodiimide hydrochloride (328 mg, 1.71 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 449 mg, 1.48 mmol) and sodium hydrogen carbonate (225 mg, 2.68 mmol). The reaction mixture was stirred at room temperature for 7 d and then concentrated in vacuo. Attempted partition between water (10 ml) and ethyl acetate (15 ml) produced a buff solid which was collected by filtration. Sonication for 5 min at room temperature in dichloromethane (5 ml) followed by filtration afforded the title compound as an off-white solid (430 mg, 72%).

NMR (DMSO, selected data): 1.18 (s, 3H), 1.95 (ddd, 2H), 2.95 (s, 3H), 3.58 (d, 1H), 3.68 (dd, 1H), 3.82 (d, 1H), 3.95 (dd, 1H), 6.78 (d, 1H), 6.98–7.05 (m, 2H), 7.10 (s, 1H), 7.22 (dd, 1H), 7.45 (d, 1H), 7.52–7.60 (m, 2H), 7.83 (m, 1H).

MS (thermospray): M/Z (MH$^+$) 403.1; C$_{20}$H$_{22}$N$_2$O$_3$S$_2$+H requires 403.1.

PREPARATION 133

N-(3-{6-Methyl-3-[(E)-3-(2-thienyl)-2-propenoyl]-3-azabicyclo[3.1.0]hex-6-yl}phenyl)methanesulfonamide

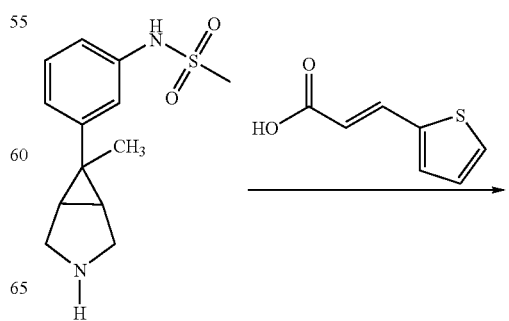

-continued

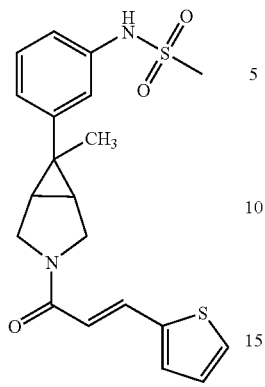

To a solution of (E)-3-(2-thienyl)-2-propenoic acid (200 mg, 1.08 mmol) in N,N-dimethylformamide (20 ml) was added 1-hydroxybenzotriazole monohydrate (225 mg, 1.47 mmol) and 1-(3-dimethylaminopropyl)-3-ethylcarbodiimide hydrochloride (328 mg, 1.71 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 449 mg, 1.48 mmol) and sodium hydrogen carbonate (225 mg, 2.68 mmol). The reaction mixture was stirred at room temperature for 7 d and then concentrated in vacuo. Attempted partition between water (15 ml) and ethyl acetate (20 ml) produced a buff solid which was collected by filtration. Sonication for 5 min at room temperature in dichloromethane (5 ml) followed by filtration afforded the title compound as an off-white solid (337 mg, 77%).

NMR (DMSO, selected data): 1.18 (s, 3H), 1.95 (ddd, 2H), 2.95 (s, 3H), 3.58 (d, 1H), 3.68 (dd, 1H), 3.80 (d, 1H), 3.95 (dd, 1H), 6.60 (d, 1H), 6.95–7.05 (m, 2H), 7.10–7.15 (m, 2H), 7.22 (dd, 1H), 7.43 (d, 1H), 7.58–7.65 (m, 2H).

MS (thermospray): M/Z (MH$^+$) 403.0; $C_{20}H_{22}N_2O_3S_2$+H requires 403.1.

PREPARATION 134

N-(3-{6-Methyl-3-[(E)-3-(3-methyl-2-thienyl)-2-propenoyl]-3-azabicyclo[3.1.0]hex-6-yl}phenyl)methanesulfonamide

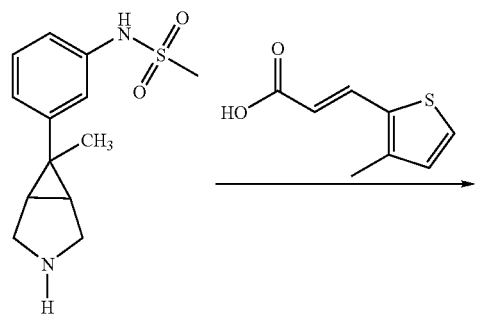

-continued

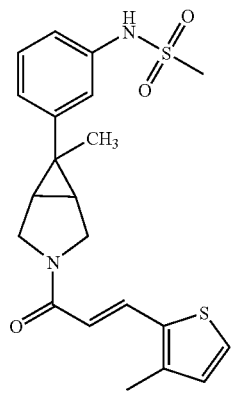

To a solution of (E)-3-(3-methyl-2-thienyl)-2-propenoic acid (200 mg, 1.00 mmol) in N,N-dimethylformamide (20 ml) was added 1-hydroxybenzotriazole monohydrate (212 mg, 1.39 mmol) and 1-(3-dimethylaminopropyl)-3-ethylcarbodiimide hydrochloride (352 mg, 1.84 mmol). After stirring at room temperature for 10 min, the mixture was treated with the hydrochloride salt of N-[3-(6-methyl-3-azabicyclo[3.1.0]hex-6-yl)phenyl]methanesulfonamide (Preparation 53, 414 mg, 1.36 mmol) and sodium hydrogen carbonate (225 mg, 2.68 mmol). The reaction mixture was stirred at room temperature for 7 d and then concentrated in vacuo. Attempted partition between water (15 ml) and ethyl acetate (20 ml) produced a buff solid which was collected by filtration. Sonication for 5 min at room temperature in dichloromethane (5 ml) followed by filtration afforded the title compound as an off-white solid (280 mg, 67%).

NMR (DMSO, selected data): 1.18 (s, 3H), 1.95 (ddd, 2H), 2.28 (s, 3H), 2.95 (s, 3H), 3.59 (d, 1H), 3.70 (dd, 1H), 3.80 (d, 1H), 3.97 (dd, 1H), 6.47 (d, 1H), 6.95 (d, 1H), 6.97–7.03 (m, 2H), 7.10 (s, 2H), 7.22 (dd, 1H), 7.43 (d, 1H), 7.58–7.65 (m, 2H).

MS (thermospray): M/Z (MH$^+$) 417.1; $C_{21}H_{24}N_2O_3S_2$+H requires 417.1.

PREPARATION 135

1-(3-Nitrophenyl)-1-ethanone hydrazone

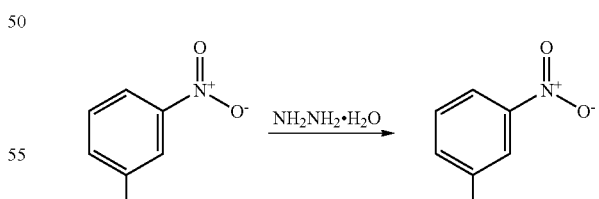

To a solution of 3-nitroacetophenone (200 g, 1.12 mol) in Industrial Methylated Spirits (1.2 l) was added hydrazine monohydrate (140 ml, 2.25 mol) and the reaction mixture was heated under reflux for 2 h. Water (1.2 l) was added and the reaction mixture was cooled to room temperature. The resulting precipitate was collected by filtration to afford the title compound as a yellow crystalline solid (180 g, 82%).

NMR (CDCl₃, selected data): 2.15 (s, 3H), 5.52 (br. s, 2H), 7.48 (dd, 1H), 7.99 (d, 1H), 8.12 (d, 1H), 8.46 (s, 1H).
MS (APCI): m/z (MH⁺) 180.5; $C_8H_9N_3O_2$+H requires 180.1.

PREPARATION 136

6-Methyl-6-(2-nitrophenyl)-3-(3-phenylpropyl)-3-azabicyclo[3.1.0]hexane-2,4-dione

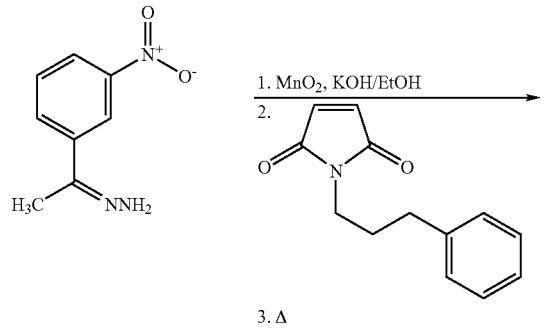

To a solution of 1-(3-nitrophenyl)-1-ethanone hydrazone (Preparation 135, 100 g, 0.56 mol) in dioxan (1 l) was added manganese (IV) oxide (200 g, 2.3 mol) and the reaction mixture was stirred at room temperature for 30 min. The suspension was filtered through Celite™ washing with dioxan (ca. 200 ml). 1-(3-Phenylpropyl)-1H-pyrrole-2,4-dione (Preparation 80, 110 g, 0.54 mol) was added to the filtrate and the reaction mixture was stirred at room temperature for 4 h before heating under reflux for 16 h. The reaction mixture was cooled to room temperature and concentrated in vacuo. The residue was triturated in methanol (500 ml) and the precipitate was collected by filtration to afford the title compound as a white crystalline solid (121 g, 65%).
NMR (CDCl₃, selected data): 1.51 (m, 3H), 1.93 (m, 2H), 2.65 (t, 2H), 2.77 (s, 2H), 3.50 (t, 2H), 7.15–7.19 (m, 3H), 7.24–7.30 (m, 2H), 7.54 (dd, 1H), 7.65 (d, 1H), 8.15 (d, 1H), 8.19 (s, 1H).
MS (APCI): m/z (MH⁺) 365.5; $C_{21}H_{20}N_2O_4$+H requires 365.2.

PREPARATION 137

1-(2-Nitrophenyl)-1-ethanone hydrazone

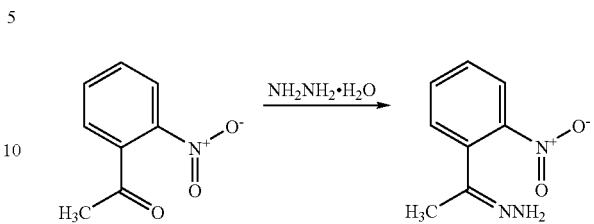

To a solution of 2'-nitroacetophenone (8.26 g, 50.00 mmol) in ethanol (50 ml) was added hydrazine monohydrate (4.85 ml, 100 mmol) and the reaction mixture was heated at 70° C. for 5 h. The reaction mixture was cooled to room temperature and water (100 ml) was added. After 5 d, the reaction mixture was concentrated in vacuo to ca. 100 ml and diethyl ether (100 ml) was added. The layers were separated and the aqueous layer was extracted with diethyl ether (100 ml). The combined extracts were dried (Na₂SO₄) and concentrated in vacuo to afford ca. 8.0 g of a crude yellow oil. This was purified by chromatography in two batches using a Biotage Flash 40M™ cartridge packed with silica gel (90 g) eluting with dichloromethane: diethyl ether (19:1) to afford the title compound as viscous yellow oil (4.20 g, 45%).
NMR (CDCl₃, selected data): 2.05 (s, 3H), 5.40 (br. s, 2H), 7.42–7.50 (m, 2H), 7.60 (dd, 1H), 7.90 (d, 1H).

PREPARATION 138

3-Hexyl-6-methyl-6-(2-nitrophenyl)-3-azabicyclo[3.1.0]hexane-2,4-dione

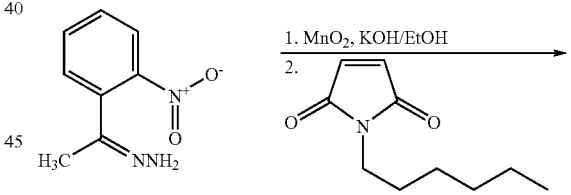

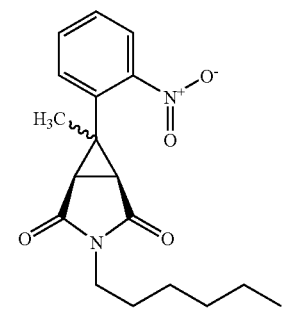

To a solution of 1-(2-nitrophenyl)-1-ethanone hydrazone (Preparation 137, 4.00 g, 22.3 mmol) in dioxan (50 ml) was added manganese (IV) oxide (4.27 g, 49.2 mmol) followed by a saturated ethanolic solution of potassium hydroxide (2.0 ml), and the reaction mixture was stirred at room temperature for 4 h. The suspension was filtered through Celite™ washing with dioxan (ca. 150 ml) to give a deep red solution. 1-Hexyl-1H-pyrrole-2,4-dione (Preparation 56, 4.05 g, 22.4 mmol) was added to the solution and the reaction mixture was stirred at room temperature overnight before heating under reflux for 24 h. The reaction mixture was cooled to room temperature, filtered through Celite™ and concentrated in vacuo a crude dark brown oil. This was purified by chromatography in two batches using a Biotage Flash 40M™ cartridge packed with silica gel (90 g) eluting with dichloromethane:hexane (2:1) to afford an 8:1 exo:endo mixture of diastereomers of the title compound as a pale brown oil (880 mg, 12%).

NMR (CDCl$_3$, selected data for the exo isomer): 0.90 (m, 3H), 1.25–1.40 (m, 6H), 1.55–1.60 (m, 5H), 2.62 (s, 2H), 3.42 (m, 2H), 7.45 (m, 1H), 7.60–7.65 (m, 2H), 7.95 (d, 1H).

NMR (CDCl$_3$, selected data for the endo isomer): 0.82 (m, 3H), 1.20–1.30 (m, 6H), 1.45 (m, 2H), 2.22 (s, 3H), 3.30–3.48 (m, 4H), 7.20 (d, 1H), 7.52 (dd, 1H), 7.62 (dd, 1H), 8.18 (d, 1H).

MS (electrospray): m/z (MH$^+$) 331.2; $C_{18}H_{22}N_2O_4$+H requires 331.2.

m/z (MNa$^+$) 353.1; $C_{18}H_{22}N_2O_4$+Na requires 353.1.

PREPARATION 139

6-(2-Aminophenyl)-3-hexyl-6-methylazabicyclo[3.1.0]hexane-2,4-dione

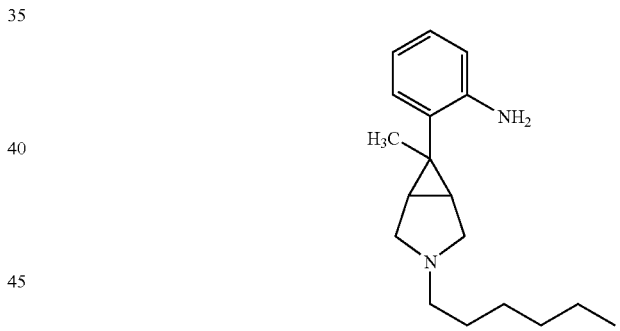

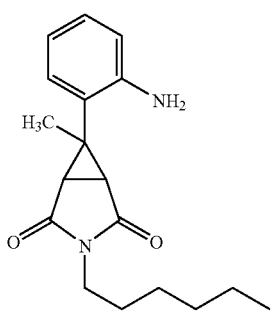

To a solution of 3-hexyl-6-methyl-6-(2-nitrophenyl)azabicyclo[3.1.0]hexane-2,4-dione (Preparation 138, 880 mg, 2.66 mmol) in tetrahydrofuran (10 ml) was added 5% palladium on charcoal (Johnsson Matthey type 87, 50 mg) and the reaction mixture was placed under an atmosphere of hydrogen (60 psi) at room temperature for 4 h. The catalyst was removed by filtration through Celite™ and the filtrate was concentrated in vacuo. The residue was flushed through a small plug of silica gel (<1 g) eluting with dichloromethane to afford only the exo isomer of the title compound as a pale yellow oil (310 mg, 39%).

NMR (CDCl$_3$, selected data): 0.90 (m, 3H), 1.15–1.40 (m, 6H), 1.45 (m, 2H), 1.60 (s, 3H), 2.75 (m, 2H), 3.45 (m, 2H), 3.90 (br. s 2H), 6.65–6.80 (m, 2H), 7.08–7.18 (m, 2H).

MS (thermospray): m/z (MH$^+$) 301.1; $C_{18}H_{22}N_2O_2$+H requires 301.2.

PREPARATION 140

2-[3-Hexyl-6-methyl-3-azabicyclo[3.1.0]hex-6-yl]phenylamine

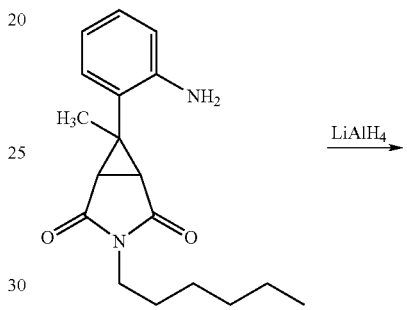

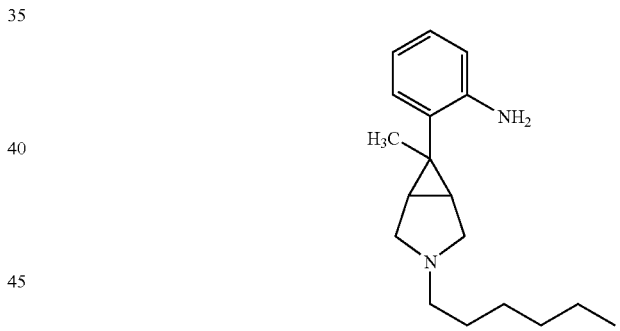

To a solution of 6-(2-aminophenyl)-3-hexyl-6-methylazabicyclo[3.1.0]hexane-2,4-dione (Preparation 139, 310 mg, 1.03 mmol) in tetrahydrofuran (10 ml) under nitrogen at 0° C. was added dropwise a 1.0M solution of lithium aluminium hydride in tetrahydrofuran (2.5 ml, 2.5 mmol), and the reaction mixture was allowed to stir at room temperature for 4 h. The rapidly stirred reaction mixture was treated sequentially with water (2.5 ml), sodium carbonate (2.5 g) and ethyl acetate (25 ml). The reaction mixture was stirred for 1 h, filtered and concentrated in vacuo. This was purified by chromatography using a Biotage Flash 12™ cartridge packed with silica gel (8 g) eluting with ethyl acetate:hexane:0.880 ammonia (25:75:1) to afford the title compound as a pale yellow oil (123 mg, 44%).

NMR (CDCl$_3$, selected data): 0.90 (m, 3H), 1.15–1.40 (m, 6H), 1.45 (m, 2H), 1.60 (s, 3H), 2.75 (m, 2H), 3.45 (m, 2H), 3.90 (br. s 2H), 6.65–6.80 (m, 2H), 7.08–7.18 (m, 2H).

MS (electrospray): m/z (MH$^+$) 267.2; $C_{18}H_{22}N_2$+H requires 267.2.

PREPARATION 141

N-(3-{6-Methyl-3-[(E)-3-(2-pyridinyl)-2-propenoyl]-3-azabicyclo[3.1.0]hex-6-yl}phenyl)methanesulfonamide

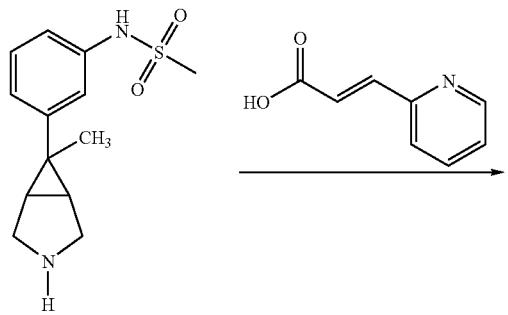

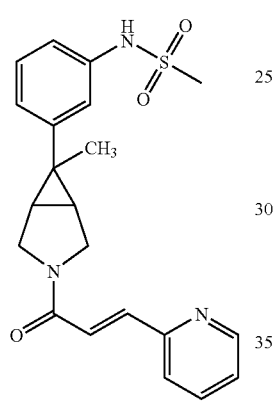

A solution of 1-hydroxybenzotriazole monohydrate (224 mg, 1.46 mmol) and 1-(3-dimethylaminopropyl)-3-ethylcarbodiimide hydrochloride (306 mg, 1.60 mmol) in N,N-dimethylformamide (10 ml) was added to (E)-3-(2-pyridinyl)-2-propenoic acid (197 mg, 1.32 mmol). After stirring at room temperature for 15 min, the mixture was added to the hydrochloride salt of N-[3-(6-methyl-3-azabicyclo[3.1.0]hex-6-yl)phenyl]methanesulfonamide (Preparation 53, 404 mg, 1.32 mmol) and sodium hydrogen carbonate (220 mg, 2.64 mmol). The reaction mixture was stirred at room temperature for overnight and then water (20 ml) and dichloromethane (10 ml) were added. The biphasic mixture was separated by filtering through a Whatman Microfiltration Device Filter Tube, and the resulting organic extract was concentrated using a stream of nitrogen to afford 377 mg of a crude dark brown oil. This was purified by chromatography using a Biotage Flash 40S™ cartridge packed with silica gel (40 g) eluting with dichloromethane:ethanol:0.880 ammonia (100:2:1) to afford the title compound as a white solid (172 mg, 33%).

NMR (CDCl$_3$, selected data): 1.25 (s, 3H), 2.02 (m, 2H), 3.00 (s, 3H), 3.80–3.95 (m, 3H), 4.05 (dd, 1H), 7.05–7.18 (m, 2H), 7.20–7.30 (m, 3H), 7.35 (d, 1H), 7.41 (d, 1H), 7.72 (dd, 1H), 7.79 (d, 1H), 8.62 (d, 1H).

MS (electrospray): M/Z (MH$^+$) 398; C$_{21}$H$_{23}$N$_3$O$_3$S+H requires 398.

PREPARATION 142

N-(3-{6-Methyl-3-[(E)-3-(2-quinolinyl)-2-propenoyl]-3-azabicyclo[3.1.0]hex-6-yl}phenyl)methanesulfonamide

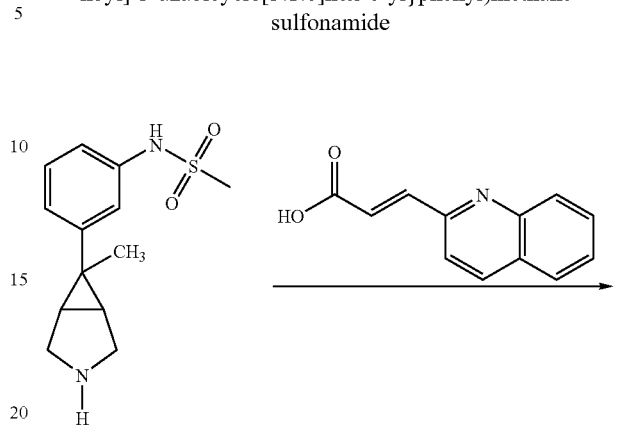

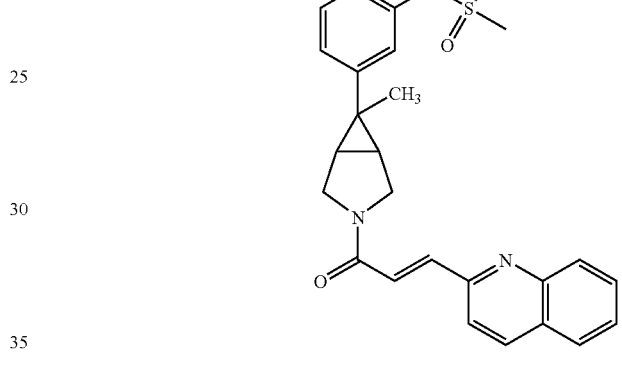

A solution of 1-hydroxybenzotriazole monohydrate (112 mg, 0.73 mmol) and 1-(3-dimethylaminopropyl)-3-ethylcarbodiimide hydrochloride (153 mg, 0.80 mmol) in N,N-dimethylformamide (5 ml) was added to (E)-3-(2-quinolinyl)-2-propenoic acid (M. Hamana, K. Funakoshi and Y. Kuchino, Chem. Pharm. Bull., 1974, 22, 1806; 131 mg, 0.66 mmol). After stirring at room temperature for 15 min, the mixture was added to the hydrochloride salt of N-[3-(6-methyl-3-azabicyclo[3.1.0]hex-6-yl)phenyl]methanesulfonamide (Preparation 53, 202 mg, 0.66 mmol) and sodium hydrogen carbonate (110 mg, 1.32 mmol). The reaction mixture was stirred at room temperature for overnight and then water (10 ml) and dichloromethane (5 ml) were added. The biphasic mixture was separated by filtering through a Whatman Microfiltration Device Filter Tube, and the resulting organic extract was concentrated using a stream of nitrogen to afford 400 mg of a crude dark red oil. This was purified by chromatography using a Biotage Flash 40S™ cartridge packed with silica gel (40 g) eluting with dichloromethane:ethanol:0.880 ammonia (100:2:1) to afford the title compound as a cream solid (206 mg, 70%).

NMR (CDCl$_3$, selected data): 1.32 (s, 3H), 2.05 (m, 2H), 3.02 (s, 3H), 3.85–3.95 (m, 2H), 4.00 (d, 1H), 4.15 (dd, 1H), 6.88 (br. s, 1H), 7.15 (dd, 1H), 7.20–7.35 (m, 2H), 7.48 (d, 1H), 7.52–7.60 (m, 2H), 7.75 (dd, 1H), 7.82 (d, 1H), 7.95 (d, 1H), 8.12 (d, 1H), 8.19 (d, 1H).

MS (electrospray): M/Z (MH$^+$) 448; C$_{25}$H$_{25}$N$_3$O$_3$S+H requires 448.

PREPARATION 143

N-(3-{3-[3-(1,3-Benzothiazol-2-yl)propanoyl]-6-methyl-3-azabicyclo[3.1.0]hex-6-yl}phenyl)methanesulfonamide

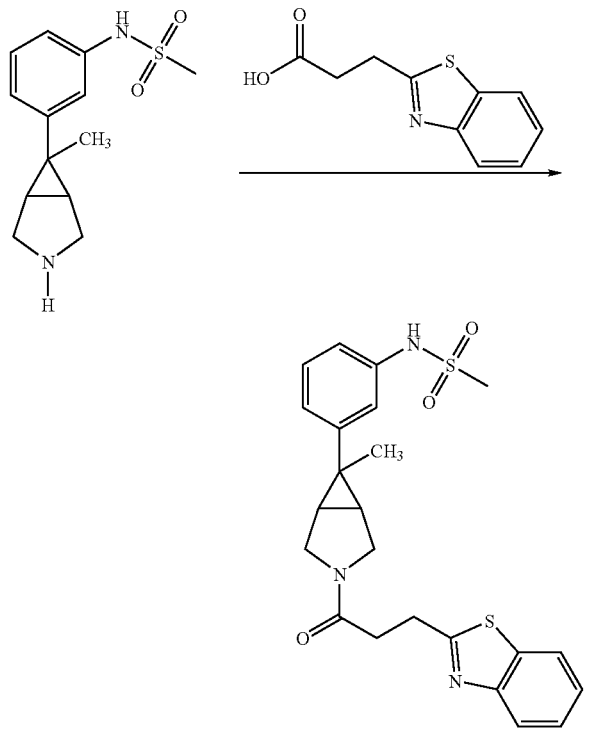

A solution of 1-hydroxybenzotriazole monohydrate (112 mg, 0.73 mmol) and 1-(3-dimethylaminopropyl)-3-ethylcarbodiimide hydrochloride (153 mg, 0.80 mmol) in N,N-dimethylformamide (5 ml) was added to 3-(1,3-benzothiazol-2-yl)propanoic acid (P. Baudet and C. Otten, Helv. Chim. Acta, 1970, 53, 1683; 137 mg, 0.66 mmol). After stirring at room temperature for 15 min, the mixture was added to the hydrochloride salt of N-[3-(6-methyl-3-azabicyclo[3.1.0]hex-6-yl)phenyl]methanesulfonamide (Preparation 53, 202 mg, 0.66 mmol) and sodium hydrogen carbonate (110 mg, 1.32 mmol). The reaction mixture was stirred at room temperature for overnight and then water (10 ml) and dichloromethane (5 ml) were added. The biphasic mixture was separated by filtering through a Whatman Microfiltration Device Filter Tube, and the resulting organic extract was concentrated using a stream of nitrogen to afford 326 mg of a crude dark green solid. This was purified by chromatography using a Biotage Flash 40S™ cartridge packed with silica gel (40 g) eluting with dichloromethane:ethanol:0.880 ammonia (100:2:1) to afford the title compound as an off-white solid (228 mg, 76%).

NMR (CDCl$_3$, selected data): 1.30 (s, 3H), 2.02 (m, 2H), 3.00 (s, 3H), 3.78–3.90 (m, 3H), 4.00 (dd, 1H), 6.47 (br. s, 1H), 6.63 (d, 1H), 7.03–7.15 (m, 3H), 7.29 (dd, 1H), 7.46 (dd, 1H), 7.56 (dd, 1H), 7.67–7.73 (m, 2H), 8.06 (d, 1H).

MS (electrospray): M/Z (MH$^+$) 456; C$_{23}$H$_{25}$N$_3$O$_3$S$_2$+H requires 456.

PREPARATION 144

N-(3-{6-Methyl-3-[(E)-3-(6-methyl-2-pyridinyl)-2-propenoyl]-3-azabicyclo[3.1.0]hex-6-yl}phenyl)methanesulfonamide

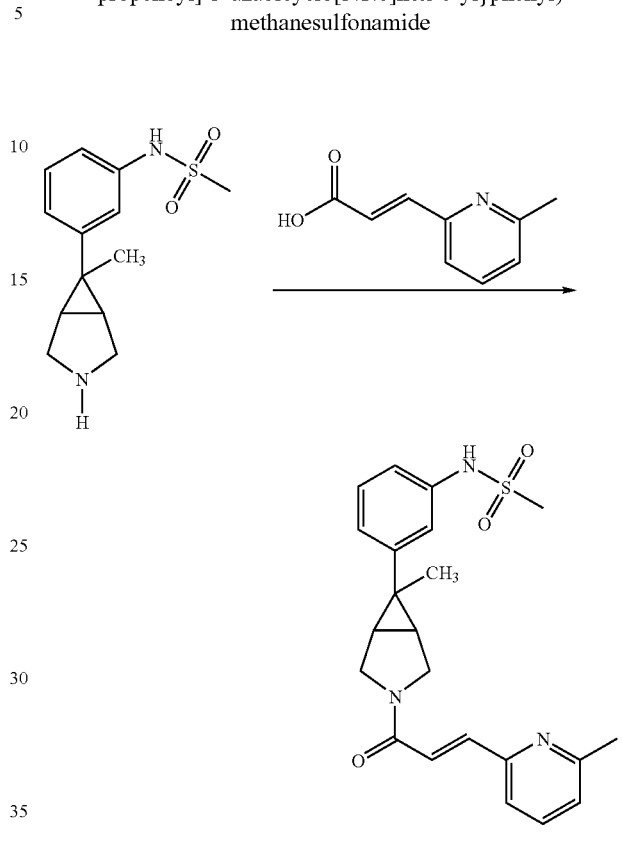

A solution of 1-hydroxybenzotriazole monohydrate (112 mg, 0.73 mmol) and 1-(3-dimethylaminopropyl)-3-ethylcarbodiimide hydrochloride (153 mg, 0.80 mmol) in N,N-dimethylformamide (5 ml) was added to (E)-3-(6-methyl-2-pyridinyl)-2-propenoic acid (F. Freeman, L. Y. Chang, J. C. Kappos and L. Sumarta, J. Org. Chem., 1987, 52, 1460; 108 mg, 0.66 mmol). After stirring at room temperature for 15 min, the mixture was added to the hydrochloride salt of N-[3-(6-methyl-3-azabicyclo[3.1.0]hex-6-yl)phenyl]methanesulfonamide (Preparation 53, 202 mg, 0.66 mmol) and sodium hydrogen carbonate (110 mg, 1.32 mmol). The reaction mixture was stirred at room temperature for overnight and then water (10 ml) and dichloromethane (5 ml) were added. The biphasic mixture was separated by filtering through a Whatman Microfiltration Device Filter Tube, and the resulting organic extract was concentrated using a stream of nitrogen to afford 290 mg of a crude cream solid. This was purified by chromatography using a Biotage Flash 40S™ cartridge packed with silica gel (40 g) eluting with dichloromethane:ethanol:0.880 ammonia (100:2:1) to afford the title compound as a white solid (191 mg, 70%).

NMR (CDCl$_3$, selected data): 1.27 (s, 3H), 2.02 (m, 2H), 2.60 (s, 3H), 3.01 (s, 3H), 3.82–3.98 (m, 3H), 4.08 (dd, 1H), 6.87 (br. s, 1H), 7.07–7.15 (m, 2H), 7.19–7.37 (m, 5H), 7.59 (dd, 1H), 7.73 (d, 1H).

MS (electrospray): M/Z (MH$^+$) 412; C$_{22}$H$_{25}$N$_3$O$_3$S+H requires 412.

PREPARATION 145

N-(3-{6-Methyl-3-[(E)-3-(2-trifluoromethyl)phenyl)-2-propenoyl]-3-azabicyclo[3.1.0]hex-6-yl}phenyl)methanesulfonamide

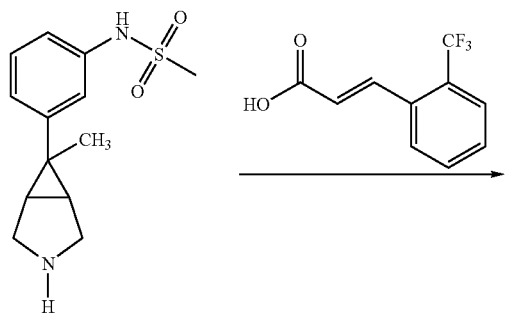

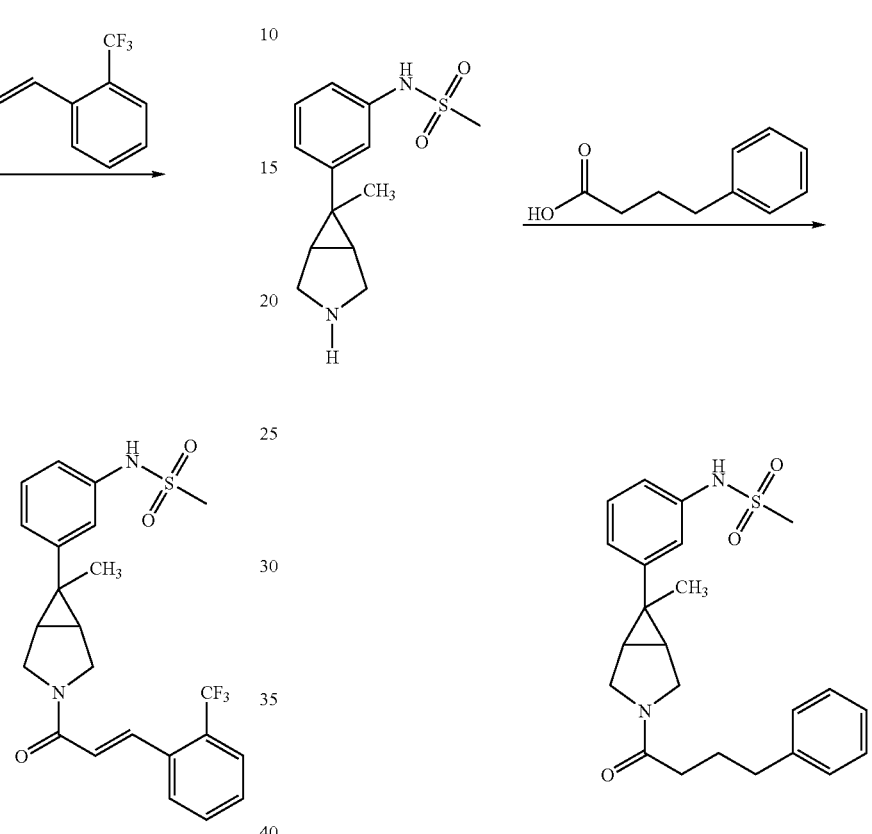

A solution of 1-hydroxybenzotriazole monohydrate (112 mg, 0.73 mmol) and 1-(3-dimethylaminopropyl)-3-ethylcarbodiimide hydrochloride (153 mg, 0.80 mmol) in N,N-dimethylformamide (5 ml) was added to (E)-3-(2-(trifluoromethyl)phenyl)-2-propenoic acid (143 mg, 0.66 mmol). After stirring at room temperature for 15 min, the mixture was added to the hydrochloride salt of N-[3-(6-methyl-3-azabicyclo[3.1.0]hex-6-yl)phenyl]methanesulfonamide (Preparation 53, 202 mg, 0.66 mmol) and sodium hydrogen carbonate (110 mg, 1.32 mmol). The reaction mixture was stirred at room temperature for overnight and then water (10 ml) and dichloromethane (5 ml) were added. The biphasic mixture was separated by filtering through a Whatman Microfiltration Device Filter Tube, and the resulting organic extract was concentrated using a stream of nitrogen to afford 364 mg of a crude brown oil. This was purified by chromatography using a Biotage Flash 40S™ cartridge packed with silica gel (40 g) eluting with dichloromethane:ethanol:0.880 ammonia (100:2:1) to afford the title compound as a yellow oil (240 mg, 78%).

NMR (CDCl$_3$, selected data): 1.30 (s, 3H), 2.02 (m, 2H), 3.00 (s, 3H), 3.78–3.90 (m, 3H), 4.00 (dd, 1H), 6.47 (br. s, 1H), 6.63 (d, 1H), 7.03–7.15 (m, 3H), 7.29 (dd, 1H), 7.46 (dd, 1H), 7.56 (dd, 1H), 7.67–7.73 (m, 2H), 8.06 (d, 1H).

MS (electrospray): M/Z (MH$^+$) 465; C$_{23}$H$_{23}$F$_3$N$_2$O$_3$S+H requires 465.

PREPARATION 146

N-{3-[6-Methyl-3-(4-phenylbutanoyl)-3-azabicyclo[3.1.0]hex-6-yl]phenyl}methanesulfonamide To a solution of 4-phenylbutanoic acid (219 mg, 1.33 mmol) in N,N-dimethylformamide (20 ml) was added 1-hydroxybenzotriazole monohydrate (225 mg, 1.48 mmol) and 1-(3-dimethylaminopropyl)-3-ethylcarbodiimide hydrochloride (382 mg, 1.98 mmol). After stirring at room temperature for 15 min the mixture was treated with the hydrochloride salt of N-[3-(6-methyl-3-azabicyclo[3.1.0]hex-6-yl)phenyl]methanesulfonamide (Preparation 53, 449 mg, 1.48 mmol) and sodium hydrogen carbonate (225 mg, 2.7 mmol). The reaction mixture was stirred at room temperature for overnight before concentrating in vacuo. Water (15 ml) was added and the reaction mixture was extracted with ethyl acetate (20, 15 ml). The combined organic extracts were washed with water (15 ml), dried (MgSO$_4$), filtered and concentrated in vacuo to give a colourless oil (540 mg). This was purified by chromatography using a Biotage Flash 12™ cartridge packed with silica gel (8 g) eluting with hexane:ethyl acetate (100:0 to 0:100 over 30 min) and then with ethyl acetate:methanol (100:0 to 0:100 over 5 min) to afford the title compound as a colourless glass (360 mg, 59%).

NMR (CDCl$_3$, selected data): 1.25 (s, 3H), 1.90–2.10 (m, 4H), 2.25 (t, 2H), 2.70 (t, 2H), 3.00 (s, 3H), 3.50 (d, 1H), 3.65–3.80 (m, 3H), 6.70 (br. s, 1H), 7.00–7.40 (m, 9H).

MS (electrospray): M/Z (MH$^+$) 413; C$_{23}$H$_{28}$N$_2$O$_3$S+H requires 413.

PREPARATION 147

N-(3-{3-[3-(2-Methoxyphenyl)propanoyl]-6-methyl-3-azabicyclo[3.1.0]hex-6-yl}phenyl)methanesulfonamide

PREPARATION 148

N-{3-[3-(1-Benzothiophen-2-ylcarbonyl)-6-methyl-3-azabicyclo[3.1.0]hex-6-yl]phenyl}methanesulfonamide

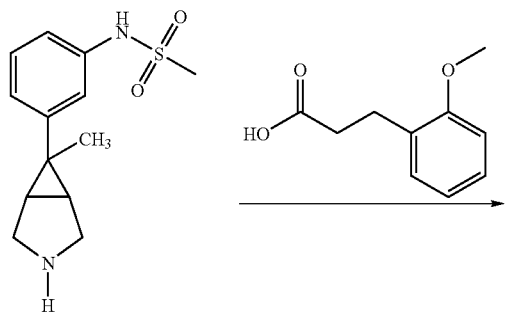

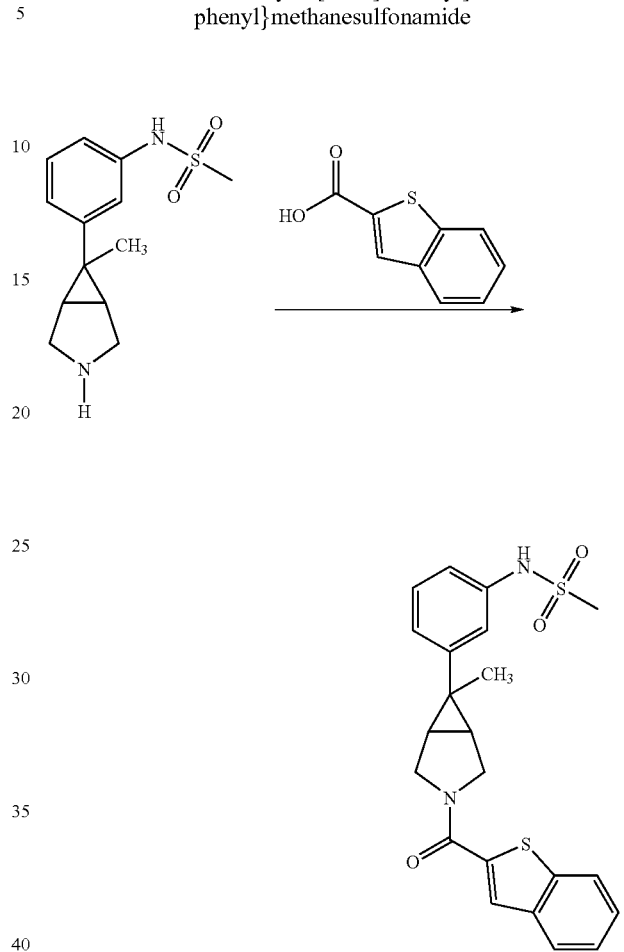

To a solution of 3-(2-methoxyphenyl)propanoic acid (240 mg, 1.33 mmol) in N,N-dimethylformamide (20 ml) was added 1-hydroxybenzotriazole monohydrate (225 mg, 1.48 mmol) and 1-(3-dimethylaminopropyl)-3-ethylcarbodiimide hydrochloride (382 mg, 1.98 mmol). After stirring at room temperature for 15 min the mixture was treated with the hydrochloride salt of N-[3-(6-methyl-3-azabicyclo[3.1.0]hex-6-yl)phenyl]methanesulfonamide (Preparation 53, 449 mg, 1.48 mmol) and sodium hydrogen carbonate (225 mg, 2.7 mmol). The reaction mixture was stirred at room temperature for overnight before concentrating in vacuo. Water (15 ml) was added and the reaction mixture was extracted with ethyl acetate (20, 15 ml). The combined organic extracts were washed with water (15 ml), dried (MgSO$_4$), filtered and concentrated in vacuo to give a dark buff solid (470 mg). The crude product was sonicated in dichloromethane (5 ml) and collected by filtration to afford the title compound as an off-white solid (220 mg, 39%).

NMR (CDCl$_3$, selected data): 1.18 (s, 3H), 1.93 (m, 2H), 2.58 (dd, 2H), 2.95–3.02 (m, 5H), 3.52 (d, 1H), 3.65–3.77 (m, 3H), 3.85 (s, 3H), 6.58 (br. s, 1H), 6.80–6.92 (m, 2H), 7.00–7.30 (m, 6H).

MS (electrospray): M/Z (MH$^+$) 429; C$_{23}$H$_{28}$N$_2$O$_4$S+H requires 429.

To a solution of 1-benzothiophene-2-carboxylic acid (236 mg, 1.33 mmol) in N,N-dimethylformamide (20 ml) was added 1-hydroxybenzotriazole monohydrate (225 mg, 1.48 mmol) and 1-(3-dimethylaminopropyl)-3-ethylcarbodiimide hydrochloride (382 mg, 1.98 mmol). After stirring at room temperature for 15 min the mixture was treated with the hydrochloride salt of N-[3-(6-methyl-3-azabicyclo[3.1.0]hex-6-yl)phenyl]methanesulfonamide (Preparation 53, 449 mg, 1.48 mmol) and sodium hydrogen carbonate (225 mg, 2.7 mmol). The reaction mixture was stirred at room temperature for overnight before concentrating in vacuo. Water (15 ml) was added and the reaction mixture was extracted with ethyl acetate (20, 15 ml). The combined organic extracts were washed with water (15 ml), dried (MgSO$_4$), filtered and concentrated in vacuo to give a buff solid (545 mg). The crude product was sonicated in dichloromethane (5 ml) and collected by filtration to afford the title compound as an off-white solid (410 mg, 72%).

NMR (DMSO, selected data): 1.20 (s, 3H), 2.03 (m, 2H), 3.00 (m, 3H), 3.80–4.00 (m, 3H), 4.25 (m, 1H), 7.00–7.08 (m, 2H), 7.12 (s, 1H), 7.24 (dd, 1H), 7.40–7.50 (m, 2H), 7.93–8.03 (m, 3H).

MS (electrospray): M/Z (MH$^+$) 427; C$_{22}$H$_{22}$N$_2$O$_3$S$_2$+H requires 427.

What is claimed is:
1. A process for the preparation of a compound of formula I

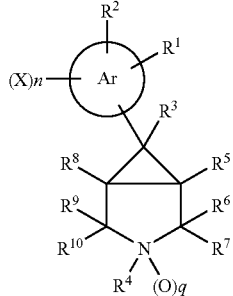

or a pharmaceutically or veterinarily acceptable derivative thereof,
wherein the "Ar" ring represents an optionally benzo-fused phenyl;
$R^1$ is H, halogen, $NO_2$, $NH_2$, $NY^2WY^1$, $CO_2R^7$, $C(O)R^8$, $C(=NOH)R^8$, or OE,
$Y^2$ is H, $C_{1-6}$ alkyl, $C_{3-6}$ alkenyl wherein each of which alkyl and alkenyl is optionally substituted by aryl, aryloxy or $Het^1$,
W is $SO_2$, CO, C(O)O, $P(Y^1)=O$, $P(Y^1)=S$,
$Y^1$ is $C_{1-10}$ alkyl (which alkyl is optionally substituted by one or more substituents independently selected from halogen, OH, $C_{1-4}$ alkoxy, $C_{1-6}$ alkanoyloxy, $CONH_2$, $C_{1-6}$ alkoxycarbonyl, $NH_2$, aryl, mono- or di($C_{1-4}$ alkyl)amino, $C_{3-8}$ cycloalkyl, phthalimidyl, and $Het^1$), $Het^1$, aryl, (which aryl is optionally substituted by one or more substituents independently selected from $C_{1-4}$ alkyl, $C_{1-4}$ haloalkyl and halogen), $NH_2$, $N(C_{1-6}$ alkyl$)_2$ or $NH(C_{1-6}$ alkyl),
$Het^1$ is a heterocyclic group containing up to 4 heteroatoms selected from N, O and S, which may comprise up to 3 rings, said $Het^1$ being optionally benzo- or pyrido-fused heteroaryl, said $Het^1$ being optionally substituted by one or more substituents independently selected from $C_{1-6}$ alkyl, $C_{1-6}$ alkoxy, $C_{3-6}$ cycloalkyl, $C_{1-6}$ haloalkoxy, $C_{1-6}$ haloalkyl, $C_{3-6}$ halocycloalkyl, =O, OH, halogen, $NO_2$, $Sir^{19a}R^{19b}R^{19c}$, $CON^{20a}R^{20b}$, $NR^{20a}R^{20b}$, $SR^{21a}$, $NR^{21b}SO_2R^{22a}$, $NR^{21c}C(O)OR^{22b}$, $NR^{21d}COR^{22d}$, and $C_{1-6}$ alkoxycarbonyl,
and if a S atom is present in a ring, it can be present as part of a —S—, S(O)— or —S(O_2)— group, and carbon atoms in the ring can be present as a part of a carbonyl moiety;
$R^{19a}$, $R^{19b}$, $R^{19c}$ each independently represent $C_{1-6}$ alkyl or aryl,
$R^{20a}$ and $R^{20b}$ each independently H, $C_{1-6}$ alkyl, aryl, ($C_{1-4}$ alkyl)phenyl, each of which alkyl, aryl and alkylphenyl are optionally substituted by one or more $C_{1-4}$ alkyl, $C_{1-4}$ alkoxy, OH, $NO_2$, $NH_2$ or halogen,
or $R^{20a}$ and $R^{20b}$ can be taken together with the N atom to which they are attached, to form a 4- to 6-membered ring optionally substituted by one or more substituents independently selected from one or more $C_{1-4}$ alkyl, $C_{1-4}$ alkoxy, OH, =O, $NO_2$, $NH_2$ and halogen,
$R^{21a, b, c \text{ and } d}$ each independently represent H, $C_{1-6}$ alkyl, aryl or $C_{1-4}$ alkylphenyl, each of which alkyl, aryl, and alkylphenyl are optionally substituted by one or more $C_{1-4}$ alkyl, $C_{1-4}$ alkoxy, OH, $NO_2$, halogen, or $NH_2$,
$R^{22a, b \text{ and } c}$ each independently represent $C_{1-6}$ alkyl, aryl or $C_{1-4}$ alkylphenyl, each of which alkyl, aryl, and alkylphenyl are optionally substituted by one or more $C_{1-4}$ alkyl, $C_{1-4}$ alkoxy, OH, $NO_2$, halogen, or $NH_2$,
E is H, $CONR^{32}R^{33}$, $CSNR^{32}R^{33}$, $COR^{34}$, $CO_2R^{34}$, $COCH(R^{34a})NH_2$, $R^{35}$, $CH_2CO_2R^{35a}$, $CHR^{35b}CO_2R^{35a}$, $CH_2OCO_2R^{35c}$, $CHR^{35d}OCO_2R^{35c}$, $COCR^{36}=CR^{37}NH_2$, $COCHR^{36}CHR^{37}NH_2$, or $PO(OR^{38})_2$,
$R^{32}$ and $R^{33}$ are each independently H, $C_{3-10}$ alkylalkenyl, $C_{3-7}$ cycloalkyl (said cycloalkyl is optionally substituted by $C_{1-4}$ alkyl), phenyl, said phenyl is optionally substituted by $(X)_n$), or $C_{1-10}$ alkyl, or $R^{32}$ and $R^{33}$ can be taken together with the N atom to which they are attached and can form a 5- to 8-membered heterocycle optionally comprising further hetero atoms selected from N, O and S, which heterocycle is optionally substituted by $C_{1-4}$ alkyl, optionally substituted by one or more halogen,
$R^{34}$ is H, $C_{4-7}$ cycloalkyl (which cycloalkyl is optionally substituted by one or more $C_{1-4}$ alkyl), phenyl (which phenyl is optionally substituted by $(X)_n$, $C_{1-4}$ alkanoyloxy, $NR^{32}R^{33}$, $CONR^{32}R^{33}$ or OH or $C_{1-6}$ alkyl,
$R^{34a}$ is H, $C_{1-6}$ alkyl, $C_{4-7}$ cycloalkyl (which is optionally substituted by one or more $C_{1-4}$ alkyl), phenyl (which is optionally substituted by $(X)_n$, $C_{1-4}$ alkanoyloxy, $NR^{32}R^{33}$, $CONR^{32}R^{33}$ or OH)] or a naturally occuring amino acid substituent,
$R^{35}$ is $C_{4-7}$ cycloalkyl optionally substituted by one or more $C_{1-4}$ alkyl, phenyl (which phenyl is optionally substituted by one or more $(X)_n$, $C_{1-4}$ alkanoyl, $NHR^{32}$, $CON(R^{32})_2$, or OH), $C_{1-6}$ alkyl, $C_{1-4}$ alkoxy($C_{1-4}$ alkyl), phenyl($C_{1-4}$)alkyloxy($C_{1-4}$)alkyl, tetrahydropyranyl, tetrahydrofuranyl, cinnamyl or trimethylsilyl,
$R^{35a, b, c \text{ and } d}$ are each independently H, $C_{4-7}$ cycloalkyl optionally substituted by one or more $C_{1-4}$ alkyl, phenyl optionally substituted by one or more $(X)_n$ or $C_{1-6}$ alkyl, which alkyl is optionally substituted by $C_{4-7}$ cycloalkyl (which cycloalkyl is optionally substituted by one or more $C_{1-4}$ alkyl, or phenyl optionally substituted by one or more $(X)_n$),
$R^{36}$ and $R^{37}$ each independently represent H, $C_{3-6}$ alkylalkenyl, $C_{4-7}$ cycloalkyl, phenyl optionally substituted by one or more $(X)_n$, or $C_{1-6}$ alkyl;
$R^{38}$ is $C_{4-7}$ cycloalkyl optionally substituted by one or more $C_{1-4}$ alkyl, phenyl, (which phenyl is optionally substituted by one or more $(X)_n$), or $C_{1-6}$ alkyl,
$R^2$ is H or halogen;
$R^3$ is H, CN, halogen, $C_{1-6}$ alkoxy, $C_{1-6}$ alkoxycarbonyl, $C_{2-6}$ alkanoyl, $C_{2-6}$ alkanoyloxy, $C_{3-8}$ cycloalkyl, $C_{3-8}$ cycloalkyloxy, $C_{4-9}$ cycloalkanoyl, aryl, aryloxy, $NR^{12}R^{13}$, $CONR^{12}R^{13}$, $NY^2WY^1$, $C_{1-6}$ alkyl, $C_{2-10}$ alkenyl, $C_{2-10}$ alkynyl, each of which alkyl, alkenyl and alkynyl groups is optionally substituted by one or more CN, halogen, OH, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl, saturated heterocycle, $NR^{12}R^{13}$, $CONR^{12}R^{13}$ or $NY^2WY^1$,
$R^4$ is $C_{1-10}$ alkyl, $C_{3-10}$ alkenyl or $C_{3-10}$ alkynyl each of which groups is linked to the N atom via a $sp^3$ carbon, and which is optionally substituted by one or more OH, CN, halogen, $C_{1-6}$ alkoxy (which alkoxy is optionally substituted by aryl), aryloxy, $C_{1-6}$ alkoxycarbonyl, $C_{2-6}$ alkanoyl, $C_{2-6}$ alkanoyloxy, $C_{3-8}$ cycloalkyl, $C_{3-8}$ cycloalkyloxy, $C_{4-9}$ cycloalkanoyl, aryl adamantyl or $ZBNR^{14}R^{15}$,
Z is a direct bond, CO or $S(O)_n$ group,
B is $(CH_2)_p$, $R^{12}$ and $R^{13}$ each independently represent H or $C_{1-4}$ alkyl, or $R^{12}$ and $R^{13}$ can be taken together with the N atom to which they are attached to form a 4- to 7-membered heterocycle optionally comprising a further hetero moiety selected from $NR^{16}$, O and/or S, and which is optionally substituted by one or more $C_{1-4}$ alkyl, $R^{14}$ and $R^{15}$ each independently represent H, $C_{1-10}$ alkyl, $C_{3-10}$ alkenyl, $C_{3-10}$ alkynyl, $C_{3-8}$ cycloalkyl, aryl or heteroaryl, or $R^{14}$ and $R^{15}$ can be taken together with the N atom to which they are attached to form a 4- to 7-membered heterocycle optionally comprising a further hetero moiety selected from $NR^{16}$, O and/or S, and which is optionally substituted by one or more $C_{1-4}$ alkyl, $R^{16}$ is H, $C_{1-6}$ alkyl, $C_{3-8}$ cycloalkyl, $(C_{1-6}$ alkylene)$(C_{3-8}$ cycloalkyl) or $(C_{1-6}$ alkylene)aryl, $R^5$ and $R^8$ when taken separately are each independently H, $C_{1-6}$ alkyl, $R^5$ and $R^8$ can be taken together with the carbon atoms to which they are joined to form a $C_{3-8}$ cycloalkyl ring, $R^6$, $R^7$, $R^9$ and $R^{10}$ when taken separately are H, $R^5$ and $R^6$ or $R^7$ can be taken together with the carbon atoms to which they are joined to form a $C_{3-8}$ cycloalkyl ring, X is halogen, $C_{1-4}$ alkyl, $C_{1-4}$ alkoxy, $C_{1-4}$ haloalkyl or $C_{1-4}$ haloalkoxy, m is 1 or 2;

n is 0, 1 or 2;

p is 0, 1, 2, 3, 4, 5, 6, 7, 8, 9 or 10; and q is 0 or 1 wherein said process comprises:

(a) for compounds of formula I in which q is 0 and $R^1$ represents $NY^2WY^1$, reacting a compound of formula II,

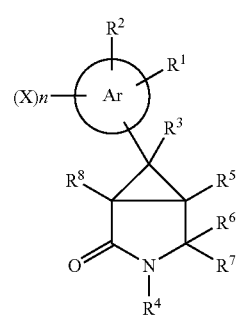

II with a compound of formula III, $Z^1$-$WY^1$        III wherein $Z^1$ is a leaving group;

(b) for compounds of formula I in which q is 0 and $R^6$ and $R^7$ both represent H, reducing of a compound of formula IV,

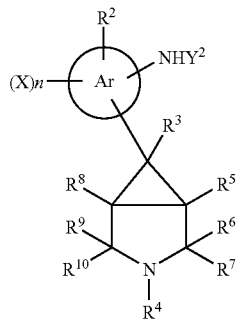

IV (c) for compounds of formula I in which q is 0 and $R^9$ and $R^{10}$ both represent H, reducing a compound of formula V,

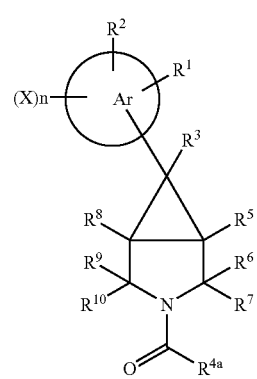

V (d) where q is 0, reacting a compound of formula VIII,

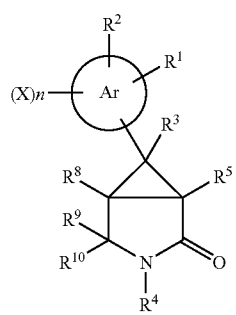

XXXI with a compound of formula IX $R^4$-Lg        IX wherein Lg is a leaving group;

(e) for compounds of formula I in which q is 0 and $R^6$, $R^7$, $R^9$ and $R^{10}$ are all H, reducing a compound of formula X,

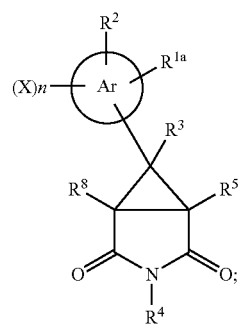

X (f) for compounds of formula I in which q is 0 and $R^1$ represents OH, reacting a compound of formula II, where $Y^2$ is H, as defined above, with fluoroboric acid and isoamyl nitrite;

(g) for compounds of formula I in which q is 0 and $R^1$ represents Cl, reacting a compound of formula II, where $Y^2$ is H, as defined above, with sodium nitrite in the presence of dilute acid, followed by reaction with copper (I) chloride in the presence of concentrated acid;

(h) for compounds of formula I in which q is 1, oxidizing a compound of formula I where q is 0; or
(i) for compounds of formula I where q is 0, by reducing the corresponding compound of formula XXXI,

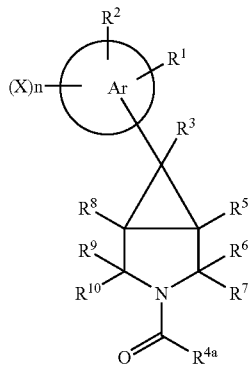

XXXI where $R^{4a}CH_2$ takes the same meaning as $R^4$ as defined above, and where desired or necessary converting the resulting compound of formula I into a pharmaceutically or veterinarily acceptable derivative.

2. The process according to claim 1 wherein (a), $Z^1$ is halogen or $Y^1SO_2$ O—.

3. The process according to claim 1 where in (b), the compound of Formula IV is reduced with lithium aluminum hydride.

4. The process according to claim 1 where in (c), the compound of Formula V is reduced with lithium aluminum hydride.

5. The process according to claim 1 where in (d), Lg is halogen or sulphate group.

6. The process according to claim 5 where in Lg is Br or tosglate.

7. The process according to claim 1 where in (e), the compound of Formula X is reduced with lithium aluminum hydride.

8. The process according to claim 1 where in (h) the compound of Formula I wherein g is O is oxidized with aqueous hydrogen peroxide.

9. The process according to claim 1 wherein $Het^1$ is aryl.

* * * * *